US012780922B2

(12) United States Patent
Murphy et al.

(10) Patent No.: US 12,780,922 B2
(45) **Date of Patent: *Nov. 3, 2026**

(54) BISPECIFIC ANTI-PSMA X ANTI-CD28 ANTIBODIES AND USES THEREOF

(71) Applicant: Regeneron Pharmaceuticals, Inc., Tarrytown, NY (US)

(72) Inventors: Andrew J. Murphy, Croton-on-Hudson, NY (US); Dimitris Skokos, New York, NY (US); Janelle Waite, Bronx, NY (US); Erica Ullman, Yorktown Heights, NY (US); Aynur Hermann, New York, NY (US); Eric Smith, New York, NY (US); Lauric Haber, Rye Brook, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/077,139

(22) Filed: Dec. 7, 2022

(65) Prior Publication Data

US 2023/0303696 A1 Sep. 28, 2023

Related U.S. Application Data

(63) Continuation of application No. 16/448,462, filed on Jun. 21, 2019, now Pat. No. 11,548,947.

(60) Provisional application No. 62/815,878, filed on Mar. 8, 2019, provisional application No. 62/781,930, filed on Dec. 19, 2018, provisional application No. 62/781,980, filed on Dec. 19, 2018, provisional application No. 62/688,227, filed on Jun. 21, 2018.

(51) Int. Cl.

| | |
|---|---|
| ***C07K 16/28*** | (2006.01) |
| ***A61K 39/00*** | (2006.01) |
| ***C07K 16/30*** | (2006.01) |

(52) U.S. Cl.

CPC ...... *C07K 16/2818* (2013.01); *C07K 16/3069* (2013.01); *A61K 2039/505* (2013.01); *C07K 2317/31* (2013.01); *C07K 2317/565* (2013.01); *C07K 2317/732* (2013.01); *C07K 2317/734* (2013.01); *C07K 2317/74* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | | |
|---|---|---|---|---|
| 7,723,482 B2 | 5/2010 | Soulillou et al. | | |
| 10,179,819 B2 | 1/2019 | Kirshner et al. | | |
| 11,396,544 B2 * | 7/2022 | Murphy | ............. | C07K 16/3061 |
| 11,453,721 B2 * | 9/2022 | Murphy | ............. | C07K 16/3069 |
| 11,548,947 B2 | 1/2023 | Murphy et al. | | |
| 11,905,332 B2 * | 2/2024 | DiLillo | .............. | C07K 16/2818 |
| 2005/0136050 A1 | 6/2005 | Kufer et al. | | |
| 2009/0297438 A1 | 12/2009 | Huang et al. | | |
| 2012/0225071 A1 | 9/2012 | Klein et al. | | |
| 2017/0051074 A1 | 2/2017 | Kirshner et al. | | |
| 2020/0199233 A1 | 6/2020 | Murphy et al. | | |
| 2020/0239576 A1 | 7/2020 | Murphy et al. | | |
| 2020/0299388 A1 | 9/2020 | Skokos et al. | | |

FOREIGN PATENT DOCUMENTS

| | | |
|---|---|---|
| WO | 17/053856 A1 | 3/2017 |
| WO | 17/121905 A1 | 7/2017 |
| WO | 19/245991 A1 | 12/2019 |

OTHER PUBLICATIONS

Buhler et al., A bispecific diabody directed against prostate-specific membrane antigen and CD3 induces T-cell mediated lysis of prostate cancer cells. Cancer Immunol Immunother. Jan. 2008;57(1):43-52.

Correnti et al., "Simultaneous Multiple Interaction T-cell Engaging (SMITE) Bispecific Antibodies Overcome Bispecific T-cell Engager (BiTe) Resistance via CD28 Co-stimulation," Leukemia, vol. 32:1239-1243, (2018).

Grosse-Hovest et al., "A Recombinant Bispecific Single-chain Antibody Induces Targeted, Supra-agonistic CD28-stimulation and Tumor Cell Killing," Euro J. Immunol, vol. 33:1334-1340, (2003).

Haas et al., "A Tumor Vaccine Containing Anti-CD3 and Anti-CD28 Bispecific Antibodies Triggers Strong and Durable Antitumor Activity in Human Lymphocytes," Int. J. Cancer, vol. 118:658-667, (2006).

(Continued)

*Primary Examiner* — Marianne P Allen

(74) *Attorney, Agent, or Firm* — Schwabe, Williamson & Wyatt PC; Aparna Patankar

(57) ABSTRACT

The present invention provides bispecific antigen-binding molecules comprising a first antigen-binding domain that specifically binds human CD28, and a second antigen-binding molecule that specifically binds human PSMA. In certain embodiments, the bispecific antigen-binding molecules of the present invention are capable of inhibiting the growth of tumors expressing PSMA, such as prostate tumors. The antibodies and bispecific antigen-binding molecules of the invention are useful for the treatment of diseases and disorders in which an up-regulated or induced targeted immune response is desired and/or therapeutically beneficial.

20 Claims, 46 Drawing Sheets

Specification includes a Sequence Listing.

(56) References Cited

OTHER PUBLICATIONS

Kroesen et al., "Bispecific Antibody-mediated Target Cell-specific Costimulation of Resting T Cells via CD5 and CD281," Cancer Research, vol. 55:4409-4415, (1995).
Jung et al., "Local Immunotherapy of Glioma Patients with a Combination of 2 Bispecific Antibody Fragments and Resting Autologous Lymphocytes: Evidence for IN Situ T-Cell Activation and Therapeutic Efficacy," Int. J. Cancer, vol. 91:225-230, (2001).
WIPO Application No. PCT/US2019/038460, PCT International Search Report and Written Opinion of the International Searching Authority mailed Nov. 7, 2019.
Zhou et al., "Strategies for Bispecific Single Chain Antibody in Cancer Immunotherapy," Journal of Cancer, vol. 8:3689-3696, (2017).
Caldas et al., "Humanization of the anti-CD18 antibody 6.7: an unexpected effect of a framework residue in binding to antigen," Science Direct, Molecular Immunology, vol. 39: 941-952, (2003).
Casadevall et al., "Immunoglobulin isotype influences affinity and specificity," PNAS, vol. 109 (No. 31): 12272-12273, (Jul. 31, 2012). [www.pnas.org/cgi/doi/10.1073/pnas.1209750109].
Du et al., "Molecular Basis of Recognition of Human Osteopontin by 23C3, a Potential therapeutic Antibody for Treatment of Rheumatoid Arthritis," J Mol Biol., vol. 382(No. 4): 835-842, (2008). [doi: 10.1016/j.jmb.2008.07.075: 10.1016/j.jmb.2008.07.075].
Kunik et al., "Structural Consensus among Antibodies Defines the Antigen Binding Site," PLoS Computational Biology, vol. 8(No. 2): pp. 1-12, (Feb. 2012).
U.S. Appl. No. 16/448,462, Non-Final Office Action mailed May 18, 2021.
U.S. Appl. No. 16/448,462, Final Office Action mailed Oct. 21, 2021.
U.S. Appl. No. 16/448,462, Non-Final Office Action mailed May 5, 2022.
U.S. Appl. No. 16/448,462, Notice of Allowance mailed Sep. 8, 2022.
U.S. Appl. No. 18/077,137, Non-Final Office Action mailed Jun. 10, 2024.

* cited by examiner

PSMAxCD28 BISPECIFIC ANTIBODIES ENHANCE THE CYTOTOXIC POTENCY OF bs13644D (PSMAxCD3) IN THE PRESENCE OF PROSTATE CARCINOMA & HUMAN OR CYNO T CELLS

C4-2 prostate carcinmoa

| | EC50 |
|---|---|
| bs13644D+bs16429D (A) (2.5ug/ml) | 1.45e-012 |
| bs13644D+bs16431D (B) (2.5ug/ml) | ~4.88e-012 |
| bs13644D | 4.347e-011 |

| | EC50 |
|---|---|
| bs13644D+bs16429D (A) (2.5ug/ml) | 1.554e-011 |
| bs13644D+bs16431D (B) (2.5ug/ml) | 7.723e-011 |

- bs13644D+bs16429D (A) (2.5ug/ml)
- bs17664D+bs16429D (A) (2.5ug/ml)
- bs17664D+bs16431D (B) (2.5ug/ml)
- bs17664D + bs16431D (B) (2.5ug/ml)
- bs13644D
- bs17664D

PSMAxCD28 BISPECIFIC ANTIBODIES ENHANCE THE CYTOTOXIC POTENCY OF bs13644D (PSMAxCD3) IN THE PRESENCE OF PROSTATE CARCINOMA & HUMAN OR CYNO T CELLS

22RV1 prostate carcinmoa

| | EC50 |
|---|---|
| bs13644D+bs16429D (A) (2.5ug/ml) | 2.287e-011 |
| bs13644D+bs16431D (B) (2.5ug/ml) | 1.669e-010 |
| bs13644D | 2.516e-009 |

| | EC50 |
|---|---|
| bs13644D+bs16429D (A) (2.5ug/ml) | 5.516e-011 |
| bs13644D+bs16431D (B) (2.5ug/ml) | 1.221e-009 |

CD28 SUPER-AGONIST TREATMENT DRIVES CYTOKINE RESPONSE AT 4 HOURS IN PBMC-ENGRAFTED NSG MICE, WHILE mAb 14226P2 (CD28 PARENTAL 'A') DOES NOT

Tumor Volume ($mm^3$) on day 21

| Ms # | Isotype | PD1 | CD28 x PSMA | CD28 x PSMA + PD1 |
|---|---|---|---|---|
| Ms 1 | 1372.0 | 1044.0 | 147.9 | 4.0 |
| Ms 2 | 1328.1 | 972.0 | 998.3 | 208.3 |
| Ms 3 | 771.8 | 500.0 | 1289.1 | 0.0 |
| Ms 4 | 976.6 | 2432.0 | 650.0 | 288.0 |
| Ms 5 | 2137.5 | 1140.8 | | 609.2 |
| Ms 6 | 1892.3 | 958.8 | | 0.0 |
| Ms 7 | 1171.9 | 526.5 | 726.0 | 211.3 |
| Ms 8 | | | | 75.0 |

FIG. 20D

% Tumor Free

| Exp # | Iso | PD1 | CD28 x PSMA | CD28 x PSMA + PD1 |
|---|---|---|---|---|
| 1 | 0 | 0 | 0 | 38 |
| 2A | 0 | 17 | 0 | 57 |
| 2B | 0 | 33 | 0 | 50 |
| 3 | 0 | 0 | 33 | 82 |
| 4 | 0 | | | 29 |
| 5 | 0 | 0 | 0 | 13 |
| 6 | 0 | 0 | 0 | 13 |

FIG. 20E

BISPECIFIC ANTI-PSMA X ANTI-CD28 ANTIBODIES AND USES THEREOF

CROSS-REFERENCE TO RELATED APPLICATIONS

This application is a continuation of US Application Ser. No. 16/448,462, filed Jun. 21, 2019, which claims the benefit of under 35 USC § 119(e) of US Provisional Application Nos.: 62/688,227, filed Jun. 21, 2018; 62/781,930, filed Dec. 19, 2018; 62/781,980, filed Dec. 19, 2018; and 62/815,878, filed Mar. 8, 2019, each of which is incorporated herein by reference in its entirety for all purposes.

REFERENCE TO A SEQUENCE LISTING

This application incorporates by reference a computer readable Sequence Listing in ST.26 XML format, titled 10367US03_Sequence, created on Dec. 7, 2022, and containing 107,656 bytes.

FIELD OF THE INVENTION

The present invention relates to bispecific antigen-binding molecules that bind CD28 and a target molecule such as PSMA, and methods of use thereof.

BACKGROUND

CD28 is a type I transmembrane protein expressed on the surface of T cells which has a single extracellular Ig-V-like domain assembled as a homodimer. CD28 is the receptor for CD80 (B7.1) and CD86 (B7.2) proteins and is activated by CD80 or CD86 expressed on APCs. The binding of CD28 to CD80 or CD86 provide co-stimulatory signals important for T cell activation and survival. T cell stimulation through CD28 in addition to the T-cell receptor (TCR) provides a potent signal for the production of various interleukins. CD28 potentiates cellular signals such as pathways controlled by the NFκB transcription factor after TCR activation. The CD28 co-signal is important for effective T-cell activation such as T cell differentiation, proliferation, cytokine release and cell-death.

Anti-CD28 antibodies have been proposed for therapeutic purposes involving the activation of T cells. One particular anti-CD28 antibody, TGN1412 (anti-CD28 superagonist), was used in a clinical trial. TGN1412 induced cytokine storm, which was not predicted by toxicology or ex vivo human PBMC studies. In 2006, six healthy volunteers were dose intravenously with TGN1412 (anti-CD28 superagonist) at a dose of 0.1 mg/kg. Within 2 hours, all six patients had significant inflammatory responses (cytokine storm). Within 16 hours, all patients were in multi-organ failure. Subjects were treated with corticosteroids, and cytokine levels returned to normal levels within 2-3 days. A starting dose of 0.1 mg/kg in a Phase 1 study (associated with CRS) was based on 500-fold multiple of the no-observed-adverse-effect-level "NOAEL" of 50 mg/kg in cynomolgus monkeys (Suntharalingam, et al., Cytokine Storm in a Phase 1 Trial of the Anti-CD28 Monoclonal Antibody TGN1412, NEJM 355:1018-1028 (2006)).

A toxicology study in cynomolgus macaques was unable to predict the cytokine response observed in humans.

PSMA (Prostate-Specific Membrane Antigen)/FOLH1 is a "well-characterized" tumor target. PSMA is a type II transmembrane glycoprotein overexpressed in prostate cancer. It is also known as glutamate carboxypeptidase II (GPC). In the normal human prostate, PSMA is associated with the cytoplasm and apical side of the epithelium surrounding prostatic ducts. Dysplastic and/or neoplastic transformation of prostate tissue results in the transfer of PSMA from the apical membrane to the luminal surface of the ducts. PSMA is constitutively endocytosed and it is not shed. PSMA is the target of various clinical ADC (antibody-drug conjugate) trial and imaging approaches. PSMA is highly expressed in Human Prostate adenocarcinoma and matches metastasis (lymph NODES). In prostate tumors, PSMA expression levels increase according to stage and grade. The transition to androgen-independent prostate cancer eventually leads to increased expression. Interestingly, PSMA expression has also been reported in the tumor neo-vasculature of some solid tumors (including colon, lung, breast, renal cancer and subtypes of bladder cancer)

PSMA is also expressed in normal tissues. Strongest expression is found in prostate epithelial cells, duodenum, renal tubular cells, salivary glands and astrocytes. PSMA is weakly expressed in fallopian tubes, breast and rarely expressed in the endothelium of cervix.

Bispecific antigen-binding molecules that bind both CD28 and a target antigen (such as PSMA) would be useful in therapeutic settings in which specific targeting and T cell-mediated killing of cells that express the target antigen is desired. There is also a need for an anti-CD28 antibody that is safe for use in a pharmaceutical composition.

BRIEF SUMMARY OF THE INVENTION

In a first aspect, the present invention provides bispecific antigen-binding molecules that bind CD28 and a target antigen. According to certain exemplary embodiments, the bispecific antigen-binding molecules bind CD28 and PSMA; such bispecific antigen-binding molecules are also referred to herein as "anti-CD28/anti-PSMA bispecific molecules." The anti-PSMA portion of the anti-CD28/anti-PSMA bispecific molecule is useful for targeting tumor cells that express PSMA (e.g., prostate tumor cell), and the anti-CD28 portion of the bispecific molecule is useful for activating T-cells. The simultaneous binding of PSMA on a tumor cell and CD28 on a T-cell facilitates directed killing (cell lysis) of the targeted tumor cell by the activated T-cell. The anti-CD28/anti-PSMA bispecific molecules of the invention are therefore useful, inter alia, for treating diseases and disorders related to or caused by PSMA-expressing tumors (e.g., prostate cancer).

The bispecific antigen-binding molecules according to this aspect of the present invention comprise a first antigen-binding domain that specifically binds human CD28, and a second antigen-binding domain that specifically binds PSMA. The present invention includes anti-CD28/anti-PSMA bispecific molecules (e.g., bispecific antibodies) wherein each antigen-binding domain comprises a heavy chain variable region (HCVR) paired with a light chain variable region (LCVR). In certain exemplary embodiments of the invention, the anti-CD28 antigen-binding domain and the anti-PSMA antigen binding domain each comprise different, distinct HCVRs paired with a common LCVR.

The present invention provides anti-CD28/anti-PSMA bispecific molecules, wherein the first antigen-binding domain that specifically binds CD28 comprises any of the HCVR amino acid sequences as set forth in Table 1. The first antigen-binding domain that specifically binds CD28 may also comprise any of the LCVR amino acid sequences as set forth in Table 1. According to certain embodiments, the first antigen-binding domain that specifically binds CD28 comprises any of the HCVR/LCVR amino acid sequence pairs as set forth in Table 1. The present invention also provides anti-CD28/anti-PSMA bispecific molecules, wherein the first antigen-binding domain that specifically binds CD28 comprises any of the heavy chain CDR1-CDR2-CDR3 amino acid sequences as set forth in Table 1, and/or any of the light chain CDR1-CDR2-CDR3 amino acid sequences as set forth in Table 1.

According to certain embodiments, the present invention provides anti-CD28/anti-PSMA bispecific molecules, wherein the first antigen-binding domain that specifically binds CD28 comprises a heavy chain variable region (HCVR) having an amino acid sequence selected from the group consisting of SEQ ID NOs: 10, 26, and 58 or a substantially similar sequence thereof having at least 90%, at least 95%, at least 98% or at least 99% sequence identity.

The present invention also provides anti-CD28/anti-PSMA bispecific molecules, wherein the first antigen-binding domain that specifically binds CD28 comprises a light chain variable region (LCVR) having an amino acid sequence selected from the group consisting of SEQ ID NOs: 18, 42, and 66, or a substantially similar sequence thereof having at least 90%, at least 95%, at least 98% or at least 99% sequence identity.

The present invention also provides anti-CD28/anti-PSMA bispecific molecules, wherein the first antigen-binding domain that specifically binds CD28 comprises a HCVR and LCVR (HCVR/LCVR) amino acid sequence pair selected from the group consisting of SEQ ID NOs: 10/18, 26/42 and 58/66.

The present invention also provides anti-CD28/anti-PSMA bispecific molecules, wherein the first antigen-binding domain that specifically binds CD28 comprises a heavy chain CDR3 (HCDR3) domain having an amino acid sequence selected from the group consisting of SEQ ID NOs: 16, 32, and 64, or a substantially similar sequence thereto having at least 90%, at least 95%, at least 98% or at least 99% sequence identity; and a light chain CDR3 (LCDR3) domain having an amino acid sequence selected from the group consisting of SEQ ID NOs: 24,48, and 72, or a substantially similar sequence thereof having at least 90%, at least 95%, at least 98% or at least 99% sequence identity.

In certain embodiments, the first antigen-binding domain that specifically binds CD28 comprises a HCDR3/LCDR3 amino acid sequence pair selected from the group consisting of SEQ ID NOs: 16/24, 32/48, and 64/72.

The present invention also provides anti-CD28/anti-PSMA bispecific antigen-binding molecules, wherein the first antigen-binding domain that specifically binds CD28 comprises a heavy chain CDR1 (HCDR1) domain having an amino acid sequence selected from the group consisting of SEQ ID NOs: 12, 28, and 60, or a substantially similar sequence thereof having at least 90%, at least 95%, at least 98% or at least 99% sequence identity; a heavy chain CDR2 (HCDR2) domain having an amino acid sequence selected from the group consisting of SEQ ID NOs: 14, 30, and 62, or a substantially similar sequence thereof having at least 90%, at least 95%, at least 98% or at least 99% sequence identity; a light chain CDR1 (LCDR1) domain having an amino acid sequence selected from the group consisting of SEQ ID NOs: 20, 44, and 68, or a substantially similar sequence thereof having at least 90%, at least 95%, at least 98% or at least 99% sequence identity; and a light chain CDR2 (LCDR2) domain having an amino acid sequence selected from the group consisting of SEQ ID NOs: 22, 46, and 70, or a substantially similar sequence thereof having at least 90%, at least 95%, at least 98% or at least 99% sequence identity.

Certain non-limiting, exemplary anti-CD28/anti-PSMA bispecific antigen-binding molecules of the invention include a first antigen-binding domain that specifically binds CD28 comprising HCDR1-HCDR2-HCDR3-LCDR1-LCDR2-LCDR3 domains, respectively, having the amino acid sequence selected from the group consisting of: SEQ ID NOs: Dec. 14, 2016-20-22-24; 28-30-32-44-46-48; and 60-62-64-68-70-72 . . .

The present invention also provides anti-CD28/anti-PSMA bispecific molecules, wherein the second antigen-binding domain that specifically binds PSMA comprises a heavy chain variable region (HCVR) having the amino acid sequence selected from the group consisting SEQ ID NOs: 2, 34 and 50, or a substantially similar sequence thereof having at least 90%, at least 95%, at least 98% or at least 99% sequence identity.

The present invention also provides anti-CD28/anti-PSMA bispecific molecules, wherein the second antigen-binding domain that specifically binds PSMA comprises a light chain variable region (LCVR) having the amino acid sequence selected from the group consisting of SEQ ID NOs: 18, 42, and 66, or a substantially similar sequence thereof having at least 90%, at least 95%, at least 98% or at least 99% sequence identity.

The present invention also provides anti-CD28/anti-PSMA bispecific molecules, wherein the second antigen-binding domain that specifically binds PSMA comprises a HCVR and LCVR (HCVR/LCVR) amino acid sequence pair selected from the group consisting of SEQ ID NOs: 2/18, 34/42 and 50/66.

The present invention also provides anti-CD28/anti-PSMA bispecific molecules, wherein the second antigen-binding domain that specifically binds PSMA comprises a heavy chain CDR3 (HCDR3) domain having the amino acid sequence selected from the group consisting of SEQ ID NOs: 8, 40 and 56, or a substantially similar sequence thereto having at least 90%, at least 95%, at least 98% or at least 99% sequence identity; and a light chain CDR3 (LCDR3) domain having an amino acid sequence selected from the group consisting of SEQ ID NOs: 24, 48 and 72, or a substantially similar sequence thereof having at least 90%, at least 95%, at least 98% or at least 99% sequence identity.

In certain embodiments, the second antigen-binding domain that specifically binds PSMA comprises a HCDR3/LCDR3 amino acid sequence pair selected from the group consisting of SEQ ID NOs: 8/24, 40/48 and 56/72.

The present invention also provides anti-CD28/anti-PSMA bispecific antigen-binding molecules, wherein the second antigen-binding domain that specifically binds PSMA comprises a heavy chain CDR1 (HCDR1) domain having the amino acid sequence selected from the group consisting of SEQ ID NOs: 4, 36 and 52, or a substantially similar sequence thereof having at least 90%, at least 95%, at least 98% or at least 99% sequence identity; a heavy chain CDR2 (HCDR2) domain having the amino acid sequence selected from the group consisting of SEQ ID NOs: 6, 38 and 54, or a substantially similar sequence thereof having at least 90%, at least 95%, at least 98% or at least 99% sequence identity; a light chain CDR1 (LCDR1) domain having an amino acid sequence selected from the group consisting of SEQ ID NOs: 20, 44 and 68, or a substantially similar sequence thereof having at least 90%, at least 95%, at least 98% or at least 99% sequence identity; and a light chain CDR2 (LCDR2) domain having an amino acid sequence selected from the group consisting of SEQ ID NOs: 22, 46 and 70, or a substantially similar sequence thereof having at least 90%, at least 95%, at least 98% or at least 99% sequence identity.

Certain non-limiting, exemplary anti-CD28/anti-PSMA bispecific antigen-binding molecules of the invention include a second antigen-binding domain that specifically binds PSMA comprising HCDR1-HCDR2-HCDR3-LCDR1-LCDR2-LCDR3 domains, respectively, having the amino acid sequences selected from the group consisting of: SEQ ID NOs: 4-6-8-20-22-24; 36-38-40-44-46-48; and 52-54-56-68-70-72.

In a related embodiment, the invention includes anti-CD28/anti-PSMA bispecific antigen binding molecules wherein the second antigen-binding domain that specifically binds PSMA comprises the heavy and light chain CDR domains contained within heavy and light chain variable region (HCVR/LCVR) sequences selected from the group consisting of SEQ ID NOs: 2/18, 34/42 and 50/66.

In another aspect, the present invention provides nucleic acid molecules encoding any of the HCVR, LCVR or CDR sequences of the anti-CD28/anti-PSMA bispecific antigen-binding molecules disclosed herein, including nucleic acid molecules comprising the polynucleotide sequences as set forth in Table 1 herein, as well as nucleic acid molecules comprising two or more of the polynucleotide sequences as set forth in Table 1 in any functional combination or arrangement thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention includes anti-CD28/anti-PSMA bispecific antigen-binding molecules wherein any of the aforementioned antigen-binding domains that specifically bind CD28 is combined, connected or otherwise associated with any of the aforementioned antigen binding domains that specifically bind PSMA to form a bispecific antigen-binding molecule that binds CD28 and PSMA.

The present invention includes anti-CD28/anti-PSMA bispecific antigen-binding molecules having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising an anti-CD28/anti-PSMA bispecific antigen-binding molecule as disclosed herein and a pharmaceutically acceptable carrier. In a related aspect, the invention features a composition which is a combination of an anti-CD28/anti-PSMA bispecific antigen-binding molecule and a second therapeutic agent. In one embodiment, the second therapeutic agent is any agent that is advantageously combined with an anti-CD28/anti-PSMA bispecific antigen-binding molecule. Exemplary agents that may be advantageously combined with an anti-CD28/anti-PSMA bispecific antigen-binding molecule are discussed in detail elsewhere herein.

In yet another aspect, the invention provides therapeutic methods for targeting/killing tumor cells expressing PSMA using an anti-CD28/anti-PSMA bispecific antigen-binding molecule of the invention, wherein the therapeutic methods comprise administering a therapeutically effective amount of a pharmaceutical composition comprising an anti-CD28/anti-PSMA bispecific antigen-binding molecule of the invention to a subject in need thereof.

The present invention also includes the use of an anti-CD28/anti-PSMA bispecific antigen-binding molecule of the invention in the manufacture of a medicament for the treatment of a disease or disorder related to or caused by PSMA expression.

In yet another aspect, the invention provides therapeutic methods for targeting/killing tumor cells expressing PSMA using an anti-CD28/anti-PSMA bispecific antigen-binding molecule of the invention, wherein the anti-CD28/anti-PSMA bispecific antigen-binding molecule is combined with other anti-tumor bispecific antigen-binding molecules that bind to CD3 (e.g., anti-CD28/anti-PSMA combined with anti-CD3/anti-PSMA antibodies).

In still another aspect, the invention provides therapeutic methods for targeting/killing tumor cells expressing PSMA using an anti-CD28/anti-PSMA bispecific antigen-binding molecule of the invention, wherein the anti-CD28/anti-PSMA bispecific antigen-binding molecule is combined with a checkpoint inhibitor targeting PD-1 or CTLA-4 (e.g., anti-CD28/anti-PSMA combined with anti-PD-1 antibodies).

In still another aspect, the invention provides therapeutic methods for targeting/killing tumor cells expressing PSMA using an anti-CD28/anti-PSMA bispecific antigen-binding molecule of the invention, wherein the anti-CD28/anti-PSMA bispecific antigen-binding molecule is combined with other anti-tumor bispecific antigen-binding molecules that binds to CD3 (e.g., anti-CD28/anti-PSMA combined with anti-CD3/anti-PSMA bispecific antibodies) and a checkpoint inhibitor targeting PD-1 or CTLA-4 (e.g., anti-CD28/anti-PSMA combined with anti-PD-1 antibodies).

Other embodiments will become apparent from a review of the ensuing detailed description.

BRIEF DESCRIPTION OF THE FIGURES

FIG. 2 is a graph showing the percentage (%) of survival. Mice were euthanized when tumors grew greater than 2000 $mm^3$.

FIG. 5A is a schematic showing bispecific antibody mode of action.

FIG. 5B is a graph showing quantification of the ratio of CD28 fluorescence in/out of the immunological synapse. PSMA engineered target cells (HEK293) and human Jurkat T cells were co-cultured with fluorescently labeled bispecific antibodies (anti-PSMAxCD28, anti-CD20×CD3) for 1 hour at 37° C., gently fixed and stained with anti-CD28. Number of cells analyzed per group is indicated on the bar graph.

FIGS. 5C and 5D shows proliferation of human T cells cultured with PSMA engineered target cells. Data shown is the average±SEM. Data is representative of at least two (2) experiments.

FIG. 5C provides a graph showing dose titration of CD20×CD3 in the presence of 0.5 nM hIgG4s isotype control or PSMAxCD28.

FIG. 5D provides a graph showing dose titration of PSMAxCD28 or indicated controls in the presence of 5 μM hIgG4s isotype control or CD20×CD3.

FIGS. 5E-5G are graphs showing proliferation and cytokine release of human T cells cultured with TAA (PSMA or CD20) engineered target cells as indicated at the top of the panel in presence of 5 μM hIgG4s isotype control (bottom panel of each figure) or CD20×CD3 (top panel of each figure). Data is average±SEM. Data is representative of at least three (3) experiments.

FIG. 5E is a graph showing proliferation.

FIG. 5F is a graph showing IL-2 release.

FIG. 5G is a graph showing IFNγ release.

FIG. 5H is a graph showing that anti-PSMAxCD28 and anti-PSMAxCD3 bispecific antibodies can bind simultaneously to PSMA-expressing cells. 22RV1 cells were preincubated 30 minutes at 4° C. in flow cytometry buffer (PBS+1% FBS) with 20 mg/ml of PSMAxCD3, or 20 mg/ml of anti-PSMA antibody harboring a similar anti-PSMA arm as the PSMAxCD28 bispecific. After incubation, the cells were washed with flow cytometry buffer and incubated for 20 minutes at 4° C. with 5 mg/ml of PSMAxCD28 directly labeled with Alexa647. After incubation, the cells were washed, resuspended in flow cytometry buffer, and analyzed by flow cytometry . . .

FIG. 7A is a graph showing the killing of tumor cells. Data shown is the percentage of viable cells.

FIG. 7B is a graph showing IFNγ release.

FIG. 7C provides graphs showing CD4 T cell counts and frequency of CD25+ cells as percentage of CD4 T cells.

FIG. 7D provides graphs showing CD8 T cell counts and frequency of CD25+ cells as percentage of CD8 T cells.

Figure 7A:
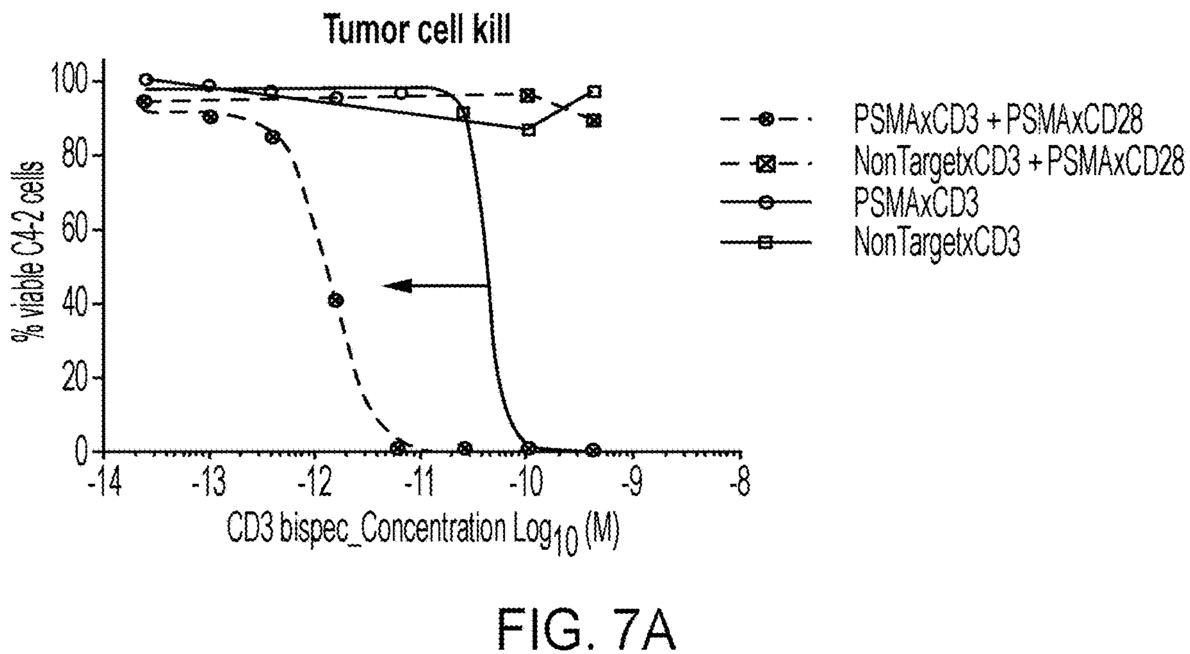
FIGS. 7A-7H provide graphs showing that, in cancer cell lines with endogenous PSMA, PSMAxCD28 bispecific antibodies potentiate T cell activation in the presence of TCR stimulation by PSMAxCD3 bispecific antibodies. For FIGS. 7A-7D, human T cells were cultured with cancer target cells with endogenous PSMA expression (prostate cancer line C4-2) and the indicated bispecific antibodies for 96 hours.
Figure 7B:
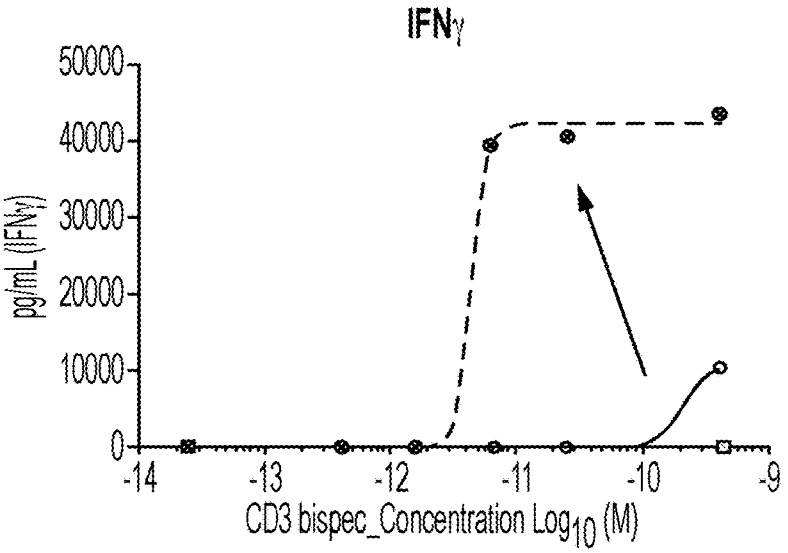
Figure 7C:
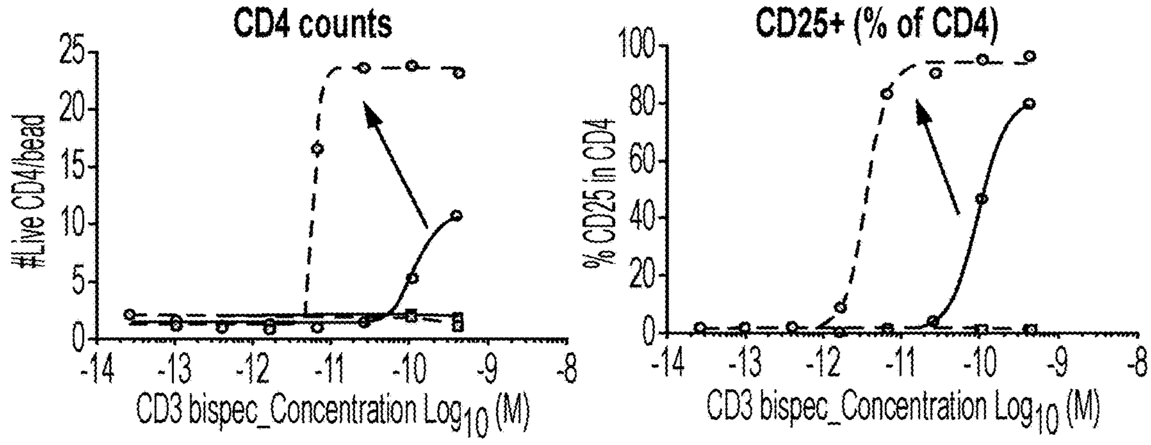
Figure 7D:
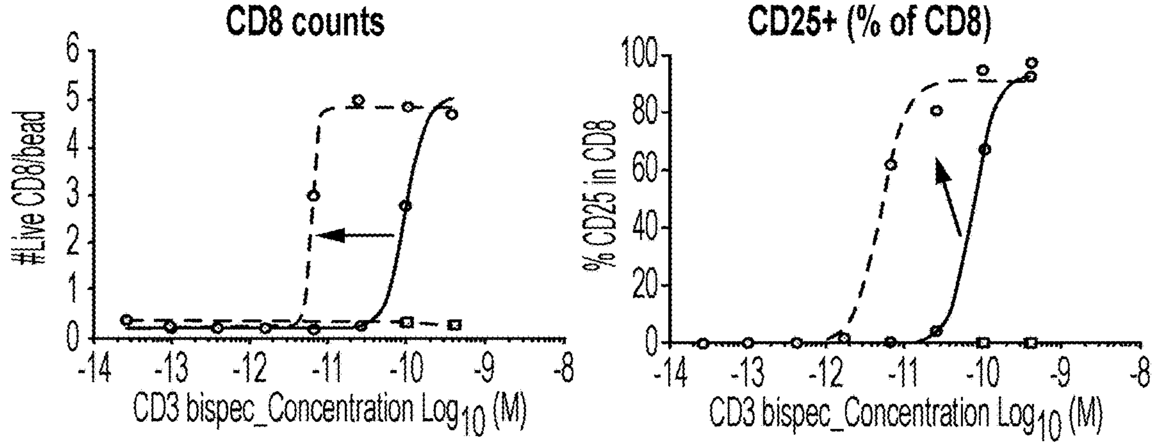
Figure 7E:
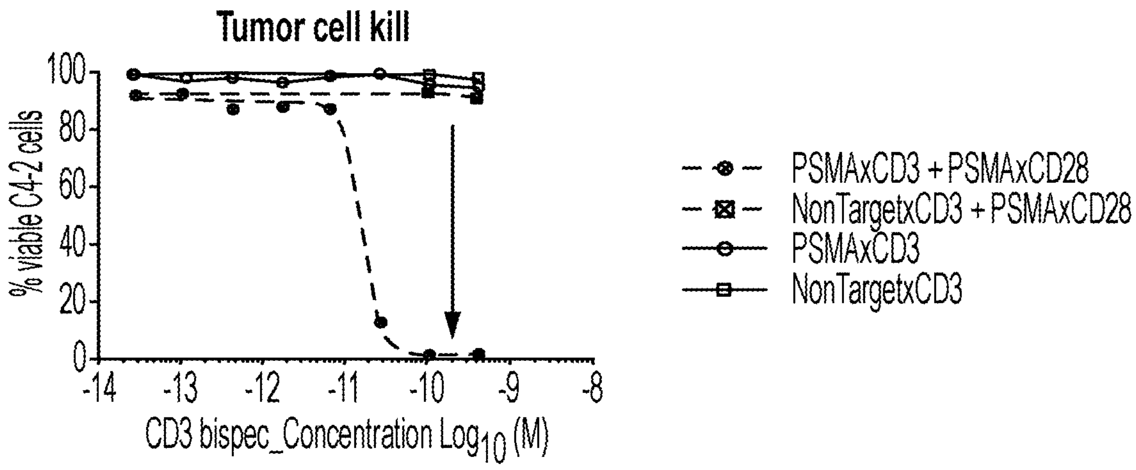
Figure 7F:
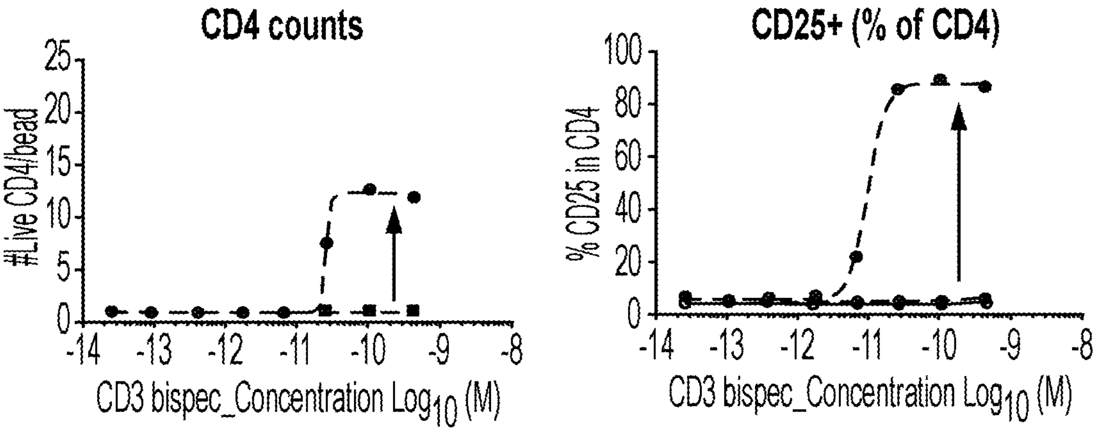
Figure 7G:
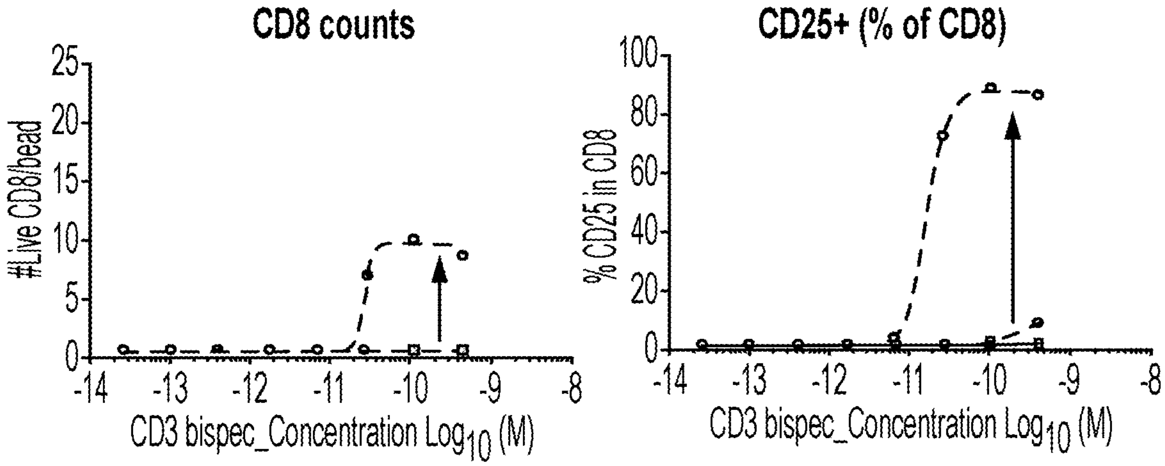

For FIGS. 7E-7G, cynomolgus T cells were culture with cancer cells with endogenous PSMA expression (prostate cancer line C4-2) and the indicated bispecific antibodies for 96 hours.

FIG. 7E is a graph showing the killing of tumor cells. Data shown is the percentage of viable cells.

FIG. 7F provides graphs showing CD4 T cell counts and frequency of CD25+ cells as percentage of CD4 T cells.

FIG. 7G provides graphs showing CD8 T cell counts and frequency of CD25+ cells as percentage of CD8 T cells.

Figure 7H:
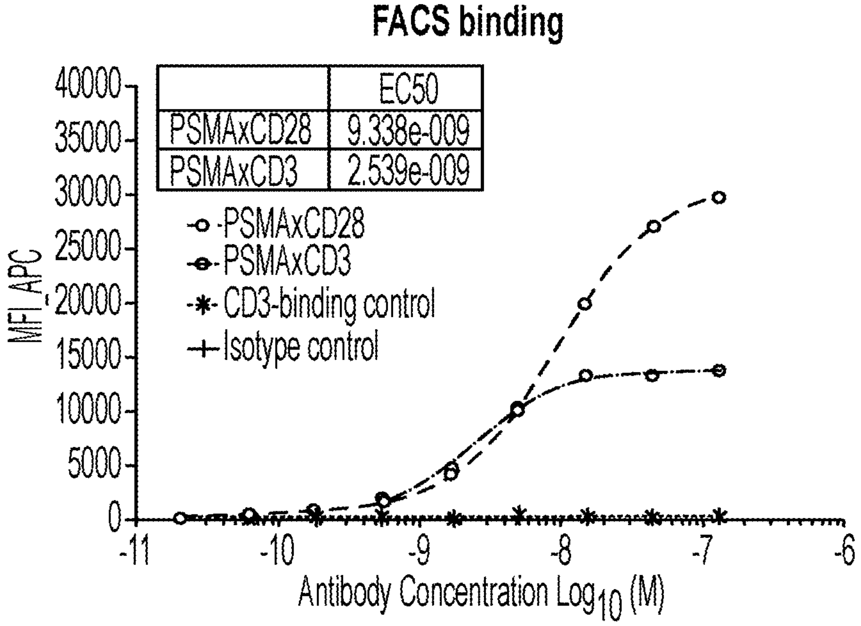

FIG. 7H provides a graph showing antibody binding to cellular targets measured by flow cytometry.

Figure 8:
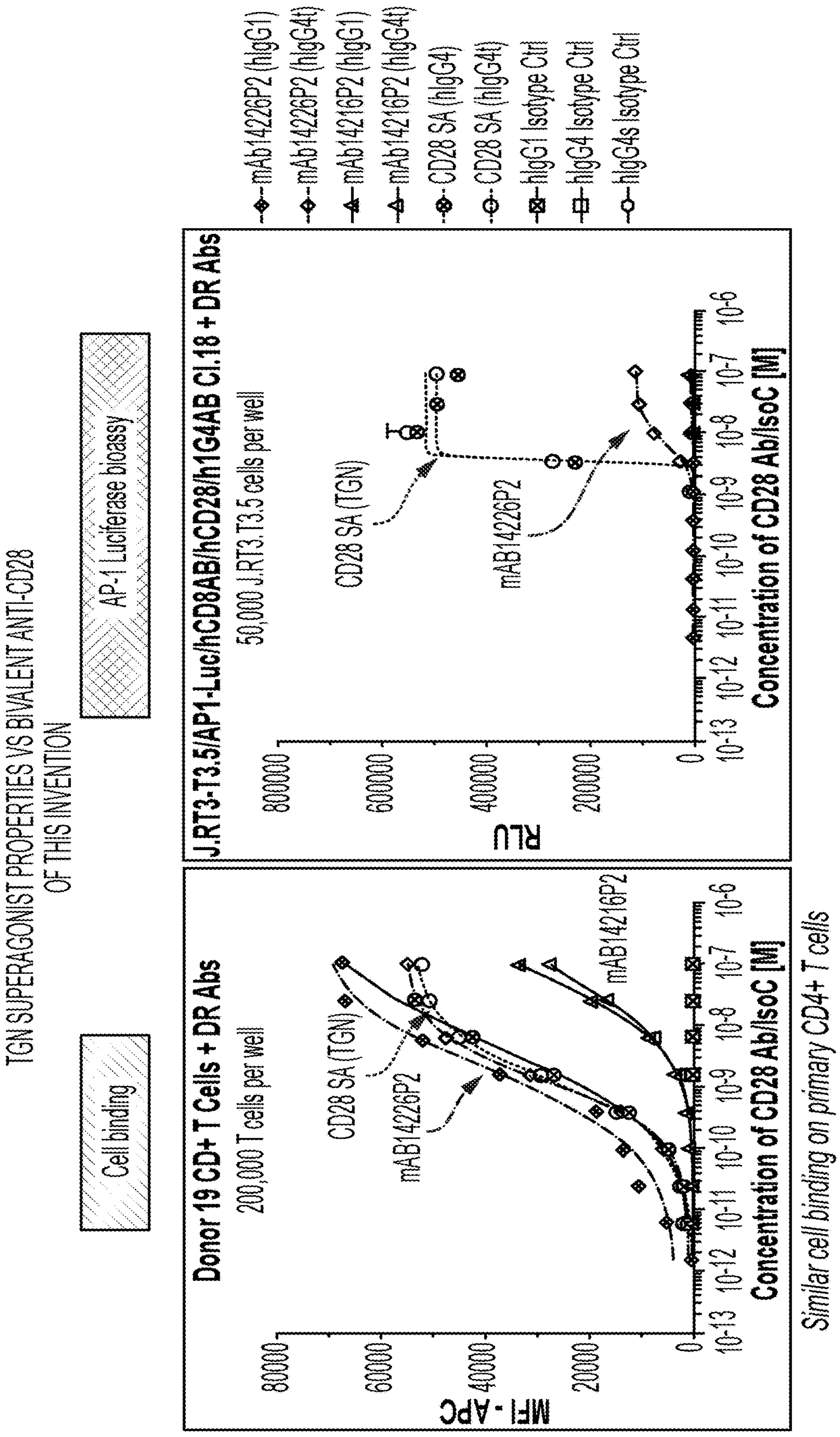

FIG. 8 shows the comparison between TGN superagonist properties and that of the anti-CD28 antibody of the invention.

Figure 9A:
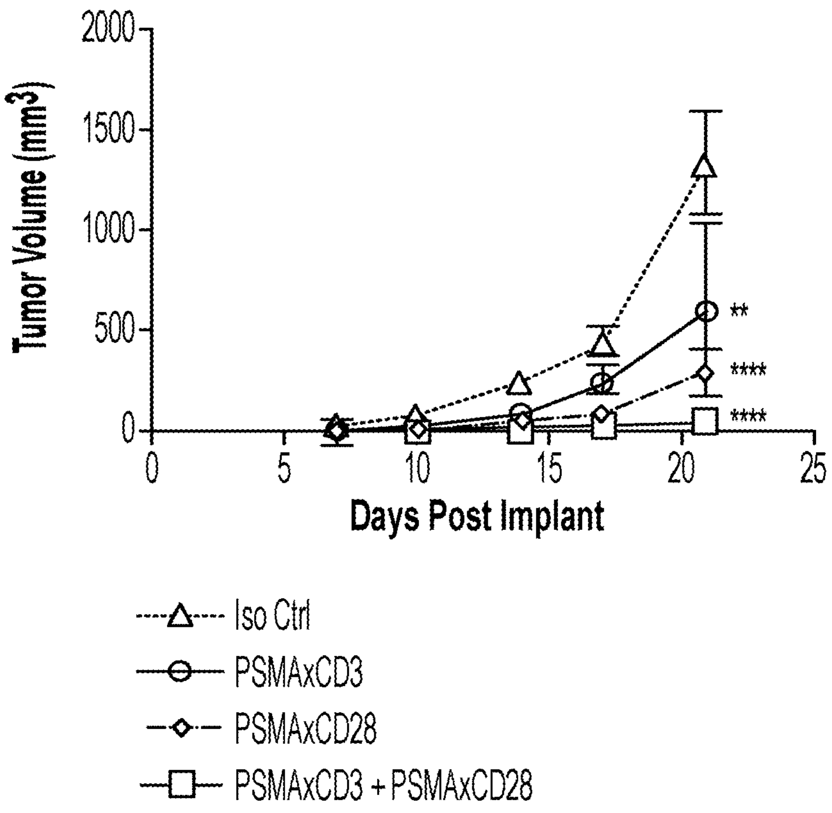
Figure 9B:
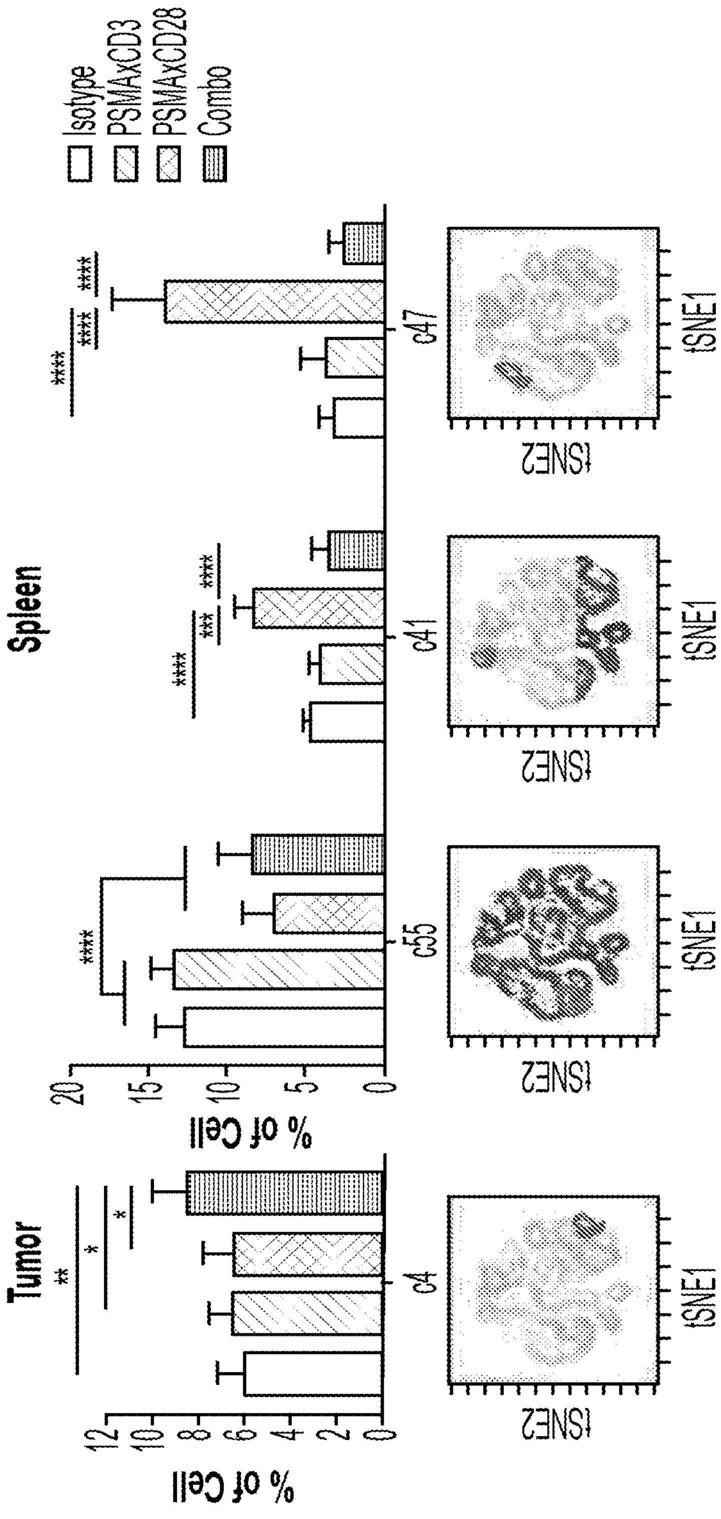

FIGS. 9A and 9B provide graphs and plots showing PSMAxCD28 bispecific antibody enhances anti-tumor immunity by PSMAxCD3 and induced T cell activation. MC38/hPSMA tumor cells were implanted subcutaneously in hCD3/hCD28/hPSMA humanized mice. Mice were treated with the indicated bispecific antibodies at 5 mg/kg on day 0, 3, and 7.

FIG. 9A shows tumor volume over time. Values represent the average±SEM and are representative of three (3) experiments with 3-7 mice per group. P values were calculated with Two-way ANOVA. (*, $p<0.05$; , $p<0.01$; *, $p<0.001$ and ****, $p<0.0001$).

FIG. 9B provides graphs showing the percentage of cells in each cluster from each treatment group (top panel); overlay of indicated cluster on viSNE plot (bottom panel).

Figures 9C, 9D, 9E:
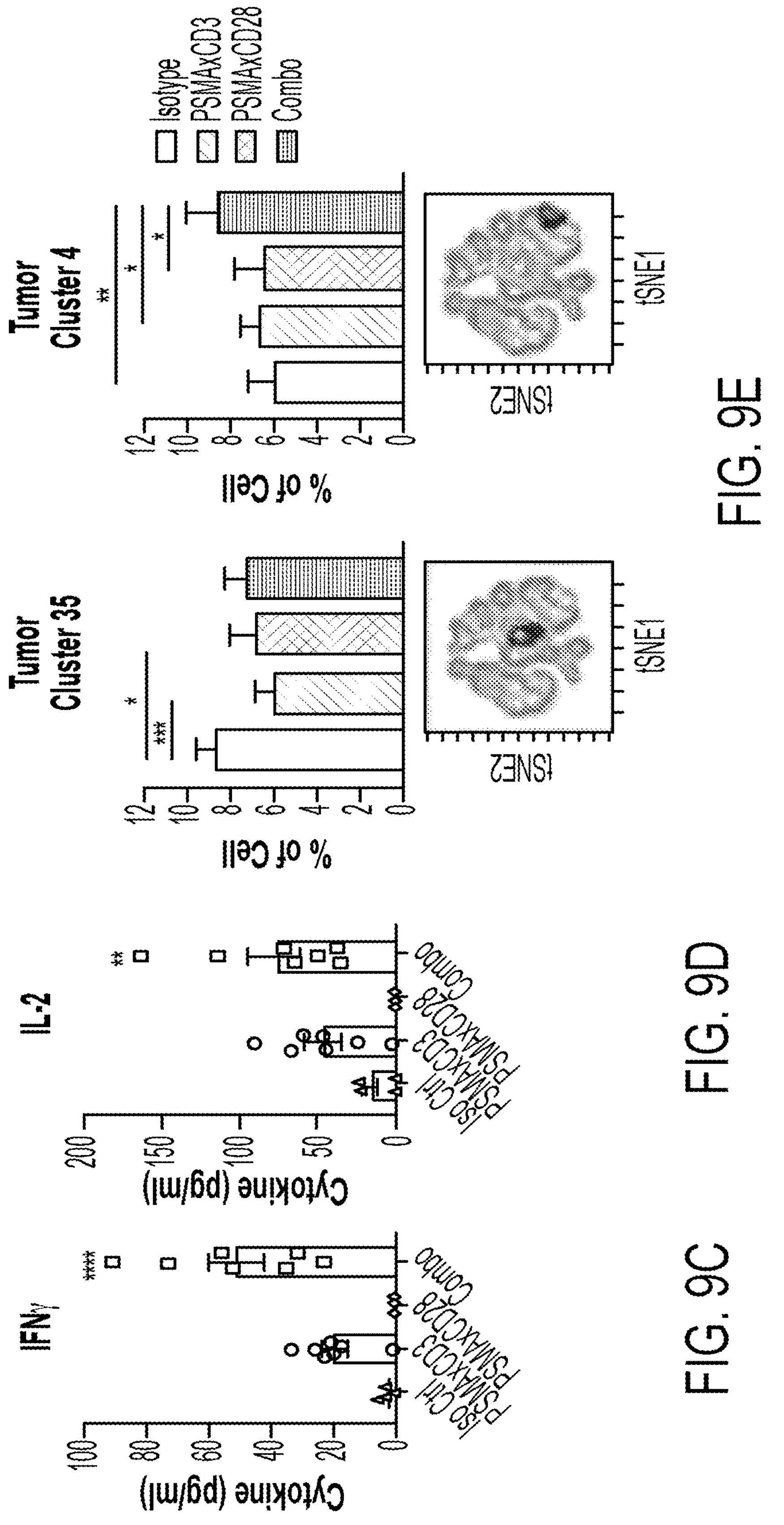

FIGS. 9C and 9D provide bar graphs showing PSMAxCD28 bispecific antibody enhances cytokine release induced by PSMAxCD3. Mice were bled for serum cytokines at 4 hours post dose on day 0. Statistical significance was calculated with 1-way ANOVA in comparison to isotype $p<0.01$ and *$p<0.0001$. n=7 mice per group. Data is representative 3 experiments.

FIG. 9E provides a graph and plot showing that PSMAxCD28 bispecific antibody enhances T cell activation induced by PSMAxCD3.

Figure 10:
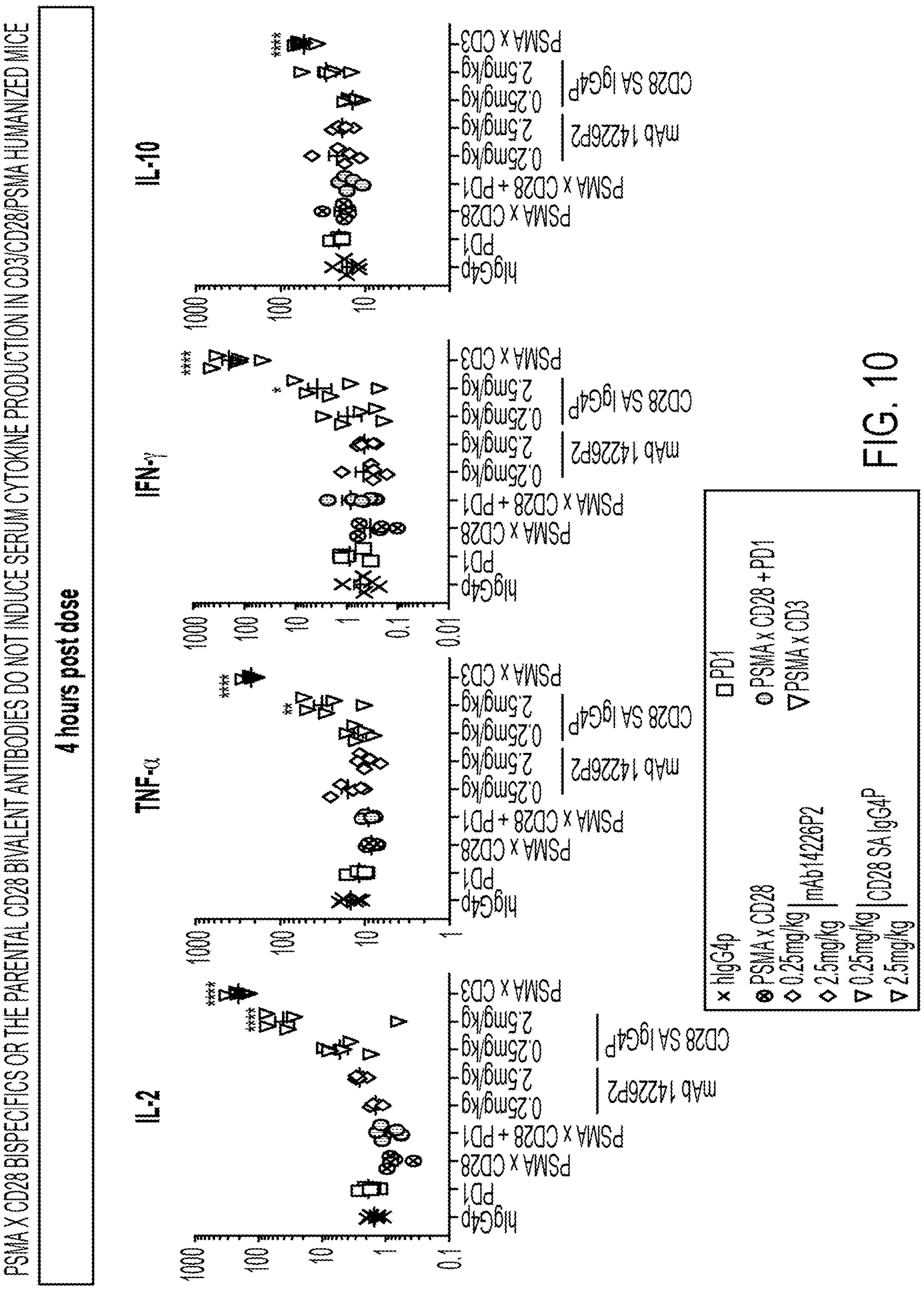

FIG. 10 shows that PSMA×CD28 bispecific antibodies or the parental CD28 bivalent antibodies did not induce serum cytokine production in CD3/CD28/PSMA humanized mice.

Figure 11:
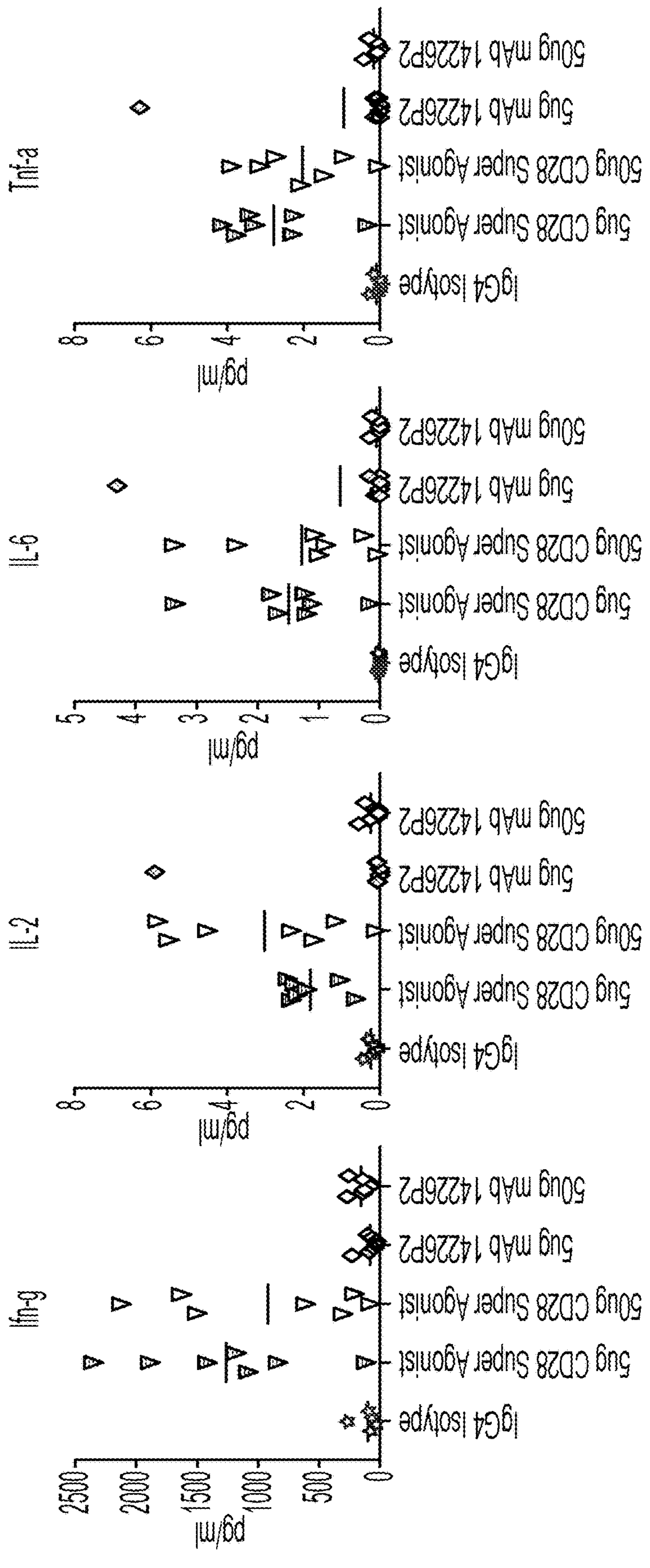

FIG. 11 shows that CD28 Super-Agonist treatment drove cytokine response at 4 hours in PBMC-engrafted NSG mice, while anti-CD28 antibody mAb14226P2 did not.

Figure 12:
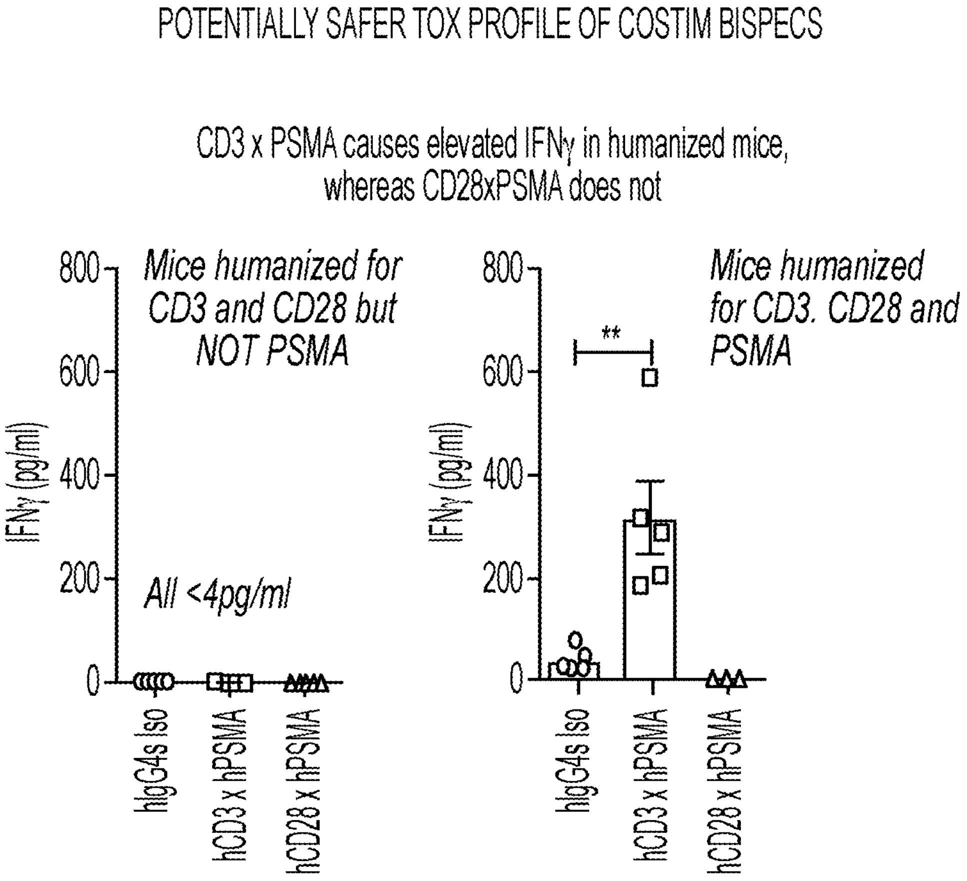

FIG. 12 shows potentially safer toxicological profile of costimulatory bispecific antigen-binding molecules of this invention. Anti-CD28×anti-PSMA did not elicit cytokine response, whereas anti-CD3×anti-PSMA did.

Figure 13A:
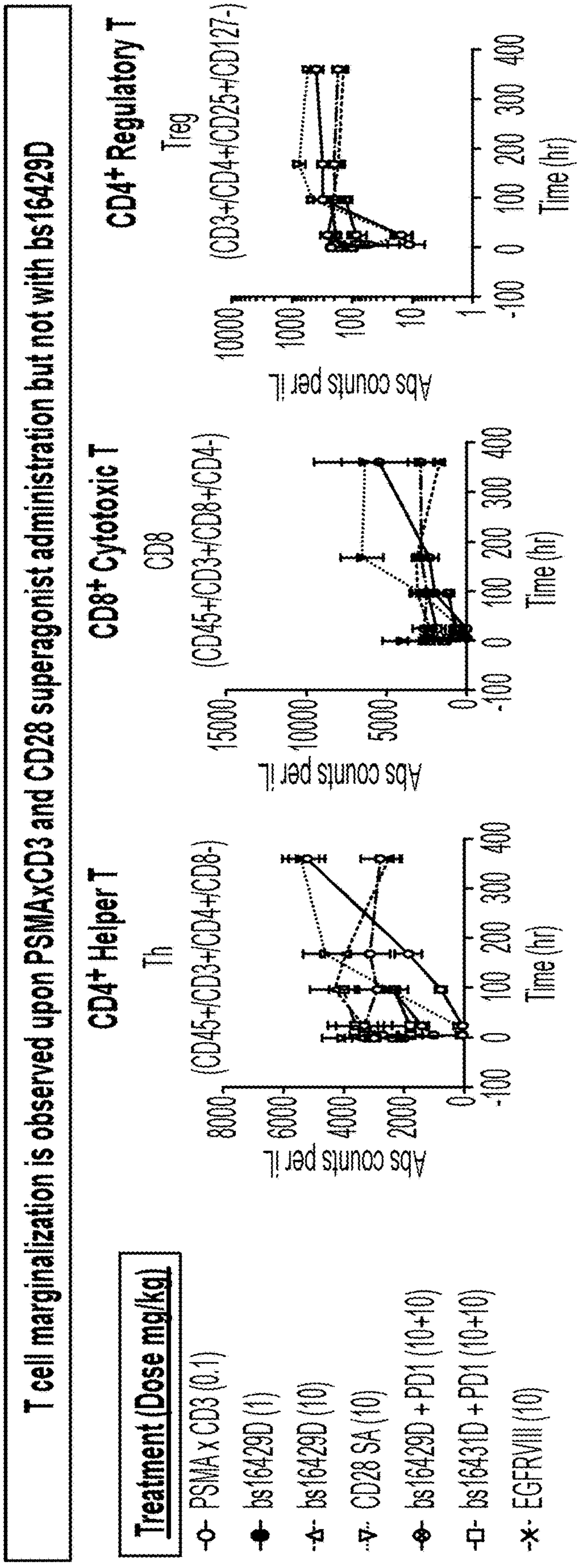
Figure 13B:
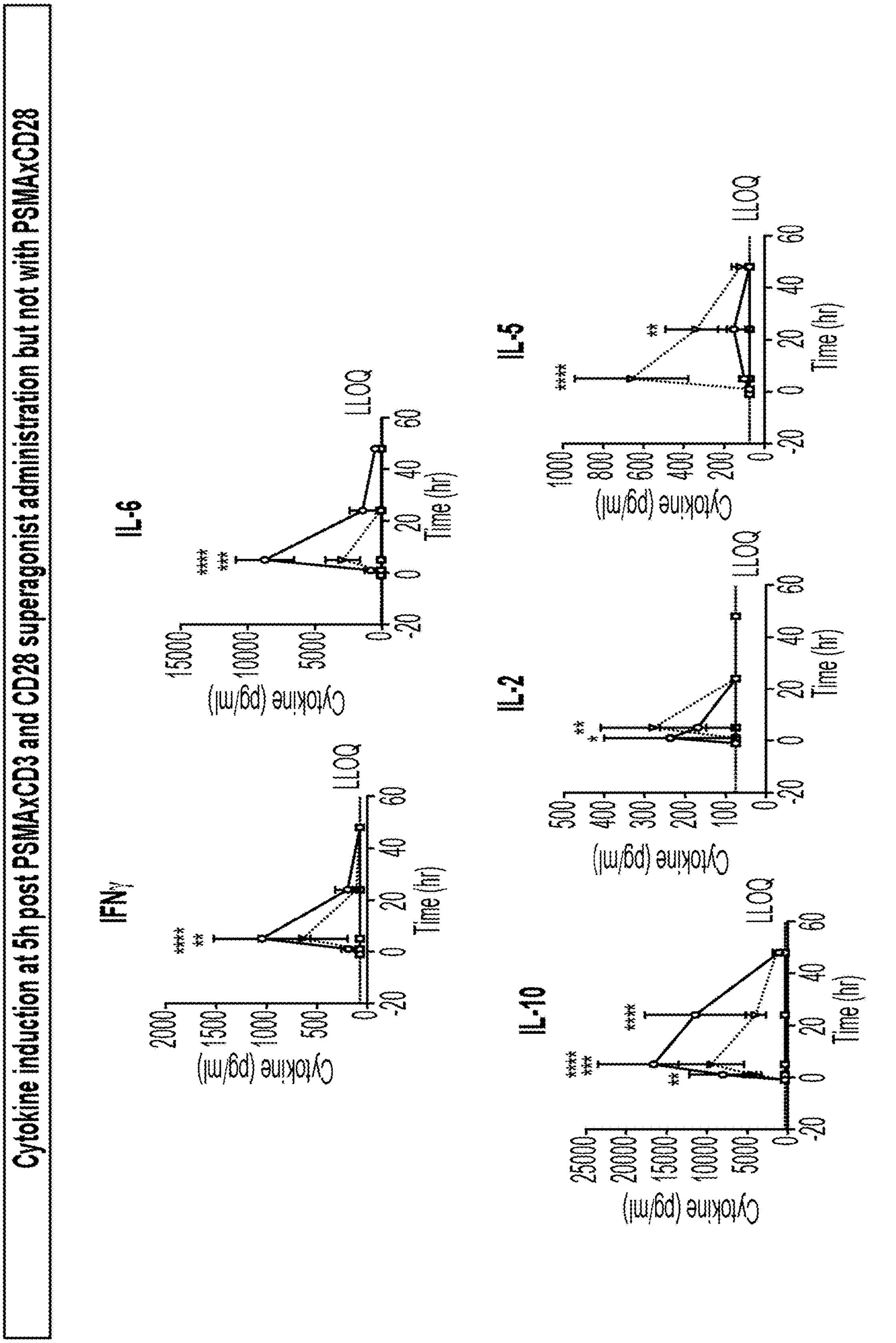

FIGS. 13A and 13B shows that PSMA×CD28 showed no cytokine production or T cell margination in comparison to PSMA×CD3 and CD28 super-agonist. LLOQ: "Lower Limit of Quantification."

Figure 14:
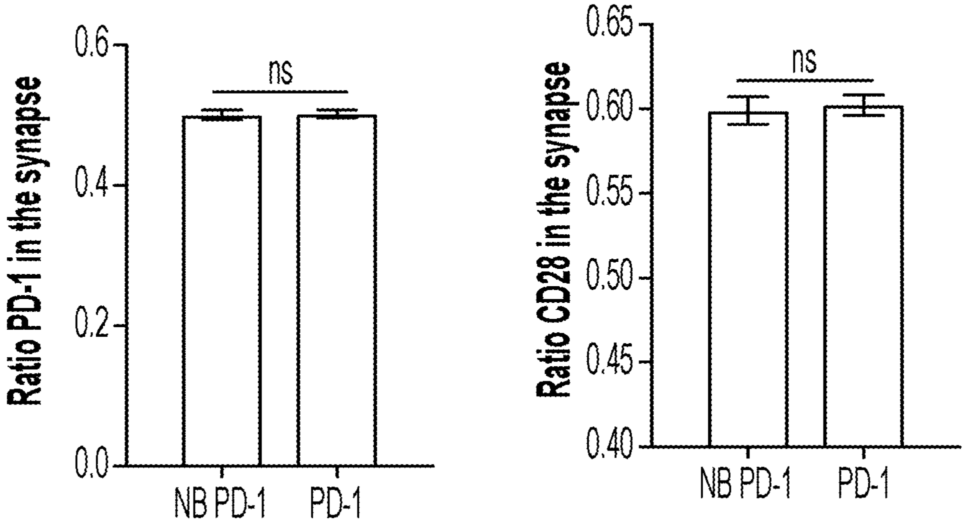
Figure 15:
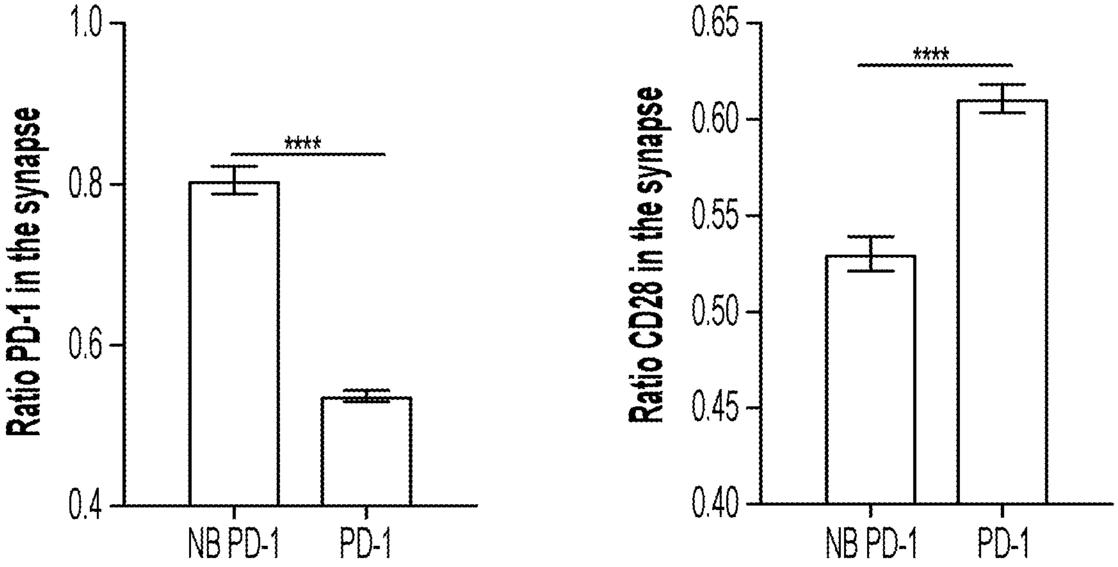
Figure 16:
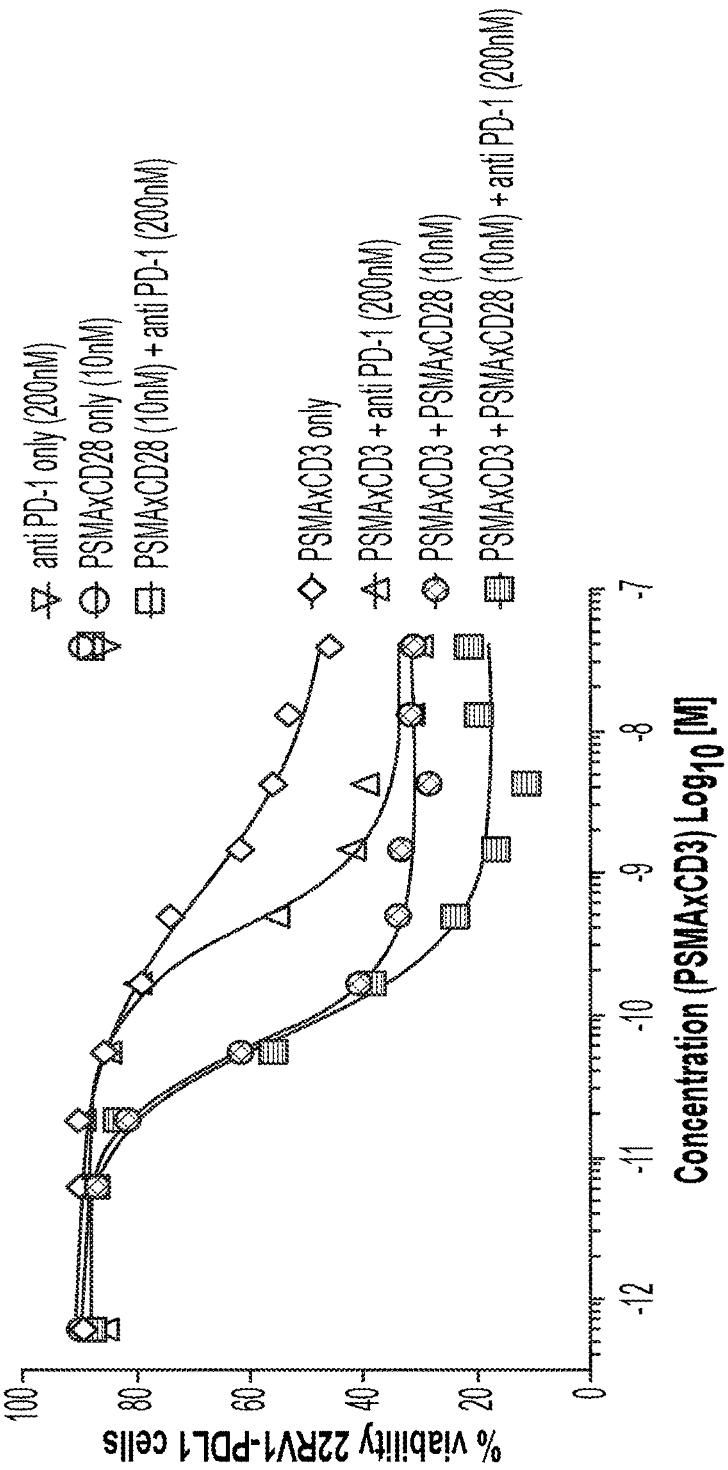
Figure 17:
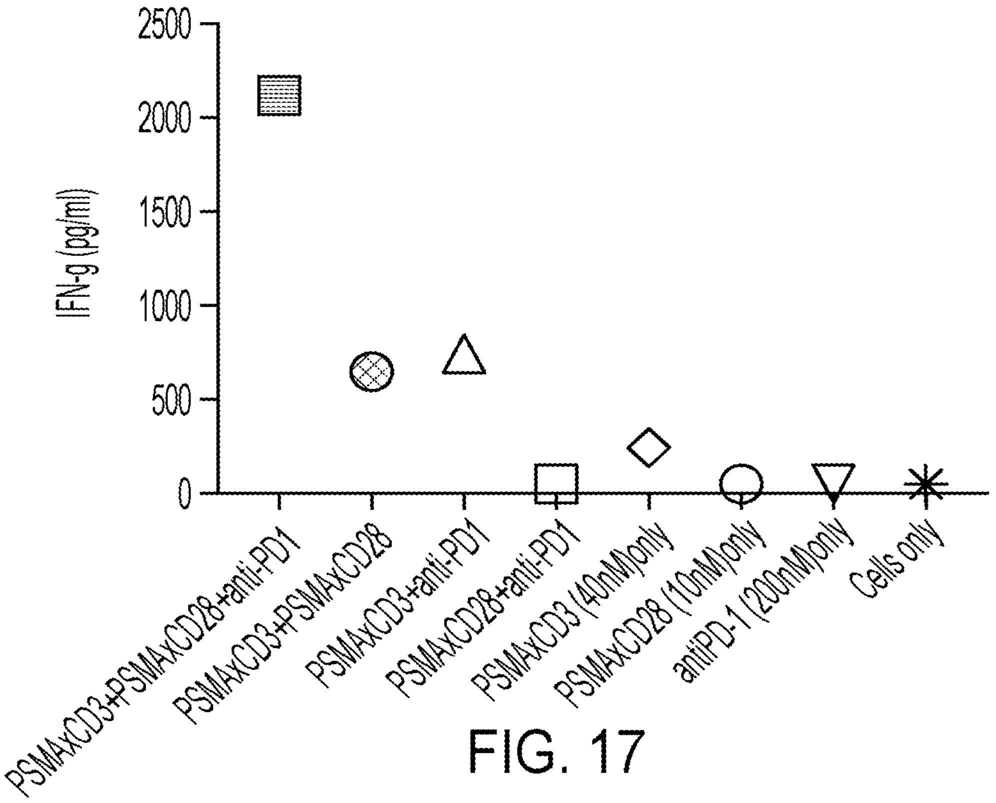
Figure 18:
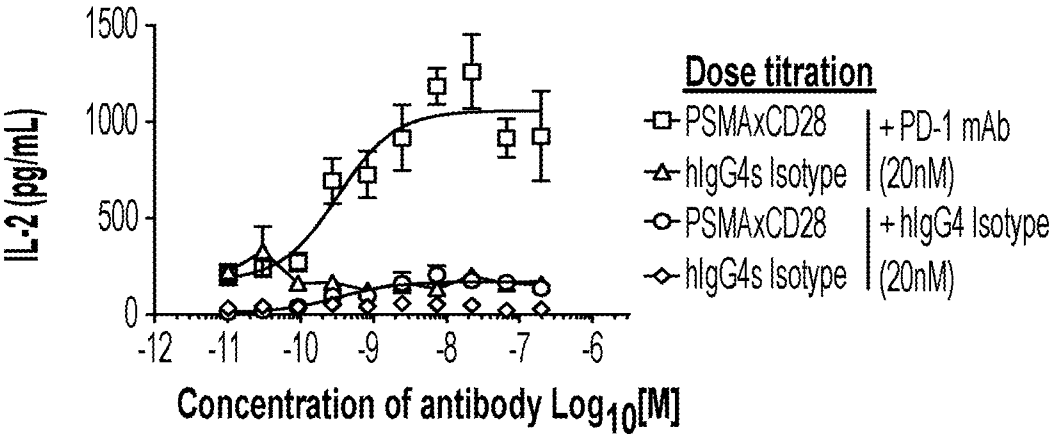

FIGS. 14, and 17 show TSAxCD28 and PD-1 blockade activates TCR/CD3 and CD28 on T cells at the tumor site. FIGS. 15, 16, and 18 show TSAxCD28 bispecific and PD-1 blockade synergistically promote T cell activation in vitro. In FIGS. 14-18, T cell (Jurkat/PD-1) and target cell (Raji WT) conjugates in the presence of a non-blocker PD-1 mAb (NB PD-1 mAb) or blocker (PD-1 mAb) and CD20×CD3 bispecific.

FIG. 14 provides bar graphs showing quantification of PD-1 and CD28 localization at the immunological synapse. Statistical significance was calculated with an unpaired t test (not significant, ns). To quantify PD-1 and CD28 localization at the immunological synapse, images of T cell (Jurkat/PD-1) and target cell (Raji WT) conjugates in the presence of a non-blocker PD-1 mAb (NB PD-1 mAb) or blocker (PD-1 mAb) and anti-CD20×CD3 bispecific antibody were taken. PD-1 mAbs were directly labeled with Alexa647, anti-CD20×CD3 bispecific antibody was directly labeled with Alexa488, CD28 mAb was directly labeled with PE and nuclei were stained with Hoechst 33342 (images not shown).

FIG. 15 provides bar graphs showing quantification of PD-1 and CD28 localization at the immunological synapse. Statistical significance was calculated with an unpaired t test ($p<0.0001$, ****). To quantify PD-1 and CD28 localization at the immunological synapse, images of T cells (Jurkat/PD-1) and target cell (Raji/PD-L1) conjugates in the presence of a non-blocker PD-1 mAb (NB PD-1 mAb) or blocker (PD-1 mAb) and anti-CD20×CD3 bispecific antibody were taken. PD-1 mAbs were directly labeled with Alexa647 (shown in red), CD20×CD3 was directly labeled with Alexa488 (shown in green), CD28 mAb was directly labeled with PE (shown in blue) and nuclei were stained with Hoechst 33342 (shown in grey). Dotted lines are outlines of cells drawn based on the brightfield image.

FIG. 16 shows the percentage (%) viability of 22RV1-PDL1 cells at 96 hours.

FIG. 17 is a graph showing IFNγ levels in the supernatant at 96 hours.

FIG. 18 is a graph showing IL-2 release at 96 hours.

FIGS. 19A-19D show that expression of a CD28 ligand (CD86) on tumor cells synergizes with anti-PD1 treatment to induce CD8 dependent anti-tumor immunity. MC38 tumor cells were transduced with the ligand for CD28, CD86 (MC38/CD86), or empty vector control (MC38/EV). WT C57BL6 mice were initially implanted with $1\times10^6$ tumor cells per mouse and treated with PD-1 mAb or rat isotype control at 5 mg/kg on day 0, 3, 7, 10 and 14 post tumor implant.

Figures 19A, 19B, 19C, 19D:
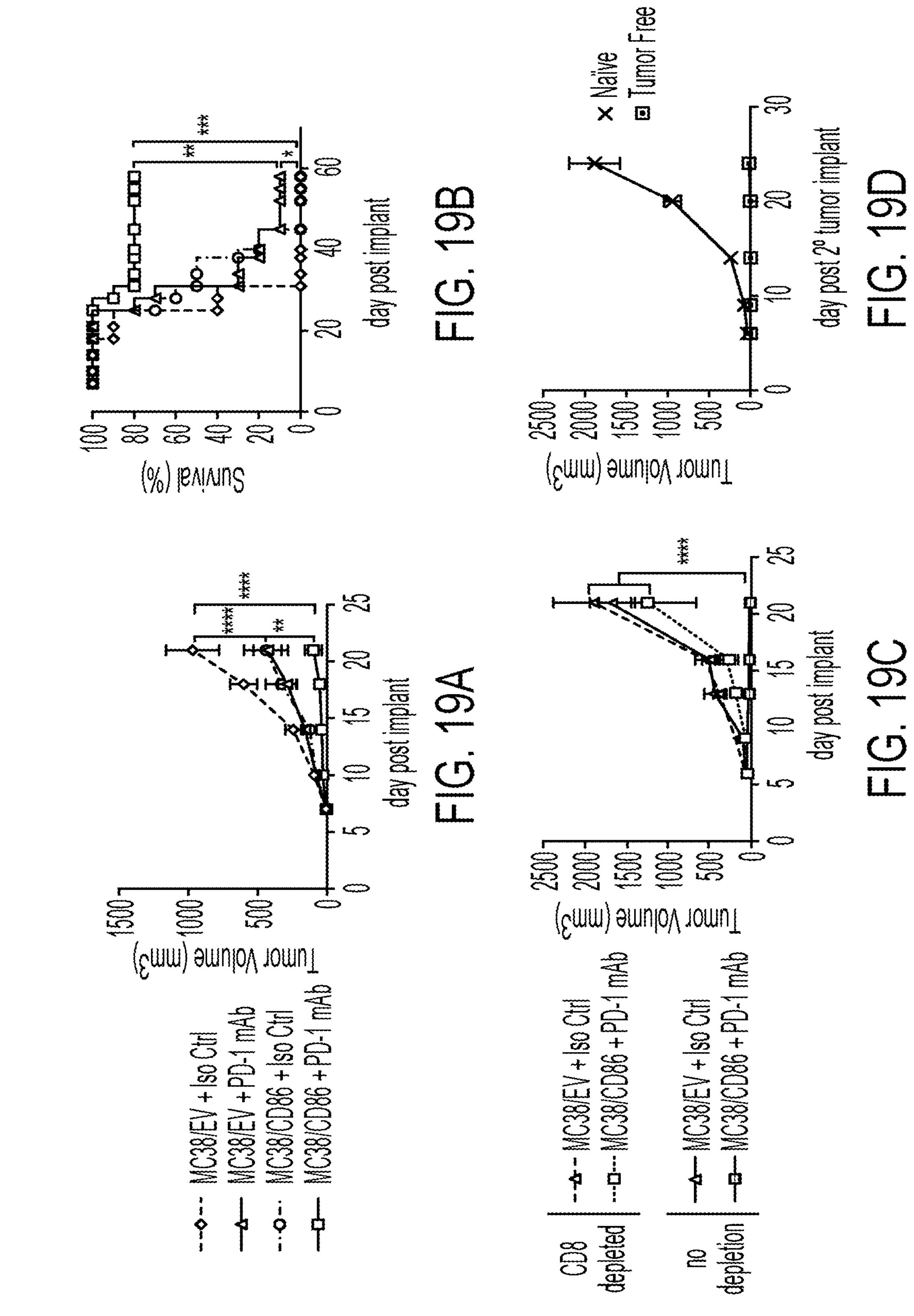

FIG. 19A shows average tumor volume over time. Error bars represent+/−SEM. Statistical significance was determined with two-way ANOVA and Tukey's multiple comparisons tests.

FIG. 19B shows survival over time (percentage of mice with tumors <2000 mm$^3$). Statistical significance at day 60 post-implantation was determined with the Log-rank (Mantel-Cox) test.

In FIG. 19C, mice were treated with CD8 depleting antibody (CD8 depleted) or isotype control (no depletion). Average tumor volume over time w/CD8 depletion (dotted lines) and no depletion (solid lines) is shown+/−SEM. Statistical significance was determined with two-way ANOVA and Tukey's multiple comparisons tests.

FIG. 19D shows secondary tumor implant (re-challenge) of tumor free mice that were implanted with MC38/CD86 and treated with PD1 mAb.

In FIGS. 19A-19D, data shown is from 1 experiment with 10 mice per group. Data is representative of at least 4 separate experiments. Statistical significance is indicated (*p<0.05, p<0.01, *p<0.001, and ****p<0.0001).

FIGS. 20A-20E, 21A, 22A-22D, 24, and 25 show that PSMAxCD28 synergizes with PD1 mAb treatment to induce anti-tumor immunity. MC38/hPSMA tumor cells were implanted in hCD3/hCD28/hPSMA mice subcutaneously. PSMAxCD28 bispecific antibody, PD-1 mAb or rat IgG2a isotype control were administered as monotherapy or in combination by intraperitoneal injection at 5 mg/kg each. FIGS. 21B and 21C show that PSMAxCD28 and PD-1 mAb combination increases the frequency of tumor specific T cells. FIGS. 23A and 23B show PSMA×CD28 synergizes with anti-PD1 treatment to induce intratumoral but not splenic or systemic cytokines.

Figure 20A:
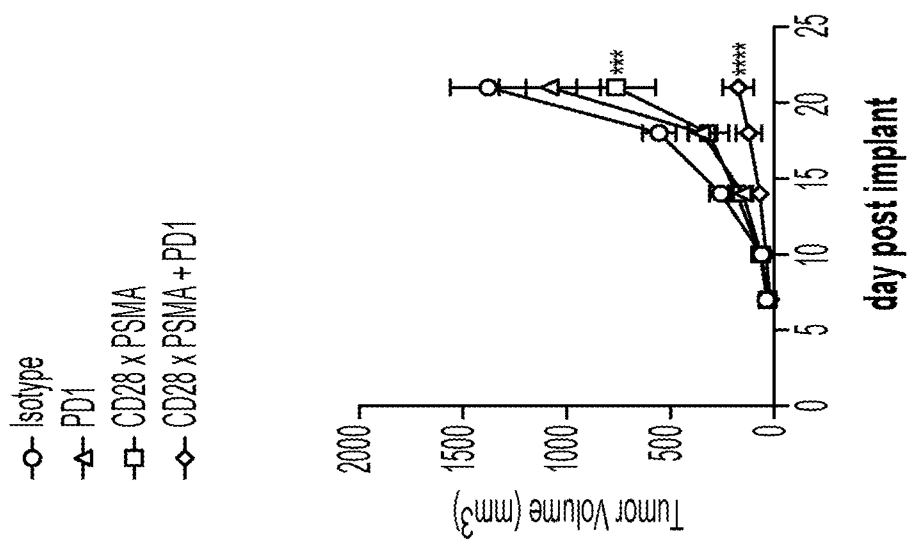
Figure 20B:
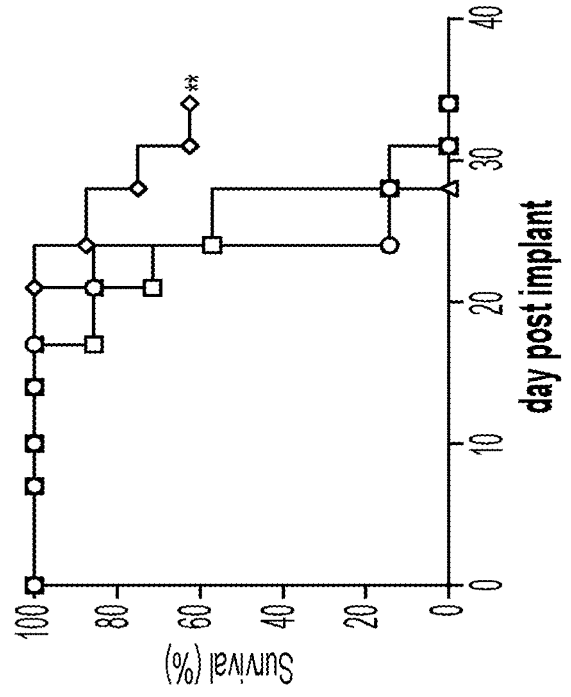
Figure 20C:
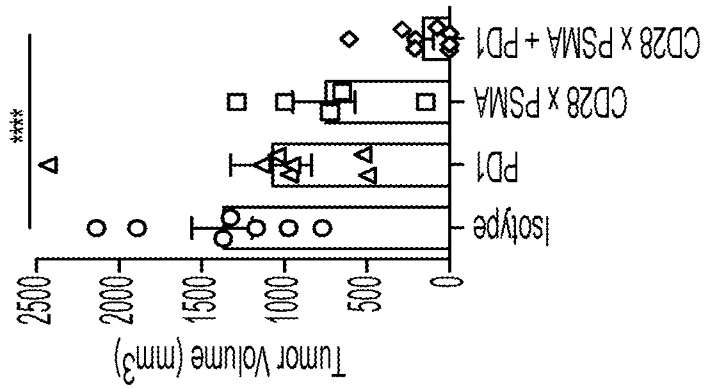

FIGS. 20A-20E show that immediate treatment with an anti-PSMA×anti-CD28 antibody enhances immunity at the tumor site and synergizes with anti-PD-1 antibodies to promote tumor rejection. FIG. 20A shows average tumor volume over time. Error bars represent+/−SEM. Statistical significance determined with 2-way ANOVA and Tukey's multiple comparisons test (*, p<0.001 and , p<0.0001). FIG. 20B shows survival over time (mice with tumors >2000 mm$^3$ are euthanized). Statistical significance determined with Log-rank (Mantel-Cox) test (, p<0.01). FIG. 20C shows average tumor volume on day 21 post implant. Error bars represent+/−SEM. Statistical significance determined with 1-way ANOVA and Holm-Sidak multiple comparisons test (**, p<0.0001). FIG. 20D shows a table of tumor volume (mm$^3$) on day 21 post implant. FIG. 20**E shows a table with the number of tumor free mice per group from 6 separate experiments.

Figure 21A:
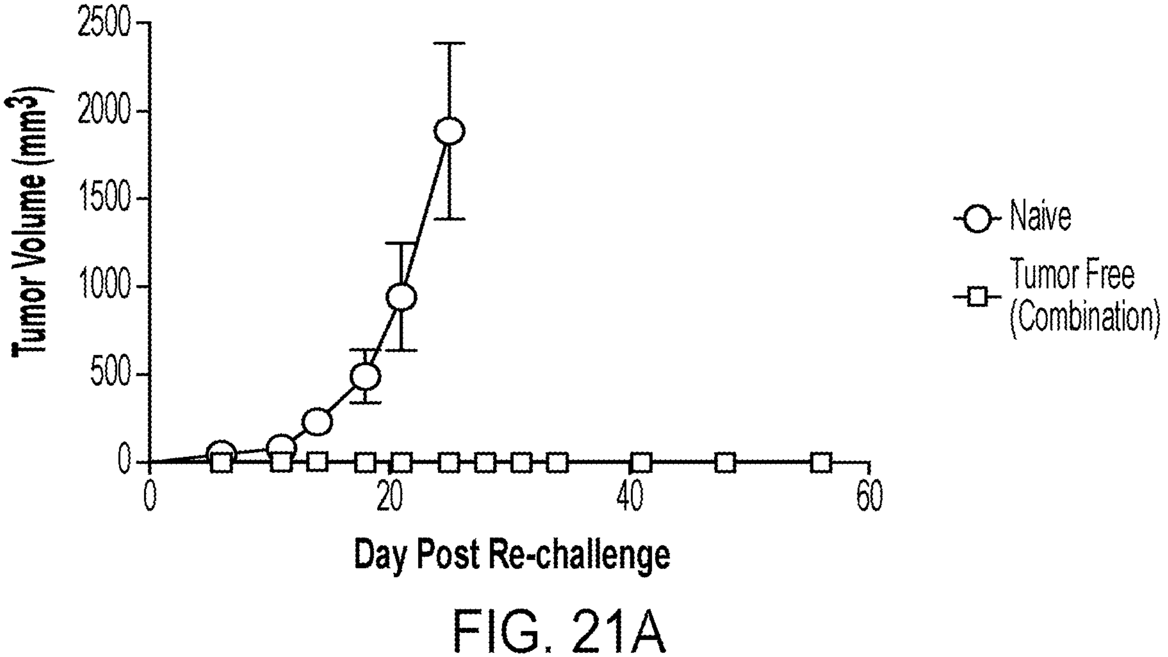
Figure 21B:
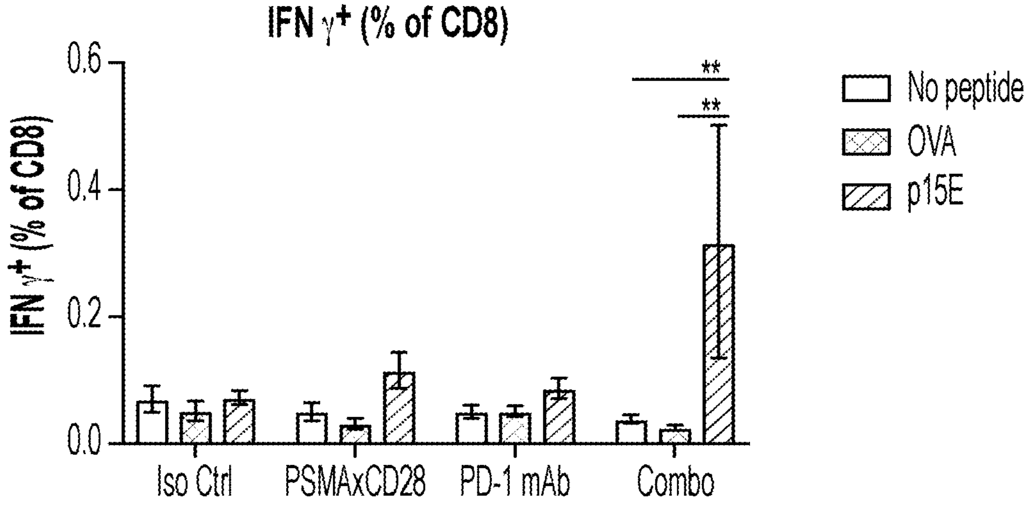
Figure 21C:
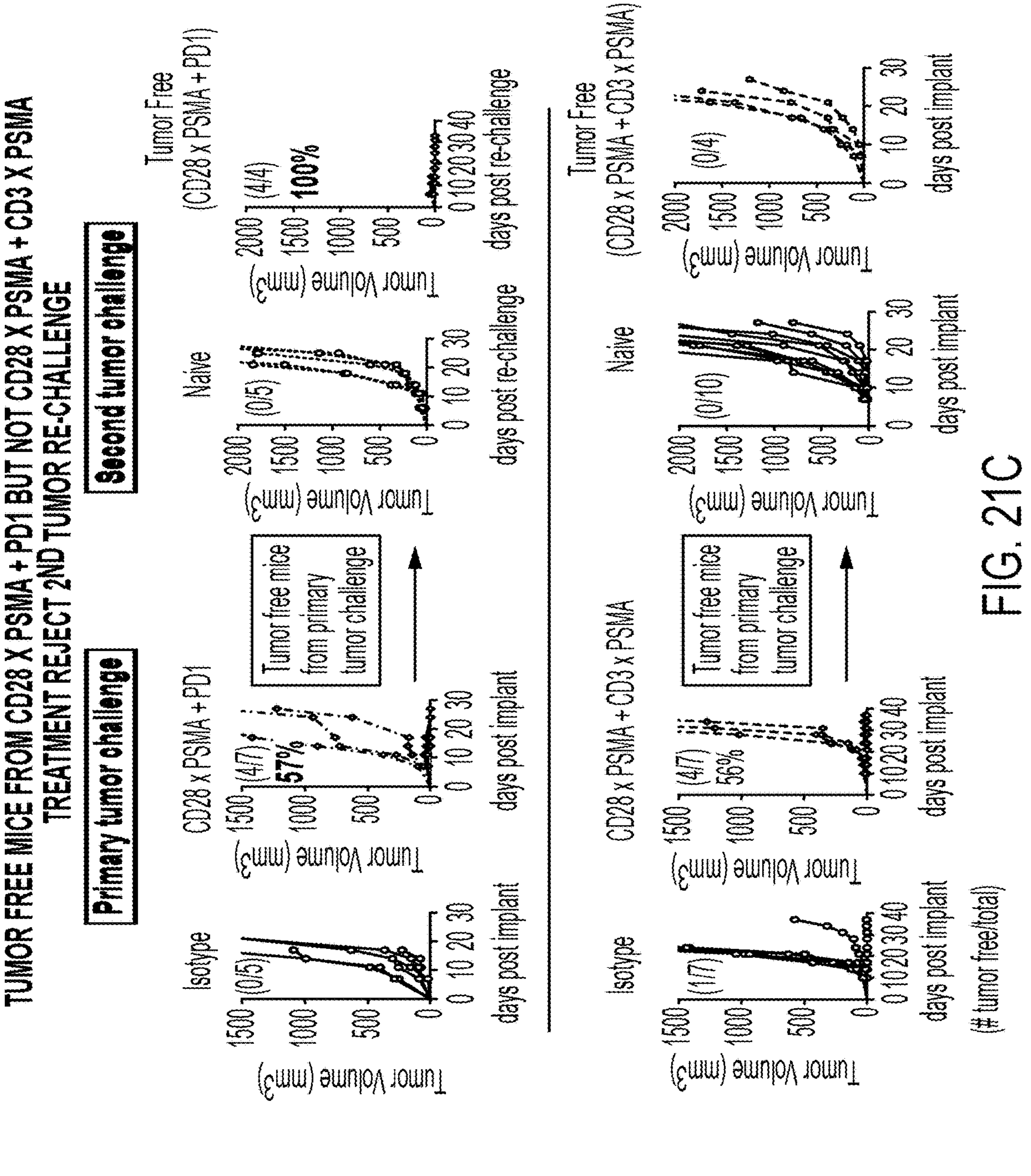

FIG. 21A shows secondary tumor challenge of tumor free mice previously treated with PSMAxCD28 and PD1 mAb combination. Error bars represent+/−SEM Data is representative of 4 experiments.

FIG. 21B shows MC38/PSMA tumor cells implanted in CD3/CD28/PSMA humanized mice and treated with Isotype control, PSMAxCD28, PD1 mAb or combination at 5 mg/kg on day 10 and 14 post implant. Spleens were harvested on day 17. Splenocytes were cultured overnight in T cell media with 10 mg/ml peptide (p15E or OVA) and 2 mg/ml anti-CD28. After overnight incubation, intracellular cytokine staining was performed following standard procedures.

FIG. 21C shows that tumor free mice from anti-CD28×PSMA and anti-PD1 but not anti-CD28×PSMA and anti-CD3×PSMA treatment rejected 2$^{nd}$ tumor re-challenge.

Figure 22B:
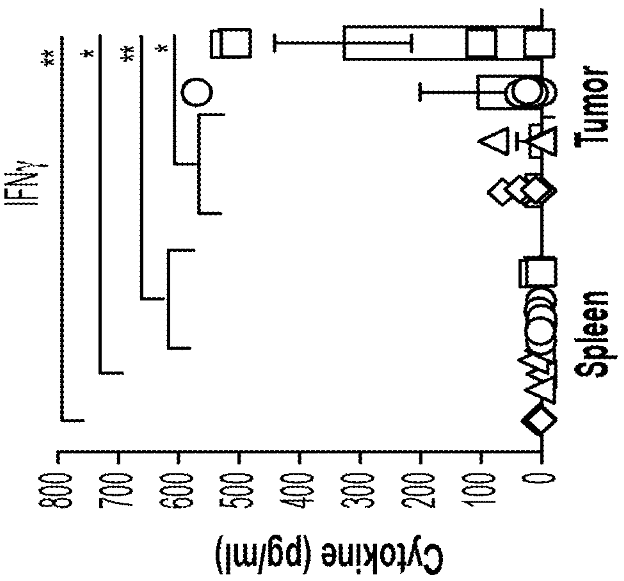
Figure 22A:
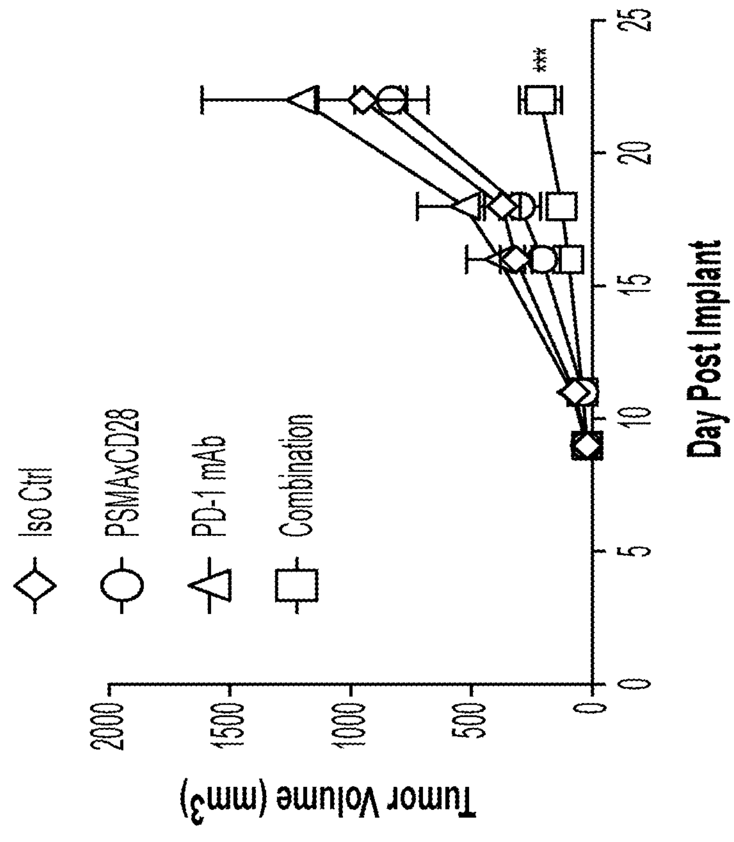
Figure 22D:
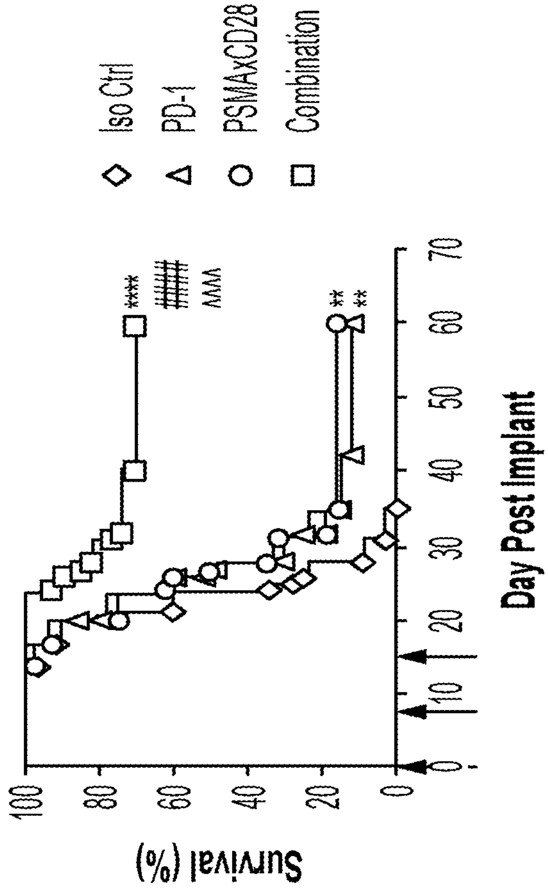
Figure 24:
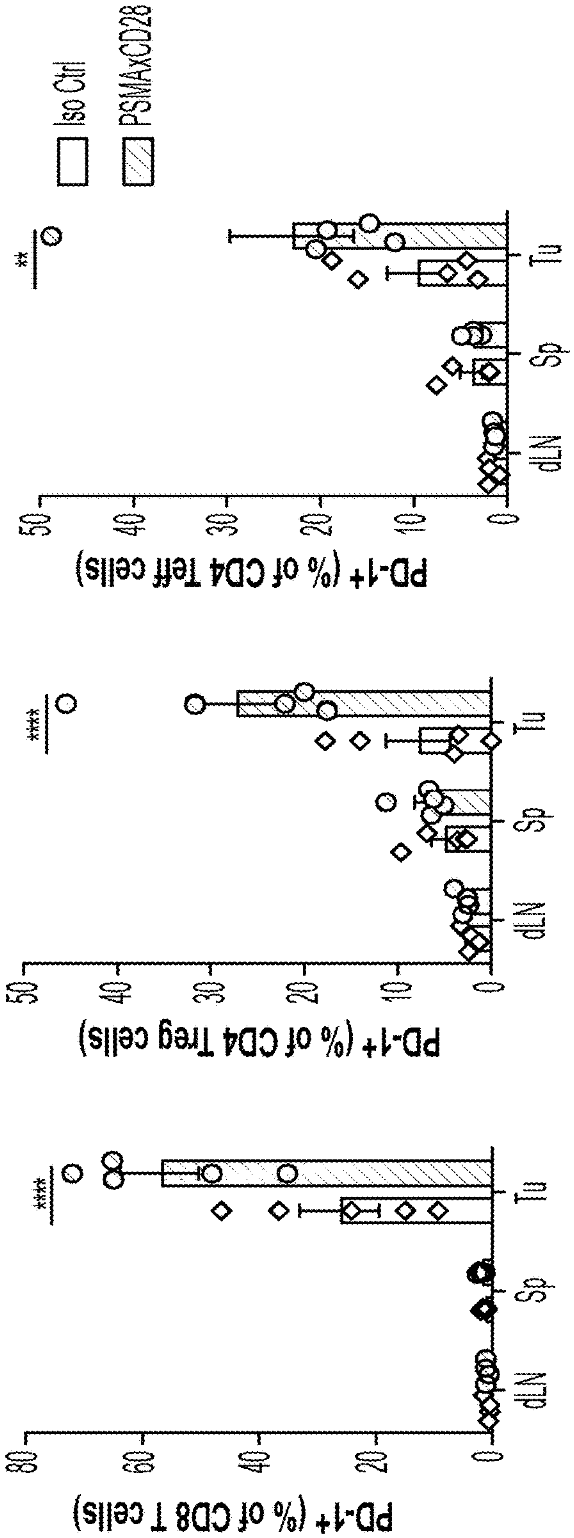
Figure 25:
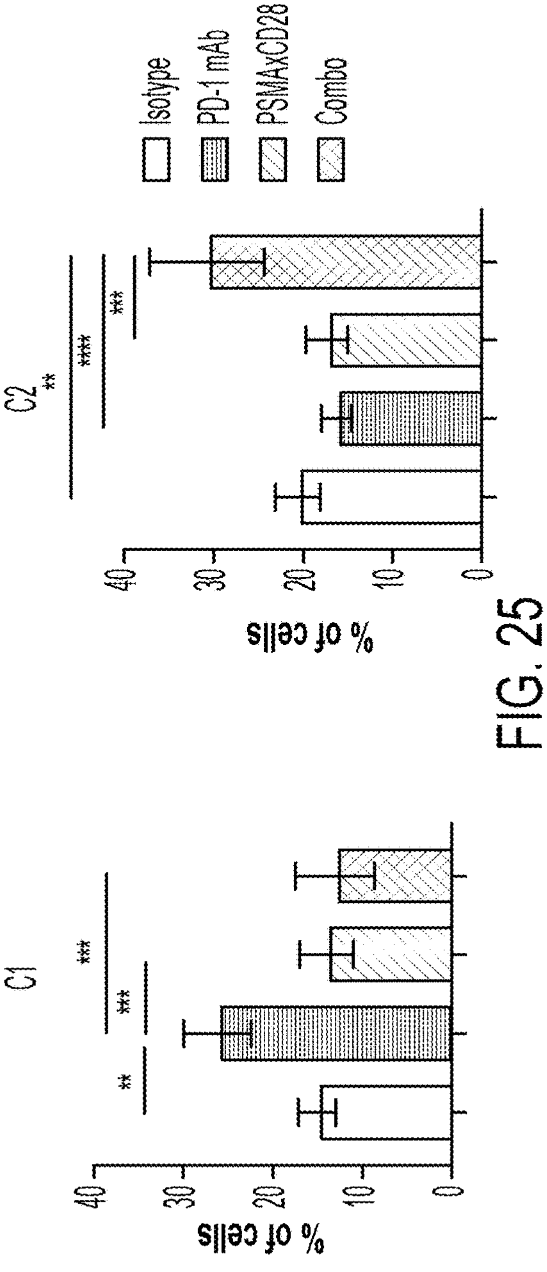

FIGS. 22A-22D, 24 and 25 show delayed/therapeutic treatment regimen (dosing indicated by arrows; FIGS. 22A and 22B on day 9, 16 and 22; FIGS. 24 and 25 on day 7, 11, and 14.

FIG. 22A shows average tumor volume over time. Error bars represent+/−SEM. Statistical significance was determined with two-way ANOVA and Tukey's multiple comparisons tests. Data is representative of 3 experiments FIG. 22B shows ex vivo splenic and intratumoral cytokines. Points represent data from individual mice. Bar is the average±/−SEM.

Figure 22C:
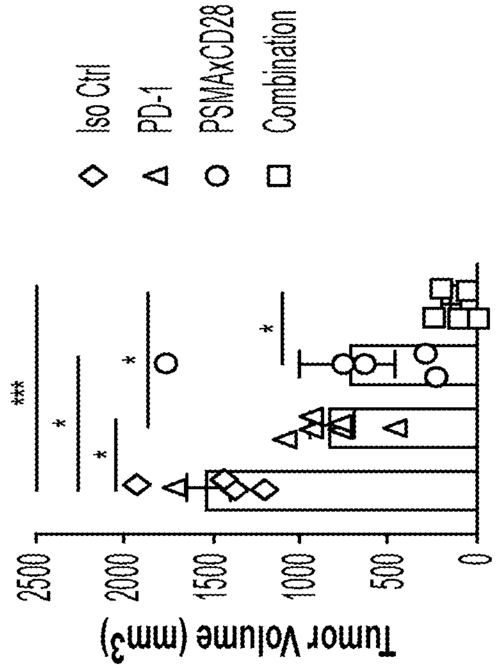
Figure 23A:
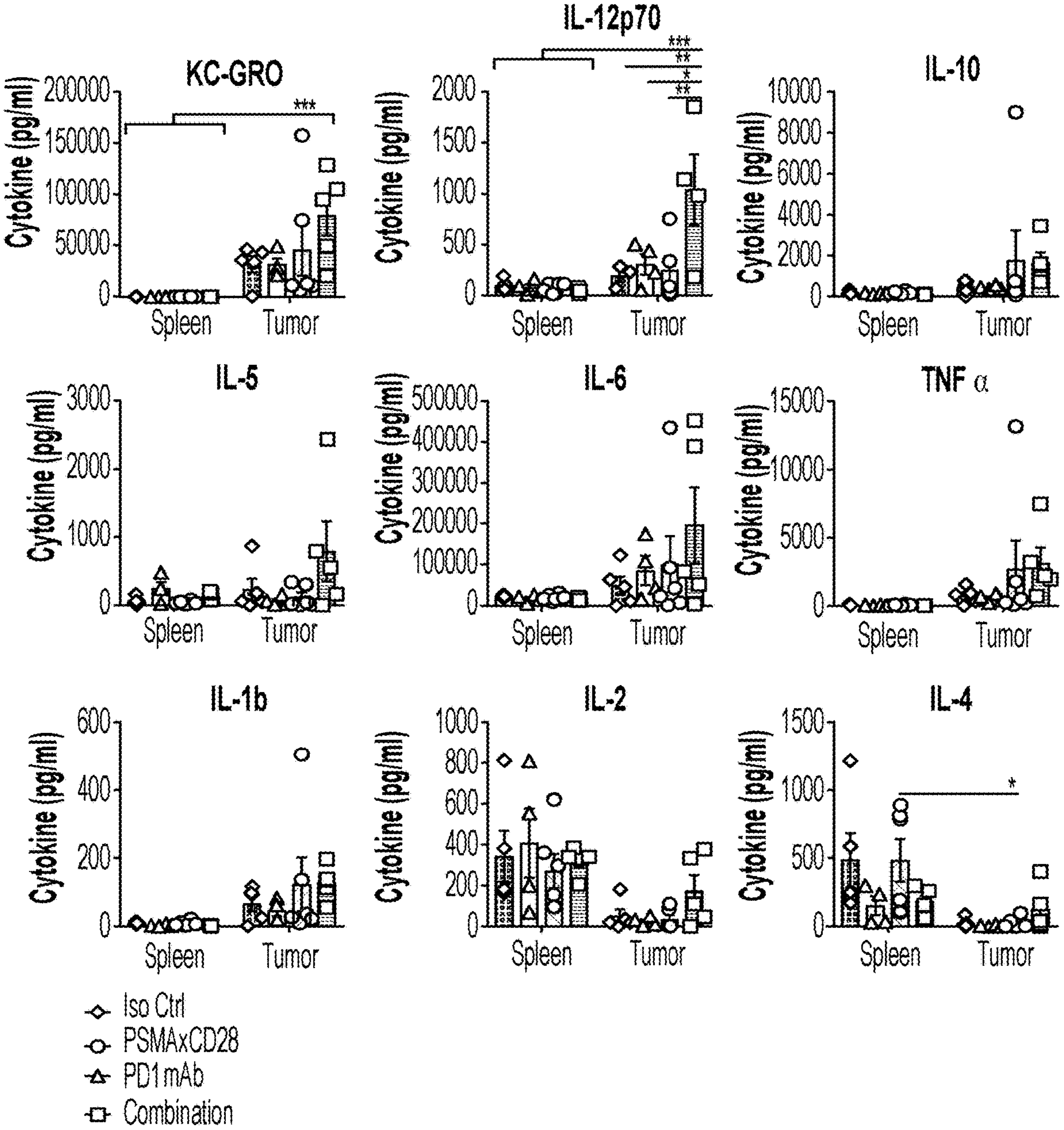
Figure 23B:
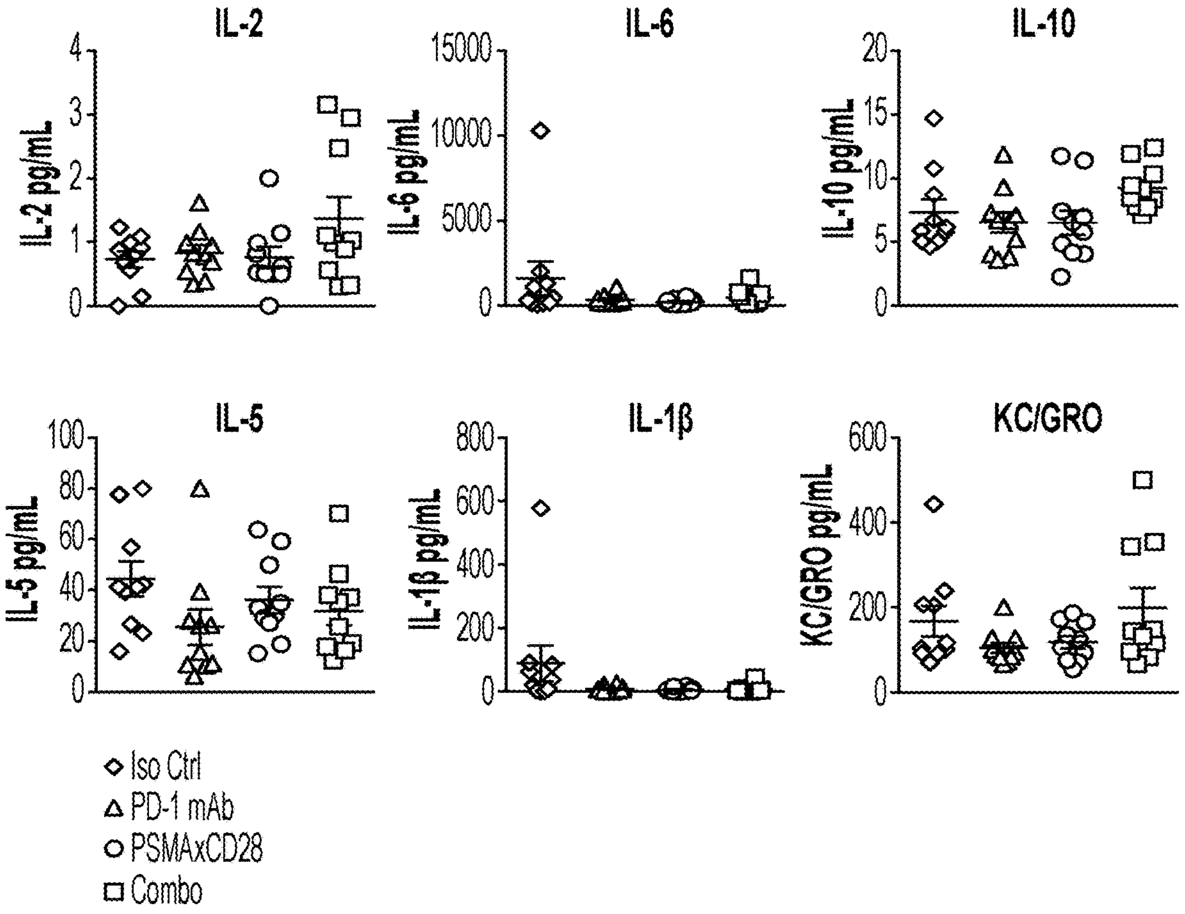

FIG. 22C shows the average tumor size at day 20.

FIG. 22D shows the survival of mice receiving different treatments.

FIGS. 23A and 23B show that PSMA×CD28 synergizes with anti-PD1 treatment to induce intratumoral but not splenic or systemic cytokines.

In FIG. 23A, data corresponds with FIG. 22B. Ex vivo splenic and intratumoral cytokines. Points represent data from individual mice. Bar is the average±/−SEM.

In FIG. 23B, CD3/CD28/PSMA triple humanized mice were implanted with MC38/hPSMA and treated with the indicated antibody at 5 mg/kg on day 0. Mice were bled and serum was collected at 4 hours post dose. In both FIGS. 23A and 23B statistical significance was calculated with 1-way ANOVA and Tukey's multiple comparisons test. *p<0.05, p<0.01, **p<0.0001

FIG. 24 shows PD1 expression on T cell subsets from draining lymph node (dLN), spleen (Sp), and tumor (Tu). Points represent data from individual mice. Bar is the average±/−SEM.

FIG. 25 shows frequency of CD8 T cells in C1 and C2 from the indicated treatment groups.

Data in FIGS. 22B, 24, and 25 from 1 experiment each. FIGS. 22B, and 24 n=4-6 mice per group. FIG. 25 n=10 mice per group.

FIGS. 26A-26C and 27 show TAAxCD28 alone or in combination with PD1 therapy does not induce systemic T cell activation in comparison to CD28 superagonist in cynomolgus monkeys. Cynomolgus monkeys were treated with a single dose of bispecifics at the indicated dose (1 or 10 mg/kg as indicated). Time is indicated post dose (hour).

Figure 26A:
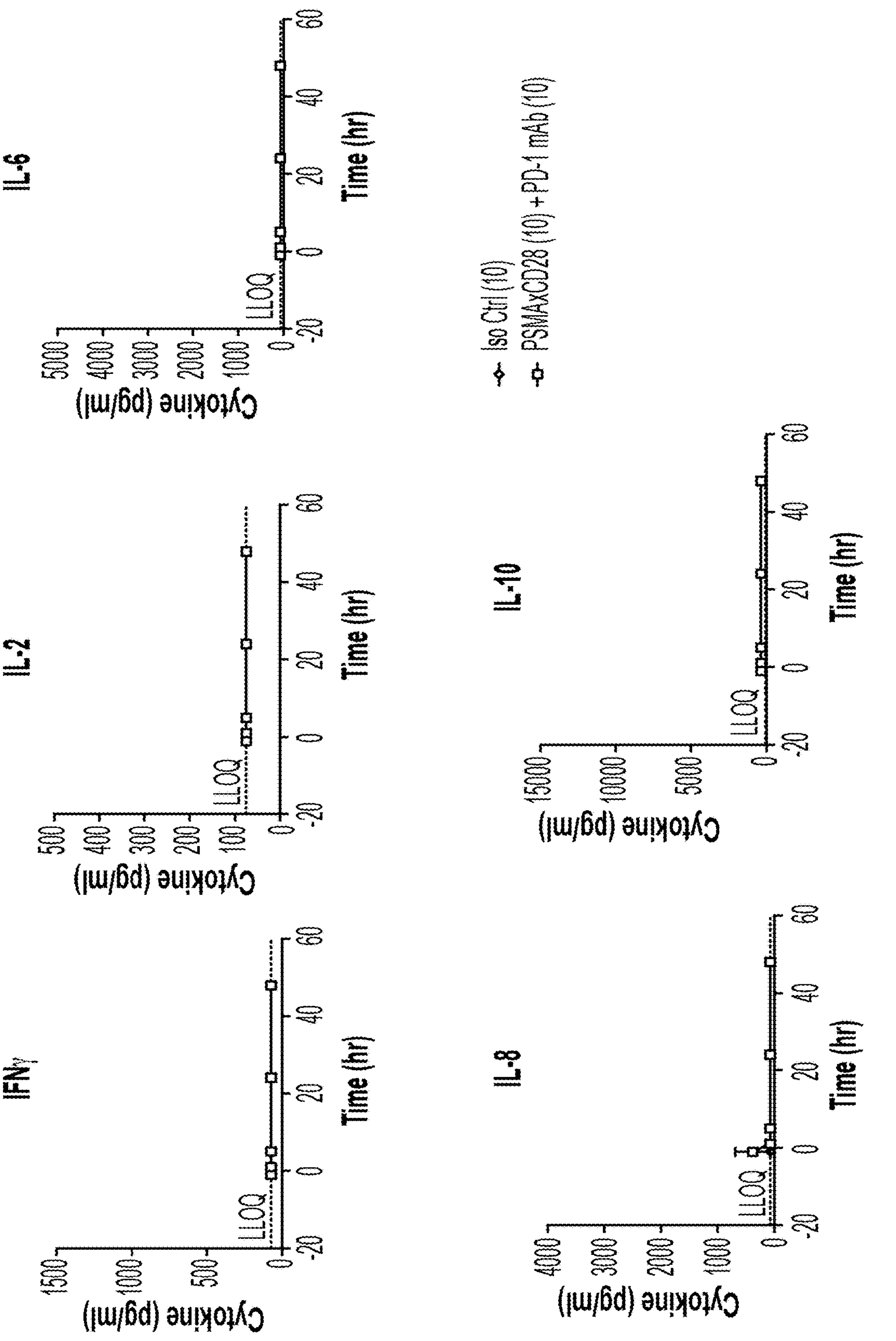

FIG. 26A shows serum cytokines.

Figure 26B:
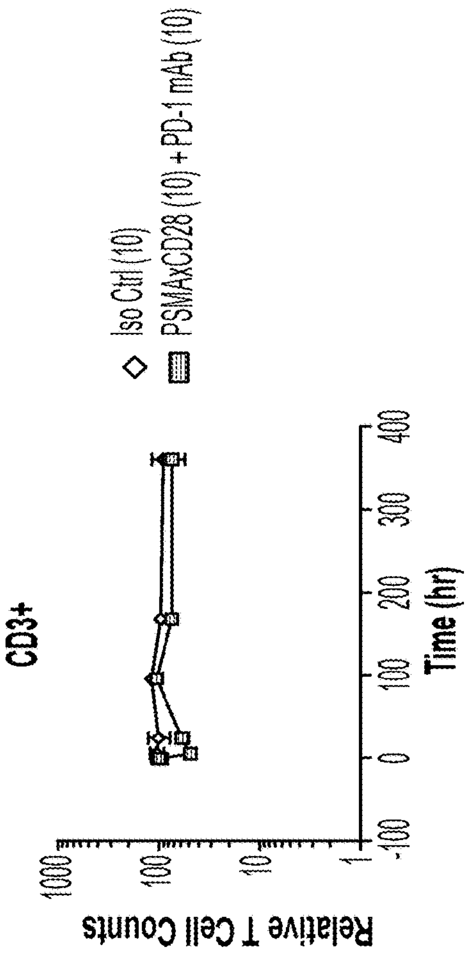

FIG. 26B shows relative peripheral blood T cell counts.

Figure 26C:
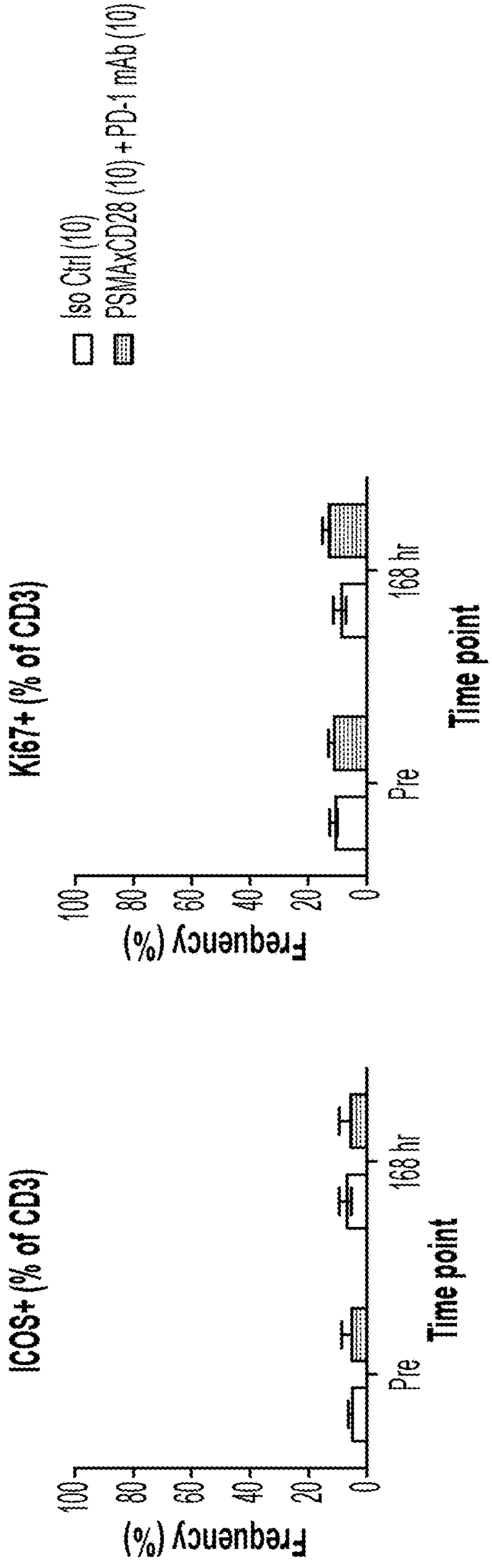

FIG. 26C shows frequency of $Ki67^+$ and $ICOS^+$ T cells (% of CD3).

In FIGS. 26A-26C, values represent the average±/−SEM. N=3 animals per group.

Figure 27:
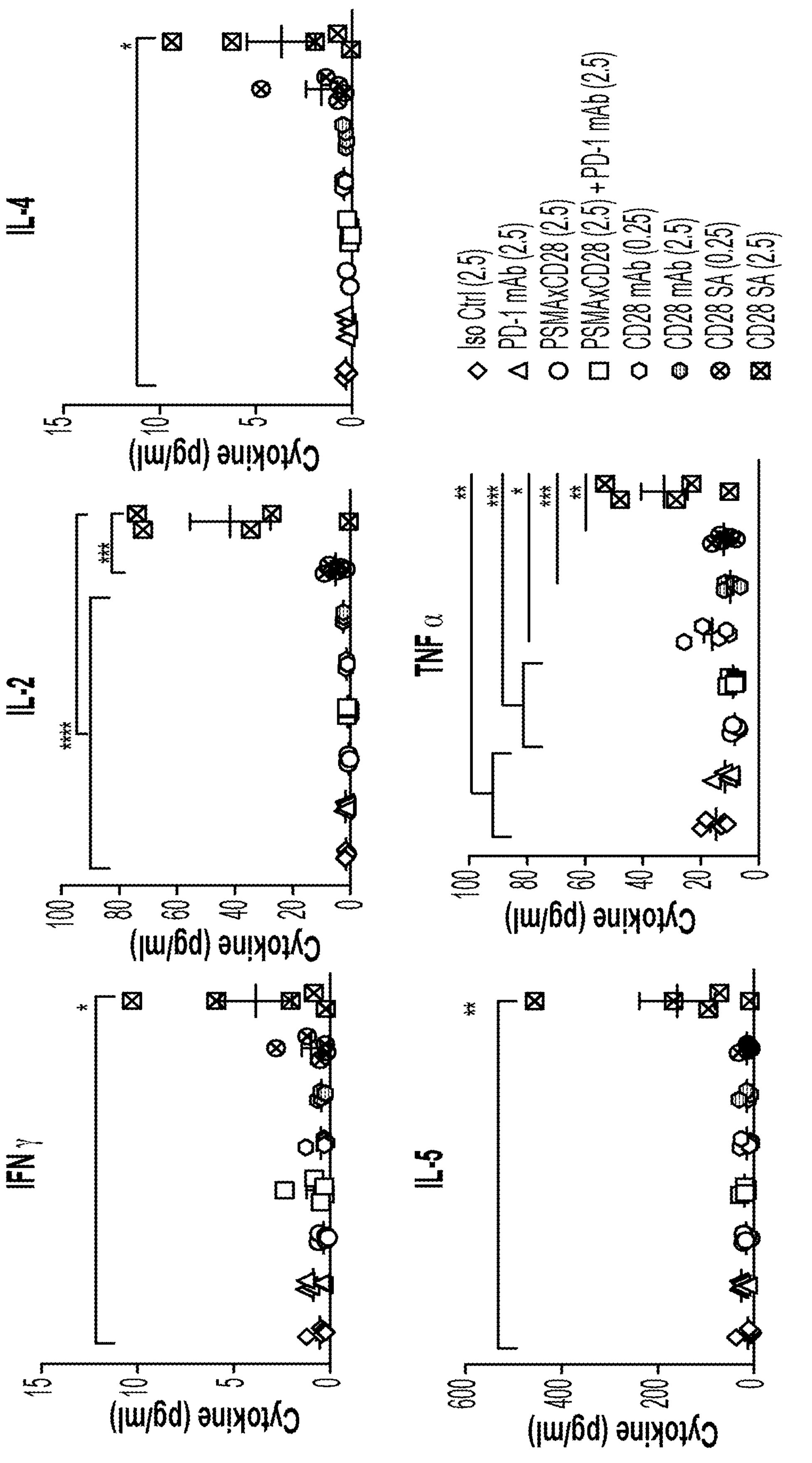

FIG. 27 shows that CD3/CD28/PSMA triple humanized mice were treated with a single dose of antibody (0.25 or 2.5 mg/kg as indicated). Mice were bled and serum was collected at 4 hours (day 0) post dose. Statistical significance was calculated with 1-way ANOVA and Holm-Sidak's multiple comparisons test. *p<0.05, p<0.01, **p<0.0001

Figure 28:
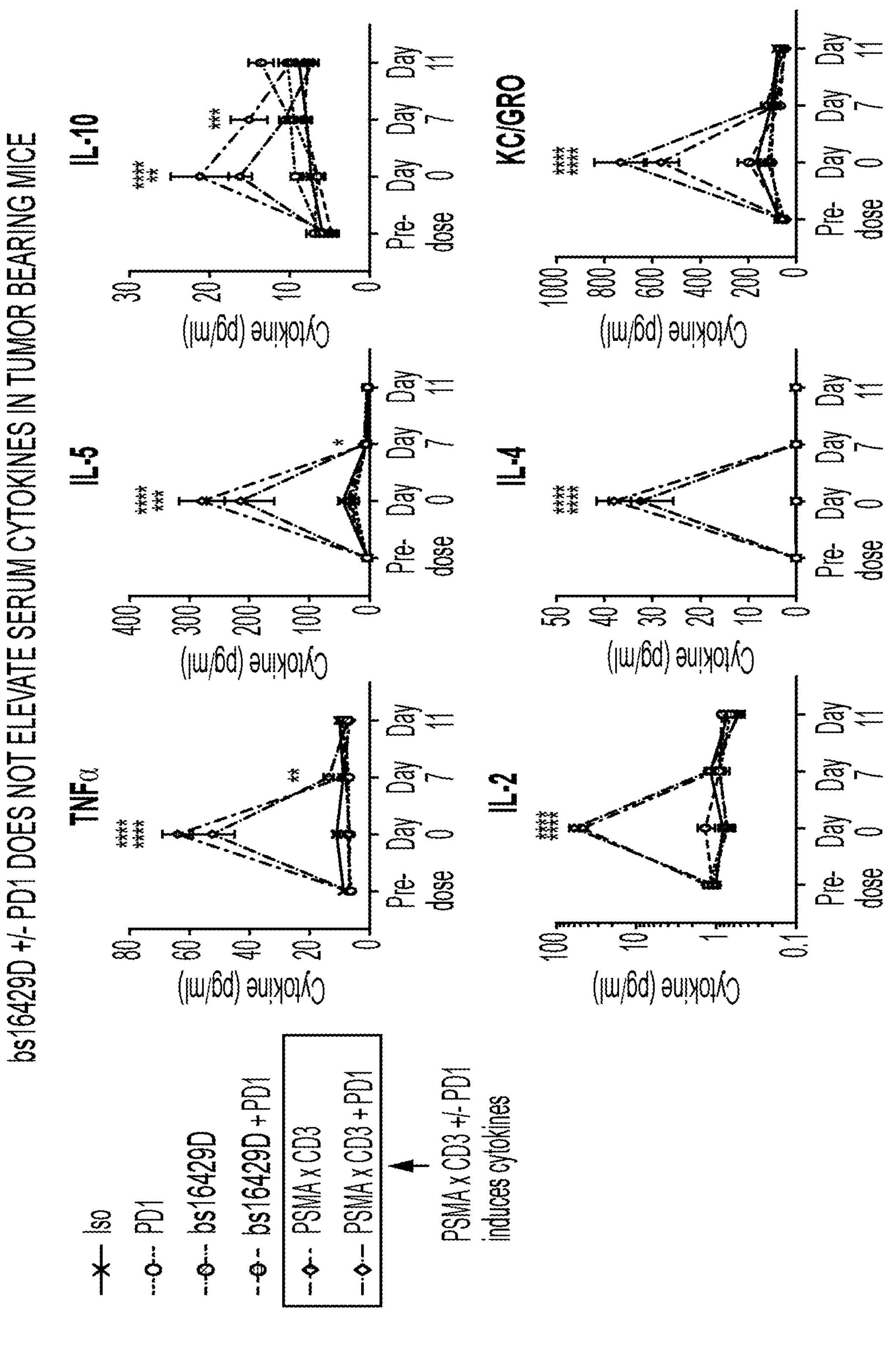

FIG. 28 shows that PSMA×CD28+/−PD1 did not elevate serum cytokines in tumor bearing mice. 29A and 29B show PSMAxCD28 alone or in combination with PD1 mAb shows safe cytokine profile in vivo in non-tumor bearing mice. Data corresponds with those FIG. 27. CD3/CD28/PSMA triple humanized mice were treated with a single dose of antibody (0.25 or 2.5 mg/kg as indicated). Mice were bled and serum was collected at 4 hours (day 0) and 72 hours (day 3) post dose. Statistical significance was calculated with 1-way ANOVA and Holm-Sidak's multiple comparisons test. *p<0.05, p<0.01, **p<0.0001

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 1 01 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "CD28," as used herein, refers to an antigen which is expressed on T cells as a costimulatory receptor. Human CD28 comprises the amino acid sequence as set forth in SEQ ID NO: 74, and/or having the amino acid sequence as set forth in NCBI accession No. NP_006130.1. All references to proteins, polypeptides and protein fragments herein are intended to refer to the human version of the respective protein, polypeptide or protein fragment unless explicitly specified as being from a non-human species. Thus, the expression "CD28" means human CD28 unless specified as being from a non-human species, e.g., "mouse CD28," "monkey CD28," etc.

As used herein, "an antibody that binds CD28" or an "anti-CD28 antibody" includes antibodies and antigen-binding fragments thereof that specifically recognize a monomeric CD28, as well as antibodies and antigen-binding fragments thereof that specifically recognize a dimeric CD28. The antibodies and antigen-binding fragments of the present invention may bind soluble CD28 and/or cell surface expressed CD28. Soluble CD28 includes natural CD28 proteins as well as recombinant CD28 protein variants such as, e.g., monomeric and dimeric CD28 constructs, that lack a transmembrane domain or are otherwise unassociated with a cell membrane.

As used herein, the expression "cell surface-expressed CD28" means one or more CD28 protein(s) that is/are expressed on the surface of a cell in vitro or in vivo, such that at least a portion of a CD28 protein is exposed to the extracellular side of the cell membrane and is accessible to an antigen-binding portion of an antibody. "Cell surface-expressed CD28" includes CD28 proteins contained within the context of a functional T cell costimulatory receptor in the membrane of a cell. The expression "cell surface-expressed CD28" includes CD28 protein expressed as part of a homodimer on the surface of a cell. A "cell surface-expressed CD28" can comprise or consist of a CD28 protein expressed on the surface of a cell which normally expresses CD28 protein. Alternatively, "cell surface-expressed CD28" can comprise or consist of CD28 protein expressed on the surface of a cell that normally does not express human CD28 on its surface but has been artificially engineered to express CD28 on its surface.

As used herein, the expression "anti-CD28 antibody" includes both monovalent antibodies with a single specificity, as well as bispecific antibodies comprising a first arm that binds CD28 and a second arm that binds a second (target) antigen, wherein the anti-CD28 arm comprises any of the HCVR/LCVR or CDR sequences as set forth in Table 1 herein. Examples of anti-CD28 bispecific antibodies are described elsewhere herein. The term "antigen-binding molecule" includes antibodies and antigen-binding fragments of antibodies, including, e.g., bispecific antibodies.

The term "antibody", as used herein, means any antigen-binding molecule or molecular complex comprising at least one complementarity determining region (CDR) that specifically binds to or interacts with a particular antigen (e.g., CD28). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, $C_H1$, $C_H2$ and $C_H3$. Each light chain comprises a light chain variable region (abbreviated herein as LCVR or VL) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-CD28 antibody (or antigen-binding portion thereof) may be identical to the human germ line sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-CD28 antibodies of the invention (monospecific or bispecific) are human antibodies. The term "human antibody", as used herein, is intended to include antibodies having variable and constant regions derived from human germ line immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germ line of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germ line $V_H$ and $V_L$ sequences, may not naturally exist within the human antibody germ line repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, CH2 or CH3 region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind CD28. As used herein, a "one-arm antibody" means an antigen-binding molecule comprising a single antibody heavy chain and a single antibody light chain. The one-arm antibodies of the present invention may comprise any of the HCVR/LCVR or CDR amino acid sequences as set forth in Table 2.

The anti-CD28 antibodies herein, or the antigen-binding domains thereof, may comprise one or more amino acid substitutions, insertions and/or deletions in the framework and/or CDR regions of the heavy and light chain variable domains as compared to the corresponding germline sequences from which the antigen-binding proteins or antigen-binding domains were derived. Such mutations can be readily ascertained by comparing the amino acid sequences disclosed herein to germline sequences available from, for example, public antibody sequence databases. The present invention includes antibodies, and the antigen-binding domains thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments, which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies, or the antigen-binding domains thereof, of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies, or the antigen-binding fragments thereof, that contain one or more germline mutations can be easily tested for one or more desired property such as, improved binding specificity, increased binding affinity, improved or enhanced antagonistic or agonistic biological properties (as the case may be), reduced immunogenicity, etc. Antibodies, or the antigen-binding fragments thereof, obtained in this general manner are encompassed within the present invention.

The present invention also includes anti-CD28 antibodies and antigen-binding molecules comprising variants of any of the HCVR, LCVR, and/or CDR amino acid sequences disclosed herein. Exemplary variants included within this aspect of the invention include variants of any of the HCVR, LCVR, and/or CDR amino acid sequences disclosed herein having one or more conservative substitutions. For example, the present invention includes anti-CD28 antibodies and antigen-binding molecules having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Bispecific Antigen-Binding Molecules

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-CD28 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

Use of the expression "anti-CD28 antibody" herein is intended to include both monospecific anti-CD28 antibodies as well as bispecific antibodies comprising a CD28-binding arm and a second arm that binds a target antigen. Thus, the present invention includes bispecific antibodies wherein one arm of an immunoglobulin binds human CD28, and the other arm of the immunoglobulin is specific for a target antigen. The target antigen that the other arm of the CD28 bispecific antibody binds can be any antigen expressed on or in the vicinity of a cell, tissue, organ, microorganism or virus, against which a targeted immune response is desired. The CD28-binding arm can comprise any of the HCVR/LCVR or CDR amino acid sequences as set forth in Table 1 herein. In certain embodiments, the CD28-binding arm binds human CD28 and induces human T cell proliferation.

In the context of bispecific antibodies of the present invention wherein one arm of the antibody binds CD28 and the other arm binds a target antigen, the target antigen can be a tumor-associated antigen, such as PSMA.

According to certain exemplary embodiments, the present invention includes bispecific antigen-binding molecules that specifically bind CD28 and PSMA. Such molecules may be referred to herein as, e.g., "anti-CD28/anti-PSMA," or "anti-CD28×PSMA," or "CD28×PSMA" or "anti-PSMA/anti-CD28," or "anti-PSMAxCD28," or "PSMAxCD28" bispecific molecules, or other similar terminology.

The term "PSMA," as used herein, refers to the human PSMA protein unless specified as being from a non-human species (e.g., "mouse PSMA," "monkey PSMA," etc.). The human PSMA protein has the amino acid sequence shown in SEQ ID NO: 73, and/or having the amino acid sequence as set forth in NCBI accession No. NP_004467.1.

Figure 1:
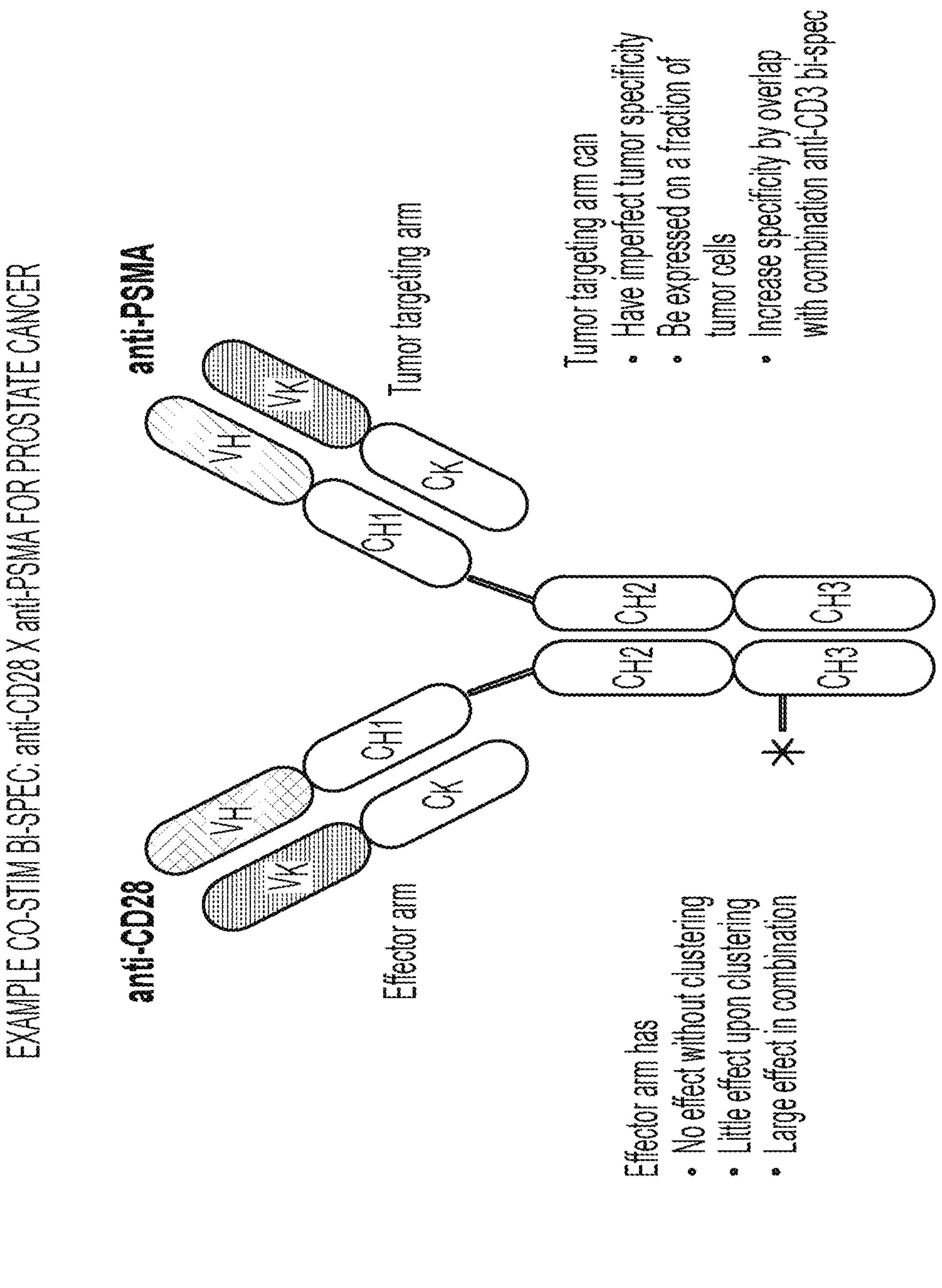
FIG. 1 is a schematic showing the structure of an exemplary anti-CD28/PSMA bispecific antibody.

According to certain exemplary embodiments as shown in FIG. 1, the bispecific antigen-binding molecules (e.g., bispecific antibody) may have an effector arm and a targeting arm. The effector arm may be the first antigen-binding domain (e.g., anti-CD28 antibody) that binds to the antigens on effector cells (e.g., T cells). The targeting arm may be the second antigen binding domain (e.g., anti-PSMA antibody) that binds to the antigens on target cells (e.g., tumor cells). According to certain exemplary embodiments, the effector arm binds to CD28 and the targeting arm binds to PSMA. The bispecific anti-CD28/PSMA may provide co-stimulatory signal to effector cells (e.g., T cells). The effector arm has no effect to stimulate T cells without clustering. Upon clustering, the effector arm alone has little effect to stimulate T cells. In combination with the targeting arm, the effector arm stimulates T cells. The tumor targeting arm may have imperfect tumor specificity. The antigen that is the target of the targeting arm (e.g., PSMA) may be expressed on a fraction of tumor cells. The specificity of the tumor targeting arm may be increased by overlapping with combination with anti-CD3 bispecific antigen-binding molecules (e.g., anti-CD3/PSMA bispecific antibody).

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD28), and the second antigen-binding domain specifically binds a second, distinct antigen (e.g., PSMA).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen binding domain (e.g., a bispecific antibody), the CDRs of the first antigen-binding domain may be designated with the prefix "D1" and the CDRs of the second antigen-binding domain may be designated with the prefix "D2". Thus, the CDRs of the first antigen-binding domain may be referred to herein as D1-HCDR1, D1-HCDR2, and D1-HCDR3; and the CDRs of the second antigen-binding domain may be referred to herein as D2-HCDR1, D2-HCDR2, and D2-HCDR3.

The first antigen-binding domain and the second antigen-binding domain may be directly or indirectly connected to one another to form a bispecific antigen-binding molecule of the present invention. Alternatively, the first antigen-binding domain and the second antigen binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of 1 to about 200 amino acids in length containing at least one cysteine residues. In other embodiments, the multimerizing domain is a cysteine residue, or a short cysteine containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (OVO)-Ig, Quadroma, knobs-into-holes, common light chain (e.g., common light chain with knobs-intoholes, etc.), CrossMab, CrossFab, (SEEO) body, leucine zipper, Ouobody, IgG1/IgG2, dual acting Fab (OAF)-IgG, and Mab2 bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., LN/FIW or T), 254 (e.g., S or T), and 256 (e.g., S/R/Q/EID or T); or a modification at position 428 and/or 433 (e.g., UR/S/P/Q or K) and/or 434 (e.g., H/F or V); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252,254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second CH3 include: D16E, L 18M, N44S, K52N, V57M, and V821 (by IMGT; D356E, L358M, N384S, K392N, V397M, and V4221 by EU) in the case of IgG1 antibodies; N44S, K52N, and V821 (IMGT; N384S, K392N, and V4221 by EU) in the case of IgG2 antibodies; and Q15R, N44S, K52N, V57M, R69K, E79Q, and V821 (by IMGT; Q355R, N384S, K392N, V397M, R409K, E419Q, and V4221 by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 CH2]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present invention are described in WO2014/022540 A1, Chimeric Fc domains having these general structural arrangements, and variants thereof, can have altered Fc receptor binding, which in turn affects Fc effector function.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germ line sequences available from, for example, public antibody sequence databases. The antigen-binding molecules of the present invention may comprise antigen binding fragments which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germ line sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germ line sequence while certain other residues that differ from the original germ line sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-1445. A "moderately conservative" replacement is any change having a nonnegative value in the PAM250 log-likelihood matrix.

The present invention also includes antigen-binding molecules comprising an antigen binding domain with an HCVR, LCVR, and/or CDR amino acid sequence that is substantially identical to any of the HCVR, LCVR, and/or CDR amino acid sequences disclosed herein. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

pH-Dependent Binding

The present invention includes anti-CD28/anti-PSMA bispecific antigen-binding molecules, with pH-dependent binding characteristics. For example, an anti-CD28 antibody of the present invention may exhibit reduced binding to CD28 at acidic pH as compared to neutral pH. Alternatively, anti-PSMA antibodies of the invention may exhibit enhanced binding to PSMA at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to CD28 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-CD28/anti-PSMA bispecific antigen binding molecules are provided comprising an Fc domain comprising one or more mutations which enhance or diminish antibody binding to the FcRn receptor, e.g., at acidic pH as compared to neutral pH. For example, the present invention includes antibodies and antigen binding molecules comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-CD28/anti-PSMA bispecific antigen binding molecules comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Antigen-Binding Molecules

The present invention includes antibodies and antigen-binding fragments thereof that bind human CD28 and/or PSMA with high affinity. The present invention also includes antibodies and antigen binding fragments thereof that bind human CD28 and/or PSMA with medium or low affinity, depending on the therapeutic context and particular targeting properties that are desired. For example, in the context of a bispecific antigen-binding molecule, wherein one arm binds CD28 and another arm binds a target antigen (e.g., PSMA), it may be desirable for the target antigen-binding arm to bind the target antigen with high affinity while the anti-CD28 arm binds CD28 with only moderate or low affinity. In this manner, preferential targeting of the antigen-binding molecule to cells expressing the target antigen may be achieved while avoiding general/untargeted CD28 binding and the consequent adverse side effects associated therewith.

According to certain embodiments, the present invention includes antibodies and antigen-binding fragments of antibodies that bind human CD28 (e.g., at 25° C.) with a $K_D$ of less than about 210 nM as measured by surface plasmon resonance, e.g., using an assay format as defined in Example 3 herein. In certain embodiments, the antibodies or antigen-binding fragments of the present invention bind CD28 with a $K_D$ of less than about 150 nM, less than about 130 nM, less than about 120 nM, less than about 100 nM, less than about 50 nM, less than about 80 nM, less than about 60 nM, less than about 40 nM, or less than about 30 nM, as measured by surface plasmon resonance, e.g., using an assay format as defined in Example 3 herein, or a substantially similar assay. In certain embodiments, the antibodies or antigen-binding fragments of the present invention bind CD28 with a $K_D$ between from about 30 nM to about 207 nM.

The present invention also includes antibodies and antigen-binding fragments thereof that bind CD28 with a dissociative half-life (t½) of greater than about 3.5 minutes as measured by surface plasmon resonance at 25° C. or 37° C., e.g., using an assay format as defined in Example 3 herein, or a substantially similar assay. In certain embodiments, the antibodies or antigen-binding fragments of the present invention bind CD28 with a t½ of greater than about 5 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1200 minutes, as measured by surface plasmon resonance at 25° C. or 37° C., e.g., using an assay format as defined in Example 3 herein, or a substantially similar assay.

The present invention includes bispecific antigen-binding molecules (e.g., bispecific antibodies) which are capable of simultaneously binding to human CD28 and human PSMA. According to certain embodiments, the bispecific antigen-binding molecules of the invention specifically interact with cells that express CD28 and/or PSMA. The extent to which a bispecific antigen-binding molecule binds cells that express CD28 and/or PSMA can be assessed by fluorescence activated cell sorting (FACS), as illustrated in Example 4 herein. For example, the present invention includes bispecific antigen-binding molecules which specifically bind human cell lines which express CD28 but not PSMA (e.g., HEK293 engineered to express CD28), and human prostatic carcinoma cell lines which express PSMA but not CD28 (e.g., C4-2). The present invention includes bispecific antigen-binding molecules which bind any of the aforementioned cells and cell lines with an $EC_{50}$ value of from about $9.6\times10^{-9}$ to about $3.5\times10^{-10}$, or less, as determined using a FACS assay as set forth in Example 4 or a substantially similar assay.

The present invention also provides anti-CD28/anti-PSMA bispecific antigen-binding molecules that induce or increase T cell-mediated killing of tumor cells. For example, the present invention includes anti-CD28×PSMA antibodies that induce or increase T cell-mediated killing of tumor cells with an $EC_{50}$ of less than about 78 μM, as measured in an in vitro T cell-mediated tumor cell killing assay, e.g., using the assay format as defined in Example 6 herein (e.g., assessing the extent of C4-2 tumor cell killing by human PBMCs in the presence of anti-CD28×PSMA antibodies), or a substantially similar assay. In certain embodiments, the antibodies or antigen-binding fragments of the present invention induce T cell-mediated tumor cell killing (e.g., PBMC mediated killing of C4-2 cells) with an $EC_{50}$ value of less than about 40 pM, less than about 20 μM, less than about 16 μM, less than about 10 μM, less than about 5.0 pM, less than about 4.0 μM, less than about 3.0 μm, less than about 2.5 μm, less than about 2.0 pM, less than about 1.5 μM, or less than about 1.45 pM, as measured by an in vitro T cell mediated tumor cell killing assay, e.g., using the assay format as defined in Example 6 herein, or a substantially similar assay.

The present invention also includes anti-CD28/anti-PSMA bispecific antigen-binding molecules which bind to CD28-expressing human T-cells with an $EC_{50}$ value of between 1.0 μM and 1000 nM. In certain embodiments, the anti-CD28/anti-PSMA bispecific antigen-binding molecules bind to CD28-expressing human T-cells with an $EC_{50}$ value of between 48 nM and 180 nM. For example, the present invention includes anti-CD28/anti-PSMA bispecific antigen-binding molecules which bind to CD28-expressing human T-cells with an $EC_{50}$ value of about 1 pM. about 10 μM, about 100 μM, about 500 μM, about 1 nM, about 2 nM, about 5 nM, about 10 nM, about 20 nM, about 30 nM, about 40 nM, about 50 nM about 60 nM, about 70 nM, about 80 nM, about 90 nM, about 100 nM, about 200 nM, about 300 nM, about 500 nM, about 800 nM, about 1000 nM, or more.

The present invention also includes anti-CD28/anti-PSMA bispecific antigen-binding molecules which exhibit one or more characteristics selected from the group consisting of: (a) inducing T-cell proliferation in vitro (see, e.g., Example 8 herein); (b) activating T-cells, inducing CD25 and PD-1 up-regulation in human PBMCs (see, e.g., Example 8 herein); (c) increasing human T-cell mediated cytotoxicity on PSMA expressing cell lines (see, e.g., Example 8 herein); (d) inducing naïve primate T cell mediated cytotoxicity on PSMA expressing cell lines (see, e.g., Example 8 herein); (e) depleting tumor cells in mice (e.g., Example 10 herein); (f) enhancing tumor clearance in mice (e.g., Example 10 herein); (g) not inducing cytokine storm (e.g., Example 10 herein); (h) not inducing systemic T cell action in cynomolgus monkey (e.g., Example 11 herein); (i) enhancing the effect of PD-1 blockade on T cell activation induced tumor cell killing (e.g., Example 13 herein); (j) enhancing the expansion of memory T cell (e.g., Example 13 herein).

The present invention includes anti-CD28/anti-PSMA bispecific antigen-binding molecules which are capable of depleting tumor cells in a subject (see, e.g., Example 8). For example, according to certain embodiments, anti-CD28/anti-PSMA bispecific antigen-binding molecules are provided, wherein a single administration of the bispecific antigen-binding molecule to a subject (e.g., at a dose of about 0.1 mg/kg, about 0.08 mg/kg, about 0.06 mg/kg about 0.04 mg/kg, about 0.04 mg/kg, about 0.02 mg/kg, about 0.01 mg/kg, or less) causes a reduction in the number of tumor cells in the subject.

Epitope Mapping and Related Technologies

The epitope on CD28 or PSMA to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD28 protein or a PSMA protein. Alternatively, the epitope may consist of a plurality of non-contiguous amino acids (or amino acid sequences) of CD28 or PSMA. The antibodies of the invention may interact with amino acids contained within a CD28 monomer, or may interact with amino acids on two different CD28 chains of a CD28 dimer. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques that can be used to determine an epitope or binding domain of a particular antibody or antigen-binding domain include, e.g., routine crossblocking assay such as that described in *Antibodies*, Harlow and Lane (Cold Spring Harbor Press, Cold Spring Harb., NY), point mutagenesis (e.g., alanine scanning mutagenesis, arginine scanning mutagenesis, etc.), peptide blots analysis (Reineke, 2004, Methods Mol Biol 248:443-463), protease protection, and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267 (2): 252-259; Engen and Smith (2001) *Anal. Chem.* 73: 256A-265A. X-ray crystal structure analysis can also be used to identify the amino acids within a polypeptide with which an antibody interacts.

The present invention further includes anti-CD28 and anti-PSMA antibodies that bind to the same epitope as any of the specific exemplary antibodies described herein (e.g. antibodies comprising any of the amino acid sequences as set forth in Table 1 herein). Likewise, the present invention also includes anti-CD28 and/or anti-PSMA antibodies that compete for binding to CD28 and/or PSMA with any of the specific exemplary antibodies described herein (e.g. antibodies comprising any of the amino acid sequences as set forth in Table 1 herein).

The present invention also includes bispecific antigen-binding molecules comprising a first antigen-binding domain that specifically binds human CD28, and a second antigen binding fragment that specifically binds human PSMA, wherein the first antigen-binding domain binds to the same epitope on CD28 as any of the specific exemplary CD28-specific antigen-binding domains described herein, and/or wherein the second antigen-binding domain binds to the same epitope on PSMA as any of the specific exemplary PSMA-specific antigen-binding domains described herein.

Likewise, the present invention also includes bispecific antigen-binding molecules comprising a first antigen-binding domain that specifically binds human CD28, and a second antigen binding fragment that specifically binds human PSMA, wherein the first antigen-binding domain competes for binding to CD28 with any of the specific exemplary CD28-specific antigen binding domains described herein, and/or wherein the second antigen-binding domain competes for binding to PSMA with any of the specific exemplary PSMA-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD28 (or PSMA) as a reference bispecific antigen-binding molecule of the present invention, the reference bispecific molecule is first allowed to bind to a CD28 protein (or PSMA protein). Next, the ability of a test antibody to bind to the CD28 (or PSMA) molecule is assessed. If the test antibody is able to bind to CD28 (or PSMA) following saturation binding with the reference bispecific antigen-binding molecule, it can be concluded that the test antibody binds to a different epitope of CD28 (or PSMA) than the reference bispecific antigen-binding molecule. On the other hand, if the test antibody is not able to bind to the CD28 (or PSMA) molecule following saturation binding with the reference bispecific antigen-binding molecule, then the test antibody may bind to the same epitope of CD28 (or PSMA) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD28 protein (or PSMA protein) under saturating conditions followed by assessment of binding of the test antibody to the CD28 (or PSMA) molecule. In a second orientation, the test antibody is allowed to bind to a CD28 (or PSMA) molecule under saturating conditions followed by assessment of binding of the reference antigen-binding molecule to the CD28 (or PSMA) molecule. If, in both orientations, only the first (saturating) antigen-binding molecule is capable of binding to the CD28 (or PSMA) molecule, then it is concluded that the test antibody and the reference antigen-binding molecule compete for binding to CD28 (or PSMA). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD28 and PSMA), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD28 or PSMA) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454 for a detailed discussion of such engineered mice and the use thereof to produce bispecific antigen-binding molecules).

Bioequivalents

The present invention encompasses antigen-binding molecules having amino acid sequences that vary from those of the described antibodies but that retain the ability to bind CD28 and/or PSMA. Such variant molecules comprise one or more additions, deletions, or substitutions of amino acids when compared to parent sequence, but exhibit biological activity that is essentially equivalent to that of the described antigen-binding molecules. Likewise, the antigen binding molecules-encoding DNA sequences of the present invention encompass sequences that comprise one or more additions, deletions, or substitutions of nucleotides when compared to the disclosed sequence, but that encode an antigen binding molecule that is essentially bioequivalent to the described antigen-binding molecules of the invention. Examples of such variant amino acid and DNA sequences are discussed above.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include the exemplary bispecific antigen-binding molecules set forth herein comprising amino acid changes which modify the glycosylation characteristics of the antibodies, e.g., mutations which eliminate or remove glycosylation.

Species Selectivity and Species Cross-Reactivity

The present invention, according to certain embodiments, provides antigen-binding molecules that bind to human CD28 but not to CD28 from other species. The present invention also provides antigen-binding molecules that bind to human PSMA but not to PSMA from other species. The present invention also includes antigen-binding molecules that bind to human CD28 and to CD28 from one or more non-human species; and/or antigen-binding molecules that bind to human PSMA and to PSMA from one or more non-human species.

According to certain exemplary embodiments of the invention, antigen-binding molecules are provide which bind to human CD28 and/or human PSMA and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD28 and or PSMA. For example, in a particular exemplary embodiment of the present invention, bispecific antigen-binding molecules are provided comprising a first antigen-binding domain that binds human CD28 and cynomolgus CD28, and a second antigen-binding domain that specifically binds human PSMA.

Immunoconjugates

The present invention encompasses antigen-binding molecules conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Therapeutic Formulation and Administration

The present invention provides pharmaceutical compositions comprising the antigen binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991*, Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-CD28 antibody or a bispecific antigen binding molecule that specifically binds CD28 and a target antigen (e.g., PSMA). The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in PSMA activity or a depletion of PSMA+ cells.

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-CD28/anti-PSMA bispecific antigen-binding molecules of the present invention may be used for the treatment, prevention and/or amelioration of any disease or disorder associated with or mediated by PSMA expression or activity or the proliferation of PSMA+ cells. The mechanisms of action by which the therapeutic methods of the invention are achieved include killing of the cells expressing PSMA in the presence of effector cells, for example, T cells. Cells expressing PSMA which can be inhibited or killed using the bispecific antigen-binding molecules of the invention include, for example, tumorigenic prostate cells.

The antigen-binding molecules of the present invention may be used to treat, e.g., primary and/or metastatic tumors arising in the colon, lung, breast, renal cancer, and subtypes of bladder cancer. According to certain exemplary embodiments, the bispecific antigen binding molecules of the present invention are used to treat a prostate cancer.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with PSMA expression (e.g., prostate cancer) comprising administering one or more of the bispecific antigen-binding molecules described elsewhere herein to a subject after the subject has been shown to be non-responsive to other types of anti-cancer therapies. For example, the present invention includes methods for treating prostate cancer comprising administering an anti-CD28/anti-PSMA bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received the standard of care for patients suffering from cancer, e.g., prostate cancer. In other aspects, a bispecific antigen-binding molecule of the invention (an anti-CD28/anti-PSMA bispecific antigen binding molecule) comprising an IgG4 Fc domain is initially administered to a subject at one or more time points (e.g., to provide robust initial depletion of prostate cancer cells), followed by administration of an equivalent bispecific antigen-binding molecule comprising a different IgG domain, such as an IgG1 Fc domain, at subsequent time points. It is envisioned that the anti-CD28/anti-PSMA antibodies of the invention may be used in conjunction with other bispecific antigen binding molecules, such as with an anti-PSMA/anti-CD3 bispecific antibody. It is also envisioned that the bispecific antibodies of the invention will be used in conjunction with checkpoint inhibitors, for example, those that target PD-1 and CTLA-4, and other targets. It may be advantageous to combine two bispecific antibodies that target the same tumor antigen (e.g., PSMA), but with one of the bispecifics targeting the CD3 on T cells and the other bispecific targeting a co-stimulator molecule like CD28. This combination may be used alone to enhance tumor cell killing, or may be used in combination with a checkpoint inhibitor.

Combination Therapies and Formulations

The present invention includes compositions and therapeutic formulations comprising any of the exemplary antibodies and bispecific antigen-binding molecules described herein in combination with one or more additional therapeutically active components, and methods of treatment comprising administering such combinations to subjects in need thereof.

Exemplary additional therapeutic agents that may be combined with or administered in combination with an antigen-binding molecule of the present invention include, e.g., chemotherapy, radiation therapy, checkpoint inhibitors that target PD-1 (e.g., an anti-PD-1 antibody such as pembrolizumab or nivolumab; see also U.S. Pat. No. 9,987,500), CTLA-4, LAG3, TIM3, and others, costimulatory agonist bivalent antibodies that target molecules such as GITR, OX40, 4-1BB, and others), CD3× bispecific antibodies (See for example WO2017/053856A1, WO2014/047231A1, WO2018/067331A1 and WO2018/058001A1), other antibodies that target PSMA×CD3 (See for example WO2017/023761A1) and other costimulatory CD28× bispecific antibodies.

Other agents that may be beneficially administered in combination with antibodies of the invention include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-CD28/anti-PSMA bispecific antigen-binding molecule as disclosed herein) may also be administered as part of a therapeutic regimen comprising one or more therapeutic combinations selected from "ICE": ifosfamide (e.g., Ifex®), carboplatin (e.g., Paraplatin®), etoposide (e.g., Etopophos®, Toposar®, VePesid®, VP-16); "DHAP": dexamethasone (e.g., Decadron®), cytarabine (e.g., Cytosar-U®, cytosine arabinoside, ara-C), cisplatin (e.g., Platinol®-AQ); and "ESHAP": etoposide (e.g., Etopophos®, Toposar®, VePesid®, VP-16), methylprednisolone (e.g., Medrol®), high-dose cytarabine, cisplatin (e.g., Platinol®-AQ).

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1 R, B-raf, PDGFR-o, PDGFR-13, FOLH1, PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; $F(ab')_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy, or treatment with a biologic, including checkpoint inhibitors or other bispecific antibodies.

The present invention includes compositions and therapeutic formulations comprising any of the antigen-binding molecules described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4 (5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-CD28 antibody or a bispecific antigen-binding molecule that specifically binds PSMA and CD28) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-CD28 antibody or a bispecific antigen-binding molecule that specifically binds PSMA and CD28). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The bispecific antibodies of the present invention may also be used to detect and/or measure CD28 or PSMA, or CD28-expressing or PSMA-expressing cells in a sample, e.g., for diagnostic purposes. For example, an anti-CD28×PSMA antibody, or fragment thereof, may be used to diagnose a condition or disease characterized by aberrant expression (e.g., over-expression, under-expression, lack of expression, etc.) of CD28 or PSMA. Exemplary diagnostic assays for CD28 or PSMA may comprise, e.g., contacting a sample, obtained from a patient, with an antibody of the invention, wherein the antibody is labeled with a detectable label or reporter molecule. Alternatively, an unlabeled antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, betagalactosidase, horseradish peroxidase, or luciferase. Specific exemplary assays that can be used to detect or measure CD28 or PSMA in a sample include enzyme-linked immunosorbent assay (ELISA), radioimmunoassay (RIA), and fluorescence-activated cell sorting (FACS). Samples that can be used in CD28 or PSMA diagnostic assays according to the present invention include any tissue or fluid sample obtainable from a patient which contains detectable quantities of CD28 or PSMA protein, or fragments thereof, under normal or pathological conditions. Generally, levels of CD28 or PSMA in a particular sample obtained from a healthy patient (e.g., a patient not afflicted with a disease or condition associated with abnormal CD28 or PSMA levels or activity) will be measured to initially establish a baseline, or standard, level of CD28 or PSMA. This baseline level of CD28 or PSMA can then be compared against the levels of CD28 or PSMA measured in samples obtained from individuals suspected of having a CD28 or PSMA related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention.

Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Abstract

The recent clinical success of tumor specific antigen (TSA) or tumor associated antigen (TAA)-CD3 bispecific antibodies, such as anti-PSMAxCD3 bispecific antibodies, is transforming cancer immunotherapy. TAA-CD3 antibodies offer relatively safe and immediately available therapeutic solutions that may prove to be an important new class of immunotherapy. However, they may not achieve the efficacy seen with CAR-T cell approaches, which engage a second co-stimulatory signal often mediated by CD28 intracellular domain. Indeed, CD28 activating antibodies are incredibly powerful but also toxic in human studies. The term TSA and TAA may be used interchangeably herein.

Herein are described a new class of bispecific antibodies, referred to as TAA-CD28, that appear to be safe, well tolerated on their own and when combined with TAA-CD3, to generate greatly amplified and highly targeted anti-tumor responses. Using TAAs, such as PSMA, expressed on prostate tumor, it has been found that TAAxCD28 enhanced T cell activation and significantly potentiated tumor cell lysis in the presence of a tumor target and a TCR/CD3 stimulus.

It has been demonstrated that TAAxCD28 bispecific antibodies of the invention significantly enhanced anti-tumor immunity mediated by TAAxCD3-induced T cell activation in syngeneic tumor models. Pairing CD3 with a tumor antigen with limited normal tissue expression, induced little to no peripheral cytokine production alone or when combined with TAAxCD28 in non-human primate and humanized mouse models. Furthermore, TAAxCD28 alone had minimal or no serum cytokine secretion and T cell activation in cynomolgus monkeys in comparison to a CD28 superagonistic antibody. These results suggest that combining this novel class of costimulatory bispecific antibodies with the emerging class of TAA-CD3 may provide safer, off the shelf biologics solutions that could markedly enhance the efficacy of the traditional TAA-CD3 bispecifics.

INTRODUCTION

Although monoclonal antibodies have been established as anti-tumor therapeutics over the last two decades, they have limited ability to mobilize T cells and efficiently exercise their cytotoxic activity at the tumor site. The ability of bispecific antibodies for T cell targeted immunotherapy and subsequent tumor cell killing has been previously demonstrated. Indeed, the bispecific antibody platform aims to recruit immune effector cells by combining an anti-CD3 with an anti-tumor target binding domain. Recently, Catumaxomab (EpCAMxCD3) and Blinatumomab (CD19×CD3), received regulatory approval for acute lymphoblastic leukemia while numerous other bispecific antibodies are undergoing investigation. Indeed, bispecific antibodies that recognize both the B cell marker CD20 and the CD3 component of the T cell repertoire have been constructed and are currently under clinical investigation for hematologic malignancies. Indeed, TAA-CD3 offer relatively safe and off the shelf therapeutic solutions that do not have to be highly and laboriously customized for individual patients. However, although TAA-CD3 bispecifics may prove to be an important new class of immunotherapy, cross study comparisons suggest they may not be achieving the efficacy seen with CAR-T approaches.

Two chimeric antigen receptor (CAR)-T cells drugs Kymriiah and Yescarta have recently received FDA approval for blood B-cell malignancies demonstrating the strong potential of this approach in the field of personalized cancer immunotherapy. Both products utilize the CD19 antigen as the tumor associated antigen (TAA), which is an ideal target for T-cell mediated killing due to its restricted expression to B-cells, which minimizes the off-target toxicity and enhances anti-tumor efficacy. However, the high potency of CAR-T cells has been associated with adverse effects such as cytokine release syndrome (CRS) and neurotoxicity. In addition, all patients do not yet benefit from the treatment, and the number of variables that could impact the clinical outcome of each patient is relatively high in both autologous and allogenic approaches. Further, attempts to target tumor associated antigens in solid tumors have achieved limited success so far showing either minimal anti-tumoral activity or severe adverse effects. The inhibiting tumor microenvironment, the poor access of CAR-T cells to the entire tumor tissue, together with the laborious manufacturing represents some of the current challenges for the promising CAR-T cell therapy.

One of the limitations of the current immunotherapeutic treatments is to optimally induce the patient's own immune response against the tumor cells via specific tumor cell recognition and induction of cytotoxicity. Effective activation of naïve T cells and induction of experienced memory T cell populations requires costimulatory signals (signal 2) in addition to the antigen-specific stimulus via the TCR/CD3 complex (signal 1). Agonism of costimulatory pathways CD28 and 4-1BB may provide significant potentiation of target cell lysis that could benefit patients' resistance to different immunotherapies. However, the broader role of costimulation remains under evaluated in clinical oncology. Many tumors lack costimulatory receptors, which prevent them from further enhancing the CD3×TAA-induced T activation.

A blinded screen of costimulatory pathways conducted herein by forced expression of costimulatory ligands on a panel of syngeneic tumors established CD28 as one of the most potent costimulatory receptors together with 4-1BB. Further, costimulatory-based bispecific antibodies bridging CD28 on the surface of T cells were constructed herein, with TAAs from prostate tissues to potentiate the anti-tumor response. Disclosed herein is data demonstrating that combination therapy with TAA-CD3 and TAA-CD28 bispecifics efficiently boosted T cell activation and cytotoxicity in the presence of both TAA and TCR stimulation, leading to enhanced anti-tumor immunity. Indeed, the data disclosed herein suggest that combining this novel class of bispecifics (TAA-CD28) with the emerging TAA-CD3 class may provide safer, off the shelf biologics solutions that may be approaching the efficacy of customized CAR-T cell therapy.

More specifically, exemplary PSMAxCD28 bispecific antibodies were generated, and it was demonstrated that exemplary anti-PSMAxCD28 potentiates PSMAxCD3 or CD20×CD3 induced T cell activation in vitro and safely enhances anti-tumor efficacy in vivo. Activity in vitro was demonstrated by showing images of bispecific antibodies localized at the immunological synapse of a T cell and target cell conjugate, enhancement of PSMAxCD3 induced proliferation, cytokine release and cytotoxicity. In vivo anti-tumor efficacy was evaluated in mouse tumor models (syngeneic). Tumor volume and serum cytokine was monitored over time to show response to bispecific antibody treatment.

A study was done in cynomolgus monkeys to determine the safety and tolerability of the exemplary PSMAxCD28 of the invention in a non-human primate. Animals were examined for toxicity by clinical observations and blood sample collections to analyze serum cytokines and T cell phenotype.

As described in details below, exemplary anti-PSMAxCD28 bispecific antibodies have been generated to potentiate the TCR/CD3-dependent T cell activation, thus mimicking the costimulation (signal 2) provided by professional APCs.

All procedures were carried out in accordance with the Guide for the Care and Use of Laboratory Animals of the NIH. The protocols were approved by the Regeneron Pharmaceuticals Institutional Animal Care and Use Committee.

Example 1. Construction of anti-PSMAxCD28 Antibodies

Generation of Anti-CD28 Antibodies

Anti-CD28 antibodies were obtained by immunizing a VELOCIMMUNE® mouse (i.e., an engineered mouse comprising DNA encoding human Immunoglobulin heavy and kappa light chain variable regions) with human CD28 protein fused to the Fc portion of mouse IgG2a, or with cells expressing CD28 or with DNA encoding CD28. The antibody immune response was monitored by a CD28-specific immunoassay. When a desired immune response was achieved splenocytes were harvested and fused with mouse myeloma cells to preserve their viability and form hybridoma cell lines. The hybridoma cell lines were screened and selected to identify cell lines that produce CD28-specific antibodies. Using this technique several anti-CD28 chimeric antibodies (i.e., antibodies possessing human variable domains and mouse constant domains) were obtained. In addition, several fully human anti-CD28 antibodies were isolated directly from antigen-positive B cells without fusion to myeloma cells, as described in US 2007/0280945A1.

Certain biological properties of the exemplary anti-CD28 antibodies generated in accordance with the methods of this Example are described in detail in the Examples set forth below.

Generation of Anti-PSMA Antibodies

Anti-PSMA antibodies were obtained by immunizing a genetically modified mouse with a human PSMA antigen or by immunizing an engineered mouse comprising DNA encoding human immunoglobulin heavy and kappa light chain variable regions with a human PSMA antigen. Alternatively, mice were immunized with human prostate cancer cells (LNCaP, ATTC, Manassas, Virginia, USA) expressing human PSMA (UniProtKB/Swiss-Prot. No. Q04609). The antibody immune response was monitored by a PSMA-specific immunoassay. When a desired immune response was achieved splenocytes were harvested from each mouse and either (1) fused with mouse myeloma cells to preserve their viability and form hybridoma cells and screened for PSMA specificity, or (2) B-cell sorted (as described in US 2007/0280945A1) using a human PSMA with an N-terminal 6-His tag (R&D, Cat #4234-ZN) as the sorting reagent that binds and identifies reactive antibodies (antigen-positive B cells). Chimeric antibodies to PSMA were initially isolated having a human variable region and a mouse constant region. The antibodies were characterized and selected for desirable characteristics, including affinity, selectivity, etc. If necessary, mouse constant regions were replaced with a desired human constant region, for example wild-type or modified IgG1 or IgG4, to generate a fully human anti-PSMA antibody.

Generation of Bispecific Antibodies that Bind CD28 and PSMA

Bispecific antibodies comprising an anti-PSMA-specific binding domain and an anti-CD28-specific binding domain were constructed using standard methodologies, wherein the anti-PSMA antigen binding domain and the anti-CD28 antigen binding domain each comprise different, distinct HCVRs paired with a common LCVR. In some instances the bispecific antibodies were constructed utilizing a heavy chain from an anti-CD28 antibody, a heavy chain from an anti-PSMA antibody and a common light chain (See table 1). In certain embodiments, the heavy chain amino acid sequence from the anti-CD28 antibody of an exemplary bispecific antibody (bs 16429D) is shown in SEQ ID NO.: 81. The heavy chain amino acid sequence from the anti-PSMA antibody of the exemplary bispecific antibody (bs 16429D) is shown in SEQ ID NO.: 82. The common light chain amino acid sequence for bs 16429D is shown in SEQ ID NO.: 83.

The bispecific antibodies created in accordance with the present Example comprise two separate antigen-binding domains (i.e., binding arms). The first antigen-binding domain comprises a heavy chain variable region derived from an anti-CD28 antibody ("CD28-VH"), and the second antigen-binding domain comprises a heavy chain variable region derived from an anti-PSMA antibody ("PSMA-VH"). Both the anti-PSMA and the anti-CD28 share a common light chain. The CD28-VH/PSMA-VH pairing creates antigen-binding domains that specifically recognize CD28 on T cells and PSMA on tumor cells.

Example 2. Heavy and Light Chain Variable Region Amino Acid and Nucleic Acid Sequences Table 1 sets forth the amino acid sequence identifiers of the heavy and light chain variable regions and CDRs of the various bispecific antibodies made in accordance with Example 1. The corresponding nucleic acid sequence identifiers are set forth in Table 2.

TABLE 1

| Amino Acid Sequence IDs | | | | | | | | | | | | |
|---|---|---|---|---|---|---|---|---|---|---|---|---|
| anti-PSMA x anti-CD28 Bispecific | Second Antigen-Binding Domain (D2, anti-PSMA) | | | | First Antigen-Binding Domain (D1, anti-CD28) | | | | Light Chain Variable Region | | | |
| Antibody PID | D2-HCVR | D2-HCDR1 | D2-HCDR2 | D2-HCDR3 | D1-HCVR | D1-HCDR1 | D1-HCDR2 | D2-HCDR3 | D3-LCVR | D3-LCDR1 | D3-LCDR2 | D3-LCDR3 |
| bs16429D | mAb11838P2 | | | | mAb14226P2 | | | | 8567 | | | |
| | 2 | 4 | 6 | 8 | 10 | 12 | 14 | 16 | 18 | 20 | 22 | 24 |

TABLE 1-continued

| Amino Acid Sequence IDs | | | | | | | | | | | | |
|---|---|---|---|---|---|---|---|---|---|---|---|---|
| anti-PSMA x anti-CD28 Bispecific | Second Antigen-Binding Domain (D2, anti-PSMA) | | | | First Antigen-Binding Domain (D1, anti-CD28) | | | | Light Chain Variable Region | | | |
| Antibody PID | D2-HCVR | D2-HCDR1 | D2-HCDR2 | D2-HCDR3 | D1-HCVR | D1-HCDR1 | D1-HCDR2 | D2-HCDR3 | D3-LCVR | D3-LCDR1 | D3-LCDR2 | D3-LCDR3 |
| bs16430D | | mAb11810P2 | | | | mAb14193P2 | | | | 10082 | | |
| | 34 | 36 | 38 | 40 | 26 | 28 | 30 | 32 | 42 | 44 | 46 | 48 |
| bs 16431D | | mAb11810P2 | | | | mAb14216P2 | | | | 10082 | | |
| | 50 | 52 | 54 | 56 | 58 | 60 | 62 | 64 | 66 | 68 | 70 | 72 |

TABLE 2

| Nucleic Acid Sequence IDs | | | | | | | | | | | | |
|---|---|---|---|---|---|---|---|---|---|---|---|---|
| anti-PSMA x anti-CD28 Bispecific | Second Antigen-Binding Domain (D2, anti-PSMA) | | | | First Antigen-Binding Domain (D1, anti-CD28) | | | | Light Chain Variable Region | | | |
| Antibody PID | D2-HCVR | D2-HCDR1 | D2-HCDR2 | D2-HCDR3 | D1-HCVR | D1-HCDR1 | D1-HCDR2 | D2-HCDR3 | D3-LCVR | D3-LCDR1 | D3-LCDR2 | D3-LCDR3 |
| bs16429D | | mAb11838P2 | | | | mAb14226P2 | | | | 8567 | | |
| | 1 | 3 | 5 | 7 | 9 | 11 | 13 | 15 | 17 | 19 | 21 | 23 |
| bs16430D | | mAb11810P2 | | | | mAb14193P2 | | | | 10082 | | |
| | 33 | 35 | 37 | 39 | 25 | 27 | 29 | 31 | 41 | 43 | 45 | 47 |
| bs16431D | | mAb11810P2 | | | | mAb14216P2 | | | | 10082 | | |
| | 49 | 51 | 53 | 55 | 57 | 59 | 61 | 63 | 65 | 67 | 69 | 71 |

Example 3. CD28 and 4-1BB Are Potent Costimulatory Receptors

Figure 2:
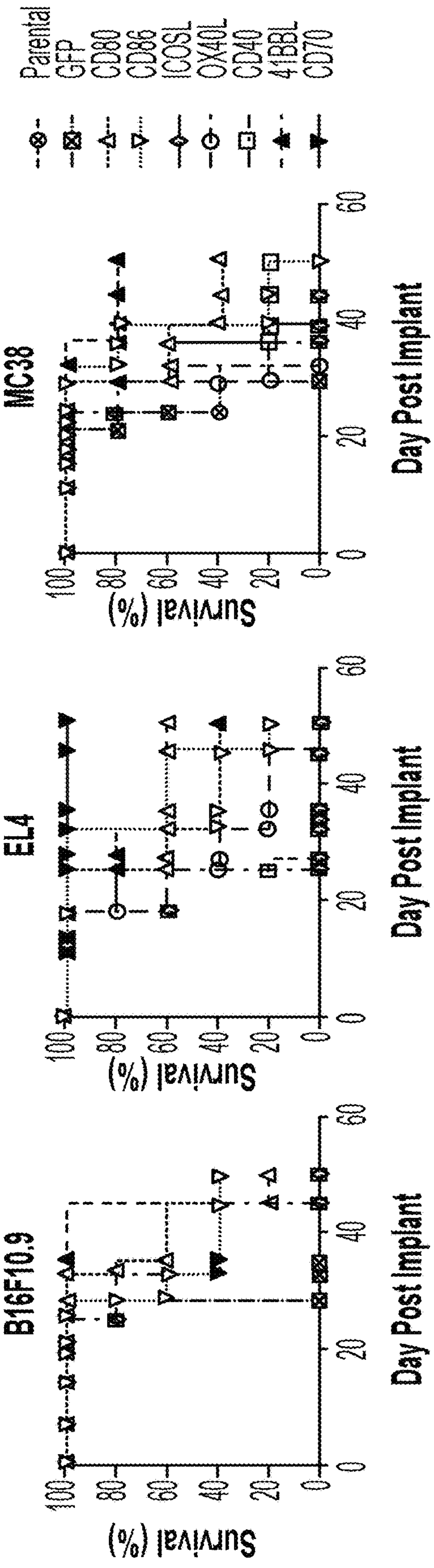
FIG. 2 is a graph showing tumor growth inhibition in engineered cell lines with introduced co-stimulatory ligand expression. Three tumor cell lines, B16F10.9, EL4, and MC 38 were engineered to express a co-stimulatory ligand or GFP as control.

To determine which costimulatory receptors are effective in providing the costimulation signal that is important to T cell activation, a blinded screen of costimulatory pathways conducted by forced expression of costimulatory ligands on a panel of syngeneic tumors (Table 3, and FIG. 2) again established CD28 as one of the most potent costimulatory receptors together with 4-1BB. Table 3 summarizes the number of tumor free mice in the blinded screen. Five (5) mice were tested in each group. The assays were conducted on three (3) different tumor cell lines which were engineered to express seven (7) different co-stimulatory ligands. Briefly, EL4, MC38 and B16F10.9 tumor cells were engineered to express individual co-stimulatory ligands by lentiviral transduction. Cells were implanted subcutaneously in WT C57BL6 mice. Tumor growth was measured on day 18, 24 and 25 post implant of EL4, MC38 and B16F10.9 tumor types, respectively. This is the time point at which tumor volumes from control groups reached maximum allowed size (>2000 mm$^3$). Tumor sizes were measured. Consistent with the data in Table 3, CD28 and 4-1BB are also among the most effective in reducing the size of tumors (data not shown).

TABLE 3

Tumor Growth Inhibition in Engineered Cell Lines with Introduced Co-Stimulator Ligand Expression

| Co-Stim. Ligand | Co-stim. Receptor | Lymphoma (EL4) | Carcinoma (MC38 | Melanoma (B16F10.9) |
|---|---|---|---|---|
| 4-1BBL | 4-BB | 3 | 4 | 1 |
| CD80 (B7.1) | CD28 | 2 | 2 | 2 |
| CD86 (B7.2) | CD28 | 1 | 0 | 2 |
| CD70 | CD27 | 5 | 0 | |
| OX40L | OX40 | 0 | 0 | 2 |
| CD40 | CD40L | 0 | 1 | 0 |
| ICOSL | ICOS | 0 | 0 | 0 |
| Empty Vector | | 0 | 0 | 0 |
| Parental | | 0 | 0 | |

Example 4. Surface Plasmon Resonance Derived Binding Affinities and Kinetic Constants of anti-PSMAxCD28 Bispecific Antibodies In order to determine the binding kinetics of anti-PSMAxCD28 bispecific monoclonal antibodies, surface plasmon resonance derived binding affinities and kinetic constants of anti-PSMAxCD28 bispecific and associated parental monoclonal antibodies to PSMA and/or CD28 were determined.

Binding Kinetics of anti-PSMAxCD28 Bispecific Monoclonal Antibodies to PSMA

Equilibrium dissociation constants ($K_D$ values) for 6 h.hPSMA (recombinant Human PSMA/FOLH1 Protein, R&D, Catalog #4234-ZN) binding to purified anti-PSMAxCD28 bispecific monoclonal antibody or anti-PSMA bivalent parental monoclonal antibody were determined using a real-time surface plasmon resonance biosensor using a Biacore T-200 instrument. The CM5 Biacore sensor surface was derivatized by amine coupling with a monoclonal mouse anti-human Fc antibody to capture purified anti-PSMAxCD28 bispecific, or anti-PSMA and anti-CD28 parental monoclonal antibodies.

This Biacore binding study was performed in a buffer composed of 0.01M HEPES pH 7.4, 0.15M NaCl, 0.5 mM $MgCl_2$, 1.0 mM $CaCl_2$), 0.05% v/v Surfactant P20 (HBS-P++ running buffer). Different concentrations of hPSMA with an N-terminal polyhistidine tag (6 h.hPSMA, R&D) were prepared in HBS-P++ running buffer, ranging from 10 nM to 0.4 nM with serially 3-fold dilutions for anti-PSMAxCD28 bispecific and anti-PSMA or anti-CD28 parental monoclonal antibodies.

The different concentrations of 6 h.hPSMA were injected over the monoclonal antibody captured surface at a flow rate of 50 μL/minute. Association of 6 h.hPSMA to the captured monoclonal antibody was monitored for 3 minutes and the dissociation of 6 h.hPSMA in HBS-P++ running buffer was monitored for 10 minutes. Kinetic association ($k_a$) and dissociation ($k_d$) rate constants were determined by fitting the real-time sensorgrams to a 1:1 binding model using Scrubber 2.0c curve fitting software (BioLogic Software). Binding dissociation equilibrium constants ($K_D$) and dissociative half-lives (t½) were calculated from the kinetic rate constants as:

$$K_D(M) = k_d/k_a, \text{ and } t1/2 \text{ (min)} = 0.693/k_d/60$$

Binding kinetic parameters for 6 h.hPSMA binding to purified monoclonal antibodies at 25° C. are shown below in Table 4.

TABLE 4

Biacore Binding Affinities of Monoclonal Antibodies to PSMA at 25 °C

| Antibody ID | Common Name | ka (1/Ms) | kd (1/s) | $K_D$ (M) | T½(min) |
|---|---|---|---|---|---|
| bs16429D | PSMA × CD28 monoclonal antibody | 1.96E+05 | 4.92E−05 | 2.51E−10 | 234.6 |
| bs16430D | PSMA × CD28 monoclonal antibody | TBD | TBD | TBD | TBD |
| bs16431D | PSMA × CD28 monoclonal antibody | 2.80E+05 | 3.85E−05 | 1.37E−10 | 300.4 |
| mAb11810P2 | anti-PSMA monoclonal antibody | 4.45E+05 | 2.99E−05 | 6.72E−11 | 386.3 |
| mAb11838P2 | anti-PSMA monoclonal antibody | TBD | TBD | TBD | TBD |
| mAb14226P2 | anti-CD28 monoclonal antibody | NB | NB | NB | NB |
| mAb14193P2 | anti-CD28 monoclonal antibody | NB | NB | NB | NB |
| mAb14216P2 | anti-CD28 monoclonal antibody | NB | NB | NB | NB |

TBD: not tested
NB: no binding observed

Binding kinetic parameters for 6 h.hPSMA binding to one purified exemplary monoclonal bispecific antibody at 37° C. are shown below in Table 5. One (1) RU (response unit) represents 1 μg of protein per $mm^2$, as defined by the manufacturer.

TABLE 5

Biacore Binding Affinities of Monoclonal Antibody to PSMA at 37 °C

| Antibody ID | mAb Capture (RU) | 10 nM hPSMA.6H Bind (RU) | Ka (1/Ms) | Kd (1/s) | $K_D$ (M) | t½ |
|---|---|---|---|---|---|---|
| bs16429D | 256.8 ± 0.9 | 43.5 | 2.00E+05 | 7.93E−05 | 3.96E−10 | 145.7 |

| Antibody ID | mAb Capture (RU) | 20 nM hPSMA.6H Bind (RU) | Ka (1/Ms) | Kd (1/s) | $K_D$ (M) | t½ |
|---|---|---|---|---|---|---|
| bs16429D | 189.7 ± 1.6 | 73.7 | 2.93E+05 | 6.36E+05 | 2.17E−10 | 181.6 |

Binding Kinetics of anti-PSMAxCD28 Bispecific Monoclonal Antibodies to CD28

Equilibrium dissociation constants ($K_D$ values) for hCD28.mmh binding to purified monoclonal antibodies were determined using a real-time surface plasmon resonance biosensor using a Biacore T-200 instrument. The CM5 Biacore sensor surface was derivatized by amine coupling with a monoclonal mouse anti-human Fc antibody to capture purified anti-PSMAxCD28 bispecific monoclonal antibodies and anti-PSMA or anti-CD28 parental monoclonal antibodies.

Different concentration of hCD28.mmh were injected over the monoclonal antibody captured surface at a flow rate of 50 μL/minute. Association of hCD28.mmh to the captured monoclonal antibody was monitored for 5 minutes and the dissociation of hCD28.mmh in HBS-P++ running buffer was monitored for 10 minutes. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = k_d/k_a, \text{ and } t1/2 \text{ (min)} = 0.693/k_d/60$$

Binding kinetic parameters for hCD28.mmh binding to purified anti-PSMAxCD28 bispecific monoclonal antibody or anti-CD28 bivalent parental monoclonal antibody at 25° C. are shown below in Table 6.

TABLE 6

| Biacore Binding Affinities of Monoclonal Antibodies to CD28 at 25 °C | | | | | |
|---|---|---|---|---|---|
| Antibody ID | Common Name | ka (1/Ms) | kd (1/s) | $K_D$ (M) | T½(min) |
| bs16429D | PSMA × CD28 monoclonal antibody | 2.26E+04 | 3.26E−03 | 1.44E−07 | 3.5 |
| bs16430D | PSMA × CD28 monoclonal antibody | TBD | TBD | TBD | TBD |
| bs16431D | PSMA × CD28 monoclonal antibody | 6.79E+03 | 1.41E−03 | 2.07E−07 | 8.2 |
| mAB11810P2 | anti-PSMA monoclonal antibody | NB | NB | NB | NB |
| mAB11838P2 | anti-PSMA monoclonal antibody | TBD | TBD | TBD | TBD |
| mAB14226P2 | anti-CD28 monoclonal antibody | 2.34E+04 | 3.28E−03 | 1.40E−07 | 3.5 |
| mAB14193P2 | anti-CD28 monoclonal antibody | 8.73E+03 | 2.64E−04 | 3.03E−08 | 43.7 |
| mAB14216P2 | anti-CD28 monoclonal antibody | 1.12E+04 | 1.41E−03 | 1.27E−07 | 8.2 |

TBD: not tested
NB: no binding observed

Binding kinetic parameters for hCD28.mmh binding to purified anti-PSMAxCD28 bispecific monoclonal antibody 37° C. are shown below in Table 7.

TABLE 7

| Biacore Binding Affinities of Monoclonal Antibodies to CD28 at 37 °C | | | | | | |
|---|---|---|---|---|---|---|
| Antibody ID | mAb Capture (RU) | 400 nM hCD28.6H Bind (RU) | Ka (1/Ms) | Kd (1/s) | $K_D$ (M) | t½ |
| bs16429D | 1576.3 ± 5.0 | 98.9 | 2.46E+04 | 6.70E−03 | 2.72E−07 | 1.7 |

As shown in Tables 4 to 7, several anti-CD28 antibodies of the present invention bind CD28 with high affinity. Several anti-PSMA antibodies of the present invention bind PSMA with high affinity. Several anti-PSMAxCD28 bispecific antibodies bind both CD28 and PSMA with high affinity.

Example 5. Potency and Specificity of Cell Binding of Anti-PSMAxCD28 Bispecific Monoclonal Antibodies to PSMA and CD28

In order to evaluate the ability of these antibodies (anti-PSMA, anti-CD28 and anti-PSMAxCD28 monoclonal antibodies) to bind specifically to the cell-surface proteins, in vitro binding assays were developed using cells expressing human PSMA or CD28 in an electrochemiluminescence based detection platform (MSD). Two studies were performed. In one study, the potency and specificity of monoclonal antibodies binding to cell surface antigens were evaluated. These antibodies (anti-PSMA, anti-CD28 and anti-PSMAxCD28 antibodies) displayed specific binding to cell lines expressing human PSMA or human CD28. In a supplemental experiment, a bridging study to IgG4s isotype was conducted.

Methods Used to Determine the Potency and Specificity of Cell Binding of Anti-PSMAxCD28 Bispecific Antibodies to PSMA and CD28

The human epithelial prostate carcinoma cell line, C4-2 (UroCor), endogenously expresses human PSMA. The HEK293/hCD28 expressing cell line was engineered by transducing human embryonic kidney cells from ATCC (CRL-1573) with the neomycin resistant lentiviral construct encoding human CD28 (hCD28 accession #NP_006130.1). To assess the specificity of binding, these two cell lines were evaluated in parallel to the parental HEK293HZ cell line (which is negative for PSMA and CD28), by fluorescence activated cell sorting (FACS) An anti-Feld1 human IgG1 antibody was included as a negative control for IgG detection.

The cell lines described above were rinsed once with 1×PBS buffer without $Ca^{2+}/Mg^{2+}$ (Irvine Scientific, Cat. #9240) and incubated for 10 minutes at 37° C. with Enzyme Free Cell Dissociation Solution (Millipore, Cat. #S-004-C) to detach cells from a flask. An additional wash with 1×PBS with $Ca^{2+}/Mg^{2+}$ (Irvine Scientific, Cat. #9236) was performed. Cells were then counted with a Cellometer™ Auto T4 cell counter (Nexcelom Bioscience, Model #Auto T4). Approximately 10,000 cells per well in the cell washing buffer were seeded separately into the 96-well carbon electrode plates (MULTI-ARRAY high bind plate, MSD, Meso Scale Discovery, Cat #L15XB-3/LX11XB-3) and incubated for 1 hour at 37° C. to allow the cells to adhere. Nonspecific binding sites were blocked by 2% BSA (w/v) (Sigma, Cat. #A8577-1L) in PBS for 1 hour at room temperature.

Solutions containing anti-PSMA, anti-CD28, anti-PSMAxCD28 or control antibodies in serial dilutions ranging from 1.7 μM to 100 nM or solutions without antibody were added to the plate-bound cells and incubated for 1 hour at room temperature. Except where indicated, analyses were performed in duplicate. The plates were then washed to remove the unbound antibodies using an AquaMax2000 plate washer with a cell washing head (MDS Analytical Technologies, Model #2000). The plate-bound antibodies were detected with a SULFO-TAG™-conjugated goat polyclonal anti-human IgG antibody specific for heavy and light chains (Jackson ImmunoResearch, Cat. #109-005-088) for 1 hour at room temperature. After washes, the plates were developed with the Read Buffer (MSD, Meso Scale Discovery, Cat. #R92TD-2) according to the manufacturer's recommended procedure and the luminescent signals were recorded with a SECTOR Imager 600 (Meso Scale Discovery, Model #600) instrument.

The direct binding signals (in Relative Light Unit, RLU) were analyzed as a function of the antibody concentration. The data were fit to a sigmoidal (four-parameter logistic) dose-response model using GraphPad Prism™ software (GraphPad Software Version #6). The EC50 values, defined as the concentration of antibody at which 50% of the maximal binding signal is detected, was determined for binding to the HEK293/hCD28 and C4-2 cells to indicate potency of each antibody binding to CD28 or PSMA, respectively. In addition, ratios of binding signals of the antibodies at 11.1 nM on HEK293/hCD28 or the C4-2 cells to the HEK293HZ cells were calculated. This representative concentration was chosen for high target cell binding, but low background signal on the CD28, PSMA negative HEK293HZ cells. The antibodies with a binding ratio of less than 3 were marked as NB in Table 8 below. NB is defined as, "no specific binding observed under assay conditions."

In a supplemental study, a separate experiment was conducted using the same protocol as described above but included an IgG4 isotype control (see U.S. Ser. No. 15/147,791) and a parental CD28 monoclonal antibody. The test solutions contained 3.4 μM to 200 nM anti-PSMA, anti-CD28, anti-PSMAxCD28 bispecific monoclonal antibodies or control antibodies in serial dilutions. Binding ratios were calculated at 7.4 nm.

Results, Summary and Conclusions

The ability of the anti-PSMAxCD28 bispecific antibodies to bind specifically to cells expressing either PSMA or CD28 was evaluated in comparison to a cell line negative for PSMA or CD28 expression using an immunobinding assay. Bivalent parental antibodies specific to PSMA or CD28 were included for comparison. Dose dependent binding of antibody to the cells on 96-well High Bind plates (MSD, Meso Scale Discovery, Cat #L15XB-3/LX11XB-3), with antibody concentrations up to 100 nM, was detected using SULFO-TAG™-conjugated anti-human IgG antibody, and the binding signals in electrochemiluminescence were recorded on a Sector Imager 600 (MSD). RLU values were determined for the antibodies binding to cells. For the CD28 or PSMA expressing cells, $EC_{50}$ values were calculated as a measure of potency. For samples that resulted in high background signal, higher concentrations were excluded from calculation of $EC_{50}$ values and values are indicated with a star in Table 8. Comparison of the binding signals of the antibodies at 11.1 nM to HEK293/hCD28 or C4-2 cells to the negative HEK293HZ cells was used to evaluate the binding specificity of the antibodies. Specific binding is defined as antibodies having a ratio of 3-fold or higher binding to CD28 or PSMA expressing cells compared to HEK293HZ cells at that concentration.

The binding results are summarized in Table 8. At a concentration of 11.1 nM, the three exemplary anti-PSMAxCD28 bispecific antibodies of the invention (bs16429D, bs16430D, and bs16431D) bound specifically to both the HEK293-hCD28 and C4-2 cells, with ratios ranging from 13-31-fold and 4-10-fold above HEK293HZ cells, respectively. The potency of the bispecific antibodies ranged from $EC_{50}$ values of 5.31-9.58 nM on HEK293-hCD28 cells and 0.35-5.24 nM on C4-2 cells.

TABLE 8

Binding of Monoclonal Antibodies to Cell Surface Antigens

| Antibody ID | HEK293-hCD28 $EC_{50}$ (M) | C4-2 $EC_{50}$ (M) | HEK293-hCD28/ HEK293HZ** | C4-2/ HEK293HZ*** |
|---|---|---|---|---|
| bs16429D | 9.58E−09 | 8.53E−10 | 31 | 10 |
| mAb14226P2 (CD28) | 1.04E−09 | NB | 68 | 1 |
| mAb11838P2 (PSMA) | NB | 7.38E−10* | <1 | 4 |
| bs16430D | 8.47E−09 | 5.24-09 | 41 | 10 |
| mAb14193P2 (CD28) | 1.02E−08 | NB | 110 | 1 |
| mAb11810P2 (PSMA)# | NB | 9.46E−10 | 1 | 25 |
| bs16431D | 5.31E−09 | 3.50E−10* | 13 | 4 |
| mAb14216P2 (CD28) | 2.47E−09 | NB | 114 | 1 |
| CONTROL | | | | |
| Anti-Feld# | NB | NB | 1 | 1 |

NB: Non-specific binding as indicated by less 3-fold ratio of cell signal to HEK293HZ at 11.1 nM
*Concentration above 11.1 nM excluded from the $EC_{50}$ calculation due to high background
#Samples run as single dilution series
**Ratio of 11.1 nM antibody cell binding signal (RLU) to HEK293-hCD28 relative to HEK293HZ parental
***Ratio of 11.1 nM antibody cell binding signal (RLU) to C4-2 relative to HEK293HZ The parental antibodies bound specifically to the cells corresponding to the antigen used to generate them, as indicated in parentheses in the Antibody ID column. $EC_{50}$ values for binding to the HEK293-hCD28 and C4-2 cells for the parental antibodies ranged from 1.04-10.2 nM on HEK293-hCD28 cells to 0.738-0.946 nM on C4-2 cells. For antibodies, mAb11838P2 and mAb11810P2 binding values at higher concentrations on C4-2 cells were excluded from calculation of $EC_{50}$ values to compensate for high background on the negative cells. The IgG control antibody did not bind specifically to the CD28 or PSMA expressing cell lines, as expected.

A supplemental experiment was conducted as described above but included an IgG4 isotype control and a parental CD28 monoclonal antibody. This data was generated as a bridging study to demonstrate that there was insignificant background signal using an hIgG4s isotype control. The data are summarized in Table 9. As shown in Table 9, anti-CD28 antibody mAb14226P2 specifically binds to human CD28 expressing cell, HEK293-hCD28 P-3. Anti-CD28 antibody mAb14226P2 does not bind to cells that do not express human CD28, regardless of whether the cells express PSMA (C4-2) or not (HEK293HZ).

TABLE 9

Binding of Monoclonal Antibodies Isotype to Cell Surface Antigen

| Antibody ID | HEK293-hCD28 P-3 $EC_{50}$ (M) | C4-2 P-7 $EC_{50}$ (M) | HEK293-hCD28/ HEK293HZ* | C4-2/ HEK293HZ** |
|---|---|---|---|---|
| mAb14226P2 | 8.41E−10 | NB | 99 | 1 |
| CONTROL | | | | |
| Anti-Feld1-hlgG1 | NB | NB | 1 | 1 |
| Anti-Feld1-hlgG4 | NB | NB | 1 | 1 |

NB: Non-specific binding as indicated by less 3-fold ratio of cell signal to HEK293HZ at 11.1 nM
*Ratio of 7.4 nM antibody cell binding signal (RLU) to HEK293-hCD28 relative to HEK293HZ parental
**Ratio of 7.4 nM antibody cell binding signal (RLU) to C4-2 relative to HEK293HZ Binding of PSMAxCD28 Bispecific Antibodies to T Cells and Target Cells Experimental Procedure Flow cytometric analysis was utilized to determine binding of anti-PSMAxCD28 bispecific antibodies to C4-2, 22RV1, RAJI, Human and Cynomolgus T cells, followed by detection with a phycoerythrin (PE)-labeled anti-human IgG antibody. Briefly, $1\times10^5$ cells/well were incubated for 30 minutes at 4° C. with a serial dilution of PSMAxCD28 bispecific antibodies or a human IgG4 antibody (see U.S. Ser. No. 15/147,791) that binds a human antigen with no cross-reactivity to human or cynomolgus CD28, ranging from 133 nM to 8.14 μM for human and cynomolgus T cells, and ranging from 133 nM to 61 μM for PSMA expressing cells. After incubation, the cells were washed twice with cold PBS containing 1% filtered FBS and a PE-conjugated anti-human secondary antibody (Jackson Immunoresearch, Cat. #709-116-149) was added to the cells and incubated for an additional 30 minutes. Live/dead dye was added to Human and Cynomolgus T cells incubations. Wells containing no antibody or secondary antibody only were used as controls.

After incubation with PSMA expressing cells, cells were washed, re-suspended in 200 UL cold PBS containing 1% filtered FBS and analyzed by flow cytometry on a BD FACS Canto II.

After incubation with Human or Cynomolgus T cells, cells were washed, and stained with a cocktail of anti-CD2 (BD, Cat. #562638), ant-CD16 (BD, Cat. #562874), anti-CD4 (BD, Cat. #564305), and anti-CD8 (BD, Cat. #563795) antibodies in Brilliant Stain Buffer (BD, Cat. #566349) for an extra 20 min incubation at 4° C. After wash, cells were re-suspended in 200 μL of cold PBS (Gibco, Cat. #14190-144) containing 1% filtered FBS (TCB, Cat. #101), gated in a Live/CD2+/CD4+/CD16− or Live/CD2+/CD8+/CD16− gate and analyzed by Flow cytometry on a BD FACS LSR-Fortessa-X20.

Results, Summary and Conclusions:

The Binding of PSMAxCD28 bispecific antibodies to the surface of Human T cells was tested by flow cytometry.

bs16429D bound to all T cells with an EC50 value of $4.80\times10^{-8}$ M. It bound to both CD4+ and CD8+ T cells, with EC50 values of $5.09\times10^{-8}$M and $5.89\times10^{-8}$M, respectively.

bs16431D bound weakly to all T cells with an EC50 value of $1.80\times10^{-7}$. It bound weakly to both CD4+ and CD8+ T cells, with EC50 values of 1.67E-07M and 1.80E-07M, respectively.

The Binding of PSMAxCD28 bispecific antibodies to the surface of cell lines expressing PSMA was tested by flow cytometry.

C4-2 is a CaP (Prostate Cancer) cell line derived from LNCaP (androgen sensitive human prostate adenocarcinoma cells derived from lymph node metastasis; see Wu et al., Int. J. Cancer, 57:406-412 (1994)) cells. Both bs16429D and bs16431D bound to C4-2 cells (see Liu et al., 2004, Prostate, 60:98-108) with EC50 values of $3.87\times10^{-9}$ M and $1.50\times10^{-9}$ M, respectively.

22RV1 is an epithelial prostate carcinoma cell line (see In Vitro Cell Dev. Biol. Anim., 1999, 35 (7): 403-409) Both bs16429D and bs16431D bound to 22RV1 cells with EC50 values of $3.05\times10^{-9}$ M and $6.33\times10^{-09}$ M, respectively.

These results are summarized in Tables 10-12.

TABLE 10

Binding of Anti-PSMA × CD28 Bispecific Antibodies to Human T Cells

| Antibody ID | Human CD2+ T cells FACS [M] | Human CD4+ T cells FACS [M] | Human CD8+ T cells FACS [M] |
|---|---|---|---|
| bs16429D | 4.80E−08 | 5.09E−08 | 5.89E−08 |
| bs16431D | (Weak) 1.80E−07 | (Weak) 1.67E−07 | (Weak) 1.80E−07 |
| Isotype Control | No binding | No binding | No binding |

TABLE 11

Binding of Anti-PSMA × CD28 Bispecific Antibodies to Cynomolgus T Cells

| Antibody ID | Cynomolgus CD2+ T cells FACS [M] | Cynomolgus CD4+ T cells FACS [M] | Cynomolgus CD8+ T cells FACS [M] |
|---|---|---|---|
| bs16429D | 1.10E−08 | 1.93E−08 | (weak) 6.84E−08 |
| bs16431D | (weak) 1.34E−07 | (weak) 2.81E−07 | Very weak binding |
| Isotype Control | No binding | No binding | No binding |

TABLE 12

Binding of Anti-PSMA × CD28 Bispecific Antibodies to PSMA Expressing Cells

| Antibody ID | C4-2 cells FACS [M] | 22RV1 cells FACS [M] | Raji cells FACS [M] |
|---|---|---|---|
| bs16429D | 3.87E−09 | 3.05E−09 | No binding |
| bs16431D | 1.50E−09 | 6.33E−09 | No binding |
| Isotype Control | No binding | No binding | No binding |

Example 6. Primary and Engineered Bioassay for PSMAxCD28 Bispecific Antibodies T-cell activation is achieved by stimulating T-cell receptors (TCR) that recognize specific peptides presented by major histocompatibility complex class I or II (MHCI or MHCII) proteins on antigen-presenting cells (APC) (Goldrath et al., Selecting and maintaining a diverse T-cell repertoire, Nature 402, 255-262 (1999)). An activated TCR in turn initiates a cascade of signaling events, which can be monitored by reporter genes, driven by various transcription factors such as activator-protein 1 (AP-1), Nuclear Factor of Activated T-cells (NFAT) or Nuclear factor kappa-light-chain-enhancer of activated B cells (NFκB). The T-cell response is then further refined via engagement of co-receptors expressed either constitutively or inducibly on T-cells such as CD28, CTLA-4 (Cytotoxic T-Lymphocyte-Associated Protein 4), PD-1 (Programmed Cell Death Protein 1), LAG-3 (Lymphocyte-Activation Gene 3) or other molecules (Sharpe et al., The B7-CD28 Superfamily, Nat. Rev. Immunol., 2 (2): 116-26 (2002)). The co-stimulatory molecule, CD28, is activated by its endogenous ligands CD80 or CD86 expressed on APCs. CD28 potentiates cellular signals such as pathways controlled by the NFκB transcription factor after TCR activation. The CD28 co-signal is important for effective T-cell activation such as T cell differentiation, proliferation, cytokine release and cell-death (Smeets et al., NFκB activation induced by T cell receptor/CD28 costimulation is mediated by protein kinase C-e, PNAS, 97 (7): 3394-3399 (2012).

Figure 3:
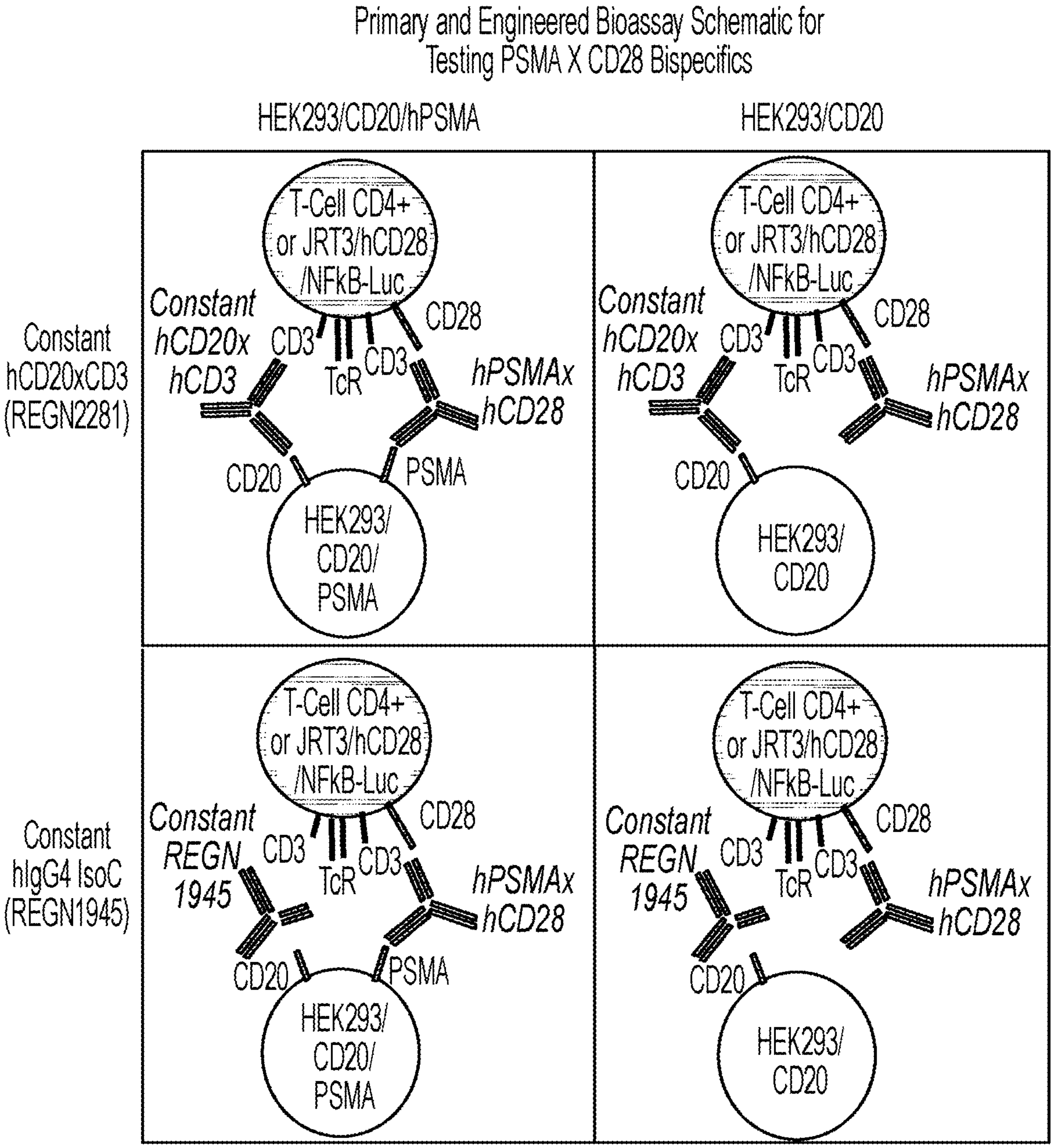
FIG. 3 is a schematic showing primary and engineered bioassay for testing anti-PSMAxCD28 bispecific antibodies.

In order to identify antibodies that enhance T cell activity in the presence of both primary stimulation and PSMA target expression, anti-CD28 antibodies and anti-PSMAxCD28 bispecific antibodies were characterized in an engineered reporter bioassay and cell-based assays using human primary T-Cells. The assays evaluate the anti-PSMA/CD28 bispecific antibody's behavior in the presence and absence of primary stimulation and in the presence and absence of target expression. The schematic of the assays is shown in FIG. 3. The assays were conducted to select anti-PSMAxCD28 bispecific antibodies that enhance T cell activity in the presence of primary stimulation and target expression. Accordingly, the assays evaluated bispecific antibodies' behavior in the presence and absence of primary stimulation and target expression.

1) Luciferase based reporter assay:

a) Engineering of reporter T-cells:

A Jurkat derived T-cell clone, JRT3.T3.5 (ATCC, #TIB-153) was transduced with an NFκB luciferase reporter construct (NFκB-Luc, SA Biosciences/Qiagen, Cat. #CLS-013L). After the isolation of a puromycin resistant clone (JRT3.T3.5/NFκB-Luc Clone 1C2), cells were further engineered to express full-length human TCR alpha (1G4A-amino acids M1 to S274) and TCR beta subunit (1G4B-amino acids M1 to G311) (Robbins et al., Single and Dual Amino Acid Substitutions in TCR CDRs Can Enhance Antigen-Specific T Cell Functions, J. Immunol. 180 (9): 6116-31 (2008)). After isolating a single clone (J.RT3-T3.5/NFκB-Luc/1G4AB Clone 1D2), cells were further engineered to express full-length human CD8 alpha (hCD8a-amino acids M1 to V235 of accession #NP_001139345) and human CD8 beta subunit (hCD8b-amino acids M1 to K210 of accession #P10966). A single clone was generated again (J.RT3-T3.5/NFκB-Luc/1G4AB/hCD8ab Clone 1D5) and further transduced with full-length human CD28 (hCD28-amino acids M1 to S220 accession #P10747). Cells were sorted for high CD28 expression and maintained in RPMI+20% FBS +penicillin/streptomycin/glutamine (P/S/G)+NEAA+NaPyr+1 ug/mL puromycin+500 μg/mL G418+250 μg/mL hygromycin+10 ug/mL blasticidin. For faster growth, the engineered reporter T-cells were kept in cell culture media without antibiotics and used for cell-based luciferase experiments as engineered reporter T-cells. The reagents information is as follows: RPMI 1640, Irvine Scientific, Cat. #9160; FBS, Seradigm, Cat. #1500-50; Penicillin/Streptomycin/Glutamine 100×(P/S/G), Thermo Fisher Scientific, Cat. #10378-016; Non-Essential Amino-Acids (NEAA), Irvine Scientific, Cat. #9304; Sodium Pyruvate (NaPyr), Millipore, Cat. #TMS-005-C; puromycin, Sigma, Cat. #P8833; Geneticin (G418), Thermo Fisher Scientific, Cat. #11811-098; hygromycin; blasticidin.

b) Engineering of APCs:

A stable HEK293 cell line (ATCC, #CRL-1573) expressing human CD20 (amino acids M1 to P297 of accession number NP_068769.2) was transduced with human PSMA (amino acids M1 to A750 of accession number Q04609). Human PSMA positive cells were isolated by fluorescence-activated cell sorting (FACS) and the resulting cell line, HEK293/CD20/hPSMA high sorted was maintained in DMEM+10%+P/S/G+NEAA supplemented with 500 ug/mL G418.

c) T-Cell/APC Stimulation:

In this experiment, engineered reporter T-cells are stimulated via two bispecific antibodies. The first stimulation is delivered by a T-cell activating bispecific antibody, anti-CD3×CD20 hIgG4, (see WO14/047231, U.S. Pat. No. 9,657,102 and U.S. Ser. No. 14/661,334) targeting CD3 molecules on engineered reporter T-cells and CD20 on HEK293 cells. Here, the first stimulation bypasses the need of activation of TCRs by their natural ligands, which are specific peptides displayed on MHC molecules. The second stimulation is driven by the CD28 bispecific antibody. This antibody mimics the CD28 activation on T-cells by its ligands, CD80/CD86, expressed on APCs. Here, the antibody interacts with CD28 on T-cells and PSMA on engineered HEK293 cells and drives the activation of CD28 on engineered reporter T-cells. The simultaneous TCR and CD28 activation leads to enhanced transcriptional activity of NFκB, which in turn induces the production of the reporter gene, luciferase.

d) Luciferase Assay Set Up:

RPMI1640 supplemented with 10% FBS and P/S/G was used as the assay medium to prepare cell suspensions and antibody dilutions for screening of the anti-PSMA×CD28 bispecific antibodies.

A day prior to screening, engineered reporter T-cells were cultured to $1\times10^6$ cells/mL in cell culture media. Three fold (1:3) serially diluted anti-PSMA×CD28 bispecific antibodies and controls were tested in the presence of constant 50 pM anti-CD20×CD3 or an hIgG4 isotype control. The 10-point dilution ranged between 15 pM to 100 nM with the final dilution containing no anti-PSMA×CD28 antibodies. Reagents were added in following order: 1) serially diluted antibodies were added to 96 well white flat bottom plates into corresponding wells; 2) A fixed concentration of 50 pM anti-CD20×CD3 or hIgG4 isotype control was added to each well; 3) APCs re-suspended to $4\times10^5$ cells/mL were added to plates with a final concentration $1\times10^4$ cells/well; 4) Overnight cultured reporter T-cells were re-suspended at $2\times10^6$/mL and added to plates with a final concentration $5\times10^4$ cells/well. Plates were incubated for 4-6 hours at 37° C./5% $CO_2$, before the addition of 100 μL ONE-Glo™ (Promega, Cat. #E6051) reagent to lyse cells and detect luciferase activity. The emitted light was captured in relative light units (RLU) on a multilabel plate reader Envision (PerkinElmer, Model 2104). All serial dilutions were tested in duplicate.

The $EC_{50}$ values of the antibodies were determined by fitting the data to a four-parameter logistic equation over a 10-point dose-response curve using GraphPad Prism™ software. Fold induction was calculated using the following equation:

$$\text{Fold induction} = \frac{\text{Mean } RLU \text{ values of antibody [100 nM]}}{\text{Mean } RLU \text{ values of antibody [0 nM]}}$$

2) IL-2 Functional Assay Using Primary Human CD4+ T-Cells:

A primary $CD4^+$ T-cell/APC functional assay was developed to evaluate the effect of CD28 activation on IL-2 production upon engagement with anti-PSMA×CD28 bispecific antibodies.

a) Human Primary CD4+ T-Cell Isolation:

Human peripheral blood mononuclear cells (PBMCs) were isolated from a healthy donor leukocyte pack. PBMC isolation was accomplished by density gradient centrifugation using 50 mL SepMate™ tubes (StemCell Technologies, Cat. #85450) following the manufacturer's recommended protocol. Briefly, 15 mL of FicollPaque PLUS was layered into 50 mL SepMate tubes, followed by addition of 30 mL of leukocytes diluted 1:2 with D-PBS (Dulbecco's Phosphate-Buffered Saline Solution, Irvine Scientific, Cat. #9240). Subsequent steps were followed according to SepMate manufacturer's protocol. CD4+ T-cells were subsequently isolated from PBMC's using human CD4 Microbead kits from Miltenyi Biotec (Cat. #130-045-101) following the manufacturer's instructions. Isolated CD4+ T-cells were frozen in FBS containing 10% DMSO (Macron Fine Chemicals, Cat. #4948-02) at a concentration of $5\times10^6$ cells per vial.

b) IL-2 Release from Primary CD4+ T-Cells Treated with CD28 Antibodies:

In this assay, primary CD4+ T-cells are activated via the crosslinking of CD3 on their surface using an anti-CD20×CD3 bispecific antibody in combination with HEK293 cells engineered to express human CD20. Binding of the CD20 arm of anti-CD20×CD3 bispecific antibodies to HEK293 cells expressing CD20 drives the clustering of the CD3 receptor, providing the first signal-important for T-cell stimulation. However, in order to detect quantifiable IL-2 release, co-stimulation, which can be provided by cross-linking CD28 molecules, is important. Here, the bispecific anti-PSMA×CD28 antibodies interact with CD28 on CD4+ T-cells and PSMA on engineered HEK293/hCD20 cells and drive the clustering-activation of CD28. The combined TCR and CD28 engagement leads to enhanced IL-2 production which is released into cell culture media. IL-2 is detected and quantified from the cell supernatant using a homogenous, no wash, AlphaLisa kit (PerkinElmer, Cat. #AL221).

Previously isolated and frozen human CD4+ T-cells from donor were thawed the day of the assay in stimulation media (X-VIVO 15 cell culture media (Lonza, Cat. #04-418Q) supplemented with 10% FBS, HEPES, NaPyr, NEAA, and 0.01 mM BME (B-mercaptoethanol, Sigma-Aldrich, Cat. #M-7522) containing 50 U/ml benzonase nuclease (EMD Millipore, Cat. #71205-3)). Cells were centrifuged at 1200 rpm for 10 minutes, resuspended in stimulation media and plated into 96-well round bottom plates at a concentration of $1\times10^5$ cells/well. HEK293 cells engineered to express human CD20 alone or in combination with human PSMA, were treated with 15 μg/mL of Mitomycin C (Sigma-Aldrich, Cat. #M4287) in primary stimulation media at a concentration of $10\times10^6$ cells/mL. After incubation for 1 hour at 37° C., 5% $CO_2$, HEK293 cells were washed 3 times with D-PBS containing 2% FBS and added to the wells containing $CD4^+$ T-cells at a final concentration of $1\times10^4$ cells per well.

Subsequently, 1:3 serially diluted anti-PSMA×CD28 bispecific or control antibodies, ranging from 15 μM to 100 nM, were added to wells in the presence of 50 μM anti-CD20×CD3 or hIgG4 isotype control. The final point of the 10-point dilution contained no anti-PSMA×CD28 or anti-CD28 antibody. After plates were incubated for 72 hours at 37° C., 5% $CO_2$, they were centrifuged to pellet the cells and 40 μL of media supernatant was collected. From this, 5 μL was tested in a human IL-2 AlphaLISA assay according to the manufacturer's protocol. The measurements were acquired on the multilabel plate reader Envision (PerkinElmer, Model 2104). A standard curve of known IL-2 concentrations was used to determine the concentrations of IL-2 generated in assay wells. All serial dilutions were tested in duplicate.

The $EC_{50}$ values of the antibodies were determined by fitting data to a four-parameter logistic equation over a 10-point dose-response curve using GraphPad Prism™ software. Fold induction was calculated using following equation:

$$\text{Fold induction} = \frac{\text{Mean } IL\text{-}2 \text{ values of antibody [100 nM]}}{\text{Mean } IL\text{-}2 \text{ values of antibody [0 nM]}}$$

Results, Summary and Conclusions

Figure 4A:
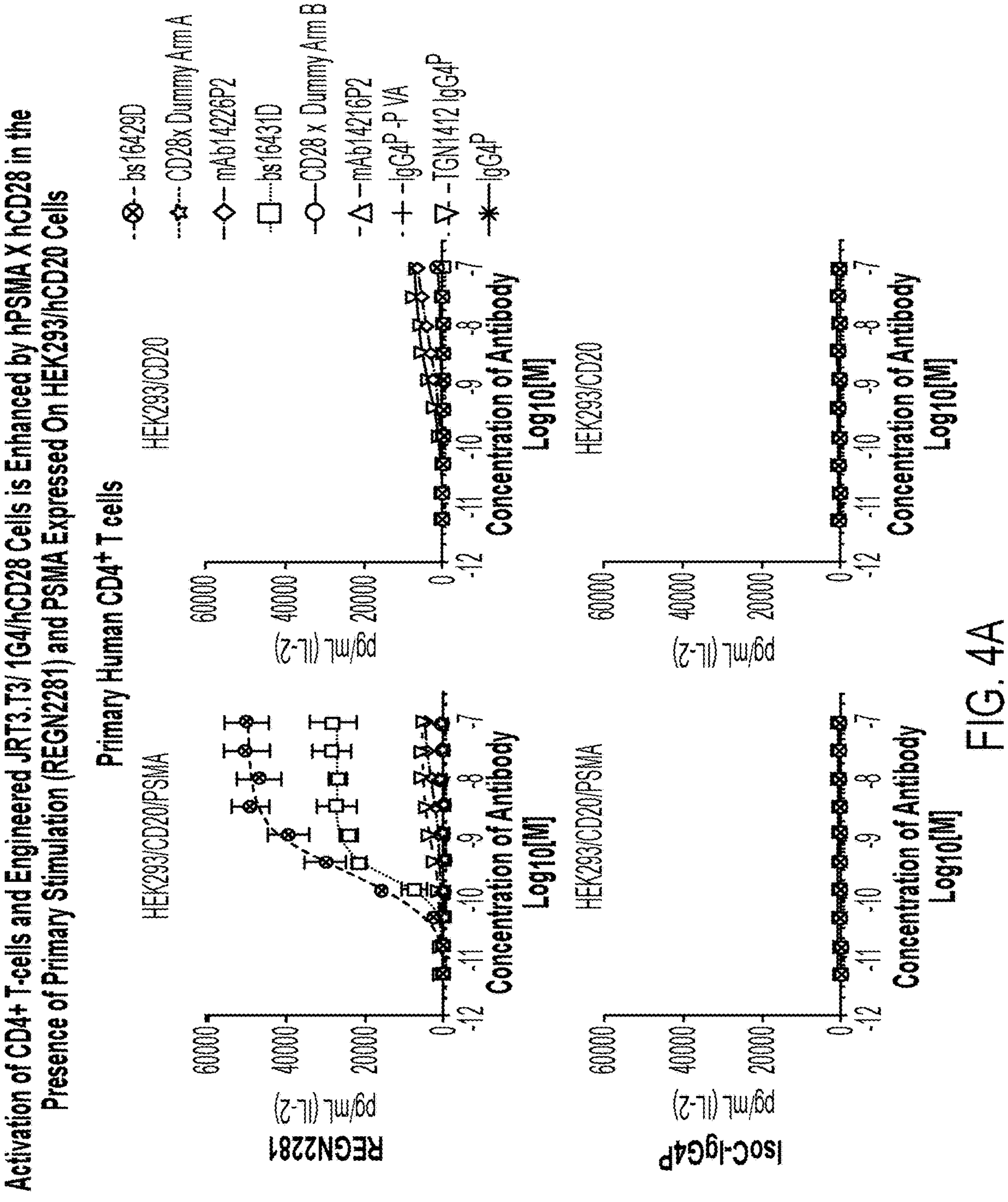
FIGS. 4A and 4B show that activation of CD4+ T-cells and engineered JRT3.T3/1G4/hCD28 cells was enhanced by anti-hPSMA×hCD28 in the presence of primary stimulation (REGN2281) and PSMA expressed on HEK293/hCD20 cells.
Figure 4B:
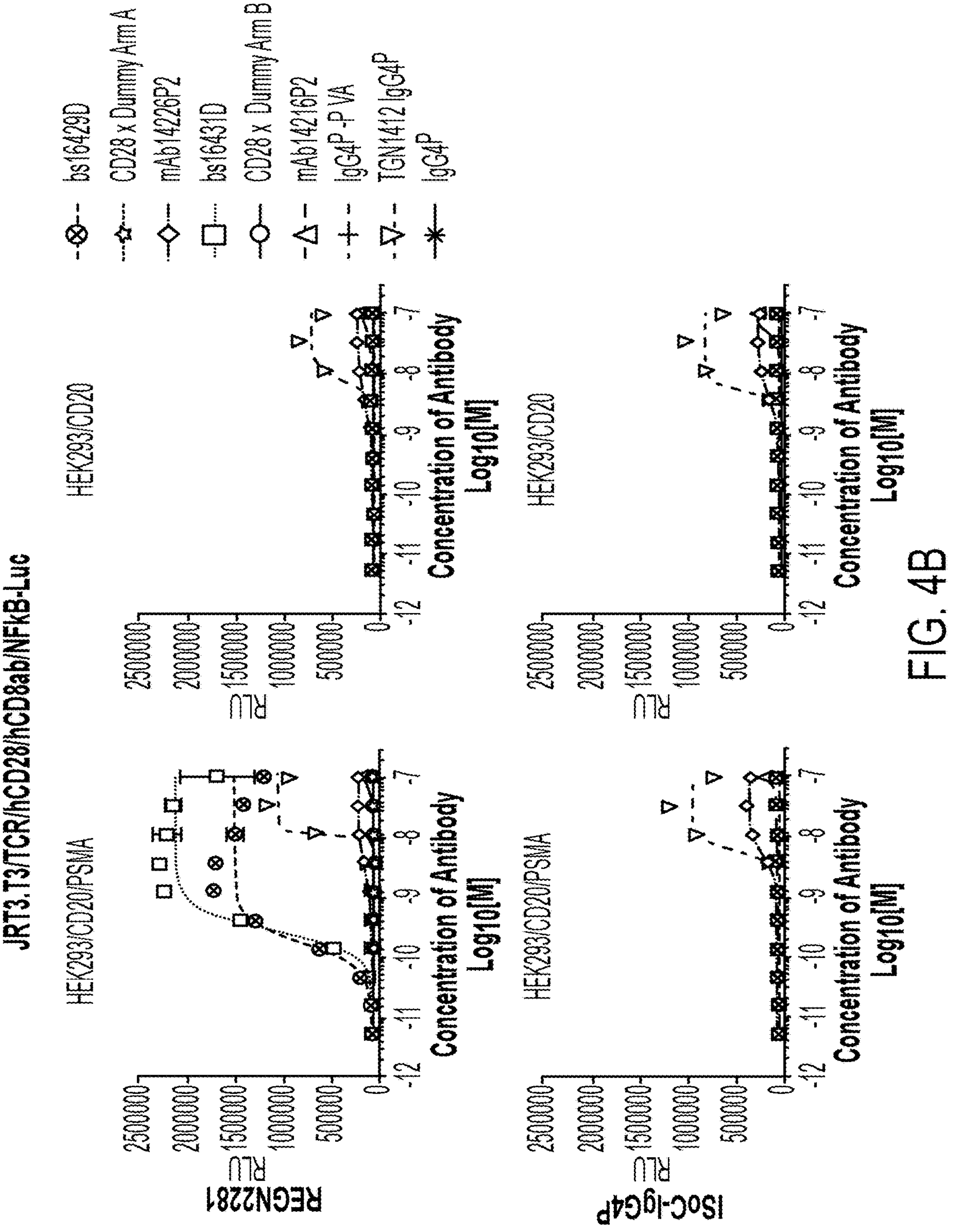

As shown in FIGS. 4A and 4B, activation of CD4+ T-cells (as measured by IL-2 release) and engineered JRT3.T3/1G4/hCD28 cells (as measured by luciferase activity) was enhanced by hPSMA×hCD28 in the presence of primary stimulation (REGN2281 anti-CD20×CD3) and PSMA expressed on HEK293/hCD20 cells. CD28 bivalent antibody, mAb14193P2, slightly enhances T cell activity in the presence of primary stimulation and slightly in the engineered bioassay in the absence of primary stimulation. The CD28 superagonist, TGN1412 enhances T cell activation in both primary and engineered assays in the presence of CD20×CD3 stimulation, albeit to a lower extent than PSMA×CD28 bispecifics in the presence of target PSMA and primary stimulation.

1) Luciferase Based Reporter Assay:

$EC_{50}$ and fold induction values are summarized in Tables 13 and 14 for engineered reporter T-cells co-incubated with HEK293/hCD20 or HEK293/hCD20/hPSMA cells in addition to either 50 μM constant hIgG4 isotype control or anti-CD3×CD20 bispecific antibody (T-cell stimulating bispecific antibody).

TABLE 13

Luciferase Activity in Engineered Reporter T-Cells in Absence of TCR Stimulation

| | HEK293/hCD20 | | HEK293/hCD20/hPSMA | |
|---|---|---|---|---|
| Antibodies | $EC_{50}$ [M] | Fold induction | $EC_{50}$ [M] | Fold induction |
| bs16429D | — | 0.81 | — | 1.04 |
| bs16430D | — | 0.87 | — | 0.89 |
| bs16431D | — | 0.94 | — | 0.98 |
| mAb14226P2 (CD28) | 5.11E−09 | 4.76 | 4.90 E−09 | 3.59 |
| mAb14193P2 (CD28) | — | 0.86 | — | 0.89 |
| mAb14216P2 (CD28) | n/c | 2.80 | n/c | 3.95 |
| one-arm mAb14226P2 | — | 0.83 | — | 0.88 |
| one-arm mAb14193P2 | — | 0.88 | — | 0.86 |
| one-arm mAb14216P2 | — | 0.89 | — | 0.91 |

Table 14 summarizes $EC_{50}$ values and fold induction results for luciferase activity in engineered T-cells co-incubated with HEK293/hCD20 or HEK293/hCD20/hPSMA cells and 50 μM constant hIgG4 isotype control.

TABLE 14

Luciferase Activity in Engineered Reporter T-cells in Presence of TCR Stimulation

| | HEK293/hCD20 | | HEK293/hCD20/hPSMA | |
|---|---|---|---|---|
| Antibodies | $EC_{50}$ [M] | Fold induction | $EC_{50}$ [M] | Fold induction |
| bs16429D | — | 1.00 | 1.72E−10 | 16.15 |
| bs16430D | — | 0.92 | 4.57E−10 | 13.61 |
| bs16431D | — | 0.95 | 2.78E−10 | 24.47 |
| mAb14226P2 (CD28) | 3.59E−09 | 3.16 | 3.27E−09 | 3.03 |
| mAb14193P2 (CD28) | 2.23E−08 | 1.27 | — | 1.37 |
| mAb14216P2 (CD28) | n/c | 3.26 | n/c | 3.15 |
| one-arm mAb14226P2 | — | 0.99 | — | 0.95 |
| one-arm mAb14193P2 | 2.24E−08 | 1.10 | — | 1.15 |
| one-arm mAb14216P2 | — | 0.96 | — | 0.94 |

Table 14 summarizes $EC_{50}$ values and fold induction results for luciferase activity in engineered T-cells co-incubated with HEK293/hCD20 or HEK293/hCD20/hPSMA cells and 50 μM constant anti-CD3×CD20.

When T-cells and APCs are treated with 50 μM hIgG4 isotype control, none of the CD28 bispecific antibodies showed an increase in luciferase activity in the absence of TCR stimulation, irrespective of the APC line used in the assay. A slight luciferase activation was observed with one of the parental CD28 antibodies (mAb14226P2) on HEK293/hCD20 cells (4.76×) and HEK293/hCD20/hSPMA cells (3.59×) shown in Table 14.

In contrast, if cells were treated with 50 μM anti-CD3×CD20 bispecific antibody, all three anti-PSMA×CD28 bispecific antibodies bs16429D, bs16430D, and bs16431D strongly induced luciferase activity when co-incubated with APCs expressing hPSMA on the surface. Very low to no activation was observed with their one-armed controls (one arm of mAb14226P2, mAb14193P2, and mAb14216P2) irrespective of the APC line. A slight luciferase activation was observed for all three parental CD28 antibodies (mAb14226P2, mAb14193P2, and mAb14216P2) as shown in Table 14.

2) IL-2 Functional Assay Using Primary Human CD4+ T-Cells:

The ability of anti-PSMA×CD28 bispecific antibodies to provide co-stimulation through CD28 on T-cells in the absence or presence of PSMA target expression was assessed in a functional primary CD4+ T-cell assay measuring IL-2 cytokine production.

$EC_{50}$ and fold induction values are summarized in Table 15 for CD4+ T-cells co-incubated with HEK293/hCD20 or HEK293/hCD20/hPSMA cells in addition to either 50 μM constant hIgG4 isotype control or anti-CD3×CD20 bispecific antibody (T-cell stimulating bispecific antibody).

As expected, no measurable IL-2 release was observed in wells containing constant amounts hIgG4 isotype control, since there was no primary T-cell stimulation.

In contrast, measurable IL-2 levels were detected in samples treated with anti-CD3×CD20 bispecific antibody. Under these conditions, if human CD4+ T-cells were co-incubated with HEK293/hCD20 cells, all CD28 monoclonal antibodies tested, including anti-CD28 antibodies and anti-PSMA×CD28 bispecific antibodies, except bs 16430D and bs16431D, showed increased IL-2 levels (Table 15). The parental antibody, mAb14226P2 showed the highest fold induction and an $EC_{50}$ around 6 nM. IL-2 release was detected with all three anti-PSMAxCD28 bispecific antibodies (bs16429D, bs16430D, and bs16431D), when CD4+ T-cells are co-cultured with hPSMA expressing APCs and anti-CD3×CD20 bispecific antibody. Lower IL-2 levels are measured with their one-armed control antibodies and parental antibodies under the same setting as shown Table 15.

TABLE 15

IL-2 Production from Primary $CD4^+$ T-cells in Presence of TCR Stimulation

| | HEK293/hCD20 | | HEK293/hCD20/hPSMA | |
|---|---|---|---|---|
| Antibodies | $EC_{50}$ [M] | Fold induction | $EC_{50}$ [M] | Fold induction |
| bs16429D | n/c | 22 | 0.27E−09 | 606 |
| bs16430D | — | 1 | 0.15E−09 | 165 |
| bs16431D | — | 1 | 0.22E−09 | 463 |
| mAb14226P2 (CD28) | 6.05E−09 | 110 | 8.69E−09 | 46 |
| mAb14193P2 (CD28) | n/c | 27 | n/c | 13 |
| mAb14216P2 (CD28) | n/c | 13 | n/c | 11 |
| one-arm mAb14226P2 | n/c | 21 | n/c | 14 |
| one-arm mAb14193P2 | 13.78E−09 | 21 | 14.52E−09 | 13 |
| one-arm mAb14216P2 | n/c | 9 | n/c | 6 |

Table 15 summarizes $EC_{50}$ values and fold induction results for IL-2 production from primary $CD4^+$ T-cells co-incubated with HEK293/hCD20 or HEK293/hCD20/hPSMA cells and 50 μm constant anti-CD3×CD20 antibody.

Example 7. Anti-PSMAxCD28 Bispecific Antibodies Potentiate T Cell Activation in the Presence of Both PSMA and TCR Stimulation by Anti-CD20×CD3

Figure 5A:
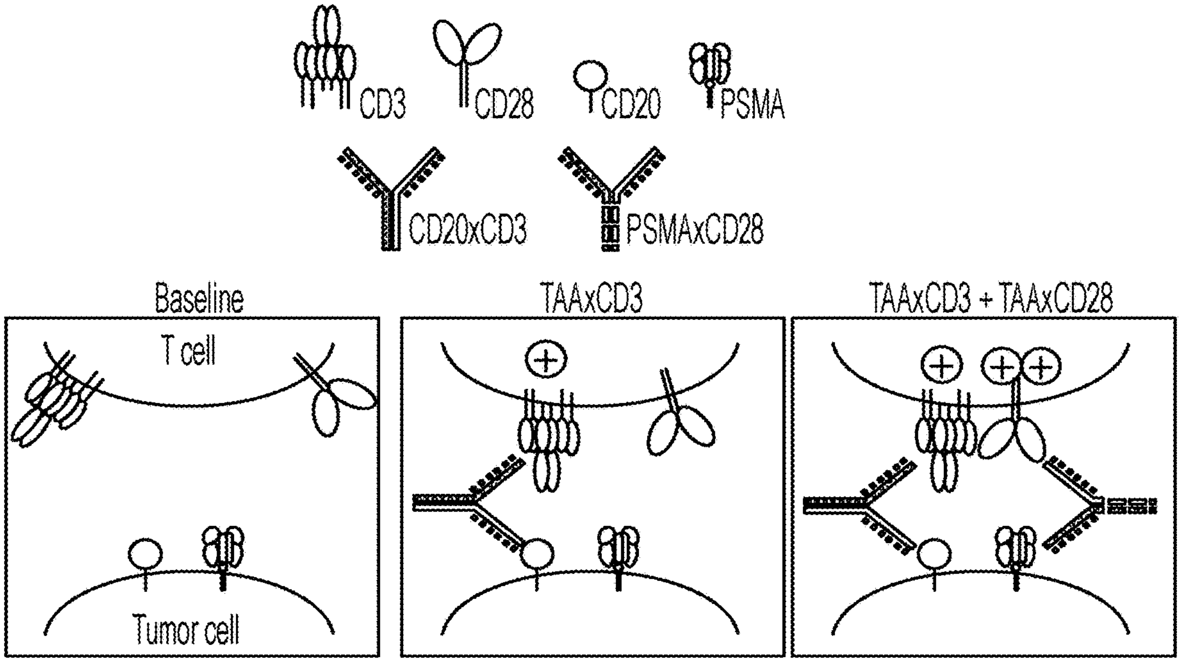
FIGS. 5A-5H show that in engineered cell lines with introduced PSMA, PSMAxCD28 bispecific antibodies potentiate T cell activation in the presence of TCR stimulation by anti-CD20×CD3 bispecific antibodies.

Exemplary anti-PSMAxCD28 bispecific antibodies have been generated and biacore validated (see, e.g., Examples 1 and 4). A pair of bispecific antibodies (CD20×CD3 and exemplary anti-PSMAxCD28 bispecific antibodies of the invention were used to induce clustering of T cells and costimulatory receptors on tumor cells by binding to PSMA (CD20 and prostate specific membrane tumor antigen-PSMA) (FIG. 5A). To show that PSMAxCD28 binds and activates CD28 in the presence of PSMA expressed on target cells and TCR activation, a series of in-vitro cell-based assays were performed.

Localization of CD28

Cell Lines

A stable HEK293 cell line (ATCC, #CRL-1573) was used in creating cell lines HEK293/hCD20, HEK293/hPSMA, and HEK293/hCD20/hPSMA. For generating the HEK293/hPSMA cell line a stable transfection was performed using a mammalian vector encoding an ubiquitin C-promoter driven PSMA (amino acids M1 to A750 of accession number Q04609) and a neomycin resistance gene. Similarly, the HEK293/hCD20 cell line was generated using a mammalian vector encoding an ubiquitin-promoter driven hCD20 (amino acids M1 to P297 of accession number NP_068769.2). Transfected cells were cultured in 500 ug/ml of Geneticin A to select for stably expressing cell lines.

For generation of HEK293/hCD20/hPSMA cells, a lentiviral plasmid encoding human PSMA (amino acids M1 to A750 of accession number Q04609) and a neomycin resistance gene was used to transfect HEK293T cells, facilitating the production of viral particles, which were subsequently used to infect HEK293/hCD20 cells. Human PSMA positive cells were isolated by fluorescence-activated cell sorting (FACS). All generated cell lines were maintained in DMEM+10% FBS+P/S/G+NEAA supplemented with 500 ug/mL G418. Jurkat Clone E6-1 (ATCC, #TIB-152) were cultured according to ATCC recommended protocol.

For generation of MC38/hPSMA cells, a lentiviral plasmid encoding human PSMA (amino acids M1 to A750 of accession number Q04609) and a neomycin resistance gene was used to transfect HEK293T cells, facilitating the production of viral particles, which were subsequently used to infect MC38 parental cells. Human PSMA positive cells were isolated by FACS. MC38/hPMA were maintained in DMEM+10% FBS+P/S/G+NEAA supplemented with 500 ug/mL G418.

Amnis Image Stream

Jurkat T cells and target cells (HEK293/hPSMA or HEK293/hPSMA/hCD20) were incubated with CD20×CD3-Alexa488 (REGN2280, 0.5 ug/ml) alone or together with PSMAxCD28-Alexa647 (bs16429D, 1 ug/ml) for 1 hour at 37° C. Cells were gently washed with FACS buffer (3% FBS, 2 mM EDTA in PBS) twice and stained with anti-CD28-Biotin (REGN1412, 2 ug/ml) at for 15 min at 4° C. and subsequently with streptavidin-PE-CF594 (BD 562284, 1 ug/ml) and Hoechst 33342 (Thermo Fisher H3570, 1 μM) for 15 min at 4° C. Cells were washed with PBS and stored in BD stabilizing fixative (BD 338036).

Images of cells were collected on Amnis® Imaging Flow Cytometer and analyzed by IDEAS® software. Cells were gated on doublet bright-field, doublet nucleus, nucleus focus, single spot count, singlet CD28. Synapse area was defined by valley mask based on nucleus staining. Cells with wrong valley mask were eliminated by gating on overlapping area between valley mask and CD28. The ratio of CD28 in/out of synapse was calculated by the following formula: CD28 in/out of synapse=intensity of CD28 in synapse/(CD28 total intensity-intensity of CD28 in synapse)*100%.

Results, Summary and Conclusions

Figure 5B:
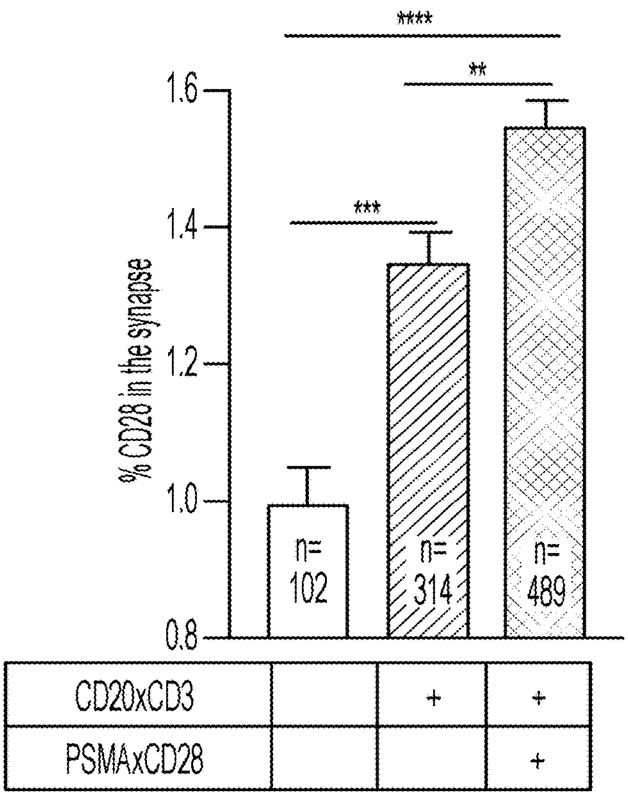
Figure 5C:
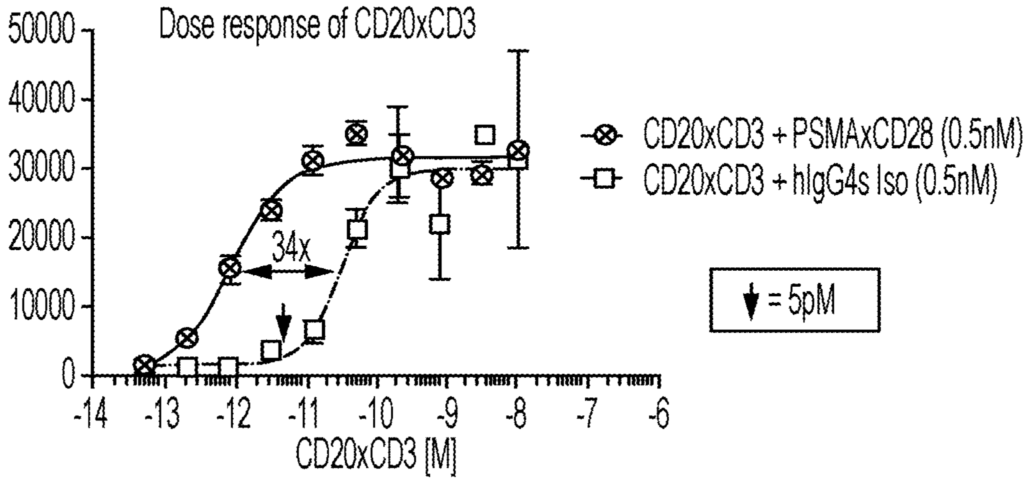
Figure 5D:
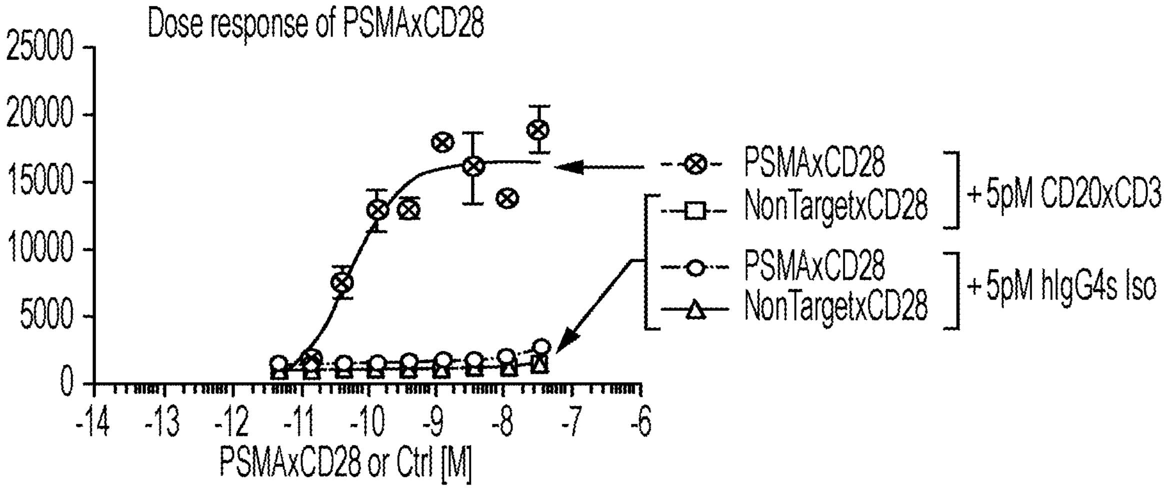

T cells were co-cultured with engineered target cells (HEK293/hPSMA or HEK293/hCD20/hPSMA) over-expressing CD20 and PSMA and fluorescently labeled bispecifics (CD20×CD3 in green, PSMAxCD28 in red). To determine the localization of CD28, cells were fixed and stained with anti-CD28 after 1-hour incubation at 37° C. Images of T cell and target cell conjugates were obtained using an Amnis ImageStream imaging flow cytometry. In the absence of PSMA expression on target cells, CD20×CD3 bispecific alone induced little to no clustering of CD28 on T cells. When PSMA was expressed on target cells, CD20×CD3 was localized at the interface of T cell and target cell conjugates and formed an immunological synapse (IS) where CD28 was localized. PSMAxCD28 together with CD20×CD3, further enhanced CD28 accumulation at the IS. The distribution of CD28 was quantified by calculating the ratio of CD28 staining inside vs. outside of the IS (FIG. 5B).

It has been concluded that PSMAxCD28 in the presence of PSMAxCD3 and PSMA expressing target cells drives a robust CD28 accumulation at the IS, the location where T cell activation signaling occurs.

Cytokine Release

Figure 5E:
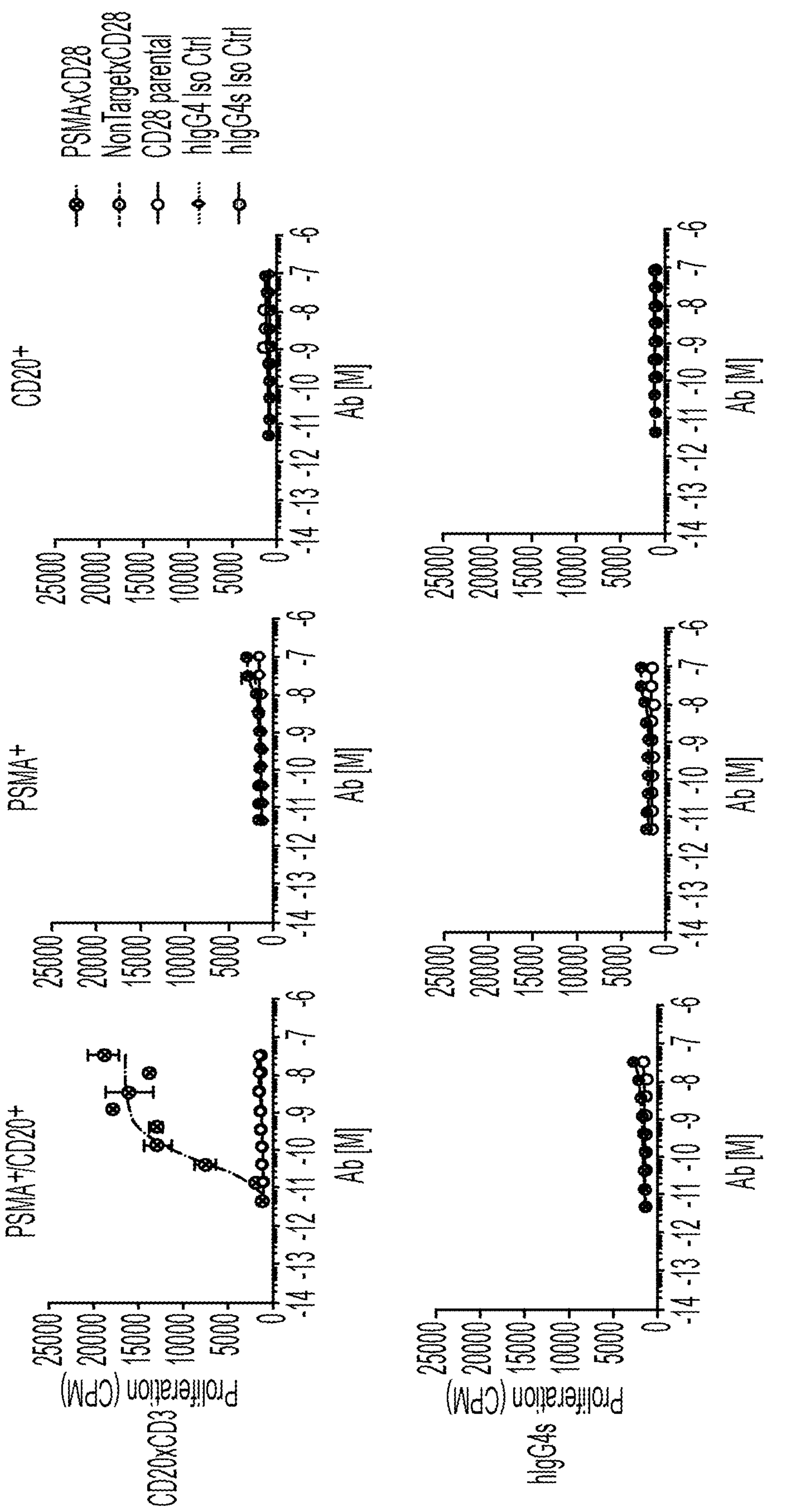
Figure 5F:
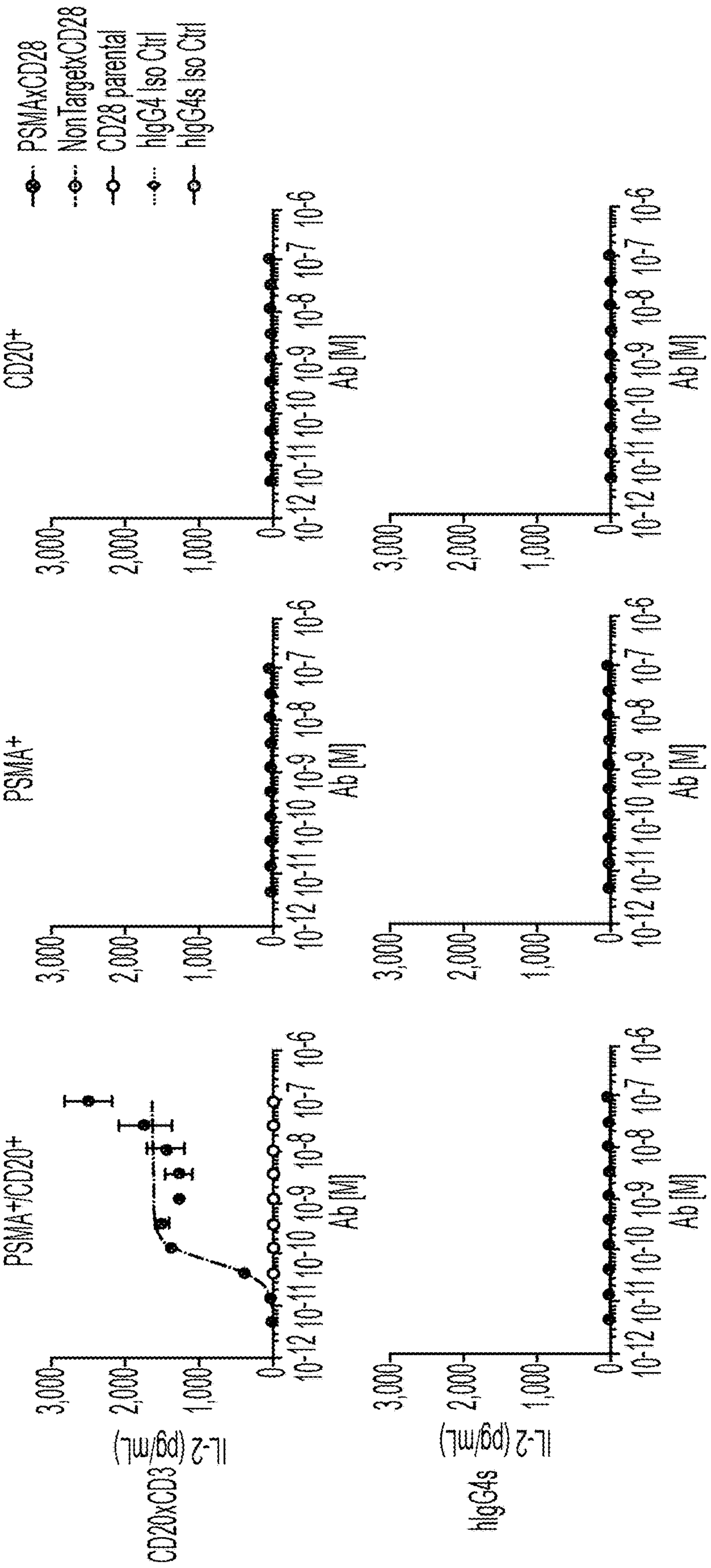
Figure 5G:
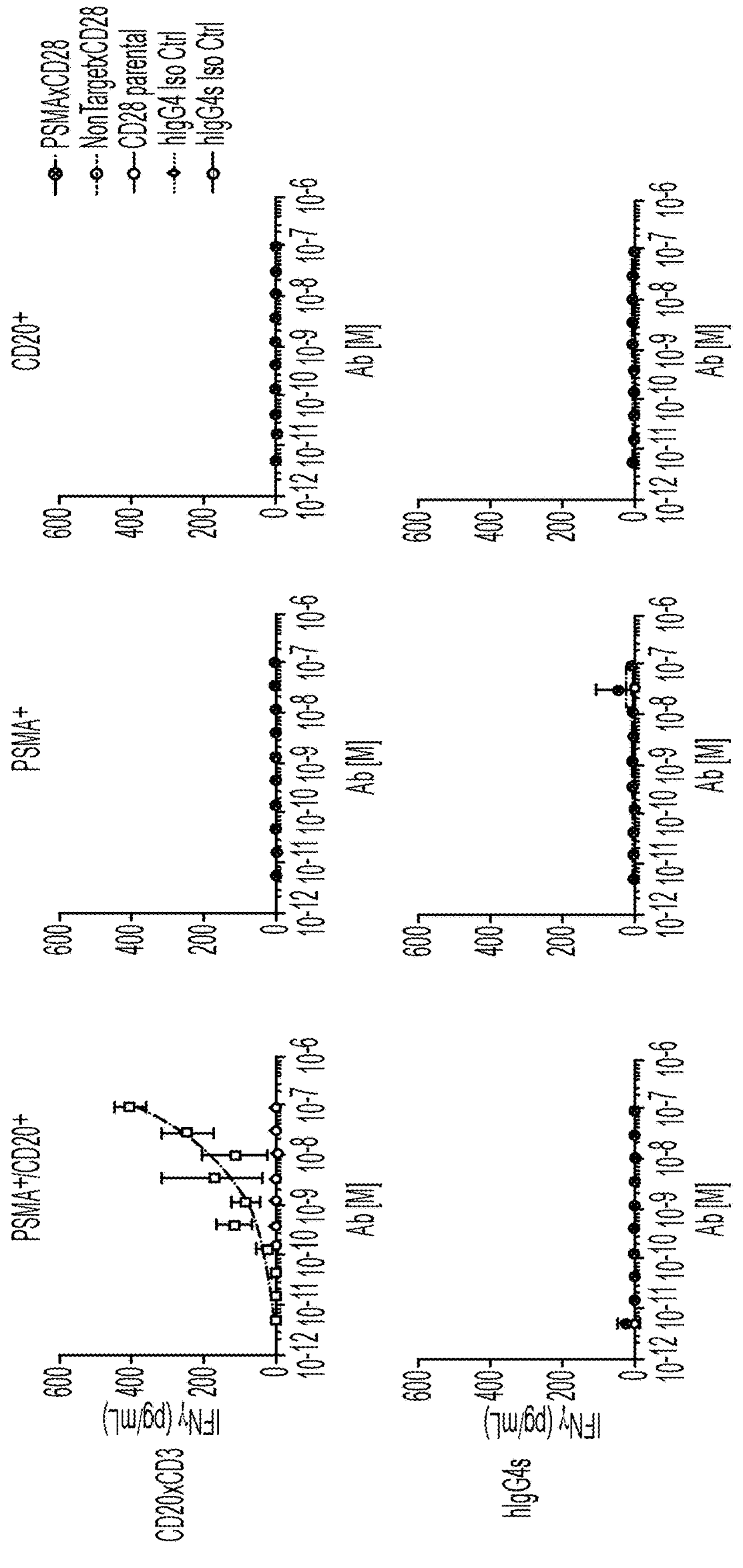
Figure 5H:
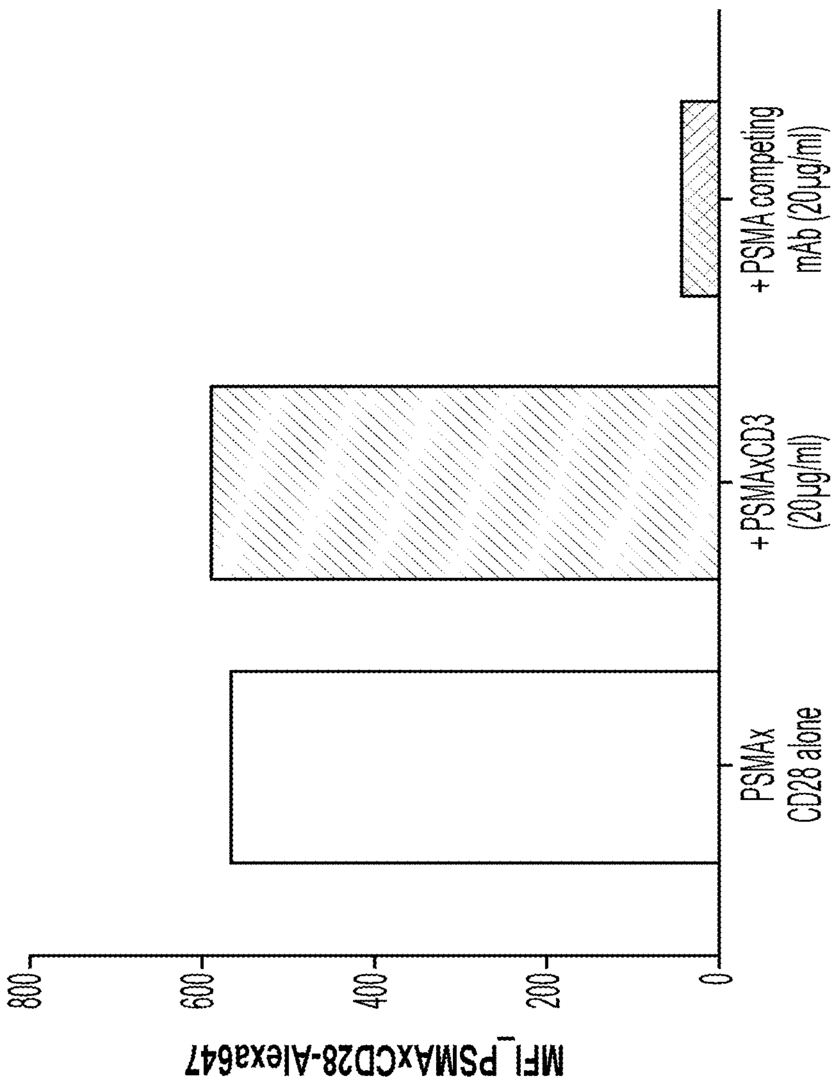

To further investigate the effect of TAAxCD28 on T cell activation, T cell proliferation and IL-2 and IFNγ cytokine release were measured after incubation with a dose titration of either CD20×CD3 or PSMAxCD28 bispecifics in co-culture with primary human T cells and engineered target cells over-expressing different TAAs (HEK293/hPSMA, HEK293/hCD20 or HEK293/hCD20/hPSMA) (FIGS. 5C-5G). It was verified that exemplary anti-PSMAxCD28 antibodies of the invention and anti-PSMAxCD3 bispecific antibodies did not compete for binding to PSMA expressing cells and therefore bind to different epitopes (FIG. 5H). It was further validated that PSMAxCD28 induced T cell activation in the presence of both CD3 stimulation and PSMA expression on the target cell (HEK293/hCD20/hPSMA plus 5 μM CD20×CD3). Activation of T cells by exemplary anti-PSMAxCD28 bispecific antibodies was not observed in the absence of PSMA expression on target cells (co-culture with HEK293/hCD20) or in the absence of CD3 stimulation (co-culture with HEK293/PSMA plus 5 μM CD20×CD3 or HEK293/hCD20/hPSMA plus 5 μM Isotype control). (FIGS. 5E-5G). Overall, it was demonstrated that exemplary anti-PSMAxCD28 antibodies of the invention drive T cell activation in the presence of PSMAxCD3 and PSMA expressing target cells, resulting in increased proliferation and cytokine secretion.

Example 8. Killing of PSMA Expressing Cells

Two FACS based cytotoxicity studies were conducted. In the first study, FACS based cytotoxicity was conducted on C4-2 cells in the presence of human peripheral blood mononuclear cells (PBMCs) in the presence or absence of anti-PSMAxCD28 stimulation. The stimulation was conducted in the presence of fixed concentration of anti-PSMAxCD28 bispecific antibody and serially diluted anti-PSMAxCD3 bispecific antibody. The second study is otherwise identical to the first study except that cynomolgus PBMCs are used instead of human PBMCs. It was concluded that PSMAxCD28 bispecific antibodies potentiate T cell activation and cytotoxicity on prostate tumor cells in the presence of TCR stimulation by PSMAxCD3.

Experimental Methods

Human Primary CD4+ T Cell Isolation

Human peripheral blood mononuclear cells (PBMCs) were isolated from a healthy donor leukocyte pack. PBMC isolation was accomplished by density gradient centrifugation using 50 mL SepMate™ tubes following the manufacturer's protocol. CD4+ T cells were subsequently isolated from PBMC's using EasySep™ Human CD4+ T Cell Isolation Kit from StemCell Technologies and following manufacturer's recommended instructions. Isolated $CD4^+$ T cells were frozen in FBS containing 10% DMSO at a concentration of $50\times10^6$ cells per vial.

Primary Human T Cell Activation Assay

Previously isolated and frozen human $CD4^+$ T cells were thawed the day of the assay in stimulation media (X-VIVO 15 cell culture media supplemented with 10% FBS, HEPES, NaPyr, NEAA, and 0.01 UM BME) containing 50 U/ml benzonase nuclease. Cells were centrifuged at 1200 rpm for 10 minutes, resuspended in stimulation media and plated out into 96-well round bottom plates at a concentration of $1\times10^5$ cells per well. HEK293 cells (HEK293/hPSMA, HEK293/hCD20 or HEK293/hPSMA/hCD20) were treated with 15 μg/mL of Mitomycin C in primary stimulation media at a concentration of $10\times10^6$ cells/mL. After incubation for 1 hour at 37° C., 5% $CO_2$, HEK293 cells were washed 3 times with D-PBS containing 2% FBS and added to the wells containing CD4+ T-cells at a final concentration of $2\times10^4$ cells per well.

To determine the suboptimal CD20×CD3 bispecific antibody concentration to activate T cells, CD20×CD3 was serially diluted 1:3, ranging from 1.5 μM to 10 nM in the presence of 500 μM PSMAxCD28 bispecific or hIgG4s isotype control. A constant 5 μM of CD20×CD3 bispecific or hIgG4 control was chosen and the following antibodies: 1) PSMA×CD28 2) nontarget×CD28 control 3) CD28 parental 4) CD28SA (super agonist) 5) hIgG4 isotype control and 6) hIgG4s isotype control, were titrated from 15 μM to 100 nM in a 1:3 dilution. The final point of the 10-point dilution contained no titrated antibody, only 5 μM of CD20×CD3 bispecific or hIgG4 control.

After plates were incubated for 48 hours at 37° C., 5% $CO_2$ they were centrifuged to pellet the cells and 50 μL of media supernatant was collected. From this, 5 μL was tested in a human IL-2 and human IFNγ AlphaLISA assay according to the manufacturer's protocol. The measurements were acquired on Perkin Elmer's multilabel plate reader Envision. A standard curve of known IL-2 or IFNγ concentrations was generated in order to extrapolate the pg/mL of IL-2 or IFNγ generated in assay wells. All serial dilutions were tested in duplicates. Pelleted cells were incubated with [Methyl-3H]-Thymidine, 0.25 uCi/well for 16 hours at 37° C., 5% $CO_2$. Cells were collected onto Perkin Elmer Unifilter plates using Perkin Elmer's Unifilter 96 Cell Harvester. After addition of 30 μl scintillation liquid, plates were sealed and counts per minute for each well acquired using the TopCount NXT from Perkin Elmer.

The $EC_{50}$ values of the antibodies were determined from a four-parameter logistic equation over a 10-point dose-response curve using GraphPad Prism™ software. FACS-based cytotoxicity assay In order to monitor the killing of PSMA+ cells in the presence of a combination of anti-PSMAxCD3 and anti-PSMAxCD28 antibodies, C4-2 cells were labeled with 1 μM of the fluorescent tracking dye Violet Cell Tracker (Invitrogen, Cat. #34557). After labeling, cells were plated overnight at 37° C. Separately, human PBMCs (New York Blood Center) or cynomolgus monkey PBMCs (Covance, Cranford NJ) were plated in supplemented RPMI media at $1\times10^6$ cells/mL and incubated overnight at 37° C. in order to enrich for lymphocytes by depleting adherent macrophages, dendritic cells, and some monocytes. The next day, the target cells were co-incubated with adherent cell-depleted naïve PBMC (Effector/Target cell 4:1 ratio), and a serial dilution of anti-PSMAxCD3 bispecific antibody or the IgG4 control (concentration range: 0.42 nM to 0.1 μM), alone or in combination with a fixed concentration of PSMAxCD28 costimulatory molecules bs16429D or bs16431D at 2.5 ug/ml (16.7 nM) for 96 hours at 37° C.

Post incubation, cells were removed from cell culture plates Trypsin-EDTA (Millipore, Cat. #SM-2004-C) dissociation buffer), and analyzed by FACS on a FACS BD LSRFortessa-X20 (BD).

For FACS analysis, cells were stained with a viability far red cell tracker (Invitrogen) and directly conjugated antibodies to CD2, CD4, CD8 and CD25 (BD). Samples were run with calibration beads for cell counting. For the assessment of specificity of killing, target cells were gated as Violet cell tracker positive populations. Percent of live target cells was calculated as follows: percentage (%) of viable cells=(R1/R2)*100, where R1=percentage (%) of live target cells in the presence of antibody, and R2=percentage (%) live target cells in the absence of test antibody. T cell activation was measured by the percent of activated ($CD25^+$) T cells out of $CD2^+/CD4^+$ or $CD2^+/CD8^+$ T cells. T cell count was measured by calculating the number of live $CD4^+$ or $CD8^+$ cells per calibration bead.

The levels of cytokines accumulated in the media were analyzed using the BD cytometric Bead Array (CBA) human Thl/Th2/Th17 Cytokine kit, following the manufacturer's protocol.

For FACS analysis, cells were stained with a dead/live Near IR Reactive (Invitrogen, Cat. #L34976) dye. Five hundred thousand ($5\times10^5$) counting beads were added to each well immediately before FACS analysis. One hundred thousand ($1\times10^5$) beads were collected for each sample. For the assessment of specificity of killing, cells were gated on live Violet labeled populations. Percent of live population was recorded and used for the calculation of survival.

T cell activation and upregulation of the PD-1 marker were assessed by incubating cells with directly conjugated antibodies to CD2, CD4, CD8, CD25 and PD-1, and by reporting the percent of late activated (CD25+/CD8+) T cells and PD-1+/CD4+ T cells out of total T cells (CD2+). The information of the directly conjugated antibodies is as follows: CD2, PE: CD2 (CI: RPA-2.1), BD, Cat. #555327; CD4, PerCP-Cy5.5: CD4 (CI: OKT-4), Biolegend, Cat. #317428; CD8, APC: CD8 (CI: RPA-T8), Biolegend, Cat. #301049; CD25, BV510: CD25 (CI:M-A251), BD, Cat. #563352; and PD-1, PE-Cy7: PD1 (CI:EH12.2H7), Biolegend, Cat. #329918.

The supernatant of the assay wells from the human PBMC assay were assessed for Thl/Th2 cytokine release using the BD cytometric bead array human kit (BD, Cat. #560484) and following the manufacturer protocol.

Results, Summary and Conclusions

Figure 6A:
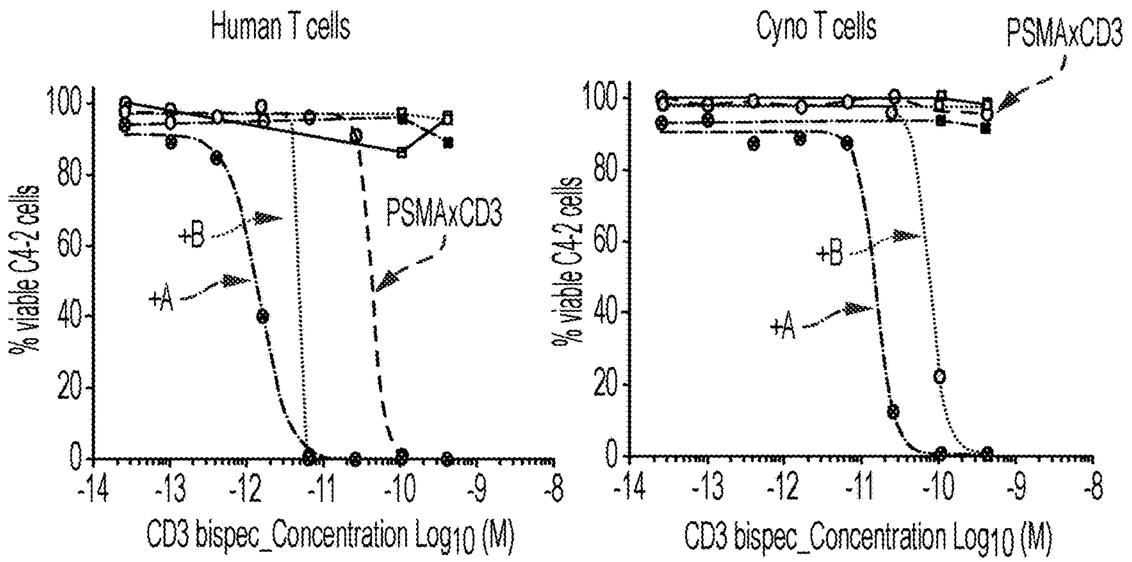
FIGS. 6A and 6B show that anti-PSMAxCD28 enhanced the cytotoxic potency of anti-PSMAxCD3 in the presence of prostate carcinoma and human or cynomolgus T cells.
Figure 6B:
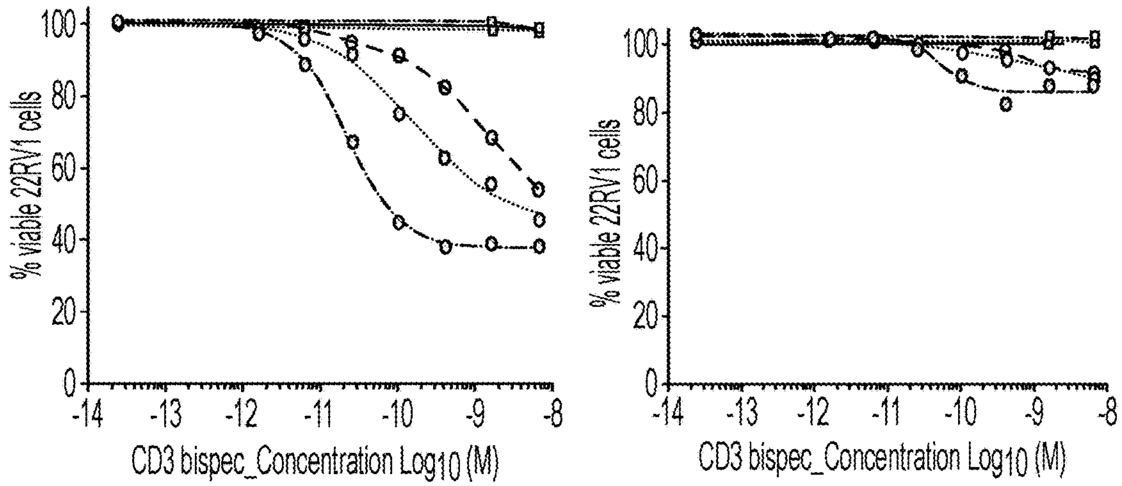

FIGS. 6A and 6B shows that anti-PSMAxCD28 enhanced the cytotoxic potency of bs13644D (anti-PSMAxCD3) in the presence of human or cynomolgus T cells. The anti-PSMAxCD3 bispecific antibody was tested for its ability to induce naïve human T cells to kill target cells expressing human PSMA as a single agent, or in the presence of a costimulatory anti-PSMAxCD28 bispecific antibody. In the study as shown in FIGS. 6A and 6B, the anti-PSMAxCD28 antibody was fixed at 2.5 μg/ml. The anti-PSMAxCD3 was serially diluted at 1:4 fold. The antibodies were incubated with cells for 96 hours. Table 16 summarizes the components of the antibodies used in this study.

TABLE 16

Components of Bispecific Antibodies in Cytotoxic Potency Studies

| AbPID | Antibody Format | PSMA arm [VH] | CD28 arm [VH] | Light Chain |
|---|---|---|---|---|
| bs16429D | PSMA × CD28 | mAb11838P2 | mAb14226P2 | 3-20 ULC |
| bs16431D | PSMA × CD28 | mAb11810P2 | mAb14216P2 | 1-39 ULC |
| bs13644D | PSMA (mAB11835P2) × CD3 (7221G) | | | 1-39 ULC |
| bs17664D | EGFRvIII × CD3(7221G) Control | | | 1-39 ULC |

Figure 6B:
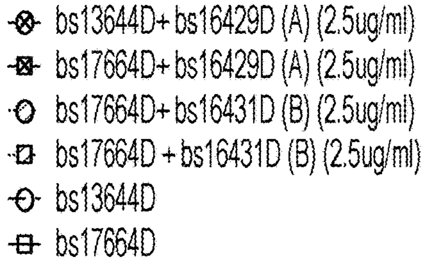

It was tested if the exemplary anti-PSMAxCD28 bispecific antibodies could enhance T cell activation and cytotoxicity on prostate cancer cells by targeting PSMA. Using the FACS based cytotoxicity and T cell activation assay, the exemplary anti-PSMAxCD28 bispecific antibodies were test in combination with PSMAxCD3 (FIGS. 6, 7A-7D). Human PBMC containing T cells were co-cultured with C4-2 prostate cancer cells expressing endogenously high levels of PSMA (Data not shown). PSMAxCD28 significantly increased the potency of cytotoxicity induced by PSMAxCD3 alone shifting the EC50 from $4.3\times10^{-11}$ to $1.5\times10^{-12}$ (over a log shift in potency) (FIGS. 6 and 7A). Concordant with the induction of T cell cytotoxicity, PSMAxCD28 boosted the levels of IFNγ release induced by PSMAxCD3 by 4-fold (FIG. 7B). Similarly, the combination of PSMAxCD28 and PSMAxCD3 increased the numbers of CD4 and CD8 T cells and expression of the activation marker CD25 (FIGS. 7C and 7D). No effect on T cell cytotoxicity or activation was observed when the exemplary anti-PSMAxCD28 bispecific antibodies were in combination with a non-targeting CD3 bispecific antibody. Furthermore, to show that the exemplary anti-PSMAxCD28 bispecific antibody can potentiate PSMAxCD3 cytotoxicity and activation of T cells from nonhuman primates, the same assays were performed obtaining similar results using PBMC from cynomolgus monkeys (FIGS. 6, 7E-7G). These results demonstrated that the exemplary anti-PSMAxCD28 bispecific antibody can potently enhance PSMAxCD3 mediated T cell activation not only by way of proliferation and cytokine release but also cytotoxicity. FIG. 7H shows that the exemplary anti-PSMAxCD28 bispecific antibody binds to cellular targets as measured by flow cytometry.

The anti-PSMA×CD3 bispecific antibody activated and directed human T cells to deplete C4-2 cells (human prostate cancer cell line). Target cell killing was observed in the presence of the anti-PSMAxCD3 bispecific antibody and C4-2 cells were killed in a dose-dependent manner with picomolar $EC_{50}S$ (Table 17). The observed target-cell lysis was associated with upregulation of CD25+ and PD-1+ cells on CD2+ T cells, again with picomolar $EC_{50}S$ (Table 17). The anti-PSMAxCD3 bispecific antibody induced the release of human cytokines. The cytotoxic activity observed with the anti-PSMAxCD3 bispecific antibody as a single agent was enhanced in the presence of a fixed concentration of anti-PSMAxCD28 costimulatory molecules (bispecific antibodies) (Table 17).

In summary, co-stimulation by anti-PSMAxCD28 bispecific antibody increased T cell activation, PD-1 upregulation, and cytokine release when compared to what was observed with anti-PSMAxCD3 bispecific antibody as a single agent. Table 16 summarizes the experiment results using human PBMCs.

TABLE 17

Effects of Anti-PSMA × CD28 on Cytotoxicity of anti-PSMA × CD3 to C4-2 Cells in the Presence of Human PBMCs

| Antibody | C4-2 Kill $EC_{50}$ [M] | T cell activation $EC_{50}$ [M] (CD8+/CD25+) | PD-1 upregulation EC50 [M] (CD4+/PD1+) |
|---|---|---|---|
| Anti-PSMA × CD3 | 4.35E−11 | 7.53E−11 | 3.03E−11 |
| Anti-PSMA × CD3 + bs16429D | 1.45E−12 | 4.95E−12 | 3.71E−12 |
| Anti-PSMA × CD3 + bs16431D | 4.88E−12 | 6.44E−12 | 4.38E−12 |

The anti-PSMAxCD3 bispecific antibody was also tested for its ability to induce naïve cynomolgus T cells to kill target cells expressing human PSMA as a single agent, or in the presence of a costimulatory anti-PSMAxCD28 bispecific antibody. At the selected antibody titration, the anti-PSMAxCD3 bispecific antibody activated human T cells but did not direct T cells to deplete C4-2 cells (Table 18). Co-stimulation with an anti-PSMAxCD28 antibody resulted in increased T-cell activation, an enhancement of cytotoxic activity, and upregulation of the PD-1 marker on T cells (Table 18).

TABLE 18

Effects of anti-PSMA × CD28 on Cytotoxicity of anti-PSMA × CD3 to C4-2 Cells in the Presence of Cynomolgus PBMCs

| Antibody | C4-2 Kill $EC_{50}$ [M] | T cell activation $EC_{50}$ [M] (CD8+/CD25+) | PD-1 upregulation EC50 [M] (CD4+/PD1+) |
|---|---|---|---|
| Anti-PSMA × CD3 | N/A | 1.71E−10 | 2.29E−10 |
| Anti-PSMA × CD3 + bs16429D | 1.55E−11 | 1.64E−11 | 5.64E−12 |
| Anti-PSMA × CD3 + bs16431D | 7.72E−11 | 2.76E−11 | 2.66E−11 |

Example 9. Cytokine Release from Cells

As stated elsewhere herein, ex vivo cytokine release assays using human PBMCS in a "soluble" format failed to predict cytokine release. Therefor, "coated" assay formats were developed.

The anti-PSMA/CD28 bispecific and anti-CD28 antibodies of this invention were evaluated for their ability to induce human PBMC proliferation and cytokine release from cells using a coated assay format. For PBMC proliferation assay, freshly isolated PBMC were used at $1\times10^5$/well. For co-culture, mitomycin C treated C4-2 cells were added at $1\times10^4$/well. Antibody dilutions are wet-coated or dry-coated onto plates overnight. Plates are washed prior to addition of PBMC. Supernatants were collected at ~54 hours for cytokine analysis by Meso Scale Diagnostics (MSD, Rockville, MD). 3H thymidine was added for 18 hours, and proliferation was measured.

Results showed that soluble anti-PSMA×CD28 bispecific antibody induced proliferation of human PBMC in the presence of a CD3 stimulus. By contrast, anti-CD28 superagonist induced proliferation of human PBMC in the absence of a CD3 stimulus (Data not shown).

Furthermore, wet-Coated bs16429D (PSMA×CD28 "A") and mAb14226P2 (CD28 Parental "A") induced less cytokine release than Wet-Coated anti-CD28 superagonist, while bs 16431D (PSMA×CD28 "B") and mAb14216P2 (CD28 Parental "B") did not induced significantly more cytokine release compared to control (Data not shown.).

The anti-CD28 antibody of the present invention shows several different properties compared to the superagonist TGN1412. Conventional CD28 agonistic mAbs (non-superagonist) are thought to bind to membrane-distal epitopes, allowing only monovalent Ab binding (Dennehy et al., Cutting Edge: monovalency of CD28 maintains the antigen dependence of T cell costimulatory responses, J. of Immunol. 176 (10): 5725-29 (2006)). CD28 antibodies drive optimal T cell activation in the presence of antigen specific recognition of peptide-MHC by TCR. CD28 signaling regulates the threshold for TCR activation and significantly decreases the number of TCR engagements needed for effective T cell activation. By contrast, TGN anti-CD28 antibody possessed a few super-agonistic properties (Luhder et al., Topological requirements and signaling properties of T cell-activating, anti-CD28 antibody superagonists, J. of Exp. Med. 197 (8): 955-966 (2003)); Riley et al., the CD28 family: a T-cell rheostat for therapeutic control of T-cell activation, Blood, 105 (1): 13-21 (2005)). For example, TGN anti-CD28 induced potent T-cell proliferation and IL2 production in vitro and in vivo even in the absence of TCR signaling, boosted NF-kB activity more effectively than conventional anti-CD28/CD3 signaling and induce AP-1/SRE activation, and bound to CD28 epitopes proximal to the cell surface allowing bivalent binding.

Accordingly, as shown in FIG. 8, CD28 superagonist TGN 1412 activated AP-1 reporter in the absence of CD3 primary stimulation. By contrast, the anti-CD28 antibody of this invention (the parent of PSMA×CD28) minimally activated AP-1 in an AP-1 luciferase bioassay.

Example 10. In Vivo Study of Anti-PSMAxCD28 Antibody

Syngeneic Tumor Model

Consistent with the in vitro study in Example 8, combining tumor antigen targeted anti-CD3×PSMA and anti-CD28×PSMA bispecific antibodies enhanced tumor clearance in a mouse model. To test the effectiveness of anti-PSMAxCD28 bispecific antibody as a monotherapy or in combination with anti-PSMAxCD3 bispecific antibody, syngeneic tumor experiments were performed in mice expressing human CD28, human CD3 and human PSMA in place of the corresponding mouse genes generated using Velocigene proprietary technology (hCD3/hCD28/hPSMA mice). It was concluded that anti-PSMAxCD28 bispecific enhances anti-tumor immunity in vivo by anti-PSMAxCD3-induced T cell activation.

T cell activation is initiated upon binding of the T Cell Receptor (TCR)/CD3 complex to peptide-MHC complexes ("signal 1"); activation is then enhanced by engagement of a second "co-stimulatory" receptor, such as the CD28 receptor on T cells binding to its cognate ligand(s) on the target cell ("signal 2"). Recently described CD3-based "bispecific antibodies" act by replacing conventional signal 1, linking T cells to tumor cells by binding a tumor-specific antigen (TSA) with one arm of the bispecific antibody, and bridging to TCR/CD3 with the other. Although some of these TSAxCD3 bispecifics have demonstrated promising anti-tumor efficacy in cancer patients, their activity remains to be optimized. As described elsewhere herein, introduced in the present invention is a novel class of bispecific antibodies that mimic signal 2, by bridging a second TSA to the co-stimulatory CD28 receptor on T cells. These bispecific antibodies are referred to as TSAxCD28 bispecifics, or anti-TSA/CD28 bispecifics. As described herein, one exemplary antibody of the present invention is specific for prostate cancer antigens (e.g., PSMA). Unlike CD28 superagonists, which broadly activate T cells and in certain cases resulted in profound toxicity in early clinical trials, these TSAxCD28 bispecifics show limited activity and no toxicity when used alone in genetically-humanized immuno-competent mouse models, or in primates. However, when combined with TSAxCD3 bispecific antibodies, the exemplary antibody of the invention enhanced the artificial synapse between a T cell and its target cell, potentiated T cell activation, and markedly improved anti-tumor activity of CD3-bispecifics in syngeneic tumor models. Combining this novel class of CD28-co-stimulatory bispecific antibodies with the emerging class of TSAxCD3 bispecifics may provide well-tolerated, "off-the shelf" antibody therapies with potentially enhanced anti-tumor efficacy.

The ability of T cells to recognize and kill their cellular targets—such as virally-infected cells or tumor cells-depends on a coordinated set of interactions. Foremost among these is the recognition and binding of the target cell by the TCR complex (which includes the associated CD3 γ, δ, ε, ζ chains); this interaction has been referred to as "signal 1" for T cell activation. The TCR can recognize viral or tumor peptide presented in the groove of an MHC proteins expressed on the surface of the target cells. This binding is typically of low-affinity; therefore for successful triggering of signal 1, it is important to have clustering of many TCR complexes along the interface between a T cell and its target cell, and this interface has been referred to as the immune synapse (J. B. Huppa, M. M. Davis, T-cell-antigen recognition and the immunological synapse. *Nat Rev Immunol* 3, 973-983 (2003)). T cell activation and proliferation are then further promoted by additional interactions with costimulatory receptors such as CD28 ("signal 2") (J. H. Esensten, Y. A. Helou, G. Chopra, A. Weiss, J. A. Bluestone, CD28 Costimulation: From Mechanism to Therapy. *Immunity* 44, 973-988 (2016)). When a T cell recognizes a target cell via the TCR complex, and engages signal 2 via CD28 binding to its cognate ligand(s) (CD80/B7.1 and/or CD86/B7.2) on a professional antigen presenting cell or the target cell, T cell activation is enhanced. As with signal 1, CD28-mediated signal 2 is thought to occur via coclustering at the immune synapse.

Conventional monoclonal antibodies targeted against tumor-specific antigens (TSAs) have been used as anti-tumor therapeutics over the last two decades (G. Salles et al., Rituximab in B-Cell Hematologic Malignancies: A Review of 20 Years of Clinical Experience. *Adv Ther* 34, 2232-2273 (2017); M. V. Mateos et al., Daratumumab plus Bortezomib, Melphalan, and Prednisone for Untreated Myeloma. *N Engl J Med* 378, 518-528 (2018): W. Eiermann, G. International Herceptin Study, Trastuzumab combined with chemotherapy for the treatment of HER2-positive metastatic breast cancer: pivotal trial data. *Ann Oncol* 12 Suppl 1, S57-62 (2001); J. M. Connors et al., Brentuximab Vedotin with Chemotherapy for Stage III or IV Hodgkin's Lymphoma. *N Engl J Med* 378, 331-344 (2018); V. Dieras et al., Trastuzumab emtansine versus capecitabine plus lapatinib in patients with previously treated HER2-positive advanced breast cancer (EMILIA): a descriptive analysis of final overall survival results from a randomised, open-label, phase 3 trial. *Lancet Oncol* 18, 732-742 (2017)). However, this class of antibodies had limited ability to induce T cell mediated cytotoxicity, and instead acted by promoting antibody-dependent cellular cytotoxicity (ADCC) and/or complement-dependent cytotoxicity (CDC), or by delivering a toxin to the tumor cells. Recently, a new class of bispecific antibodies (TSAxCD3) has emerged that can efficiently trigger T cell-mediated killing of tumor cells, by linking a T cell to a tumor cell and activating the CD3/TCR complex (usually via the e chain of CD3) via a surrogate mechanism, thus mimicking signal 1. An early version of such a bispecific (one arm binding to CD19 on leukemia cells, while the other binds to CD3) recently received regulatory approval for B cell acute lymphoblastic leukemia (R. Bargou et al., Tumor regression in cancer patients by very low doses of a T cell engaging antibody. *Science* 321, 974-977 (2008); H. Kantarjian et al., Blinatumomab versus Chemotherapy for Advanced Acute Lymphoblastic Leukemia. *N Engl J Med* 376, 836-847 (2017)). Recently, more advanced versions of bispecifics have been shown to have good activity against non-Hodgkin's Lymphomas, targeting CD20 on these lymphomas (E. J. Smith et al., A novel, native-format bispecific antibody triggering T-cell killing of Bcells is robustly active in mouse tumor models and cynomolgus monkeys. *Sci Rep* 5, 17943 (2015); L. L. Sun et al., Anti-CD20/CD3 T cell-dependent bispecific antibody for the treatment of B cell malignancies. *Sci Transl Med* 7, 287ra270 (2015); M. Bacac et al., CD20-TCB with Obinutuzumab Pretreatment as Next-Generation Treatment of Hematologic Malignancies. *Clin Cancer Res* 24, 4785-4797 (2018); R. Bannerji et al., Emerging Clinical Activity of REGN1979, an Anti-CD20×Anti-CD3 Bispecific Antibody, in Patients with Relapsed/Refractory Follicular Lymphoma (FL), Diffuse Large B-Cell Lymphoma (DLBCL), and Other B-Cell Non-Hodgkin Lymphoma (B-NHL) Subtypes. *American Society of Hematology*, (2018); L. Budde et al., Mosunetuzumab, a Full-Length Bispecific CD20/CD3 Antibody, Displays Clinical Activity in Relapsed/Refractory B-Cell Non-Hodgkin Lymphoma (NHL): Interim Safety and Efficacy Results from a Phase 1 Study. *American Society of Hematology*, (2018)). However, although TSAxCD3 bispecifics are emerging as an important new class of immunotherapy in hematologic malignancies, cross-study comparisons (E. A. Zhukovsky, R. J. Morse, M. V. Maus, Bispecific antibodies and CARs: generalized immunotherapeutics harnessing T cell redirection. *Curr Opin Immunol* 40, 24-35 (2016)) suggest that in some cases they may not be achieving the level of efficacy seen with the personalized chimeric antigen receptor T cell (CAR-T) therapies.

One of the reasons for the strong efficacy of CAR-T therapies is that the chimeric antigen receptor (CAR) is engineered to provide both signal 1 (via a portion of the CD3z cytodomain) and signal 2 (e.g., via a portion of the CD28 cytodomain) upon binding to its target on a tumor cell. Two CAR-T cell therapies have recently received FDA approval for B-cell malignancies, both of which act by binding and targeting the antigen CD19 (S. S. Neelapu et al., Axicabtagene Ciloleucel CAR T-Cell Therapy in Refractory Large B Cell Lymphoma. *N Engl J Med* 377, 2531-2544 (2017); S. J. Schuster et al., Chimeric Antigen Receptor T Cells in Refractory B-Cell Lymphomas. *N Engl J Med* 377, 2545-2554 (2017)). CAR-T cell approaches can be associated with severe adverse effects such as cytokine release syndrome (CRS) and neurotoxicity (S. S. Neelapu et al., Chimeric antigen receptor T-cell therapy-assessment and management of toxicities. *Nat Rev Clin Oncol* 15, 47-62 (2018); J. Gust et al., Endothelial Activation and Blood-Brain Barrier Disruption in Neurotoxicity after Adoptive Immunotherapy with CD19 CAR-T Cells. *Cancer Discov* 7, 1404-1419 (2017); A. Shimabukuro-Vornhagen et al., Cytokine release syndrome. *J Immunother Cancer* 6, 56 (2018)); and due to the highly-personalized manufacturing processes and requirement for preconditioning chemotherapeutic regimens (S. S. Neelapu et al., Axicabtagene Ciloleucel CAR T-Cell Therapy in Refractory Large B Cell Lymphoma. *N Engl J Med* 377, 2531-2544 (2017); S. J. Schuster et al., Chimeric Antigen Receptor T Cells in Refractory B-Cell Lymphomas. *N Engl J Med* 377, 2545-2554 (2017); P. Salmikangas, N. Kinsella, P. Chamberlain, Chimeric Antigen Receptor T-Cells (CART-Cells) for Cancer Immunotherapy—Moving Target for Industry? *Pharm Res* 35, 152 (2018)), many patients are not deemed suitable candidates.

The advantages of TSAxCD3 bispecifics as relatively well-tolerated and “off-the-shelf” therapeutic solutions for broader patient populations would be enhanced if their anti-tumor activity could be further optimized, especially if this could be done without sacrificing tolerability, or perhaps even increase, specificity for tumor cells as opposed to normal cells. Towards this end, it was hypothesized that pairing TSAxCD3 bispecifics with a novel class of bispecifics that independently activates signal 2 could provide potential increased efficacy as well as an opportunity for enhanced specificity. Therefore, a second class of bispecifics were designed. These bispecifics could either engage a second epitope on the same tumor-specific antigen or a second separate tumor antigen, with the co-stimulatory receptor CD28 (TSAxCD28 Bispecifics) expressed on T cells. It was reasoned that combining TSA1×CD3 with a TSA2×CD28 should allow directed and enhanced surrogate activation of T cells by triggering both signal 1 and signal 2, with specificity targeted only against tumor cells expressing both epitopes or both antigens, allowing for greater anti-tumor activity together with an opportunity for increased specificity.

Described herein are the generation and testing of TSAxCD28 co-stimulatory bispecific antibodies targeted to prostate cancer (PSMAxCD28, which binds prostate-specific membrane tumor antigen). Toxicology studies in genetically-humanized immunocompetent mice as well as in cynomolgus monkeys demonstrate that these bispecifics exhibit limited activity and no toxicity as single agents. However, these novel co-stimulatory bispecifics can be effectively combined with the emerging class of TSAxCD3 bispecifics to potentiate anti-tumor responses in syngeneic tumor models. Collectively, these data suggest that combining this novel class of CD28-based bispecifics (TSAxCD28) with the CD3-based bispecifics (TSAxCD3) may provide well-tolerated, “off-the-shelf” biologics solutions with markedly enhanced and synergistic anti-tumor activity.

Materials and Methods

The following materials and methods were used in Examples 10 and 13.

Syngeneic Tumor Studies

Mice expressing human CD28, human CD3 and human PSMA in place of the corresponding mouse genes were generated using Velocigene® technology (referred to as hCD3/hCD28/hPSMA humanized mice), as described previously (Valenzuela (2003), Nat Biotechnol, Jun; 21 (6): 652-9; Crawford et al. 2018, Manuscript in preparation). For each humanized mouse, correct gene targeting in F1H4 (C57BL/6×129 hybrid) embryonic stem (ES) cell clones was identified by a loss of allele assay as described previously (Poueymirou et al (2007), Nat Biotechnol, Jan; 25 (1): 91-9). Targeted ES cells were injected into 8-cell stage Swiss Webster embryos to produce fully F0 generation heterozygous mice for breeding with C57BL/6N mice (Taconic, Rensselaer, NY) to homozygosity. hCD3/hCD28/hPSMA mice (4-8 mice/group, 8-16 weeks old) were injected subcutaneously with $1\times10^6$ MC38/hPSMA tumor cells. Anti-PSMAxCD28 bispecific antibody, anti-PSMAxCD3 bispecific antibody or a human IgG4 isotype control were administered as a monotherapy or in combination by intraperitoneal injection on day 0, 3 and 7 at 5 mg/kg.

Tumor growth was monitored over time using caliper measurements of X and Y diameter. Tumor volume was calculated (X*Y*(X/2)). Mice were euthanized when tumor size was greater than 2000 $mm^3$.

Measurement of Serum Cytokine Levels in Mice

At the indicated time points, blood was collected by submandibular puncture into microtainer serum tubes (BD 365967). Cytokine levels were analyzed using a V-plex Human ProInflammatory-10 Plex kit following the manufacturer’s instructions (Meso Scale Diagnostics, Rockville, MA).

Results, Summary and Conclusions

The expression of human CD28 on T and NK cells was validated by FACS (Data not shown). The triple humanized mice were functionally validated using in vitro T cell proliferation assay (Data not shown). PSMA expression was confirmed by QPCR (Data not shown). MC38/hPSMA tumor growth was monitored in the triple humanized hCD3/hCD28/hPSMA mice (described above) over time (FIG. 9A). Compared to isotype control, both PSMAxCD3 and PSMAxCD28 monotherapy treatments significantly inhibited tumor growth ($p<0.001$ and $p<0.0001$, respectively). Tumor growth was further significantly inhibited by combination therapy ($p<0.00001$). Compared to isotype control, the combination of PSMAxCD3 and PSMAxCD28 bispecifics provided the greatest cytokine production (FIGS. 9C and 9D). To further understand the role of combination therapy on the activation state of intra-tumoral CD8+ T cells, viSNE analysis was performed (FIG. 9B). viSNE is a tool to map high dimensional cytometry data onto 2D, while conserving high dimensional structure. Each treatment drove unique CD8+ T cell clusters in the spleen and tumor. Combination therapy drove the expansion of an activated/memory T cell phenotype (expressing TCF1, CD1-2, CD127, PD-1, ICOS, KLRG1 and CD38), as shown in cluster 4 in the tumor.

Studies were conducted to determine the levels of serum cytokines (IFNγ, IL-2, IL-6, IL-10, TNFα, IL-4, and IL-5) in both $hCD3^{+/+}/hPSMA^{+/+}/hCD28^{+/+}$ mice and $hCD3^{+/-}/hPSMA^{+/-}/hCD28^{+/-}$ mice. Blood were obtained at day 0 (4 hours), 3, 7, and 11 after the treatments. Except for IL-10 in hCD3$^{+/+}$/hPSMA$^{+/+}$/hCD28$^{+/+}$ mice, at day 0, the cytokine levels increased significantly in treatments that include anti-PSMAxCD3 antibodies, with the combination therapy with anti-PSMAxCD3 and anti-PSMAxCD28 providing the greatest cytokine release. By contrast, IgG control and anti-PSMAxCD28 monotherapy did not cause increased cytokine production. Except for IL-5 and IL-10, cytokine productions decreased after three (3) days to similar level in all the treatment group. IL-5 production had significantly higher production on day 3, although lower than day 0, in hCD3$^{+/+}$/hPSMA$^{+/+}$/hCD28$^{+/+}$, but not in hCD3$^{+/-}$/hPSMA$^{+/-}$/hCD28$^{+/-}$ mice that received combination treatment. In hCD3$^{+/+}$/hPSMA$^{+/+}$/hCD28$^{+/+}$ mice, the production of IL-10 were similar for all treatment group on day 0 and day 3, but the combination therapy produced significantly higher level in combination therapy on day 7 and day 11. In hCD3$^{+/-}$/hPSMA$^{+/-}$/hCD28$^{+/-}$ mice, combination therapy produced significantly more IL-10 at day 0, day 3, and day 11, but not day 7. Anti-PSMAxCD3 monotherapy produced significantly more IL-10 at day 0, and day 3, but not day 7 and day 11. Anti-PSMAxCD28 monotherapy only produced significantly more IL-10 at day 11 (Data not shown).

As shown in FIG. 9A, unlike the previous in vitro analyses in which the CD28-bispecifics had very limited single-agent activity (see above Example 8), the CD28-bispecifics in this syngeneic MC38/hPSMA models had more notable activity as single agents. This suggested that "signal 1" was already being activated to some degree in this MC38 model. Consistent with this, it has been previously shown that MC38 tumor cells express high levels of re-activated endogenous retroviral proteins such as p15E, and that C57BL6 mice can generate endogenous T cells that recognize and respond to this neo-epitope (J. C. Yang, D. Perry-Lalley, The envelope protein of an endogenous murine retrovirus is a tumor-associated T-cell antigen for multiple murine tumors. *J Immunother* 23, 177-183 (2000); H. J. Zeh, 3rd, D. Perry-Lalley, M. E. Dudley, S. A. Rosenberg, J. C. Yang, High avidity CTLs for two self-antigens demonstrate superior in vitro and in vivo antitumor efficacy. *J Immunol* 162, 989-994 (1999)). Indeed, it was confirmed that in the MC38 models, intratrumoral T cells responsive to this p15E neo-antigen could easily be detected. Thus, CD28-bispecifics in this syngeneic tumor models can boost endogenous TCR/CD3-dependent T cell responses, which can then further be enhanced by providing additional "signal 1" activation via a CD3-bispecific antibody.

To determine the cellular mechanism underlying the combination therapy, tumor-infiltrating and spleen CD8+ T cells were profiled from these experiments by high-dimensional flow cytometry and used unsupervised clustering approaches. It was found that each treatment drove unique CD8+ T cell clusters in spleen and tumor. Single treatment regimens reduced intra-tumoral CD8+ T cells with less activated phenotype (lower ICOS, KLRG1, Ki67, PD1, CD38, and LAG3, FIG. 9E) as shown in cluster C35. However, combination therapy significantly drove the expansion of a more activated/memory T cell phenotype (expressing Tcf1, CD122, CD127, PD1, ICOS, KLRG1 and CD38, FIG. 9B) as shown in cluster C4.

Anti-CD28×Anti-PSMA does not Induce Elevation in Serum Cytokine in CD28/CD3/PSMA Humanized Mice in Absence and Presence of Tumor As stated elsewhere herein, TGN1412, the superagonist anti-CD28 antibody, induced "cytokine storm" detrimental to the patient. The anti-CD28 antibody and the anti-CD28×PSMA bispecific antibody of the invention did not cause cytokine storm. In this study, several antibodies (summarized in Table 19) were administered to hCD3/hCD28/hPSMA humanized mice at either 2.5 mg/kg or 0.25 mg/kg dosage. Blood was drawn from mice at 4 hours and 3 days after the antibody administrations. As shown in FIG. 10, anti-PSMAxCD28 bispecific antibodies or the parental CD28 bivalent antibodies did not induce serum cytokine production in CD3/CD28/PSMA humanized mice in absence of tumor.

TABLE 19

Antibodies for Cytokine Storm Study in hCD3/hCD28/hPSMA Humanized Mice

| Antibody ID | Lot # | Name |
|---|---|---|
| REGN1945 | REGN1945-L49 | hIgG4 |
| mAb14226P2 | REGN5705-L1 | CD28 mAb |
| REGN2329 (TeGenero) | REGN2329-L3 | CD28 SA |
| bs16429D | bs16429D-L2 | PSMA × CD28 |
| BE0146 | 614216J2B | PD1, RMP1-14 |
| bs15780D | bs15780D-L2 | PSMA × CD3 |

At 2.5 mg/kg, TGN1412 can cause significant increase in the blood level of IL-2, IL-4, IL-5, and TNF α (data not shown).

Furthermore, as shown in FIG. 28, anti-PSMAxCD28 treatment alone or combined treatment with anti-PD1 did not elevate serum cytokines in tumor bearing mice. By contrast, anti-PSMAxCD3 treatment, alone or in combination with anti-PD1, increased serum cytokine level, such as TNFα, IL-5, IL-10, IL-2, and IL-4 in tumor bearing mice. Anti-PSMAxCD3 treatment induced cytokine expression at 4 hours post dose. Cytokine elevation was not sustained past day 7. This study was done in MC38/hPSMA tumor bearing hCD3/hCD28/hPSMA humanized mice. Serum was collected from MC38/hPSMA tumor bearing hCD3/hCD28/hPSMA humanized mice at 4 hours post dose on day 0 and day 7, 4 days later with 5 mg/kg of the indicated antibodies or bispecifics. Serum cytokines were measured using a 10-plex mouse cytokine MSD kit following the manufacturer protocol.

In addition, as shown in FIG. 11, CD28 superagonist treatment drove cytokine response at 4 hours in PBMC-engrafted NSG mice, while anti-CD28 antibody of the invention did not. In the study as shown in FIG. 11, immunodeficient NSG mice were engrafted with $5\times10^6$ PBMC from a normal healthy donor on day-10. On day-1, systemic engraftment of T cells was confirmed by staining peripheral blood for human T cell markers. On day 0, the mice were injected i.p. with either 50 μg of an IgG4 isotype control antibody, 5 μg or 50 μg of anti-CD28 superagonist, or 5 μg or 50 μg of anti-CD28 mAb14226P2 antibody. Four hours after antibody injections, blood was harvested from the animals and serum was prepared. Cytokine concentrations in the serum were analyzed by multiplex assay (Meso Scale Discovery V-PLEX kit). While anti-CD28 superagonist drove increased serum levels of interferon gamma (IFN-γ), IL-2, IL-6, and TNFα compared to isotype control antibody-treated animals, no increase in cytokine response was seen in the serum of animals treated with anti-CD28 mAb14226P2. Accordingly, the bispecific anti-CD28×PSMA has a potentially safer toxicology profile among costimulatory bispecific antigen-binding molecules. The bispecific anti-CD28×PSMA did not elicit a cytokine response, whereas anti-CD3×PSMA did. As shown in FIG. 12, anti-CD3×PSMA caused elevated IFNγ in humanized mice, whereas anti-CD28×PSMA did not. In this study, serum was collected from MC38/hPSMA tumor bearing CD3/CD28/PSMA or CD3/CD28 humanized mice at 4 hours after dosing with 5 mg/kg of the indicated bispecifics. Serum cytokines were measured using a 10-plex mouse cytokine MSD kit following the manufacturer protocol. Data points represent individual cytokine levels per mouse. Bars on the graph represent the average per treatment group. Error bars represent+/−SEM. Statistical significance determined with 1-way ANOVA and Holm-Sidak multiple comparisons test using isotype treated mice as controls (**, $p<0.01$)

Consistent with the humanized mice data, anti-CD3×PSMA bispecific antibody caused elevated CRP and systemic cytokine release in non-human primates, cynomolgus monkey. In the monkey study, anti-CD3×PSMA bispecific antibody was administered into cynomolgus monkey at 0.01, 0.1, and 0.5 mg/kg dosage. The monkey showed the following symptoms: clinical signs by day one such as vomitus, hunched, red/discolored skin; elevated CRP (about 10 vs 1 mg/dL in control mice); elevated plasma cytokines (IL-6, TNF-α, IFN-γ, IL-2, and MCP); and drop in absolute T cell number in blood (data not shown).

Moreover, mice receiving anti-CD28×PSMA treatment showed no cytokine production or T cell margination in comparison to anti-PSMAxCD3 or anti-CD28 superagonist treatment (FIGS. 13A and 13B).

SUMMARY

It has long been appreciated that T cell activation via the TCR complex ("signal 1") can be markedly enhanced by co-stimulatory signals such as those mediated when the CD28 receptor on T cells engages its ligands (CD80/B7.1 and CD86/B7.2) on target cells ("signal 2") (J. H. Esensten, Y. A. Helou, G. Chopra, A. Weiss, J. A. Bluestone, CD28 Costimulation: From Mechanism to Therapy. *Immunity* 44, 973-988 (2016)). In agreement with the data disclosed herein, the potential for CD28-costimulation to enhance the anti-tumor activity of T cells was first demonstrated by studies in which B7 ligands were over-expressed on tumor cells (R. H. Schwartz, Costimulation of T lymphocytes: the role of CD28, CTLA-4, and B7/BB1 in interleukin-2 production and immunotherapy. Cell 71, 1065-1068 (1992); L. Chen et al., Costimulation of antitumor immunity by the B7 counterreceptor for the T lymphocyte molecules CD28 and CTLA-4. *Cell* 71, 1093-1102 (1992)), which showed improved T cell rejection of such B7-expressing tumors. This potential inspired efforts to evaluate CD28-activating antibodies in human trials. Tragically, the 2006 trial of such an antibody (TGN1412) resulted in life-threatening complications in all six human volunteers (G. Suntharalingam et al., Cytokine storm in a phase 1 trial of the anti-CD28 monoclonal antibody TGN1412. *N Engl J Med* 355, 1018-1028 (2006)), due to multi-organ failure resulting from massive cytokine release syndrome (CRS). This catastrophe led to cessation of any further testing of CD28-activating antibodies in humans.

Described herein is a novel class of CD28 costimulatory bispecific antibodies that can markedly and safely promote anti-tumor activity by providing a co-stimulatory "signal 2". These CD28-bispecifics have limited activity on their own (in the absence of "signal 1"), but can markedly enhance anti-tumor activity in the setting of "signal 1", as can be provided by pairing these CD28-bispecifics with the emerging class of CD3-bispecifics (or if these CD28-bispecifics are used in settings where there are already endogenous populations of tumor-specific T cells). Described herein are the generation and testing of TSAxCD28 co-stimulatory bispecific antibodies targeted against prostate cancer (PSMAxCD28). It was shown showed that, in the absence of "signal 1", these CD28-bispecifics have minimal activity, in vitro or in vivo. However, these CD28-bispecifics can be paired with CD3-bispecifics to form artificial "immune synapses" containing the tumor antigens as well as the TCR and CD28 complexes. Moreover, when paired with appropriate CD3-bispecifics in vitro, these CD28-bispecifics can efficiently and specifically promote T cell activation and tumor cell killing in an antigen-dependent manner. Furthermore, these CD28-bispecifics also efficiently enhance the anti-tumor activity of CD3-bispecifics in vivo, in a tumor antigen-specific manner, in syngeneic tumor models; in such models, the CD28-bispecifics have minimal single-agent activity unless tumor-specific T cells are already present, and in such settings they appear to enhance this specific activity in a tumor-antigen-dependent manner. In addition, TSAxCD28 and TSAxCD3 combination therapy significantly drives expansion of an intratumoral activated/memory T cell phenotype in vivo. Finally, toxicology studies in genetically-humanized immunocompetent mice, as well as in cynomolgus monkeys, demonstrate that these bispecifics exhibit limited activity and no toxicity as single agents, as directly compared to conventional CD28-activating antibodies.

Often, the characterization of human-specific clinical candidates in the field of immunooncology is limited to testing in xenogeneic tumor models with engrafted human immune cells. Although these xenogenic models can be very useful, they have limitations. The mice used in such xenogenic models do not express the human tumor target in their normal tissues, thereby precluding assessment of the test agent in the setting of normal tissue expression of the target. Indeed, if a target is normally also expressed at high levels in normal tissues, this could limit anti-tumor efficacy by diverting the test agent from the tumor, and could result in toxicity on these normal tissues-none of this could be assessed in a xenogenic model. An additional limitation could involve the activity of the engrafted human peripheral blood mononuclear cells (PBMCs) transferred to an immunodeficient mouse, which could differ from that of normal host T cells found in a immune-competent system. To overcome these limitations and provide better models for testing human-specific clinical candidates, double and triple genetically-humanized mice were created herein. In these models, the tumor antigens were genetically humanized to allow for their normal expression in appropriate host tissues, and the CD3 and/or CD28 components were genetically-humanized to allow immunocompetent host cells to respond to the human-specific clinical candidates. In these genetically-humanized immunocompetent syngeneic animal models, it was found that the CD28-bispecifics for the PSMA tumor target enhanced the anti-tumor activity of their appropriate CD3-bispecifics. The similar enhancement of anti-tumor efficacy by the different TSAxCD28 bispecifics across multiple preclinical models suggests that this therapeutic modality is robust and not limited to a specific tumor model, and could have broader utility as a novel combination target class for immunotherapy. Overall, the findings highlight that TSAxCD28 bispecifics can synergize with TSAxCD3 bispecifics and may provide a biologic solution that could markedly enhance the efficacy of the well studied TSAxCD3 bispecifics, in a reasonably safe and well-tolerated manner, justifying testing in human trials.

TSAxCD3 bispecifics represent a promising emerging class of immunotherapy, but further optimization of anti-tumor activity will surely be important in many cases. Just as CAR-T approaches have employed chimeric receptors that artificially activate both "signal 1" and "signal 2" so as to improve their anti-tumor activity (E. A. Zhukovsky, R. J. Morse, M. V. Maus, Bispecific antibodies and CARs: generalized immunotherapeutics harnessing T cell redirection. *Curr Opin Immunol* 40, 24-35 (2016); S. L. Maude et al., Tisagenlecleucel in Children and Young Adults with B-Cell Lymphoblastic Leukemia. *N Engl J Med* 378, 439-448 (2018)), it is shown now the potential benefit of combining CD3-specifics (which provide "signal 1") with CD28-bispecifics (which provide "signal 2") to enhance anti-tumor activity. In addition to the practical benefits that such an approach might have over CAR-T therapies—in that it does not require a laborious cell therapy preparation that must be individually customized for each patient, nor does it require that patients be preemptively "lymphodepleted" via toxic chemotherapy so that they can accept this cell therapy often associated with adverse effects (A. Shimabukuro-Vornhagen et al., Cytokine release syndrome. *J Immunother Cancer* 6, 56 (2018); C. H. June, R. S. O'Connor, O. U. Kawalekar, S. Ghassemi, M. C. Milone, CAR T cell immunotherapy for human cancer. Science 359, 1361-1365 (2018))—the bispecific approach according to the invention offers the potential for increased efficacy as well as increased safety and specificity of action. That is, it is possible to take advantage of "combinatorial targeting", by pairing a CD3-bispecific for one antigen with a CD28-bispecific specific for a second antigen—increased efficacy will only occur on tumor cells expressing both antigens—thus focusing T cell killing only to tumor cells expressing both antigens, while limiting "off target toxicity" in normal tissues expressing only one of the antigens. Collectively, the data disclosed herein suggest that combining CD28-based bispecifics with CD3-based bispecifics may provide well-tolerated, "off-the-shelf" biologics solutions with markedly enhanced and synergistic anti-tumor activity. Initial testing of this possibility in human trials will occur this year.

Example 11. Cynomolgus Toxicology Studies

These studies demonstrated that PSMAxCD28 alone or in combination therapy does not induce systemic T cell action in comparison to CD28 superagonist in cynomolgus monkeys. The exemplary anti-PSMAxCD28 bispecific antibodies of the invention potentiated TAAxCD3 activation of T cells from cynomolgus monkeys (Example 8, FIGS. 7E-7G). To determine the safety and tolerability of the exemplary anti-PSMAxCD28 bispecific antibodies of the invention alone or in combination with anti-PSMAxCD3, a single dose toxicity study was performed in cynomolgus monkeys. Female or male cynomolgus monkeys were assigned to treatment groups as indicated in Table 20.

TABLE 20

Exploratory Single-Dose Monkey Toxicology Study with Anti-PSMA × CD28

| Group | Treatment (single dose) | Total No. of Animals Males | Dose Levels/Dose Escalation (30 minutes IV Infusion) |
|---|---|---|---|
| 1 | PSMA × CD3 | 3 | 0.1 mg/kg |
| 2 | bs16429D | 3 | 1 mg/kg |
| 3 | bs 16429D | 3 | 10 mg/kg |
| 4 | Anti-CD28 Super Agonist "SA" | 3 | 10 mg/kg |
| 5 | bs16429D + anti-PD-1 | 3 | 10 mg/kg + 10 mg/kg |
| 6 | bs16431D + anti-PD-1 | 3 | 10 mg/kg + 10 mg/kg |
| 7 | Isotype Control Ab | 3 | 10 mg/kg |

The cynomolgus monkey study was conducted in accordance with IACUC guidelines. Male cynomolgus monkeys (3 animals/group) received a single dose of each test article via intravenous infusion for approximately 30 minutes (combination treatment was administered as separate infusion for total of 1 hour). Assessment of toxicity was based on clinical observations, qualitative food consumption, body weight, neurological examinations, vital signs (body temperature, heart rate, pulse oximetry, and respiration rate), and clinical and anatomic pathology. Blood and tissue samples were collected for cytokine analysis, FACS immunophenotyping analysis, histopathology and toxicokinetic evaluation. CRP levels were analyzed on a Roche Modular P 800 system. Cytokines were measured by Meso Scale Diagnostics (MSD, Rockville, MD). For peripheral blood flow cytometry, blood was collected into potassium EDTA tubes, lysed, stained with the indicated antibodies such as, anti-CD3, anti-Ki67 and anti-ICOS (BD Biosciences), and analyzed with FACS Canto II. No significant cytokine release, T cell marginalization or T cell activation marker upregulation were observed following single dose administration of PSMAxCD28 at 1 or 10 mg/kg did not induce significant cytokine release, T cell margination or T cell activation marker upregulation (Table 21).

TABLE 21

Cynomolgus Monkey Toxicity Study Summary

| | | Dose | Day 1-clin- | Any Obs. | Absolute T-Cells (E3/μL) | | Proliferating T-Cells Ki67 + (E3/μL) | | CRP (mg/dL) | Plasma Cytokine at 5 hrs post-dose (pg/ml) | | | | | | | |
|---|---|---|---|---|---|---|---|---|---|---|---|---|---|---|---|---|---|
| Molecule | Description | (mg/kg) | ical Obs | Days 2-4 | Pre-test | 5 hr | Pre-test | 168 hr | 24 hr | IL-6 | IL-8 | IL-10 | IFN-γ | TNF-α | IL-2 | IL-4 | IL-5 |
| bs16429D | anti-PSMAxCD28 | 1 | — | — | 6.58 | 7.22 | 0.62 | 0.59 | 0.5 | BLQ* | BLQ | BLQ | BLQ | BLQ | BLQ | BLQ | BLQ |
| | | | — | — | 4.91 | 5.09 | 0.42 | 0.32 | 0.5 | BLQ | BLQ | BLQ | BLQ | BLQ | BLQ | BLQ | BLQ |
| | | | — | — | 4.50 | 4.04 | 0.63 | 0.48 | 1.1 | BLQ | BLQ | BLQ | BLQ | BLQ | BLQ | BLQ | BLQ |

TABLE 21-continued

Cynomolgus Monkey Toxicity Study Summary

| Molecule | Description | Dose (mg/kg) | Day 1-clinical Obs | Any Obs. Days 2-4 | Absolute T-Cells (E3/μL) Pre-test | Absolute T-Cells (E3/μL) 5 hr | Proliferating T-Cells Ki67 + (E3/μL) Pre-test | Proliferating T-Cells Ki67 + (E3/μL) 168 hr | CRP (mg/dL) 24 hr | Plasma Cytokine at 5 hrs post-dose (pg/ml) IL-6 | IL-8 | IL-10 | IFN-γ | TNF-α | IL-2 | IL-4 | IL-5 |
|---|---|---|---|---|---|---|---|---|---|---|---|---|---|---|---|---|---|
| bs16429D | anti | 10 | — | — | 6.03 | 5.73 | 0.33 | 0.35 | 0.2 | BLQ | BLQ | BLQ | BLQ | BLQ | BLQ | BLQ | BLQ |
| | PSMAxCD28 | | — | — | 4.64 | 4.53 | 0.38 | 0.64 | 0.2 | BLQ | BLQ | BLQ | BLQ | BLQ | BLQ | BLQ | BLQ |
| | | | — | — | 10.06 | 7.16 | 0.88 | 0.39 | 1.3 | BLQ | BLQ | BLQ | BLQ | BLQ | BLQ | BLQ | BLQ |
| REGN2329 | anti-CD28 | 10 | — | — | 7.02 | 0.26 | 0.60 | 5.66 | 15.4 | 764 | BLQ | 3364 | BLQ | BLQ | BLQ | BLQ | 1169 |
| (TeGenero) | Super | | — | — | 7.06 | 0.19 | 0.79 | 7.29 | 15 | 2907 | 1095 | 17155 | 333 | BLQ | 238 | BLQ | 615 |
| | agonist | | — | — | 11.87 | 0.66 | 1.13 | 10.96 | 15.3 | 5226 | 5324 | 7918 | 1509 | 163 | 522 | 342 | 198 |
| mAb10154P3 | EGFRVIIIAb | | — | — | 6.39 | 5.62 | 0.62 | 0.39 | 0.8 | BLQ | BLQ | BLQ | BLQ | 151 | BLQ | 335 | BLQ |
| | | | — | — | 7.43 | 7.72 | 0.86 | 0.52 | 11 | BLQ | BLQ | BLQ | BLQ | 267 | BLQ | 378 | BLQ |
| | | | — | — | 3.66 | 4.61 | 0.52 | 0.69 | 0.2 | BLQ | BLQ | BLQ | BLQ | BLQ | BLQ | BLQ | BLQ |

BLQ: Below lower limit of quantification

In contrast, significant cytokine release, lymphocyte marginalization and T cell activation was seen in monkeys administered CD28 superagonist. Further, these findings were validated using dry- and wet-coated human T cell proliferation assay (Example 9). Indeed, it was not observed that the exemplary anti-PSMAxCD28 bispecific antibodies as well as the parent bivalent CD28 antibodies induced human T cell proliferation as compared to the CD28 superagonist antibody. Overall, the exploratory single-dose toxicology study in monkeys and in vitro human T cell-based assays suggest that the exemplary anti-PSMAxCD28 bispecific antibodies of the invention are safe and well tolerated.

As shown in Table 21, TGN1412, the CD28 superagonist, caused modest cytokine release and transient increases in T Cells (measured on D15). The study was done on male cynomolgus monkey with weekly dosing 5 to 50 mg/kg for 4 weeks. FACS of leukocyte subsets analysis was performed on a male cynomolgus monkey following I.V. injection of weekly (d1, 8, 15, 22) escalating doses (5, 10, 25, 50 mg/kg) of TGN1412. Modest increases in IL-2, IL-5, IL-6, IFN-γ in first 2 to 24 hr (2 to 20-fold) were observed. There were no substantive changes in IL-4 or TNF-α. Exploratory single-dose monkey toxicology study with anti-CD28×PSMA was conducted to establish the safety and pharmacokinetic profile of anti-CD28×PSMA bispecific antibody.

In summary, it has been shown that anti-CD28×PSMA antibodies enhanced immunity at the tumor site. The anti-CD28×PSMA turned tumor cells into antigen presenting cells (APCs). Anti-CD28×PSMA antibodies do not induce T cell proliferation or stimulate cytokine release compared to anti-CD28 superagonist.

Example 12. Epitope Mapping of mAb14226P2 binding to CD28 by Hydrogen Deuterium Exchange H/D exchange epitope mapping with mass spectrometry (HDX-MS) was performed to determine the amino acid residues of CD28 (recombinant human CD28, shown as hCD28 ecto (N19-P152).mmh; SEQ ID NO: 75) interacting with anti-hCD28 monoclonal antibody. A general description of the H/D exchange method is set forth in e.g., Ehring (1999) *Analytical Biochemistry* 267 (2): 252-259; and Engen and Smith (2001) *Anal. Chem.* 73: 256A-265A.

The HDX-MS experiments were performed on an integrated HDX/MS platform, consisting of a Leaptec HDX PAL system for the deuterium labeling and quenching, a Waters Acquity M-Class (Auxiliary solvent manager) for the sample digestion and loading, a Waters Acquity M-Class (uBinary solvent manager) for the analytical gradient, and Thermo Q Exactive HF mass spectrometer for peptide mass measurement.

The labeling solution was prepared as PBS buffer in $D_2O$ at pD 7.0 (10 mM phosphate buffer, 140 mM NaCl, and 3 mM KCl, equivalent to pH 7.4 at 25° C.). For deuterium labeling, 11 μL of CD28.mmH (Regeneron in house protein REGN2011, 127 UM) or CD28.mmH premixed with REGN5705 in 1:0.6 molar ratio (Ag-Ab complex) was incubated at 20° C. with 44 UL $D_2O$ labeling solution for various time-points in duplicates (e.g., Undeuterated control=0 second; deuterium-labeled for 5 minutes and 10 minutes). The deuteration reaction was quenched by adding 55 μL of pre-chilled quench buffer (0.5 M TCEP-HCl, 8 M urea and 1% formic acid) to each sample for a 5-minute incubation at 20° C. The quenched sample was then injected into a Waters HDX Manager for online pepsin/protease XIII digestion. The digested peptides were separated by a C8 column (1.0 mm×50 mm, NovaBioassays) with a 13-minute gradient from 10%-32% B (mobile phase A: 0.5% formic acid in water, mobile phase B: 0.1% formic acid in acetonitrile). The eluted peptides were analyzed by Q Exactive HF mass spectrometry in LC-MS/MS or LC-MS mode.

The LC-MS/MS data of undeuterated CD28 sample were searched against a database including CD28 and its randomized sequence using Byonic search engine (Protein Metrics). The search parameters (in ELN) were set as default using non-specific enzymatic digestion and human glycosylation as common variable modification. The list of identified peptides was then imported into the HDX Workbench software (version 3.3) to calculate the deuterium uptake of each peptide detected by LC-MS from all deuterated samples. For a given peptide, the centroid mass (intensity-weighted average mass) at each time point was used to calculate the deuterium uptake (D) and percentage of deuterium uptake (% D).

$$\text{Deuterium Uptake } (D\text{–Uptake}) =. \text{ Average Mass(Deuterated)} - \text{Average Mass(Undeuterated)}$$

$$\text{Percentage of Deuterium Uptake}(\%\ D) = \frac{D\text{–Uptake for Peptide at each Time Point} \times 100\%}{\text{Maximun } D\text{–Uptake of the Peptide(defined in } ELN)}$$

A total of 73 peptides from hCD28.mmH (SEQ ID NO: 75) were identified from both hCD28.mmH alone and hCD28.mmH in complex with anti-CD28 antibody samples, representing 85.8% sequence coverage of hCD28. Any peptide which exhibited a differential percent D-uptake value above 5% was defined as significantly protected. For hCD28.mmH (SEQ ID NO: 75), regions corresponding to amino acids 5-20 (VKQSPMLVAYDNAVNL; SEQ ID NO: 77), 29-38 (FSREFRASLH; SEQ ID NO: 78), 80-84 (YLQNL; SEQ ID NO: 79), and 91-108 (IYFCKIEVMYPPPYLDNE; SEQ ID NO: 80) were significantly protected by anti-CD28 antibody, with amino acids 91-108 (IYFCKIEVMYPPPYLDNE; SEQ ID NO: 80) defined as the primary epitope on CD28. Protection of these residues by anti-CD28 antibody was confirmed using hCD28.mFc (SEQ ID NO: 76). See also Table 22 below for a summary of the results of this study.

TABLE 22

Selected CD28.mmH peptides with significant protection upon binding to an Anti-CD28 Antibody

| | | 5 min | | | 10 min | | | |
|---|---|---|---|---|---|---|---|---|
| | | REGN2011 | REGN2011 + mAb14226P2 | | REGN2011 | REGN2011 + mAb14226P2 | | |
| CD28 Residues | Charge (+) | Centroid $MH^+$ | Centroid $MH^+$ | ΔD | Centroid $MH^+$ | Centroid $MH^+$ | ΔD | Δ % D |
| 5-11 | 1 | 805.74 | 805.53 | −0.21 | 805.83 | 805.58 | −0.25 | −7.1 |
| 5-11 | 2 | 806.69 | 806.48 | −0.21 | 806.76 | 806.51 | −0.24 | −7.1 |
| 8-11 | 1 | 449.28 | 449.11 | −0.16 | 449.33 | 449.16 | −0.17 | −10.5 |
| 12-19 | 1 | 869.61 | 869.30 | −0.31 | 869.72 | 869.33 | −0.39 | −7.2 |
| 12-19 | 2 | 869.95 | 869.72 | −0.23 | 870.08 | 869.69 | −0.39 | −6.4 |
| 12-20 | 1 | 982.96 | 982.54 | −0.42 | 983.05 | 982.63 | −0.41 | −7.4 |
| 15-20 | 1 | 648.02 | 647.61 | −0.40 | 648.06 | 647.68 | −0.38 | −12.3 |
| 29-32 | 1 | 540.44 | 540.06 | −0.38 | 540.51 | 540.08 | −0.44 | −25.4 |
| 29-37 | 2 | 1116.66 | 1116.15 | −0.51 | 1116.79 | 1116.20 | −0.60 | −9.9 |
| 29-37 | 3 | 1117.61 | 1117.74 | −0.50 | 1117.11 | 1117.17 | −0.57 | −9.6 |
| 30-37 | 2 | 969.13 | 968.85 | −0.28 | 969.23 | 968.90 | −0.33 | −6.4 |
| 30-38 | 3 | 1107.35 | 1106.93 | −0.42 | 1107.48 | 1107.02 | −0.46 | −7.8 |
| 33-37 | 1 | 595.17 | 595.23 | −0.12 | 595.05 | 595.08 | −0.15 | −5.8 |
| 33-38 | 1 | 732.40 | 732.24 | −0.16 | 732.45 | 732.25 | −0.19 | −5.5 |
| 33-38 | 2 | 733.43 | 733.25 | −0.18 | 733.48 | 733.29 | −0.19 | −5.7 |
| 80-84 | 1 | 652.81 | 652.51 | −0.30 | 652.91 | 652.60 | −0.31 | −12.6 |
| 81-84 | 1 | 489.26 | 488.99 | −0.28 | 489.34 | 489.04 | −0.30 | −17.9 |
| 91-93 | 1 | 443.49 | 443.50 | −0.07 | 443.42 | 443.41 | −0.09 | −10.1 |
| 93-97 | 1 | 641.40 | 641.48 | −0.58 | 640.83 | 640.89 | −0.59 | −24.4 |
| 94-105 | 2 | 1458.33 | 1456.70 | −1.63 | 1458.63 | 1456.83 | −1.80 | −30.7 |
| 94-107 | 2 | 1688.09 | 1686.36 | −1.73 | 1688.33 | 1686.43 | −1.90 | −25.2 |
| 94-108 | 2 | 1817.69 | 1816.15 | −1.54 | 1817.88 | 1816.19 | −1.69 | −20.2 |
| 96-107 | 2 | 1455.75 | 1455.07 | −0.68 | 1455.91 | 1455.09 | −0.82 | −13.4 |
| 98-107 | 2 | 1212.67 | 1212.07 | −0.60 | 1212.78 | 1212.07 | −0.70 | −16.3 |
| 98-108 | 2 | 1342.17 | 1341.57 | −0.60 | 1342.10 | 1341.61 | −0.48 | −5.0 |

Example 13. PSMA×CD28 Bispecific Antibodies Potently Enhance the Anti-Tumor Efficacy of PD-1 Immunotherapy Abstract T cell activation is enhanced by engaging a second co-stimulatory receptor ("signal 2") in addition to the antigen specific TCR/CD3 activation ("signal 1"). The goal of cancer immunotherapy is to optimally activate and mobilize T cells to detect and kill tumor cells. However, current treatments tend not to activate T cells efficiently and selectively at the tumor site, often failing to achieve durable responses and/or leading to undesirable toxicities. Herein, a novel tumor-targeted immunotherapeutic modality combining PD-1 inhibition together with bispecific antibodies was introduced. The bispecific antibodies bind a tumor-specific antigen (TSA) (e.g., PSMA) with one arm and the co-stimulatory receptor CD28 on T cells with the other arm. Indeed, PD-1-PD-L1 signaling inhibition significantly increases the ratio of CD28 accumulated in the immunological synapse, enabling TSAxCD28 bispecific to exercise its effect. This combination immunotherapy was validated using a bispecific antibody specific for prostate antigen (e.g., PSMA). Unlike non-specific CD28 superagonists, which broadly activate T cells, the TSAxCD28 bispecifics were well-tolerated when used alone or in combination with a PD-1 blocker in genetically-humanized immuno-competent mouse models, or in primates. Importantly, in the presence of endogenous TCR/CD3 triggering, TSAxCD28 strikingly improved the anti-tumor activity of PD-1 antibody, associated with durable anti-tumor responses. Combination therapy specifically potentiated intra-tumoral T cell activation, promoting an effector memory-like T cell phenotype without systemic cytokine secretion in a variety of syngeneic and human tumor xenograft models. Combining this class of CD28-co-stimulatory bispecific antibodies with the clinically validated anti-PD-1 treatment may provide well-tolerated, "off the shelf" antibody therapies with markedly enhanced anti-tumor efficacy.

INTRODUCTION

Numerous monoclonal antibodies (mAbs) aimed at enhancing T cell activation are under clinical development as anti-tumor therapeutics (M. K. Callahan, M. A. Postow, J. D. Wolchok, Targeting T Cell Co-receptors for Cancer Therapy. *Immunity* 44, 1069-1078 (2016)). However, the majority of current treatments are challenged by overcoming the inhibitory nature of tumor microenvironment, thus failing to generate efficient tumor-specific T cell activation and subsequent tumor cell killing (K. G. Anderson, I. M. Stromnes, P. D. Greenberg, Obstacles Posed by the Tumor Microenvironment to T cell Activity: A Case for Synergistic Therapies. *Cancer Cell* 31, 311-325 (2017)). Several blocking mAbs directed against checkpoint inhibitors such as cytotoxic T lymphocyte-associated protein (CTLA-4) and programmed cell death 1 (PD-1)/programmed cell death ligand 1 (PD-L1) have been clinically approved for melanoma, renal cell carcinoma, non-small lung cancer and advanced metastatic cutaneous squamous cell carcinoma (J. S. Weber et al., Nivolumab versus chemotherapy in patients with advanced melanoma who progressed after anti-CTLA-4 treatment (CheckMate 037): a randomised, controlled, open-label, phase 3 trial. *Lancet Oncol* 16, 375-384 (2015); S. L. Topalian et al., Survival, durable tumor remission, and long-term safety in patients with advanced melanoma receiving nivolumab. *J Clin Oncol* 32, 1020-1030 (2014); M. A. Postow, M. K. Callahan, J. D. Wolchok, Immune Checkpoint Blockade in Cancer Therapy. *J Clin Oncol* 33, 1974-1982 (2015); M. R. Migden et al., PD-1 Blockade with Cemiplimab in Advanced Cutaneous Squamous-Cell Carcinoma. *N Engl J Med* 379, 341-351 (2018)). Blocking PD-1 releases the break on T cell activation, but its efficacy as a single agent often it is not sufficient to get tumor clearance and durable anti-tumor responses. When combined, anti-PD-1/PD-L1 and anti-CTLA-4 do yield high response rates in certain tumors types, but high-grade toxicities are often observed (J. Larkin et al., Combined Nivolumab and Ipilimumab or Monotherapy in Untreated Melanoma. *N Engl J Med* 373, 23-34 (2015); D. B. Johnson et al., Fulminant Myocarditis with Combination Immune Checkpoint Blockade. *N Engl J Med* 375, 1749-1755 (2016); M. H. Pollack et al., Safety of resuming anti-PD-1 in patients with immune-related adverse events (irAEs) during combined anti-CTLA-4 and anti-PD1 in metastatic melanoma. *Ann Oncol* 29, 250-255 (2018); J. D. Wolchok et al., Nivolumab plus ipilimumab in advanced melanoma. *N Engl J Med* 369, 122-133 (2013)). Consequently, considerable effort to identify patients who are more likely to respond to checkpoint inhibition through identification of biomarkers that predict responsiveness are ongoing (R. Cristescu et al., Pan-tumor genomic biomarkers for PD-1 checkpoint blockade-based immunotherapy. *Science* 362, (2018)). Furthermore, combination therapies aiming to improve the efficacy of PD-1 blockade and the durability of the anti-tumor response by combining agonistic antibodies triggering costimulatory receptors or with other modalities such as chemotherapy or radiotherapy are undergoing preclinical and clinical evaluation (S. Hu-Lieskovan, A. Ribas, New Combination Strategies Using Programmed Cell Death 1/Programmed Cell Death Ligand 1 Checkpoint Inhibitors as a Backbone. *Cancer J* 23, 10-22 (2017); Y. K. Chae et al., Current landscape and future of dual anti-CTLA4 and PD-1/PD-L1 blockade immunotherapy in cancer; lessons learned from clinical trials with melanoma and non-small cell lung cancer (NSCLC). *J Immunother Cancer* 6, 39 (2018); P. S. Chowdhury, K. Chamoto, T. Honjo, Combination therapy strategies for improving PD-1 blockade efficacy: a new era in cancer immunotherapy. *J Intern Med* 283, 110-120 (2018); B. Wang et al., Combination cancer immunotherapy targeting PD-1 and GITR can rescue CD8(+) T cell dysfunction and maintain memory phenotype. *Sci Immunol* 3, (2018); S. Chen et al., Combination of 4-1BB agonist and PD-1 antagonist promotes antitumor effector/memory CD8 T cells in a poorly immunogenic tumor model. *Cancer Immunol Res* 3, 149-160 (2015)). Microsatellite instability and high mutational burden generate potential endogenous antigens that are expressed in certain cancers (K. W. Mouw, M. S. Goldberg, P. A. Konstantinopoulos, A. D. D'Andrea, DNA Damage and Repair Biomarkers of Immunotherapy Response. *Cancer Discov* 7, 675-693 (2017)). T cells recognize these mutated peptides as neo-antigens (M. Efremova, F. Finotello, D. Rieder, Z. Trajanoski, Neoantigens Generated by Individual Mutations and Their Role in Cancer Immunity and Immunotherapy. *Front Immunol* 8, 1679 (2017)). However, in isolation, the presentation of these antigens is not sufficient to promote robust T cell activation to generate antitumor activity (S. Spranger, R. Bao, T. F. Gajewski, Melanoma-intrinsic beta-catenin signaling prevents anti-tumour immunity. *Nature* 523, 231-235 (2015)). This is likely due to the immune inhibitory microenvironment of the tumor.

Described herein is a novel immunotherapeutic modality using TSAxCD28 bispecifics targeted against prostate cancer TSA PSMAxCD28, that when combined with PD-1 blocking antibody induced long lived anti-tumor immunity and promoted robust intra-tumoral T cell activation and T cell memory with no signs of systemic cytokine release in animal tumor models. Toxicology studies in genetically-humanized immunocompetent mice and in cynomolgus monkeys demonstrated that these bispecifics exhibit no toxicity on their own or in combination with anti-PD-1 antibody. Collectively, these data suggest that combining this class of CD28-based bispecifics (TSAxCD28) with PD-1 inhibition may provide well-tolerated, "off-the-shelf" biologics solutions with markedly enhanced, specific and synergistic anti-tumor activity.

Material and Methods

The following materials and methods were used in Example 13.

Study Design

One exemplary objective of this invention was to develop TSAxCD28 bispecific antibody and demonstrate that TSAxCD28 potentiates PD-1 induced T cell activation in vitro and safely enhances anti-tumor efficacy in vivo. Activity in vitro was demonstrated by showing images bispecific antibodies, PD-1 and CD28 localized at the immunological synapse of a T cell and target cell conjugates, enhancement of PD-1 T cell cytokine release. In vivo anti-tumor efficacy was evaluated in syngeneic mouse tumor model. Tumor volume and serum cytokine was monitored over time to show response to bispecific antibody treatment. One purpose of the cynomolgus studies was to determine the safety and tolerability (pharmacologic and toxicologic profile) of TSAxCD28 as monotherapy or in combination with PD-1 in non-human primate. Animals were examined for toxicity by clinical observations and blood sample collections to analyze serum cytokines and T cell phenotype.

Animal Studies

All procedures were carried out in accordance with the Guide for the Care and Use of Laboratory Animals of the NIH. The protocols were approved by the Regeneron Pharmaceuticals Institutional Animal Care and Use Committee.

Cells Lines

Jurkat Clone E6-1 (ATCC, #TIB-152), Raji (ATCC, #CCL-86™), HEK293 cell line (ATCC, #CRL-1573) and A-431 (ATCC, CRL-1555™) were cultured according to ATCC recommended protocol. The HEK293/hCD20 cell line was generated using a mammalian vector encoding a ubiquitin-promoter driven hCD20 (amino acids M1 to P297 of accession number NP_068769.2). Transfected cells were cultured in 500 μg/ml of Geneticin A (G418) to select for stably expressing cell lines. To generate hCD80 or hPDL1 expressing cell, a lentiviral plasmid encoding human CD80

(288aa long; accession #NM_005191.4) and a neomycin resistance gene or human PDL1 (290aa long; accession #NM_14143.4) and a puromycin resistance gene was used to transfect HEK293T cells, facilitating the production of viral particles, which were subsequently used to infect HEK293/hCD20 or Raji cells. Human CD80 or PDL1 positive cells were isolated by FACS. Jurkat cells were transduced with NFκB-Luc using a lentivirus from Qiagen (Cat #CLS-013L) and a lentiviral plasmid encoding human PD-1 and a puromycin resistance gene. All generated cell lines were maintained in DMEM+10% FBS+P/S/G+NEAA supplemented with 500 ug/mL G418 and/or 0.5 ug/ml Puromycin.

The DU145/hPSMA cell line was generated by transducing DU145 cells (ATCC, HTB-81) with viral particles that were produced by HEK293T cells transfected with a lentiviral plasmid encoding human PSMA (amino acids M1 to A750 of accession number Q04609) and a neomycin resistance gene. After infection, cells were cultured in 500 ug/ml of Geneticin A (G418) to select for cells stably expressing PSMA. The generated cell line, DU145/PSMA, was maintained in MEM+10% FBS+P/S/G with 500 ug/mL G418.

To generate tumor cell lines engineered to express co-stimulatory ligands, the pLVX lentiviral plasmid with EF1a promoter encoding mouse CD86 or empty vector and a puromycin resistance gene (pLVX.EF1a.CD86-puro and pLVX.EF1a.EV-puro, respectively) was used to transfect HEK293T cells, facilitating the production of viral particles, which were subsequently used to infect MC38 (National Cancer Institute, Laboratory of Tumor Immunology & Biology). Engineered cell lines expressing CD86 were isolated by fluorescence-activated cell sorting (FACS). Cells were maintained under conditions recommended by ATCC in the presence of 0.5 ug/ml Puromycin. Resulting cell lines were designated MC38/CD86 and MC38/EV.

For generation of MC38/hPSMA cells, a lentiviral plasmid encoding human PSMA (amino acids M1 to A750 of accession number Q04609) and a neomycin resistance gene was used to transfect HEK293T cells, facilitating the production of viral particles, which were subsequently used to infect MC38 parental cells. Human PSMA positive cells were isolated by FACS. MC38/hPMA were maintained in DMEM+10% FBS+P/S/G+NEAA supplemented with 500 ug/mL G418.

Amnis Image Stream

Amnis Image Stream was performed as described in Example 7.

Human Primary CD3+ T-Cell Isolation

T cell isolation was performed as described in Example 8.

IL-2 release from primary CD3+ T-cells in an MLR reaction with DU145/PSMA cells

Previously isolated and frozen human CD3+ T-cells were thawed the day of the assay in stimulation media (X-VIVO 15 cell culture media supplemented with 10% FBS, HEPES, NaPyr, NEAA, and 0.01 mM BME) containing 50 U/ml benzonase nuclease. Cells were centrifuged at 1200 rpm for 10 minutes, resuspended in stimulation media and plated out into 96-well round bottom plates at a concentration of $1\times10^5$ cells/well. DU145 parental cells or DU145 cells engineered to express human PSMA, were treated with 25 µg/mL of Mitomycin C in primary stimulation media at a concentration of $10\times10^6$ cells/mL. After incubation for 1 hour at 37° C., 5% $CO_2$, mitomycin C-treated cells were washed 3 times with D-PBS containing 2% FBS and added to the wells containing CD3+ T-cells at a final concentration of $5\times10^4$ cells per well. To prevent possible CD28 agonistic activity through Fc-anchoring of CD28 antibody to Fc-receptors from occurring, a saturating amount of non-specific human IgG antibody (100 nM of each: hIgG1, hIgG4, and hIgG4s) was included into each assay well. Subsequently, PSMA×CD28, nontarget×CD28 control, or hIgG4s isotype control, antibodies were titrated from 30 µM to 200 nM in a 1:3 dilution and added to wells. The final point of the 10-point dilution contained no titrated antibody. As DU145 cells endogenously express PD-L1, the impact of PD-1 suppression of T-cell activity was evaluated by adding a constant 20 nM of the PD-1 antagonist REGN2810 to wells. Also included was a condition in the absence of PD-1 inhibition, where in its place 20 nM of a matched hIgG4 isotype control was used. Plates were incubated for 72 hours at 37° C., 5% $CO_2$ and subsequently centrifuged to pellet the cells. 50 µL of media supernatant was collected and from this, 5 µL was tested in a human IL-2 AlphaLISA assay according to the manufacturer's protocol. The measurements were acquired on Perkin Elmer's multilabel plate reader Envision. A standard curve of known IL-2 concentrations was generated in order to extrapolate the pg/mL of IL-2 generated in assay wells. All serial dilutions were tested in duplicates. The $EC_{50}$ values of the antibodies were determined from a four-parameter logistic equation over a 10-point dose-response curve using GraphPad Prism™ software.

FACS-Based Cytotoxicity Assay

FACS-based cytotoxicity assay was performed as described previously (Example 8).

Syngeneic Tumor Studies

MC38/EV and MC38/CD86 were culture according to ATCC guideline. $1\times10^6$ MC38/EV or MC38/CD86 were implanted subcutaneously on C57BL/6 mice. Mice were treated with PD-1 antibody (RPM1-14, BioXcell) or rat IgG2a isotype control (BioXcell) at 5 mg/kg by intraperitoneal injection on day 0, 3, 7, 10 and 14 post tumor implant. Tumor sizes were measured twice per week using calipers (Roboz RS-6466). Tumor volume was calculated using the formula X*Y*(X/2), where Y is the longest dimension and X is the perpendicular dimension. Mice with tumors larger than 2000 $mm^3$ or with ulcerated tumors were euthanized by $CO_2$ asphyxiation.

hCD3/hCD28/hPSMA humanized mice were generated as described in Example 10. Antibody treatments were also similar except that indicated antibodies or bispecific antibodies were administered as a monotherapy or in combination by intraperitoneal injection on day 0, 7, and 14 (prophylactic treatment) or day 9, 13 and 22 (delayed treatment) at 5 mg/kg.

Ex Vivo Tissue Cytokine Analysis

On day 29 post implant, MC38/hPSMA tumor bearing CD3/CD28/PSMA mice were euthanized by carbon dioxide asphyxiation. Spleens and tumors were collected and stored in media on ice. All following steps were performed on ice or at 4° C. unless noted differently. Tumors were cut into small pieces and fragments were processed into single cell suspension using Miltenyi mouse tumor dissociation kit following manufacturing protocol (Miltenyi 130-096-730). Spleens were processed into single cells suspension using gentle MACS mechanical dissociation (spleen 4 program) and mashing through a 70-micron filter using the rubber end of a 3 ml syringe. Cells were pelleted by centrifugation at 1200 rpm for 5 minutes. Red blood cells were lysed by resuspending the cell pellet in 1 ml ACK lysis buffer and incubating on ice for 5 minutes. ACK lysis buffer was quenched w/FACS buffer. Cells were pelleted by centrifugation at 1200 rpm for 5 minutes. Cell suspension was resuspended in 1 ml of media and 0.2 ml were plated in 96-well plates (20-400K tumor cells or 50-70K spleen cells.

Cells were incubated overnight at 37° C. and culture supernatant was collected. Cytokine levels in tissue culture supernatant was measured using V-Plex Proinflammatory MSD kit following manufacturer protocol (Meso Scale Diagnostics K15048D-4). The number of cells plated per well was determined by FACS analysis. The levels of cytokines were normalized to the number of cells plated. Calibration beads were run together with cells to accurately measure the number of cells using the following calculation:

Cell #=(#input beads×#cells counted by FACS)/#of beads counted by FACS

Measurement of Serum Cytokine Levels in Mice

Measurements of serum cytokine levels in mice were performed as described previously (Example 10).

Flow Cytometry Analysis

For flow cytometry analysis of in vivo experiments, tumors were harvested, single cell suspensions were prepared, and red blood cells were lysed using ACK Lysis buffer (ThermoFisher Scientific). Live/dead cell discrimination was performed using Live/dead fixable blue dead cell staining kit (ThermoFisher Scientific). Samples were acquired on Symphony (BD Bioscience) and analyzed using Cytobank software (Cytobank, Santa Clara, CA). Analysis were performed with equal numbers of events per sample. The range in events was determined by the sample with the fewest events acquired. To cluster T cells automatically based on specific markers, CITRUS analysis from Cytobank was used.

Cynomolgus Toxicology Studies

The cynomolgus monkey study was conducted as described previously (Example 11).

Results

PD-1 Checkpoint Inhibition Increases the Relative Ratio of CD28 within the Immunological Synapse, Allowing TSAxCD28 Bispecifics to Markedly Enhance the Ability of Anti-PD-1 to Promote T Cell Activation In Vitro To test whether costimulatory bispecific agonists could complement checkpoint inhibition, an exemplary PSMAxCD28 bispecific of the present invention (bs16429D) was tested with respect to its ability to enhance the effectiveness of PD-1 blockade in a TCR/CD3-dependent T cell activation manner. Indeed, efficient T cell activation depends on co-clustering of TCR/CD3 and CD28 complexes at the "immune synapse" (IS). However, activation signals from both TCR/CD3 and CD28 are directly inhibited by PD-1-Shp-2 phosphorylation followed PD-1/PD-L1 clustering at the synapse (E. Hui et al., T cell costimulatory receptor CD28 is a primary target for PD-1-mediated inhibition. *Science* 355, 1428-1433 (2017); J. M. Chemnitz, R. V. Parry, K. E. Nichols, C. H. June, J. L. Riley, SHP-1 and SHP-2 associate with immunoreceptor tyrosine-based switch motif of programmed death 1 upon primary human T cell stimulation, but only receptor ligation prevents T cell activation. *J Immunol* 173, 945-954 (2004)). To determine the relative localization of CD28 and PD-1 at the IS, an in vitro assay, Amnis Image Stream as described in Example 7, was developed using Jurkat T cells overexpressing PD-1 and Raji tumor target cells engineered to overexpress PD-L1. A fluorescently labeled bispecific CD20×CD3 antibody (E. J. Smith et al., A novel, native-format bispecific antibody triggering T-cell killing of B-cells is robustly active in mouse tumor models and cynomolgus monkeys. *Sci Rep* 5, 17943 (2015)) was used to replicate the peptide MHC/TCR binding and to visualize T cell interactions with the target cells forming an IS. Two different fluorescently labeled monoclonal PD-1 antibodies (PD-1 mAb), a blocker (PD-1 mAb, REGN2810, (E. Burova et al., Characterization of the Anti-PD-1 Antibody REGN2810 and Its Antitumor Activity in Human PD-1 Knock-In Mice. *Mol Cancer Ther* 16, 861-870 (2017)) and a non-blocker (NB PD-1 mAb) were used to simultaneously block the interaction with PD-L1 and visualize the localization of PD-1. It was found that in the absence of PD-L1 expression on the target cells, and in the presence of either PD-1 mAb, there was no change in the relative amount of PD-1 or CD28 at the IS (FIG. 14). However, PD-L1 expression on target cells in the presence of a non-blocking PD-1 mAb, decreased CD28 at the synapse and promoted high PD-1 accumulation, at the IS. Conversely, in the presence of a blocking PD-1 mAb, PD-1 localization was significantly reduced and relative CD28 levels were maintained at the IS. The distribution of PD-1 and CD28 was quantified by calculating the ratio of antibody staining inside versus outside of the IS (FIG. 15). This data shows that expression of PD-L1 on target cells enhances PD-1 localization at the IS while decreasing CD28. Furthermore, a PD-1 blocking mAb reduces the relative amount of PD-1 at the IS and rescues the level of CD28, therefore increasing the relative ratio of CD28 to PD-1.

It was next tested if PSMAxCD28 can enhance the effect of PD-1 blockade on T cell activation induced tumor cell killing. Towards this end the prostate cancer line 22RV1 was utilized. 22RV1 cells endogenously express PSMA and were engineered to express PD-L1 (22RV1/PD-L1). Due to an absence of TCR/CD3 stimulation through an allogenic T cell response, PSMAxCD3 (U.S. Pat. No. 10,179,819) was used to provide a primary stimulus. In co-cultures of human peripheral blood mononuclear cells (PBMCs, containing human T cells) and 22RV1/PD-L1 cells, PSMAxCD3 alone induced ~40% tumor cell killing (FIG. 16, diamonds, $EC_{50}$ of 8E-10). Addition of PD-1 mAb to PSMAxCD3 enhanced tumor cell killing to ~55% (FIG. 16, solid triangles, $EC_{50}$ of 4E-10). Interestingly, PSMAxCD28 combination with PSMAxCD3 similarly enhanced the depth of tumor cell killing to ~55% with increased potency (FIG. 16, solid circles, $EC_{50}$ of 6E-11), suggesting that PSMAxCD28 can override PD-1/PD-L1 mediated inhibition. Interestingly PSMAxCD28, PD-1 mAb and PSMAxCD3 triple combination had the strongest tumor cell killing at ~70% demonstrating the synergistic effect of this combination (FIG. 16, solid squares, $EC_{50}$ of 7E-11). As expected, neither PSMAxCD28 alone, PD-1 mAb nor PSMAxCD28 plus PD-1 mAb combination induced any tumor cell killing (FIG. 16, open symbols). In agreement, it was observed the maximum increase in IFNγ release with the triple combination treatment (FIG. 17).

It was next determined the effect of PSMAxCD28 and PD-1 mAb combination on primary human T cell activation in vitro. To replicate physiological PD-L1 expression and TCR/CD3 stimulation, a mixed lymphocyte reaction (MLR) was employed. In a one-way MLR, incompatibility of allogeneic determinants leads to T-cell activation, which can be quantified by cytokine production. Here T-cells from healthy donors were incubated with DU145/PSMA cells, an engineered prostate cancer cell line that endogenously expresses PD-L1 and over expresses PSMA, and the indicated antibodies (FIG. 18). In the presence of DU145/PSMA cells and T cells, the PSMAxCD28 bispecific lead to a dose dependent increase in IL-2 release ~3-4 fold over the IgG4 isotype control (FIG. 18, circles). Similarly, the addition of 20 nM PD-1 mAb into the MLR assay also increased IL-2 release ~3-4 fold over IgG4 isotype control (FIG. 18, triangles). In combination, PSMAxCD28 and 20 nM PD-1 mAb markedly potentiated the activation induced by PSMAxCD28 bispecific with max IL-2 levels that were increased ~20 fold over isotype control (FIG. 18, squares), demonstrating that the PSMAxCD28 bispecific in combination with a PD-1 blocking mAb potently and synergistically activates T cells in the presence of tumor cells with endogenous levels TCR/CD3 activation and PD-L1 inhibition.

Altogether these results demonstrated that the PSMAxCD28 bispecific can potently enhance the ability of PD-1 mAb to promote T cell activation in the presence of TCR/CD3 signaling (driven by a CD3-bispecific or an allo-response), resulting in increased cytokine release and killing of tumor cells expressing PSMA and PD-L1 in vitro.

Over-Expression of a Natural CD28 Ligand on Tumor Cells Synergizes with PD-1 mAb Treatment to Induce CD8 T Cell-Dependent Durable Anti-Tumor Immunity In Vivo To determine if CD28 engagement by its natural ligand(s) could potentiate the anti-tumor efficacy of PD-1 mAb in vivo, MC38 tumor cells were engineered to over-express CD86, one of the co-stimulatory ligands for CD28 (Data not shown). Combination of MC38/CD86 cells and PD-1 mAb treatment significantly inhibited tumor growth (FIG. 19A), resulting in complete tumor regression associated with robust survival benefit (FIG. 19B) when compared with a negative control MC38 cells transfected with an empty vector control (MC38/EV). Depletion of CD8+ T cells during the course of treatment completely abrogated the anti-tumor efficacy elicited by combining PD-1 mAb therapy with MC38/CD86 cells demonstrating a dependence on CD8+ T cells (FIG. 19C). Of note, tumor free mice that were initially implanted with MC38/CD86 cells and treated with PD-1 mAb rejected a second MC38 parental tumor that was implanted more than 60 days after the implantation of the primary tumor, indicating the presence of a T cell memory response (FIG. 19D). Consequently, these data demonstrate that the synergistic effect of constitutive expression CD28 ligand and anti-PD-1 therapy can result in a durable CD8-dependent anti-tumor immunity in vivo.

PSMAxCD28 Synergizes with PD-1 mAb Treatment to Induce Anti-Tumor Immunity in a Syngeneic Tumor Model The findings described above were next extended to demonstrate the anti-tumor efficacy of treatment using a TSAxCD28 bispecific antibody alone or in combination with a PD-1 mAb in syngeneic tumor models. Using the established C57BL6 syngeneic MC38 tumor model as described herein, the hPSMA gene (pLVX.EF1a.hPSMA) was genetically-introduced into the MC38 cells, creating tumor specific antigen MC38/hPSMA as described herein. To avoid the possibility that the mice would spontaneously reject these otherwise syngeneic tumors expressing an introduced human tumor antigen, PSMA was genetically-humanized in these mice. In addition, the CD3γ-δ-ε and CD28 genes were also humanized using VelociGene technology as previously described (D. M. Valenzuela et al., High-throughput engineering of the mouse genome coupled with high-resolution expression analysis. *Nat Biotechnol* 21, 652-659 (2003); W. T. Poueymirou et al., FO generation mice fully derived from gene-targeted embryonic stem cells allowing immediate phenotypic analyses. *Nat Biotechnol* 25, 91-99 (2007)), so that the bispecifics would recognize the host T cells (via hCD3 or hCD28), as well as the human tumor antigens in both normal tissues and in the tumors (i.e., hPSMA), representing the actual clinical situation (Y. Kinoshita et al., Expression of prostate-specific membrane antigen in normal and malignant human tissues. *World J Surg* 30, 628-636 (2006)). In this model the combination of the PSMAxCD28 bispecific and PD-1 mAb provided the greatest tumor growth control which translated into a robust survival benefit Immediate Treatment with a Combination of Anti-CD28× Anti-PSMA and Anti-PD1 Synergistically Inhibit Tumor Growth In an immediate treatment study, anti-CD28×anti-PSMA, anti-PD1 or rat IgG2a isotype control were administered as monotherapy or in combination by intraperitoneal injection on day 0, 7 and 14 at 5 mg/kg. Tumor growth was monitored over time using caliper measurements of X and Y diameter. Tumor volume was calculated (X*Y*(X/2)). Mice were euthanized when tumor size was greater than 2000 $mm^3$.

As shown in FIGS. 20A through 20E the anti-CD28×anti-PSMA antibodies suppressed tumor growth and increased survival in mice when used alone, but also synergized with anti-PD-1 antibodies to promote tumor rejection and increase survival even more so than when used in the absence of a PD-1 antibody.

Treatment with a Combination of CD28×PSMA and PD1 Induces Long Lived Anti-Tumor Immunity to Secondary Tumor Challenge Furthermore, tumor free mice that were implanted and treated with PSMAxCD28 bispecific and PD-1 mAb combination rejected a second MC38 parental tumor line that was implanted more than 60 days after primary tumor implant, demonstrating the generation of immune memory (FIG. 21A) consistent with observation described herein. These results suggests that an endogenous antigen specific TCR signal (Signal 1) is being generated from peptide MHC complex on the MC38/PSMA implanted tumor cells. It has been shown that MC38 tumor cells express high levels of re-activated endogenous retroviral proteins such as p15E, and that intra-tumoral T cells in C57BL6 mice are responsive to this p15E antigen (J. C. Yang, D. Perry-Lalley, The envelope protein of an endogenous murine retrovirus is a tumor-associated T-cell antigen for multiple murine tumors. *J Immunother* 23, 177-183 (2000); H. J. Zeh, 3rd, D. Perry-Lalley, M. E. Dudley, S. A. Rosenberg, J. C. Yang, High avidity CTLs for two self-antigens demonstrate superior in vitro and in vivo antitumor efficacy. *J Immunol* 162, 989-994 (1999)). Consistent with this finding, it was found that PSMAxCD28 and PD-1 mAb combination therapy induced peripheral T cells reactive to at least one endogenous antigen P15E, supporting the generation of anti-tumor immune memory (FIG. 21B). Notably, in similar experiments where treatment with PSMAxCD28 in combination with PSMAxCD3 induced MC38/hPSMA tumor rejection, those tumor free mice failed to reject secondary tumor re-challenge (FIG. 21C). Altogether, this data shows that CD28-bispecifics synergize with PD-1 mAb in this PSMA syngeneic tumor model and can boost endogenous TCR/CD3-dependent T cell responses.

Therapeutic Treatment with a Combination of Anti-CD28Xanti-PSMA and Anti-PD1 Synergistically Inhibits Tumor Growth Similarly, in a delayed treatment protocol, the combination of PSMAxCD28 and PD-1 mAb 10 days post implantation inhibited growth of established MC38/hPSMA tumors (FIG. 22A) and also resulted in a significant increase in survival (FIG. 22C) and reduction in tumor volume (FIG. 22D). Interestingly, tumor-targeted combination therapy selectively increased intratumoral cytokines as shown for IFNγ (FIG. 22B). No splenic or systemic cytokine induction was observed in the same mice (FIGS. 23A and 23B). Furthermore, expression profiling of T cell activation markers showed that intra-tumoral PD-1 expression was increased upon PSMAxCD28 treatment (FIG. 24) in support of this combination treatment. To further characterize the responding T cell subsets upon combination treatment, tumor infiltrating CD8$^+$ T cells were profiled day 17 post tumor challenge by high-dimensional flow cytometry. Using CITRUS (cluster identification, characterization, and regression) to independently stratify statistically significant different T cell clusters. Importantly, it was found that PD-1 blockade expanded effector (CD44$^{high}$CD62L$^{low}$) CD8$^+$ T cell (cluster C1) expressing high level of activation/exhaustion markers (PD-1, TIM3, LAG3, Ki67) (FIG. 25). However, only combination treatment was able to drive an expansion of intra-tumoral CD8$^+$ T cell (cluster C2) with memory-like phenotype (high Tcf1, EOMES, CD62L, intermediate CD122 and CD127) and less exhausted phenotype (Low PD-1, LAG3, TIM3, CD38, KLRG1, higher CD5) (FIG. 25) (M. Philip et al., Chromatin states define tumour-specific T cell dysfunction and reprogramming. *Nature* 545, 452-456 (2017)). These data demonstrate that PSMAxCD28 bispecific and anti-PD-1 combination therapy drive robust anti-tumor immunity associated with intra-tumoral T cell activation with a memory-like phenotype, and survival benefit.

TSAxCD28 Alone or in Combination with PD-1 mAb Therapy does not Induce Systemic T Cell Activation in Comparison to CD28 Superagonist in Cynomolgus Monkeys Early clinical trial data showed that bivalent CD28-activating antibodies, termed "CD28 superagonists" (CD28-SA), broadly activated T cells and resulted in profound toxicity associated with cytokine release syndrome (CRS) in a group of healthy volunteers (G. Suntharalingam et al., Cytokine storm in a phase 1 trial of the anti-CD28 monoclonal antibody TGN1412. *N Engl J Med* 355, 1018-1028 (2006)). To evaluate the tolerability of TSAxCD28 bispecifics alone, or the potential for synergistic pharmacology in combination with PD-1 mAb, exploratory studies in genetically-engineered triple humanized mice and cynomolgus monkeys were conducted. Three monkeys per treatment group received single dose (10 mg/kg) of PSMAxCD28 alone or in combination with PD-1 mAb (REGN2810) (10 mg/kg) via intravenous infusion (combination groups received sequential infusions) (Table 20, FIGS. 26A-26C, and 27).

Figure 29A:
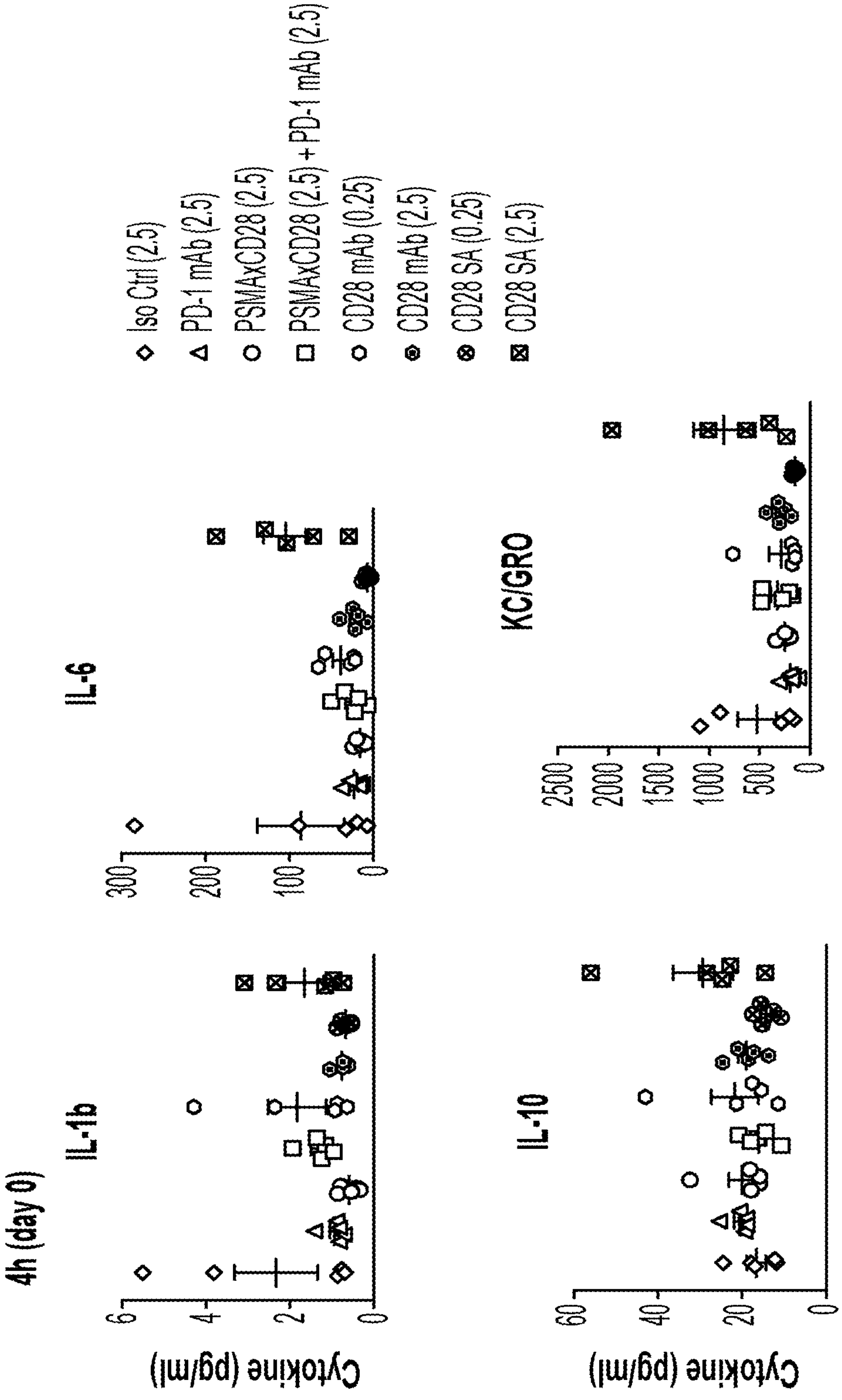
Figure 29B:
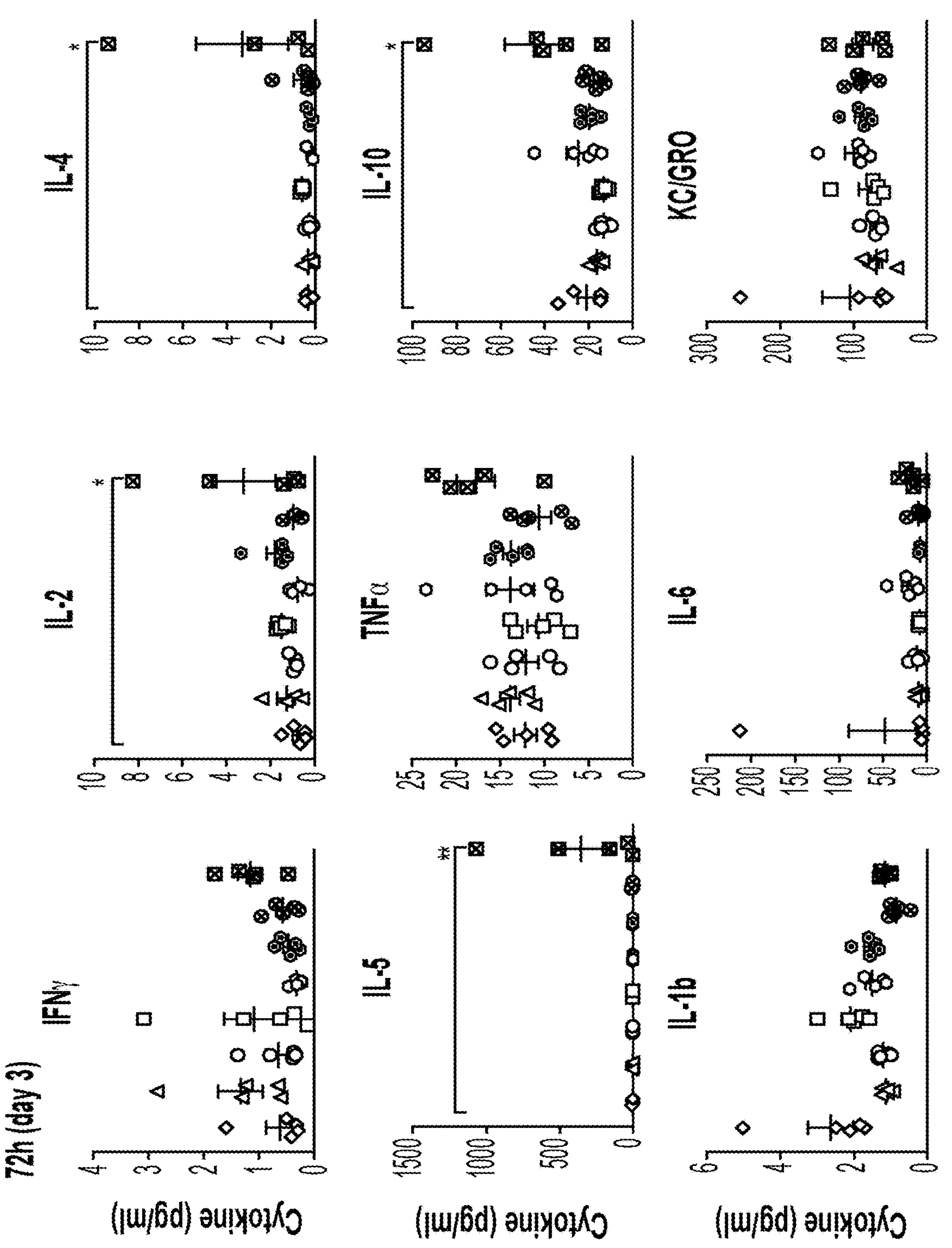

In addition, three monkeys per group received single dose (01 mg/kg) anti-PSMAxCD3 bispecific antibody and single dose (10 mg/kg) of CD28 superagonist antibody as described herein (Table 20, FIGS. 26A-26C, and 27). Assessment of toxicity was based on clinical observations, qualitative food consumption, body weight, vital signs (body temperature, heart rate, pulse oximetry, and respiration rate), clinical and anatomic pathology upon completion of the experiment. Blood samples were collected for cytokine and FACS immunophenotyping analysis. PSMAxCD28 alone or in combination with PD-1 was well tolerated and all the animals survived for the study duration. There was no test article related clinical-observations observed (data not shown). No changes in organ weights were found, nor were any macroscopic changes noted at the terminal necropsy (data not shown). Furthermore, no significant cytokine release, T cell margination or activation were observed (Table 23, FIGS. 26A-26C). In contrast, significant cytokine release, lymphocyte margination and T cell activation was seen in monkeys administered CD28 "superagonist" alone (FIGS. 29A and 29B). Massive infiltration of immune cells were observed in the kidney, brain and seminal vesicles of animals treated with CD28 superagonist. In contrast, no significant treatment-related histological changes were observed in animals that were administered with PSMAxCD28 alone or in combination with PD-1 (data not shown).

TABLE 23

No Significant Clinical Observations or Cytokine Release Were Observed with anti-PSMAxCD28 Alone or in Combination with Anti-PD-1 in the Exploratory Single-Dose Monkey Toxicology Study

| Molecule | Description | Dose (mg/kg) | Day 1 - clinical Obs | Any Obs. Days 2-4 | Absolute T-Cells (E3/µL) Pre-test | Absolute T-Cells (E3/µL) 5 hr | Proliferating T-Cells Ki67 + (E3/µL) Pre-test | Proliferating T-Cells Ki67 + (E3/µL) 96 hr | Activated T-cells (E3/µL)-ICOS Pre-test | Activated T-cells (E3/µL)-ICOS 96 hr |
|---|---|---|---|---|---|---|---|---|---|---|
| bs15780D | anti-PSMAxCD3 | 0.1 | | HUN | 4.15 | 0.11 | 0.24 | 1.21 | 0.42 | 0.82 |
| | | | | | 7.41 | 0.15 | 0.88 | 1.69 | 0.40 | 0.64 |
| | | | | | 5.68 | 0.01 | 0.42 | 3.87 | 0.68 | 3.75 |
| bs16429D | anti-PSMAxCD28 | 1 | — | — | 6.58 | 7.22 | 0.62 | 0.41 | 0.33 | 0.32 |
| | | | — | — | 4.91 | 5.09 | 0.42 | 0.23 | 0.26 | 0.17 |
| | | | — | — | 4.50 | 4.04 | 0.63 | 0.39 | 0.51 | 0.48 |
| bs16429D | anti-PSMAxCD28 | 10 | — | — | 6.03 | 5.73 | 0.33 | 0.44 | 0.33 | 0.22 |
| | | | — | — | 4.64 | 4.53 | 0.38 | 0.60 | 0.58 | 0.50 |
| | | | — | — | 10.06 | 7.16 | 0.88 | 0.49 | 0.84 | 0.48 |
| REGN2329 (TeGenero) | anti-CD28 Super agonist | 10 | — | — | 7.02 | 0.26 | 0.60 | 2.57 | 0.51 | 1.94 |
| | | | — | — | 7.06 | 0.19 | 0.79 | 1.55 | 0.43 | 1.11 |
| | | | — | — | 11.87 | 0.66 | 1.13 | 3.61 | 0.48 | 2.09 |
| bs16429D + REGN2810 | anti-PSMAxCD28 + PD-1 | 10 + 10 | — | — | 3.76 | 1.90 | 0.38 | 0.37 | 0.34 | 0.28 |
| | | | — | — | 3.66 | 2.07 | 0.54 | 0.52 | 0.22 | 0.20 |
| | | | — | — | 3.54 | 1.34 | 0.39 | 0.40 | 0.12 | 0.10 |
| bs16431D + REGN2810 | anti-PSMAxCD28 + PD-1 | 10 + 10 | — | — | 3.63 | 4.23 | 0.36 | 0.42 | 0.24 | 0.38 |
| | | | — | — | 3.53 | 1.90 | 0.35 | 0.19 | 0.13 | 0.15 |
| | | | — | — | 4.16 | 3.16 | 0.42 | 0.32 | 0.26 | 0.33 |
| mAb10154P3 | EGFRVIIIAb | | — | — | 6.21 | 5.62 | 0.60 | 0.58 | 0.32 | 0.39 |
| | | | — | — | 7.22 | 7.72 | 0.84 | 0.77 | 0.39 | 0.41 |
| | | | — | — | 3.55 | 4.61 | 0.51 | 0.75 | 0.26 | 0.44 |

TABLE 23-continued

| Molecule | Description | CRP (mg/dL) 24 hr | Plasma Cytokine at 5 hrs post-dose (pg/ml) | | | | | | | |
|---|---|---|---|---|---|---|---|---|---|---|
| | | | IL-6 | IL-8 | IL-10 | IFN-γ | TNF-α | IL-2 | IL-4 | IL-5 |
| bs15780D | anti- | 13.6 | 4449 | 531 | 2878 | 159 | BLQ* | BLQ | BLQ | BLQ |
| | PSMAxCD3 | 14.9 | 11239 | 3910 | 22140 | 1800 | BLQ | 357 | BLQ | 152 |
| | | 15.4 | 10529 | 776 | 24784 | 1176 | BLQ | BLQ | BLQ | BLQ |
| bs16429D | anti- | 0.5 | BLQ | BLQ | BLQ | BLQ | BLQ | BLQ | BLQ | BLQ |
| | PSMAxCD28 | 0.5 | BLQ | BLQ | BLQ | BLQ | BLQ | BLQ | BLQ | BLQ |
| | | 1.1 | BLQ | BLQ | BLQ | BLQ | BLQ | BLQ | BLQ | BLQ |
| bs16429D | anti- | 0.2 | BLQ | BLQ | BLQ | BLQ | BLQ | BLQ | BLQ | BLQ |
| | PSMAxCD28 | 0.2 | BLQ | BLQ | BLQ | BLQ | BLQ | BLQ | BLQ | BLQ |
| | | 1.3 | BLQ | BLQ | BLQ | BLQ | BLQ | BLQ | BLQ | BLQ |
| REGN2329 | anti-CD28 | 15.4 | 764 | BLQ | 3364 | BLQ | BLQ | BLQ | BLQ | 1169 |
| (TeGenero) | Super | 15 | 2907 | 1095 | 17155 | 333 | BLQ | 238 | BLQ | 615 |
| | agonist | 15.3 | 5226 | 5324 | 7918 | 1509 | 163 | 522 | 342 | 198 |
| bs16429D + | anti- | 10.8 | BLQ | BLQ | BLQ | BLQ | BLQ | BLQ | BLQ | BLQ |
| REGN2810 | PSMAxCD28 + | 1 | BLQ | BLQ | BLQ | BLQ | 195 | BLQ | 323 | BLQ |
| | PD-1 | 11.9 | BLQ | BLQ | BLQ | BLQ | BLQ | BLQ | BLQ | BLQ |
| bs16431D + | anti- | 5.1 | BLQ | BLQ | BLQ | BLQ | BLQ | BLQ | 333 | BLQ |
| REGN2810 | PSMAxCD28 + | 2.9 | BLQ | BLQ | BLQ | BLQ | BLQ | BLQ | BLQ | BLQ |
| | PD-1 | 0.2 | BLQ | BLQ | BLQ | BLQ | 187 | BLQ | 323 | BLQ |
| mAb10154P3 | EGFRVIIIAb | 0.8 | BLQ | BLQ | BLQ | BLQ | 151 | BLQ | 335 | BLQ |
| | | 11 | BLQ | BLQ | BLQ | BLQ | 267 | BLQ | 378 | BLQ |
| | | 0.2 | BLQ | BLQ | BLQ | BLQ | BLQ | BLQ | BLQ | BLQ |

*BLQ: Below lower limit of quantification

Consistent with the above studies in cynomolgus monkeys, no cytokine elevation was observed in tumor bearing or non-tumor bearing naïve triple humanized mice (hCD3/hCD28/hPSMA) dosed with PSMAxCD28 alone or in combination PD-1 (FIG. 27 and FIGS. 29A and 29B). In contrast, dosing with CD28 superagonist induced a significant increase in IFNγ, TNFα, IL-2, IL-4 and IL-5 at 4 hours post dose (FIG. 27 and FIGS. 29A and 29B). Consistent with the results described above it has been previously shown that TSAxCD28 bispecific (as well as the parent bivalent non superagonistic CD28 antibodies used to make these bispecifics), failed to induce human T cell proliferation in the FDA recommended in vitro dry- and wet-coated assay (R. Stebbings, D. Eastwood, S. Poole, R. Thorpe, After TGN1412: recent developments in cytokine release assays. *J Immunotoxicol* 10, 75-82 (2013)) in comparison to the strong proliferation induced by CD28-SA (data not shown). Overall, these data suggest that TSAxCD28 bispecifics are well tolerized.

Furthermore, as described previously (Example 10, FIG. 28), anti-PSMAxCD28 treatment alone or in combination with anti-PD1 did not elevate serum cytokines in tumor bearing mice, while anti-PSMAxCD3 treatment, alone or in combination with anti-PD1, increased serum cytokine level in tumor bearing mice.

Discussion

Introduced and validated herein is a novel tumor-targeted immunotherapy using TSAxCD28 bispecifics in combination with PD-1 blocking mAb, that induces long lived anti-tumor immunity and promotes robust intra-tumoral T cell activation in animal tumor models. Toxicology studies in genetically-humanized immunocompetent mice and in cynomolgus monkeys demonstrated that these bispecifics exhibit no toxicity on their own or in combination with PD-1 mAb, suggesting that this therapeutic approach may provide well-tolerated, "off-the-shelf" biologic solutions with markedly enhanced, specific and synergistic anti-tumor activity.

Checkpoint inhibition with PD-1 blocking mAb are known to release the break on T cell activation, but their efficacy as a single agent is often not sufficient to get tumor clearance and a durable anti-tumor response in many cancers. Several approaches to improve the response rate to PD-1 inhibition are currently being evaluated. Indeed, identification of biomarkers to predict responsiveness to PD-1 mAbs (R. Cristescu et al., Pan-tumor genomic biomarkers for PD-1 checkpoint blockade-based immunotherapy. Science 362, (2018)), non-tumor targeted combination therapies using PD-1 inhibition together with agonistic antibodies triggering costimulatory receptors to improve T cell activation, or with chemotherapy or radiotherapy are all currently undergoing pre-clinical and clinical testing (S. Hu-Lieskovan, A. Ribas, New Combination Strategies Using Programmed Cell Death 1/Programmed Cell Death Ligand 1 Checkpoint Inhibitors as a Backbone. *Cancer J* 23, 10-22 (2017); Y. K. Chae et al., Current landscape and future of dual anti-CTLA4 and PD-1/PD-L1 blockade immunotherapy in cancer; lessons learned from clinical trials with melanoma and non-small cell lung cancer (NSCLC). *J Immunother Cancer* 6, 39 (2018); P. S. Chowdhury, K. Chamoto, T. Honjo, Combination therapy strategies for improving PD-1 blockade efficacy: a new era in cancer immunotherapy. *J Intern Med* 283, 110-120 (2018)). The challenge however is that many of these combinations are often based on the availability of pre-existing drug and a post-hoc rational to combine therapies, rather than a truly hypothesis driven approach, which in some cases has led to worse outcomes for the patient (M. J. Ahn, J. M. Sun, S. H. Lee, J. S. Ahn, K. Park, EGFR TKI combination with immunotherapy in non-small cell lung cancer. *Expert Opin Drug Saf* 16, 465-469 (2017)). It is evident that checkpoint inhibition and reactivation of the immune system offers the potential of long term remission in a number of patients (J. S. Weber et al., Nivolumab versus chemotherapy in patients with advanced melanoma who progressed after anti-CTLA-4 treatment (CheckMate 037): a randomised, controlled, open-label, phase 3 trial. *Lancet Oncol* 16, 375-384 (2015); S. L. Topalian et al., Survival, durable tumor remission, and long-term safety in patients with advanced melanoma receiving nivolumab. *J Clin Oncol* 32, 1020-1030 (2014); M. A. Postow, M. K. Callahan, J. D. Wolchok, Immune Checkpoint Blockade in Cancer Therapy. *J Clin Oncol* 33, 1974-1982 (2015); M. R. Migden et al., PD-1 Blockade with Cemiplimab in Advanced Cutaneous Squamous-Cell Carcinoma. *N Engl J Med* 379, 341-351 (2018)), therefore methods to further improve or enhance T cell activity to promote a more durable response are warranted. Here, to improve the anti-tumor efficacy of PD-1 mAb, the concept of using a TSAxCD28 bispecific to enhance T cell signaling and activation was introduced. Indeed, this novel combination immunotherapy was validated using a tumor target (e.g., PSMA) and demonstrated that CD28 costimulatory bispecific antibodies synergize with PD-1 mAb to not only generate robust T cell activation but also to provide durable anti-tumor responses without systemic toxicity. Consequently, this tumor-targeted combination therapy may provide a considerable advantage over the non-targeted approaches described previously. Using CD28-bispecific antibodies, which do not directly activate CD28 unless clustered on tumor cell surfaces, offered the possibility of promoting co-stimulation only at the tumor site, avoiding the systemic toxicity of conventional CD28-activating antibodies (G. Suntharalingam et al., Cytokine storm in a phase 1 trial of the anti-CD28 monoclonal antibody TGN1412. *N Engl J Med* 355, 1018-1028 (2006)), the toxicity often observed with the combination of CLTA-4 and PD-1 blockade (J. Larkin et al., Combined Nivolumab and Ipilimumab or Monotherapy in Untreated Melanoma. *N Engl J Med* 373, 23-34 (2015); D. B. Johnson et al., Fulminant Myocarditis with Combination Immune Checkpoint Blockade. *N Engl J Med* 375, 1749-1755 (2016); M. H. Pollack et al., Safety of resuming anti-PD-1 in patients with immune-related adverse events (irAEs) during combined anti-CTLA-4 and anti-PD1 in metastatic melanoma. *Ann Oncol* 29, 250-255 (2018)) or other costimulatory agonist bivalent antibodies (N. H. Segal et al., Results from an Integrated Safety Analysis of Urelumab, an Agonist Anti-CD137 Monoclonal Antibody. *Clin Cancer Res* 23, 1929-1936 (2017)). Toxicology studies in genetically-humanized immunocompetent mice, as well as in cynomolgus monkeys, showed that these bispecifics exhibit no toxicity as single agents or in combination with PD-1 mAb. The safety profile together with the enhancement of anti-tumor efficacy by the anti-PSMAxCD28 bispecific antibodies of the invention with PD-1 mAb in syngeneic models suggests that this therapeutic modality is robust, and could have broader utility as a novel combination class for immunotherapy.

To enhance T cell-mediated killing of tumor cells, tumor-targeted approaches are being developed (E. Dahlen, N. Veitonmaki, P. Norlen, Bispecific antibodies in cancer immunotherapy. *Ther Adv Vaccines Immunother* 6, 3-17 (2018)). Indeed, CD3-based bispecific antibodies represent an emerging class of antibodies that can efficiently trigger T cell activation, by linking a T cell to a tumor cell and activating TCR/CD3 (E. J. Smith et al., A novel, native-format bispecific antibody triggering T-cell killing of B-cells is robustly active in mouse tumor models and cynomolgus monkeys. *Sci Rep* 5, 17943 (2015)), thus mimicking normal "signal 1". However, despite their promising clinical efficacy, CD3-bispecifics can be associated with cytokine release syndrome (CRS) due to direct T cell activation and lack of tumor only specificity (S. L. Maude, D. Barrett, D. T. Teachey, S. A. Grupp, Managing cytokine release syndrome associated with novel T cell-engaging therapies. *Cancer J* 20, 119-122 (2014)). Here it was demonstrated for the first time that TSAxCD28 bispecific and PD-1 mAb combination therapy induces a tumor specific T cell activation associated with long term memory response in immunocompetent mouse tumor model. TSAxCD28 bispecific antibodies have limited or no activity in the absence of "signal 1" and PD-1 blockade relies on the endogenous antigen specific T cell response to tumor peptides (W. Hugo et al., Genomic and Transcriptomic Features of Response to Anti-PD-1 Therapy in Metastatic Melanoma. *Cell* 165, 35-44 (2016); N. A. Rizvi et al., Cancer immunology. Mutational landscape determines sensitivity to PD-1 blockade in non-small cell lung cancer. *Science* 348, 124-128 (2015); J. M. Mehnert et al., Immune activation and response to pembrolizumab in POLE-mutant endometrial cancer. *J Clin Invest* 126, 2334-2340 (2016); D. T. Le et al., Mismatch repair deficiency predicts response of solid tumors to PD-1 blockade. *Science* 357, 409-413 (2017)). Therefore, "signal 1" provided by endogenous tumor antigens is important to PSMAxCD28 and PD-1 mAb combination treatment. This is in contrast to CD3-bispecifics that activate T cells independently of their TCR specificity and therefore may not generate long-lived tumor specific immunity. Indeed, it was found that although PSMAxCD3 and PSMAxCD28 combination treatment induces strong anti-tumor efficacy, it did not generate a strong memory response. Further, it has been shown that MC38 tumor cells express high levels of re-activated endogenous retroviral peptides such as p15E, and C57BL6 mice can generate endogenous T cells that recognize and respond to this neo-epitope (J. C. Yang, D. Perry-Lalley, The envelope protein of an endogenous murine retrovirus is a tumor-associated T-cell antigen for multiple murine tumors. *J Immunother* 23, 177-183 (2000); H. J. Zeh, 3rd, D. Perry-Lalley, M. E. Dudley, S. A. Rosenberg, J. C. Yang, High avidity CTLs for two self-antigens demonstrate superior in vitro and in vivo antitumor efficacy. *J Immunol* 162, 989-994 (1999)). In MC38 model described herein, it was demonstrated that PSMAxCD28 and PD-1 mAb combination therapy increased the number of T cells responsive to this p15E neo-antigen. In addition, it was found herein through extensive profiling of tumor infiltrating T cells that PSMAxCD28 and PD-1 mAb combination results in a less dysfunctional CD8 T cell and promotes a strong intra-tumoral memory T cell phenotype. Thus, CD28-bispecifics together with PD-1 blockade can boost endogenous TCR/CD3-dependent T cell responses driving durable anti-tumor responses.

The data herein demonstrate that PD-1 is accumulated at the immune synapse when PD-L1 is expressed by target cells and its accumulation is associated with a reduction of CD28 at the synapse, suggesting that PD-1 could exercise T cell inhibition, by preventing CD28 localization to the synapse. In addition, it was found herein that PD-1 blockade prevented PD-1 synaptic localization while CD28 accumulation at the synapse was increased, allowing TSAxCD28 bispecific to markedly enhance the ability of PD-1 mAb to promote T cell activation. This may be one of the mechanisms by which PD-1 blocking antibody promotes T cell activation. Overall, the visualization of PD-1 and CD28 localization in the immunological synapse following PD-1-PD-L1 interaction and/or PD-1 inhibition, enables better understanding of the effect of PD-1 blockade on T cell activation, as well as the synergy between TSAxCD28 and PD-1 mAb at the level of the immune synapse.

Although PD-1 mAbs are an important new class of immunotherapy, further optimization of anti-tumor activity will surely be important in many cases. Just as CAR-T approaches have employed chimeric receptors that artificially activate both "signal 1" and "signal 2" so as to improve their anti-tumor activity (E. A. Zhukovsky, R. J. Morse, M. V. Maus, Bispecific antibodies and CARs: generalized immunotherapeutics harnessing T cell redirection. *Curr Opin Immunol* 40, 24-35 (2016); A. I. Salter et al., Phosphoproteomic analysis of chimeric antigen receptor signaling reveals kinetic and quantitative differences that affect cell function. *Sci Signal* 11, (2018)), it is now shown the potential benefit of combining PD-1 inhibition with CD28-bispecifics (which provide "signal 2") to enhance anti-tumor activity. This approach has several practical benefits over CAR-T therapies in that it does not require a laborious cell therapy preparation that must be individually customized for each patient, nor does it require that patients be pre-emptively "lymphodepleted" via toxic chemotherapy that is often associated with adverse effects so that they can't accept cell therapy (C. H. June, R. S. O'Connor, O. U. Kawalekar, S. Ghassemi, M. C. Milone, CAR T cell immunotherapy for human cancer. *Science* 359, 1361-1365 (2018)). This bispecific approach offers the potential for increased efficacy as well as increased safety through its specificity of action. Collectively, these data suggest that combining CD28-based bispecifics with the clinically validated PD-1 mAb, such as cemiplimab, may provide well-tolerated, "off-the-shelf" biologics solutions with markedly enhanced and synergistic anti-tumor activity.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

TABLE 24

Sequences Excluded from ST.26-Formatted Sequence Listing

| SEQ ID NO: | Sequence |
|---|---|
| 45 | gctgcatcc |
| 46 | AAS |
| 69 | gctgcatcc |
| 70 | AAS |

What is claimed is:

1. An antibody or antigen-binding fragment thereof that binds human CD28, wherein the antibody or antigen-binding fragment comprises three heavy chain complementarity determining regions (HCDR1, HCDR2 and HCDR3) contained within a heavy chain variable region (HCVR), and three light chain complementarity determining regions (LCDR1, LCDR2 and LCDR3) contained within a light chain variable region (LCVR), wherein the HCDR1, HCDR2, HCDR3, LCDR1, LCDR2, and LCDR3 comprise the amino acid sequences of:

(a) SEQ ID NOs: 12, 14, 16, 20, 22, and 24, respectively; or (b) SEQ ID NOs: 28, 30, 32, 44, 46, and 48, respectively; or (c) SEQ ID NOs: 60, 62, 64, 68, 70, and 72, respectively.

2. The antibody or antigen-binding fragment of claim 1, wherein the HCVR comprises the amino acid sequence of SEQ ID NO: 10, and the LCVR comprises the amino acid sequence of SEQ ID NO: 18.

3. A pharmaceutical composition comprising the antibody or antigen-binding fragment of claim 2 formulated with a suitable carrier.

4. The antibody or antigen-binding fragment of claim 1, wherein the HCVR comprises the amino acid sequence of SEQ ID NO: 26, and the LCVR comprises the amino acid sequence of SEQ ID NO: 42.

5. A pharmaceutical composition comprising the antibody or antigen-binding fragment of claim 4 formulated with a suitable carrier.

6. The antibody or antigen-binding fragment of claim 1, wherein the HCVR comprises the amino acid sequence of SEQ ID NO: 58, and the LCVR comprises the amino acid sequence of SEQ ID NO: 66.

7. A pharmaceutical composition comprising the antibody or antigen-binding fragment of claim 6 formulated with a suitable carrier.

8. The antibody or antigen-binding fragment of claim 1 that is an antibody consisting of two immunoglobulin heavy chains and two immunoglobulin light chains interconnected by disulfide bonds, wherein each immunoglobulin heavy chain comprises the HCVR and a heavy chain constant region comprising CH1, CH2 and CH3 domains, and each immunoglobulin light chain comprises the LCVR and a light chain constant region.

9. The antibody of claim 8, wherein the heavy chain constant region is a human IgG heavy chain constant region.

10. The antibody of claim 9, wherein the heavy chain constant region is human IgG1 or human IgG4 isotype.

11. A pharmaceutical composition comprising the antibody of claim 8 formulated with a suitable carrier.

12. The antibody of claim 1 that is a bispecific antibody or bispecific antigen-binding fragment thereof.

13. A pharmaceutical composition comprising the bispecific antibody or antigen-binding fragment of claim 12 formulated with a suitable carrier.

14. The antibody or antigen-binding fragment of claim 1, wherein the HCDR1, HCDR2, HCDR3, LCDR1, LCDR2, and LCDR3 comprise, respectively, the amino acid sequences of SEQ ID NOs: 12, 14, 16, 20, 22, and 24.

15. A pharmaceutical composition comprising the antibody or antigen-binding fragment of claim 14 formulated with a suitable carrier.

16. The antibody or antigen-binding fragment of claim 1, wherein the HCDR1, HCDR2, HCDR3, LCDR1, LCDR2, and LCDR3 comprise, respectively, the amino acid sequences of SEQ ID NOs: 28, 30, 32, 44, 46, and 48.

17. A pharmaceutical composition comprising the antibody or antigen-binding fragment of claim 16 formulated with a suitable carrier.

18. The antibody or antigen-binding fragment of claim 1, wherein the HCDR1, HCDR2, HCDR3, LCDR1, LCDR2, and LCDR3 comprise, respectively, the amino acid sequences of SEQ ID NOs: 60, 62, 64, 68, 70, and 72.

19. A pharmaceutical composition comprising the antibody or antigen-binding fragment of claim 18 formulated with a suitable carrier.

20. A pharmaceutical composition comprising the antibody or antigen-binding fragment of claim 1 formulated with a suitable carrier.

* * * * *

SEQUENCE LISTING

```
Sequence total quantity: 83
SEQ ID NO: 1            moltype = DNA  length = 372
FEATURE                 Location/Qualifiers
misc_feature            1..372
                        note = synthetic
source                  1..372
                        mol_type = other DNA
                        organism = synthetic construct
SEQUENCE: 1
caggtgcagc tggtggagtc tgggggaggc gtggtccagc ctgggaggtc cctgagactc  60
tcctgtgcag cctctggatt caccttcagt agttatggca tgcactgggt ccgccaggct  120
ccaggcaagg ggctggagtg ggtggcattt atgtcatatg atggaagtaa taaattctat  180
tcagactccg tgaagggccg attcaccatc tccagagaca attccaggaa aatgctgttt  240
ctgcaaatga acaacctgag agctgaggac acggctgtgt attactgtgc aagagatcag  300
tattacgatt ttttgactga tcacggggtc tttgactact ggggccaggg aaccctggtc  360
accgtctcct ca                                                       372

SEQ ID NO: 2            moltype = AA  length = 124
FEATURE                 Location/Qualifiers
REGION                  1..124
                        note = synthetic
source                  1..124
                        mol_type = protein
                        organism = synthetic construct
SEQUENCE: 2
QVQLVESGGG VVQPGRSLRL SCAASGFTFS SYGMHWVRQA PGKGLEWVAF MSYDGSNKFY  60
SDSVKGRFTI SRDNSRKMLF LQMNNLRAED TAVYYCARDQ YYDFLTDHGV FDYWGQGTLV  120
TVSS                                                                124

SEQ ID NO: 3            moltype = DNA  length = 24
FEATURE                 Location/Qualifiers
misc_feature            1..24
                        note = synthetic
source                  1..24
                        mol_type = other DNA
                        organism = synthetic construct
SEQUENCE: 3
ggattcacct tcagtagtta tggc                                          24

SEQ ID NO: 4            moltype = AA  length = 8
FEATURE                 Location/Qualifiers
REGION                  1..8
                        note = synthetic
source                  1..8
                        mol_type = protein
                        organism = synthetic construct
SEQUENCE: 4
```

```
GFTFSSYG                                                    8

SEQ ID NO: 5            moltype = DNA  length = 24
FEATURE                 Location/Qualifiers
misc_feature            1..24
                        note = synthetic
source                  1..24
                        mol_type = other DNA
                        organism = synthetic construct
SEQUENCE: 5
atgtcatatg atggaagtaa taaa                                  24

SEQ ID NO: 6            moltype = AA  length = 8
FEATURE                 Location/Qualifiers
REGION                  1..8
                        note = synthetic
source                  1..8
                        mol_type = protein
                        organism = synthetic construct
SEQUENCE: 6
MSYDGSNK                                                    8

SEQ ID NO: 7            moltype = DNA  length = 51
FEATURE                 Location/Qualifiers
misc_feature            1..51
                        note = synthetic
source                  1..51
                        mol_type = other DNA
                        organism = synthetic construct
SEQUENCE: 7
gcaagagatc agtattacga ttttttgact gatcacgggg tctttgacta c     51

SEQ ID NO: 8            moltype = AA  length = 17
FEATURE                 Location/Qualifiers
REGION                  1..17
                        note = synthetic
source                  1..17
                        mol_type = protein
                        organism = synthetic construct
SEQUENCE: 8
ARDQYYDFLT DHGVFDY                                          17

SEQ ID NO: 9            moltype = DNA  length = 366
FEATURE                 Location/Qualifiers
misc_feature            1..366
                        note = synthetic
source                  1..366
                        mol_type = other DNA
                        organism = synthetic construct
SEQUENCE: 9
caggtgcagc tgcaggagtc gggcccagga ctggtgaagc cttcggagac cctgtccctc  60
acctgcactg tctctggtgg ctccatcagt agttactact ggagctggat ccggcagccc  120
ccagggaagg gactggagtg gattgggtat atctattaca gtgggatcac ccactacaac  180
ccctccctca agagtcgagt caccatatca gtagacacgt ccaagatcca gttctccctg  240
aagctgagtt ctgtgaccgc tgcggacacg gccgtgtatt actgtgcgag atggggggtt  300
cggagggact actactacta cggtatggac gtctggggcc aagggaccac ggtcaccgtc  360
tcctca                                                      366

SEQ ID NO: 10           moltype = AA  length = 122
FEATURE                 Location/Qualifiers
REGION                  1..122
                        note = synthetic
source                  1..122
                        mol_type = protein
                        organism = synthetic construct
SEQUENCE: 10
QVQLQESGPG LVKPSETLSL TCTVSGGSIS SYYWSWIRQP PGKGLEWIGY IYYSGITHYN  60
PSLKSRVTIS VDTSKIQFSL KLSSVTAADT AVYYCARWGV RRDYYYYGMD VWGQGTTVTV  120
SS                                                          122

SEQ ID NO: 11           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 11
ggtggctcca tcagtagtta ctac                                  24
```

```
SEQ ID NO: 12          moltype = AA  length = 8
FEATURE                Location/Qualifiers
REGION                 1..8
                       note = synthetic
source                 1..8
                       mol_type = protein
                       organism = synthetic construct
SEQUENCE: 12
GGSISSYY                                                             8

SEQ ID NO: 13          moltype = DNA  length = 21
FEATURE                Location/Qualifiers
misc_feature           1..21
                       note = synthetic
source                 1..21
                       mol_type = other DNA
                       organism = synthetic construct
SEQUENCE: 13
atctattaca gtgggatcac c                                              21

SEQ ID NO: 14          moltype = AA  length = 7
FEATURE                Location/Qualifiers
REGION                 1..7
                       note = synthetic
source                 1..7
                       mol_type = protein
                       organism = synthetic construct
SEQUENCE: 14
IYYSGIT                                                              7

SEQ ID NO: 15          moltype = DNA  length = 48
FEATURE                Location/Qualifiers
misc_feature           1..48
                       note = synthetic
source                 1..48
                       mol_type = other DNA
                       organism = synthetic construct
SEQUENCE: 15
gcgagatggg gggttcggag ggactactac tactacggta tggacgtc                 48

SEQ ID NO: 16          moltype = AA  length = 16
FEATURE                Location/Qualifiers
REGION                 1..16
                       note = synthetic
source                 1..16
                       mol_type = protein
                       organism = synthetic construct
SEQUENCE: 16
ARWGVRRDYY YYGMDV                                                    16

SEQ ID NO: 17          moltype = DNA  length = 324
FEATURE                Location/Qualifiers
misc_feature           1..324
                       note = synthetic
source                 1..324
                       mol_type = other DNA
                       organism = synthetic construct
SEQUENCE: 17
gaaatagttt tgacacagag tcccggcaca ctgtcactct ctcccgggga aagagccacc  60
ttgtcatgta gagcaagtca gtcagtctct agctcttatc tcgcctggta ccagcagaag  120
ccgggacagg cccctagact gctgatctac ggggcaagtt ccagggccac cggaatcccc  180
gaccggttca gtggaagcgg aagcggaacc gattttactt tgacgatttc tagactggag  240
ccagaggatt tcgccgttta ctattgtcaa cagtacggaa gcagcccgtg gacgtttggc  300
cagggcacga aggtagaaat caag                                           324

SEQ ID NO: 18          moltype = AA  length = 108
FEATURE                Location/Qualifiers
REGION                 1..108
                       note = synthetic
source                 1..108
                       mol_type = protein
                       organism = synthetic construct
SEQUENCE: 18
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK                 108

SEQ ID NO: 19          moltype = DNA  length = 36
FEATURE                Location/Qualifiers
```

```
misc_feature          1..36
                      note = synthetic
source                1..36
                      mol_type = other DNA
                      organism = synthetic construct
SEQUENCE: 19
agagcaagtc agtcagtctc tagctcttat ctcgcc                              36

SEQ ID NO: 20         moltype = AA  length = 12
FEATURE               Location/Qualifiers
REGION                1..12
                      note = synthetic
source                1..12
                      mol_type = protein
                      organism = synthetic construct
SEQUENCE: 20
RASQSVSSSY LA                                                        12

SEQ ID NO: 21         moltype = DNA  length = 21
FEATURE               Location/Qualifiers
misc_feature          1..21
                      note = synthetic
source                1..21
                      mol_type = other DNA
                      organism = synthetic construct
SEQUENCE: 21
ggggcaagtt ccagggccac c                                              21

SEQ ID NO: 22         moltype = AA  length = 7
FEATURE               Location/Qualifiers
REGION                1..7
                      note = synthetic
source                1..7
                      mol_type = protein
                      organism = synthetic construct
SEQUENCE: 22
GASSRAT                                                              7

SEQ ID NO: 23         moltype = DNA  length = 27
FEATURE               Location/Qualifiers
misc_feature          1..27
                      note = synthetic
source                1..27
                      mol_type = other DNA
                      organism = synthetic construct
SEQUENCE: 23
caacagtacg gaagcagccc gtggacg                                        27

SEQ ID NO: 24         moltype = AA  length = 9
FEATURE               Location/Qualifiers
REGION                1..9
                      note = synthetic
source                1..9
                      mol_type = protein
                      organism = synthetic construct
SEQUENCE: 24
QQYGSSPWT                                                            9

SEQ ID NO: 25         moltype = DNA  length = 387
FEATURE               Location/Qualifiers
misc_feature          1..387
                      note = synthetic
source                1..387
                      mol_type = other DNA
                      organism = synthetic construct
SEQUENCE: 25
gaggtgcagc tggtggagtc tgggggaggc ttggtacagc cggggggggtc cctgagactc  60
tcctgtgcag cctctggatt cacctttagc acctatgcca tgacctgggt ccgccaggct  120
ccagggaagg ggctggagtg ggtctcattt attagtggta gtggtgataa cacgtattac  180
gcagactccg tgaagggccg attcaccatc tccagagaca attccaagaa cacgctgtat  240
ctgcaaatga acagcctgag agccgacgat tcggccatat atcactgtgc gaaagattcc  300
ggatattgta gtagtggtgg gtgctccctc tacttctact acggtatgga cgtctggggc  360
caagggacca cggtcaccgt ctcctca                                        387

SEQ ID NO: 26         moltype = AA  length = 129
FEATURE               Location/Qualifiers
REGION                1..129
                      note = synthetic
source                1..129
```

```
                        mol_type = protein
                        organism = synthetic construct
SEQUENCE: 26
EVQLVESGGG LVQPGGSLRL SCAASGFTFS TYAMTWVRQA PGKGLEWVSF ISGSGDNTYY  60
ADSVKGRFTI SRDNSKNTLY LQMNSLRADD SAIYHCAKDS GYCSSGGCSL YFYYGMDVWG  120
QGTTVTVSS                                                          129

SEQ ID NO: 27           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 27
ggattcacct ttagcaccta tgcc                                         24

SEQ ID NO: 28           moltype = AA  length = 8
FEATURE                 Location/Qualifiers
REGION                  1..8
                        note = synthetic
source                  1..8
                        mol_type = protein
                        organism = synthetic construct
SEQUENCE: 28
GFTFSTYA                                                           8

SEQ ID NO: 29           moltype = DNA  length = 24
FEATURE                 Location/Qualifiers
misc_feature            1..24
                        note = synthetic
source                  1..24
                        mol_type = other DNA
                        organism = synthetic construct
SEQUENCE: 29
attagtggta gtggtgataa cacg                                         24

SEQ ID NO: 30           moltype = AA  length = 8
FEATURE                 Location/Qualifiers
REGION                  1..8
                        note = synthetic
source                  1..8
                        mol_type = protein
                        organism = synthetic construct
SEQUENCE: 30
ISGSGDNT                                                           8

SEQ ID NO: 31           moltype = DNA  length = 66
FEATURE                 Location/Qualifiers
misc_feature            1..66
                        note = synthetic
source                  1..66
                        mol_type = other DNA
                        organism = synthetic construct
SEQUENCE: 31
gcgaaagatt ccggatattg tagtagtggt gggtgctccc tctacttcta ctacggtatg  60
gacgtc                                                             66

SEQ ID NO: 32           moltype = AA  length = 22
FEATURE                 Location/Qualifiers
REGION                  1..22
                        note = synthetic
source                  1..22
                        mol_type = protein
                        organism = synthetic construct
SEQUENCE: 32
AKDSGYCSSG GCSLYFYYGM DV                                           22

SEQ ID NO: 33           moltype = DNA  length = 372
FEATURE                 Location/Qualifiers
misc_feature            1..372
                        note = synthetic
source                  1..372
                        mol_type = other DNA
                        organism = synthetic construct
SEQUENCE: 33
caggtgcagc tggtggagtc tgggggaggc gtggtccagc ctgggaggtc cctgagactc  60
tcctgtgcag cctctggatt caccttcagt agctatggca tgcactgggt ccgccaggct  120
ccaggcaagg ggctggagtg ggtggcagtc atttcatatg ctggaaacaa taaatactat  180
```

```
gcagactccg tgaaaggccg attcaccgtt tccagagaca attcgaagaa aacattgtat  240
ctgcaaatga acagcctgag atctgaggac acggctgtgt attactgtgc gaaagattcg  300
tattatgatt ttttgactga tcccgatgtt ttggatatct ggggccaagg gacaatggtc  360
accgtctctt ca                                                      372

SEQ ID NO: 34          moltype = AA  length = 124
FEATURE                Location/Qualifiers
REGION                 1..124
                       note = synthetic
source                 1..124
                       mol_type = protein
                       organism = synthetic construct
SEQUENCE: 34
QVQLVESGGG VVQPGRSLRL SCAASGFTFS SYGMHWVRQA PGKGLEWVAV ISYAGNNKYY  60
ADSVKGRFTV SRDNSKKTLY LQMNSLRSED TAVYYCAKDS YYDFLTDPDV LDIWGQGTMV  120
TVSS                                                               124

SEQ ID NO: 35          moltype = DNA  length = 24
FEATURE                Location/Qualifiers
misc_feature           1..24
                       note = synthetic
source                 1..24
                       mol_type = other DNA
                       organism = synthetic construct
SEQUENCE: 35
ggattcacct tcagtagcta tggc                                         24

SEQ ID NO: 36          moltype = AA  length = 8
FEATURE                Location/Qualifiers
REGION                 1..8
                       note = synthetic
source                 1..8
                       mol_type = protein
                       organism = synthetic construct
SEQUENCE: 36
GFTFSSYG                                                           8

SEQ ID NO: 37          moltype = DNA  length = 24
FEATURE                Location/Qualifiers
misc_feature           1..24
                       note = synthetic
source                 1..24
                       mol_type = other DNA
                       organism = synthetic construct
SEQUENCE: 37
atttcatatg ctggaaacaa taaa                                         24

SEQ ID NO: 38          moltype = AA  length = 8
FEATURE                Location/Qualifiers
REGION                 1..8
                       note = synthetic
source                 1..8
                       mol_type = protein
                       organism = synthetic construct
SEQUENCE: 38
ISYAGNNK                                                           8

SEQ ID NO: 39          moltype = DNA  length = 51
FEATURE                Location/Qualifiers
misc_feature           1..51
                       note = synthetic
source                 1..51
                       mol_type = other DNA
                       organism = synthetic construct
SEQUENCE: 39
gcgaaagatt cgtattatga tttttttgact gatcccgatg ttttggatat c          51

SEQ ID NO: 40          moltype = AA  length = 17
FEATURE                Location/Qualifiers
REGION                 1..17
                       note = synthetic
source                 1..17
                       mol_type = protein
                       organism = synthetic construct
SEQUENCE: 40
AKDSYYDFLT DPDVLDI                                                 17

SEQ ID NO: 41          moltype = DNA  length = 324
FEATURE                Location/Qualifiers
```

```
misc_feature          1..324
                      note = synthetic
source                1..324
                      mol_type = other DNA
                      organism = synthetic construct
SEQUENCE: 41
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 42         moltype = AA  length = 108
FEATURE               Location/Qualifiers
REGION                1..108
                      note = synthetic
source                1..108
                      mol_type = protein
                      organism = synthetic construct
SEQUENCE: 42
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK               108

SEQ ID NO: 43         moltype = DNA  length = 18
FEATURE               Location/Qualifiers
misc_feature          1..18
                      note = synthetic
source                1..18
                      mol_type = other DNA
                      organism = synthetic construct
SEQUENCE: 43
cagagcatta gcagctat                                                18

SEQ ID NO: 44         moltype = AA  length = 6
FEATURE               Location/Qualifiers
REGION                1..6
                      note = synthetic
source                1..6
                      mol_type = protein
                      organism = synthetic construct
SEQUENCE: 44
QSISSY                                                             6

SEQ ID NO: 45         moltype =   length =
SEQUENCE: 45
000

SEQ ID NO: 46         moltype =   length =
SEQUENCE: 46
000

SEQ ID NO: 47         moltype = DNA  length = 30
FEATURE               Location/Qualifiers
misc_feature          1..30
                      note = synthetic
source                1..30
                      mol_type = other DNA
                      organism = synthetic construct
SEQUENCE: 47
caacagagtt acagtacccc tccgatcacc                                   30

SEQ ID NO: 48         moltype = AA  length = 10
FEATURE               Location/Qualifiers
REGION                1..10
                      note = synthetic
source                1..10
                      mol_type = protein
                      organism = synthetic construct
SEQUENCE: 48
QQSYSTPPIT                                                         10

SEQ ID NO: 49         moltype = DNA  length = 372
FEATURE               Location/Qualifiers
misc_feature          1..372
                      note = synthetic
source                1..372
                      mol_type = other DNA
                      organism = synthetic construct
```

SEQUENCE: 49
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtc atttcatatg ctggaaacaa taaatactat 180
gcagactccg tgaaaggccg attcaccgtt tccagagaca attcgaagaa aacattgtat 240
ctgcaaatga acagcctgag atctgaggac acggctgtgt attactgtgc gaaagattcg 300
tattatgatt ttttgactga tcccgatgtt ttggatatct ggggccaagg gacaatggtc 360
accgtctctt ca 372

SEQ ID NO: 50 moltype = AA length = 124
FEATURE Location/Qualifiers
REGION 1..124
note = synthetic
source 1..124
mol_type = protein
organism = synthetic construct
SEQUENCE: 50
QVQLVESGGG VVQPGRSLRL SCAASGFTFS SYGMHWVRQA PGKGLEWVAV ISYAGNNKYY 60
ADSVKGRFTV SRDNSKKTLY LQMNSLRSED TAVYYCAKDS YYDFLTDPDV LDIWGQGTMV 120
TVSS 124

SEQ ID NO: 51 moltype = DNA length = 24
FEATURE Location/Qualifiers
misc_feature 1..24
note = synthetic
source 1..24
mol_type = other DNA
organism = synthetic construct
SEQUENCE: 51
ggattcacct tcagtagcta tggc 24

SEQ ID NO: 52 moltype = AA length = 8
FEATURE Location/Qualifiers
REGION 1..8
note = synthetic
source 1..8
mol_type = protein
organism = synthetic construct
SEQUENCE: 52
GFTFSSYG 8

SEQ ID NO: 53 moltype = DNA length = 24
FEATURE Location/Qualifiers
misc_feature 1..24
note = synthetic
source 1..24
mol_type = other DNA
organism = synthetic construct
SEQUENCE: 53
atttcatatg ctggaaacaa taaa 24

SEQ ID NO: 54 moltype = AA length = 8
FEATURE Location/Qualifiers
REGION 1..8
note = synthetic
source 1..8
mol_type = protein
organism = synthetic construct
SEQUENCE: 54
ISYAGNNK 8

SEQ ID NO: 55 moltype = DNA length = 51
FEATURE Location/Qualifiers
misc_feature 1..51
note = synthetic
source 1..51
mol_type = other DNA
organism = synthetic construct
SEQUENCE: 55
gcgaaagatt cgtattatga tttttttgact gatcccgatg ttttggatat c 51

SEQ ID NO: 56 moltype = AA length = 17
FEATURE Location/Qualifiers
REGION 1..17
note = synthetic
source 1..17
mol_type = protein
organism = synthetic construct
SEQUENCE: 56

```
AKDSYYDFLT DPDVLDI                                              17

SEQ ID NO: 57          moltype = DNA  length = 354
FEATURE                Location/Qualifiers
misc_feature           1..354
                       note = synthetic
source                 1..354
                       mol_type = other DNA
                       organism = synthetic construct
SEQUENCE: 57
gaggtgcagc tggtggagtc tgggggaggc ttggtccagc ctggggggtc cctgagactc  60
tcctgtgcag cctccggatt caccttcagt aggaataata tgcactgggt ccgccaggct  120
ccagggaagg gactggaata tgtttcaggt attagtagta atgggggtcg cacatattat  180
gcagactctg tgaagggcag attcaccatc tccagagaca attccaagaa cacgctgtat  240
cttcaaatgg gcggcctgag agctgcggac atggctgtgt atttctgtac gagagatgac  300
gagctgcttt cctttgacta ctggggccag ggaaccctgg tcactgtctc ctca        354

SEQ ID NO: 58          moltype = AA  length = 118
FEATURE                Location/Qualifiers
REGION                 1..118
                       note = synthetic
source                 1..118
                       mol_type = protein
                       organism = synthetic construct
SEQUENCE: 58
EVQLVESGGG LVQPGGSLRL SCAASGFTFS RNNMHWVRQA PGKGLEYVSG ISSNGGRTYY  60
ADSVKGRFTI SRDNSKNTLY LQMGGLRAAD MAVYFCTRDD ELLSFDYWGQ GTLVTVSS    118

SEQ ID NO: 59          moltype = DNA  length = 24
FEATURE                Location/Qualifiers
misc_feature           1..24
                       note = synthetic
source                 1..24
                       mol_type = other DNA
                       organism = synthetic construct
SEQUENCE: 59
ggattcacct tcagtaggaa taat                                      24

SEQ ID NO: 60          moltype = AA  length = 8
FEATURE                Location/Qualifiers
REGION                 1..8
                       note = synthetic
source                 1..8
                       mol_type = protein
                       organism = synthetic construct
SEQUENCE: 60
GFTFSRNN                                                        8

SEQ ID NO: 61          moltype = DNA  length = 24
FEATURE                Location/Qualifiers
misc_feature           1..24
                       note = synthetic
source                 1..24
                       mol_type = other DNA
                       organism = synthetic construct
SEQUENCE: 61
attagtagta atgggggtcg caca                                      24

SEQ ID NO: 62          moltype = AA  length = 8
FEATURE                Location/Qualifiers
REGION                 1..8
                       note = synthetic
source                 1..8
                       mol_type = protein
                       organism = synthetic construct
SEQUENCE: 62
ISSNGGRT                                                        8

SEQ ID NO: 63          moltype = DNA  length = 33
FEATURE                Location/Qualifiers
misc_feature           1..33
                       note = synthetic
source                 1..33
                       mol_type = other DNA
                       organism = synthetic construct
SEQUENCE: 63
acgagagatg acgagctgct ttcctttgac tac                            33

SEQ ID NO: 64          moltype = AA  length = 11
```

```
FEATURE                Location/Qualifiers
REGION                 1..11
                       note = synthetic
source                 1..11
                       mol_type = protein
                       organism = synthetic construct
SEQUENCE: 64
TRDDELLSFD Y                                                   11

SEQ ID NO: 65          moltype = DNA  length = 324
FEATURE                Location/Qualifiers
misc_feature           1..324
                       note = synthetic
source                 1..324
                       mol_type = other DNA
                       organism = synthetic construct
SEQUENCE: 65
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                     324

SEQ ID NO: 66          moltype = AA  length = 108
FEATURE                Location/Qualifiers
REGION                 1..108
                       note = synthetic
source                 1..108
                       mol_type = protein
                       organism = synthetic construct
SEQUENCE: 66
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK            108

SEQ ID NO: 67          moltype = DNA  length = 18
FEATURE                Location/Qualifiers
misc_feature           1..18
                       note = synthetic
source                 1..18
                       mol_type = other DNA
                       organism = synthetic construct
SEQUENCE: 67
cagagcatta gcagctat                                            18

SEQ ID NO: 68          moltype = AA  length = 6
FEATURE                Location/Qualifiers
REGION                 1..6
                       note = synthetic
source                 1..6
                       mol_type = protein
                       organism = synthetic construct
SEQUENCE: 68
QSISSY                                                         6

SEQ ID NO: 69          moltype =   length =
SEQUENCE: 69
000

SEQ ID NO: 70          moltype =   length =
SEQUENCE: 70
000

SEQ ID NO: 71          moltype = DNA  length = 30
FEATURE                Location/Qualifiers
misc_feature           1..30
                       note = synthetic
source                 1..30
                       mol_type = other DNA
                       organism = synthetic construct
SEQUENCE: 71
caacagagtt acagtacccc tccgatcacc                               30

SEQ ID NO: 72          moltype = AA  length = 10
FEATURE                Location/Qualifiers
REGION                 1..10
                       note = synthetic
source                 1..10
                       mol_type = protein
```

```
                         organism = synthetic construct
SEQUENCE: 72
QQSYSTPPIT                                                10

SEQ ID NO: 73            moltype = AA  length = 750
FEATURE                  Location/Qualifiers
REGION                   1..750
                         note = Human PSMA (FOLH1) NP_004467.1 glutamate
                          carboxypeptidase 2 isoform 1
source                   1..750
                         mol_type = protein
                         organism = synthetic construct
SEQUENCE: 73
MWNLLHETDS AVATARRPRW LCAGALVLAG GFFLLGFLFG WFIKSSNEAT NITPKHNMKA  60
FLDELKAENI KKFLYNFTQI PHLAGTEQNF QLAKQIQSQW KEFGLDSVEL AHYDVLLSYP  120
NKTHPNYISI INEDGNEIFN TSLFEPPPPG YENVSDIVPP FSAFSPQGMP EGDLVYVNYA  180
RTEDFFKLER DMKINCSGKI VIARYGKVFR GNKVKNAQLA GAKGVILYSD PADYFAPGVK  240
SYPDGWNLPG GGVQRGNILN LNGAGDPLTP GYPANEYAYR RGIAEAVGLP SIPVHPIGYY  300
DAQKLLEKMG GSAPPDSSWR GSLKVPYNVG PGFTGNFSTQ KVKMHIHSTN EVTRIYNVIG  360
TLRGAVEPDR YVILGGHRDS WVFGGIDPQS GAAVVHEIVR SFGTLKKEGW RPRRTILFAS  420
WDAEEFGLLG STEWAEENSR LLQERGVAYI NADSSIEGNY TLRVDCTPLM YSLVHNLTKE  480
LKSPDEGFEG KSLYESWTKK SPSPEFSGMP RISKLGSGND FEVFFQRLGI ASGRARYTKN  540
WETNKFSGYP LYHSVYETYE LVEKFYDPMF KYHLTVAQVR GGMVFELANS IVLPFDCRDY  600
AVVLRKYADK IYSISMKHPQ EMKTYSVSFD SLFSAVKNFT EIASKFSERL QDFDKSNPIV  660
LRMMNDQLMF LERAFIDPLG LPDRPFYRHV IYAPSSHNKY AGESFPGIYD ALFDIESKVD  720
PSKAWGEVKR QIYVAAFTVQ AAAETLSEVA                                750

SEQ ID NO: 74            moltype = AA  length = 220
FEATURE                  Location/Qualifiers
REGION                   1..220
                         note = Human CD28 NP_006130.1 T-cell-specific surface
                          glycoprotein CD28 isoform 1 precursor
source                   1..220
                         mol_type = protein
                         organism = synthetic construct
SEQUENCE: 74
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                      220

SEQ ID NO: 75            moltype = AA  length = 162
FEATURE                  Location/Qualifiers
REGION                   1..162
                         note = hCD28 ecto (N19-P152).mmH (REGN2011): Monomeric
                          human CD28 (amino acids N19-P152, Accession # NM_006139),
                          with a C-terminal myc-myc-hexahistidine (mmH) tag
source                   1..162
                         mol_type = protein
                         organism = synthetic construct
SEQUENCE: 75
NKILVKQSPM LVAYDNAVNL SCKYSYNLFS REFRASLHKG LDSAVEVCVV YGNYSQQLQV  60
YSKTGFNCDG KLGNESVTFY LQNLYVNQTD IYFCKIEVMY PPPYLDNEKS NGTIIHVKGK  120
HLCPSPLFPG PSKPEQKLIS EEDLGGEQKL ISEEDLHHHH HH                    162

SEQ ID NO: 76            moltype = AA  length = 367
FEATURE                  Location/Qualifiers
REGION                   1..367
                         note = hCD28 ecto (N19-P152).mFc (REGN2012): Dimeric human
                          CD28 (amino acids N19-P152, Accession # NM_006139), with a
                          C-terminal mouse IgG2a Fc (amino acids E98-K330, Accession
                          # P01863) tag
source                   1..367
                         mol_type = protein
                         organism = synthetic construct
SEQUENCE: 76
NKILVKQSPM LVAYDNAVNL SCKYSYNLFS REFRASLHKG LDSAVEVCVV YGNYSQQLQV  60
YSKTGFNCDG KLGNESVTFY LQNLYVNQTD IYFCKIEVMY PPPYLDNEKS NGTIIHVKGK  120
HLCPSPLFPG PSKPEPRGPT IKPCPPCKCP APNLLGGPSV FIFPPKIKDV LMISLSPIVT  180
CVVVDVSEDD PDVQISWFVN NVEVHTAQTQ THREDYNSTL RVVSALPIQH QDWMSGKEFK  240
CKVNNKDLPA PIERTISKPK GSVRAPQVYV LPPPEEEMTK KQVTLTCMVT DFMPEDIYVE  300
WTNNGKTELN YKNTEPVLDS DGSYFMYSKL RVEKKNWVER NSYSCSVVHE GLHNHHTTKS  360
FSRTPGK                                                         367

SEQ ID NO: 77            moltype = AA  length = 16
FEATURE                  Location/Qualifiers
REGION                   1..16
                         note = amino acids 5-20 of SEQ ID NO: 76
source                   1..16
```

```
                        mol_type = protein
                        organism = synthetic construct
SEQUENCE: 77
VKQSPMLVAY DNAVNL                                                  16

SEQ ID NO: 78           moltype = AA  length = 10
FEATURE                 Location/Qualifiers
REGION                  1..10
                        note = amino acids 29-38 of SEQ ID NO: 76
source                  1..10
                        mol_type = protein
                        organism = synthetic construct
SEQUENCE: 78
FSREFRASLH                                                         10

SEQ ID NO: 79           moltype = AA  length = 5
FEATURE                 Location/Qualifiers
REGION                  1..5
                        note = amino acids 80-84 of SEQ ID NO: 76
source                  1..5
                        mol_type = protein
                        organism = synthetic construct
SEQUENCE: 79
YLQNL                                                              5

SEQ ID NO: 80           moltype = AA  length = 18
FEATURE                 Location/Qualifiers
REGION                  1..18
                        note = amino acids 91-108 of SEQ ID NO: 76
source                  1..18
                        mol_type = protein
                        organism = synthetic construct
SEQUENCE: 80
IYFCKIEVMY PPPYLDNE                                                18

SEQ ID NO: 81           moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 81
QVQLQESGPG LVKPSETLSL TCTVSGGSIS SYYWSWIRQP PGKGLEWIGY IYYSGITHYN  60
PSLKSRVTIS VDTSKIQFSL KLSSVTAADT AVYYCARWGV RRDYYYYGMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPPVAGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNRFTQK SLSLSPGK                                     448

SEQ ID NO: 82           moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 82
QVQLVESGGG VVQPGRSLRL SCAASGFTFS SYGMHWVRQA PGKGLEWVAF MSYDGSNKFY  60
SDSVKGRFTI SRDNSRKMLF LQMNNLRAED TAVYYCARDQ YYDFLTDHGV FDYWGQGTLV  120
TVSSASTKGP SVFPLAPCSR STSESTAALG CLVKDYFPEP VTVSWNSGAL TSGVHTFPAV  180
LQSSGLYSLS SVVTVPSSSL GTKTYTCNVD HKPSNTKVDK RVESKYGPPC PPCPAPPVAG  240
PSVFLFPPKP KDTLMISRTP EVTCVVVDVS QEDPEVQFNW YVDGVEVHNA KTKPREEQFN  300
STYRVVSVLT VLHQDWLNGK EYKCKVSNKG LPSSIEKTIS KAKGQPREPQ VYTLPPSQEE  360
MTKNQVSLTC LVKGFYPSDI AVEWESNGQP ENNYKTTPPV LDSDGSFFLY SRLTVDKSRW  420
QEGNVFSCSV MHEALHNHYT QKSLSLSLGK                                   450

SEQ ID NO: 83           moltype = AA  length = 215
FEATURE                 Location/Qualifiers
REGION                  1..215
                        note = Description of Artificial Sequence: Synthetic
                         polypeptide
source                  1..215
                        mol_type = protein
                        organism = synthetic construct
```

-continued

```
SEQUENCE: 83
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215
```